(12) United States Patent
Bolen et al.

(10) Patent No.: US 11,903,973 B2
(45) Date of Patent: *Feb. 20, 2024

(54) GENETICALLY ENGINEERED HEMATOPOIETIC STEM CELLS AND USES THEREOF

(71) Applicant: VOR BIOPHARMA INC., Cambridge, MA (US)

(72) Inventors: Joseph Bolen, Boston, MA (US); Aleksandar Filip Radovic-Moreno, Evanston, IL (US); John Lydeard, Sharon, MA (US)

(73) Assignee: VOR BIOPHARMA INC., Cambridge, MA (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/176,610

(22) Filed: Feb. 16, 2021

(65) Prior Publication Data

US 2022/0008476 A1  Jan. 13, 2022

Related U.S. Application Data

(63) Continuation of application No. 16/701,818, filed on Dec. 3, 2019, now Pat. No. 10,925,902, which is a continuation of application No. 16/554,520, filed on Aug. 28, 2019, now Pat. No. 11,389,485.

(60) Provisional application No. 62/809,202, filed on Feb. 22, 2019, provisional application No. 62/789,440, filed on Jan. 7, 2019, provisional application No. 62/728,061, filed on Sep. 6, 2018, provisional application No. 62/723,993, filed on Aug. 28, 2018.

(51) Int. Cl.
| | | |
|---|---|---|
| *A61P 35/02* | (2006.01) | |
| *A61K 35/17* | (2015.01) | |
| *A61K 35/28* | (2015.01) | |
| *A61K 39/395* | (2006.01) | |
| *C07K 16/28* | (2006.01) | |
| *C07K 14/705* | (2006.01) | |
| *C12N 5/0789* | (2010.01) | |
| *C12N 15/90* | (2006.01) | |
| *C12N 15/113* | (2010.01) | |
| *C12N 15/11* | (2006.01) | |
| *A61K 38/17* | (2006.01) | |
| *C12N 9/22* | (2006.01) | |
| *A61P 35/00* | (2006.01) | |
| *A61K 35/12* | (2015.01) | |
| *A61K 39/00* | (2006.01) | |

(52) U.S. Cl.
CPC .............. *A61K 35/28* (2013.01); *A61K 35/17* (2013.01); *A61K 38/178* (2013.01); *A61K 38/1774* (2013.01); *A61K 39/3955* (2013.01); *A61P 35/00* (2018.01); *A61P 35/02* (2018.01); *C07K 14/7056* (2013.01); *C07K 14/70596* (2013.01); *C12N 5/0647* (2013.01); *C12N 9/22* (2013.01); *C12N 15/11* (2013.01); *C12N 15/907* (2013.01); *A61K 2035/124* (2013.01); *A61K 2039/505* (2013.01); *C12N 2310/20* (2017.05); *C12N 2510/00* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 9,777,061 B2 | 10/2017 | Ebersbach et al. | |
| 9,803,029 B2 | 10/2017 | Ellwanger et al. | |
| 10,137,155 B2 | 11/2018 | Mukherjee et al. | |
| 10,201,606 B2 | 2/2019 | Lutteropp et al. | |
| 10,548,922 B2 | 2/2020 | Gill et al. | |
| 10,660,919 B2 | 5/2020 | Mukherjee et al. | |
| 10,668,103 B2 | 6/2020 | Mukherjee et al. | |
| 10,786,535 B2 | 9/2020 | Mukherjee et al. | |
| 10,912,799 B2 | 2/2021 | Mukherjee et al. | |
| 10,925,902 B2 | 2/2021 | Bolen et al. | |
| 11,033,619 B2 | 6/2021 | Lutteropp et al. | |
| 11,382,932 B2 * | 7/2022 | Bolen | A61K 35/17 |
| 11,389,485 B2 * | 7/2022 | Bolen | A61P 35/00 |
| 11,419,935 B2 | 8/2022 | Lutteropp et al. | |
| 11,464,807 B2 * | 10/2022 | Bolen | A61P 35/00 |
| 11,559,551 B2 * | 1/2023 | Bolen | C12N 5/0647 |
| 11,571,445 B2 * | 2/2023 | Bolen | A61K 35/17 |
| 11,718,659 B2 | 8/2023 | Mukherjee et al. | |
| 2013/0309223 A1 | 11/2013 | Sutherland et al. | |
| 2015/0283255 A1 | 10/2015 | McDonagh et al. | |

(Continued)

FOREIGN PATENT DOCUMENTS

| | | |
|---|---|---|
| CA | 2944528 A1 | 10/2015 |
| CN | 108290939 A | 7/2018 |

(Continued)

OTHER PUBLICATIONS

[No Author Listed], Clinical Trial NCT03795779. CLL1-CD33 cCar in Patients with Relapsed and/or Refractory, High Risk Hematologic Malignancies. Access at ClincialTrials.gov on Mar. 27, 2020. 8 pages.

(Continued)

*Primary Examiner* — Ilia I Ouspenski
(74) *Attorney, Agent, or Firm* — Wolf, Greenfield & Sacks, P.C.

(57) ABSTRACT

Genetically engineered hematopoietic cells such as hematopoietic stem cells having one or more genetically edited genes of lineage-specific cell-surface proteins and therapeutic uses thereof, either alone or in combination with immune therapy that targets the lineage-specific cell-surface proteins.

31 Claims, 67 Drawing Sheets
Specification includes a Sequence Listing.

(56) References Cited

U.S. PATENT DOCUMENTS

| | | |
|---|---|---|
| 2016/0051651 A1 | 2/2016 | Brogdon et al. |
| 2016/0096892 A1 | 4/2016 | Brogdon et al. |
| 2016/0144026 A1 | 5/2016 | Lutteropp et al. |
| 2016/0272999 A1 | 9/2016 | Duchateau et al. |
| 2016/0311907 A1 | 10/2016 | Brogdon et al. |
| 2016/0368994 A1 | 12/2016 | Kelley et al. |
| 2017/0145094 A1 | 5/2017 | Galetto et al. |
| 2017/0326179 A1 | 11/2017 | Mukherjee et al. |
| 2017/0329179 A1 | 11/2017 | Cho et al. |
| 2018/0002397 A1 | 1/2018 | Shah et al. |
| 2018/0009895 A1 | 1/2018 | Smith et al. |
| 2018/0111993 A1 | 4/2018 | Pule et al. |
| 2018/0162939 A1 | 6/2018 | Ma et al. |
| 2018/0187173 A1 | 7/2018 | Cost et al. |
| 2018/0207295 A1 | 7/2018 | Fotin-Mleczek et al. |
| 2018/0250339 A1 | 9/2018 | Gill et al. |
| 2018/0282762 A1 | 10/2018 | Gori |
| 2018/0312825 A1 | 11/2018 | Liu et al. |
| 2018/0312828 A1 | 11/2018 | Liu et al. |
| 2018/0355044 A1 | 12/2018 | Jiang et al. |
| 2019/0046580 A1 | 2/2019 | Mukherjee et al. |
| 2019/0046581 A1 | 2/2019 | Mukherjee et al. |
| 2019/0112380 A1 | 4/2019 | Chaudhary et al. |
| 2019/0280502 A1 | 9/2019 | Hsieh et al. |
| 2019/0309075 A1 | 10/2019 | Chiffoleau et al. |
| 2019/0314418 A1 | 10/2019 | Mukherjee et al. |
| 2019/0321410 A1 | 10/2019 | Mukherjee et al. |
| 2019/0365806 A1 | 12/2019 | Jeker et al. |
| 2020/0030381 A1 | 1/2020 | Bolen et al. |
| 2020/0093865 A1 | 3/2020 | Bolen et al. |
| 2020/0138869 A1 | 5/2020 | Bolen et al. |
| 2020/0262891 A1 | 8/2020 | Mukherjee et al. |
| 2020/0276244 A1 | 9/2020 | Mukherjee et al. |
| 2020/0281975 A1 | 9/2020 | Gill et al. |
| 2020/0318071 A1 | 10/2020 | Bolen et al. |
| 2020/0338130 A9 | 10/2020 | Bolen et al. |
| 2021/0220407 A1 | 7/2021 | Bolen et al. |
| 2021/0252073 A1 | 8/2021 | Mukherjee et al. |
| 2021/0260130 A1 | 8/2021 | Mukherjee et al. |
| 2021/0315936 A1 | 10/2021 | Bolen et al. |
| 2021/0338814 A1 | 11/2021 | Lutteropp et al. |
| 2022/0008476 A1 | 1/2022 | Bolen et al. |
| 2022/0228153 A1* | 7/2022 | Lydeard .................. C12N 9/22 |
| 2022/0290160 A1 | 9/2022 | Bolen et al. |
| 2022/0333116 A1 | 10/2022 | Lydeard et al. |
| 2023/0053285 A1 | 2/2023 | Bolen et al. |

FOREIGN PATENT DOCUMENTS

| | | |
|---|---|---|
| CN | 109715207 A | 5/2019 |
| EA | 202191979 A1 | 11/2021 |
| EP | 3025719 A1 | 6/2016 |
| JP | 2017-522879 A | 8/2017 |
| WO | WO 2009/052431 A2 | 4/2009 |
| WO | WO 2011/048350 A1 | 4/2011 |
| WO | WO 2012/012667 A2 | 1/2012 |
| WO | WO 2013/176772 A1 | 11/2013 |
| WO | WO 2014/093694 A1 | 6/2014 |
| WO | WO 2014/191128 A1 | 12/2014 |
| WO | WO 2015/014535 A1 | 2/2015 |
| WO | WO 2015/090229 A1 | 6/2015 |
| WO | WO 2015/121454 A1 | 8/2015 |
| WO | WO 2015/140268 A1 | 9/2015 |
| WO | WO 2015/150526 A2 | 10/2015 |
| WO | WO 2015/157070 A1 | 10/2015 |
| WO | WO 2015/164740 A1 | 10/2015 |
| WO | WO 2015/195547 A1 | 12/2015 |
| WO | WO 2016/014576 A1 | 1/2016 |
| WO | WO 2016/089433 A1 | 6/2016 |
| WO | WO 2016/115482 A1 | 7/2016 |
| WO | WO 2016/164356 A1 | 10/2016 |
| WO | WO 2016/176651 A2 | 11/2016 |
| WO | WO 2016/182959 A1 | 11/2016 |
| WO | WO 2017/066760 A1 | 4/2017 |
| WO | WO 2017/079400 A1 | 5/2017 |
| WO | WO 2017/091615 A1 | 6/2017 |
| WO | WO 2017/172981 A2 | 10/2017 |
| WO | WO 2017/186718 A1 | 11/2017 |
| WO | WO 2017/214460 A1 | 12/2017 |
| WO | WO 2017/222593 A1 | 12/2017 |
| WO | WO 2018/007263 A1 | 1/2018 |
| WO | WO 2018/083071 A1 | 5/2018 |
| WO | WO 2018/126176 A1 | 7/2018 |
| WO | WO 2018/160768 A1 | 9/2018 |
| WO | WO 2018/165629 A1 | 9/2018 |
| WO | WO 2018/200562 A1 | 11/2018 |
| WO | WO 2019/046285 A1 | 3/2019 |
| WO | WO 2019/152519 A1 | 8/2019 |
| WO | WO 2019/157326 A1 | 8/2019 |
| WO | WO 2020/047164 A1 | 3/2020 |
| WO | WO 2020/095107 A1 | 5/2020 |
| WO | WO 2020/150478 A1 | 7/2020 |
| WO | WO 2020/150534 A2 | 7/2020 |
| WO | WO 2020/168122 A1 | 8/2020 |
| WO | WO 2021/041971 A1 | 3/2021 |
| WO | WO 2021/041977 A1 | 3/2021 |
| WO | WO 2023/091954 A2 | 5/2023 |
| WO | WO 2023/118608 A1 | 6/2023 |
| WO | WO 2023/159136 A2 | 8/2023 |

OTHER PUBLICATIONS

[No Author Listed], Myeloid cell surface antigen CD33. Uniprot No. P20138. Retrieved from https://www.uniprot.org/uniprot/P20138. Feb. 1, 1991. 10 pages.

Abrahimi et al., Efficient gene disruption in cultured primary human endothelial cells by CRISPR/Cas9. Circ Res. Jul. 3, 2015;117(2):121-8. doi: 10.1161/CIRCRESAHA.117.306290. Epub May 4, 2015.

ADLI, The CRISPR tool kit for genome editing and beyond. Nat Commun. May 15, 2018;9(1):1911. doi: 10.1038/s41467-018-04252-2.

Angata et al., Large-scale sequencing of the CD33-related Siglec gene cluster in five mammalian species reveals rapid evolution by multiple mechanisms. Proc Natl Acad Sci U S A. Sep. 7, 2004;101(36):13251-6. Epub Aug. 26, 2004.

Bakker et al., C-type lectin-like molecule-1: a novel myeloid cell surface marker associated with acute myeloid leukemia. Cancer Res. 2004;64(22):8443-8450. doi:10.1158/0008-5472.CAN-04-1659.

Borot et al., Gene-edited stem cells enable CD33-directed immune therapy for myeloid malignancies. Proc Natl Acad Sci U S A. Jun. 11, 2019;116(24):11978-11987. doi: 10.1073/pnas.1819992116. Epub May 28, 2019.

Brinkman-Van Der Linden et al., CD33/Siglec-3 binding specificity, expression pattern, and consequences of gene deletion in mice. Mol Cell Biol. Jun. 2003;23(12):4199-206.

Brown et al., CAR T cell therapy: inroads to response and resistance. Nat Rev Immunol. Feb. 2019;19(2):73-74. doi: 10.1038/s41577-018-0119-y.

Chatterjee et al., Minimal PAM specificity of a highly similar SpCas9 ortholog. Sci Adv. Oct. 24, 2018;4(10):eaau0766. doi: 10.1126/sciadv.aau0766. eCollection Oct. 2018.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Cong et al., Multiplex genome engineering using CRISPR/Cas systems. Science. Feb. 15, 2013;339(6121):819-23. doi: 10.1126/science.1231143. Epub Jan. 3, 2013.

Cradick et al., CRISPR/Cas9 systems targeting β-globin and CCR5 genes have substantial off-target activity. Nucleic Acids Res. Nov. 2013;41(20):9584-92. doi: 10.1093/nar/gkt714. Epub Aug. 11, 2013.

Dabrowska et al., Precise Excision of the CAG Tract from the Huntingtin Gene by Cas9 Nickases. Front Neurosci. Feb. 26, 2018;12:75. doi: 10.3389/fnins.2018.00075. eCollection 2018.

De Oliveira et al., Modification of hematopoietic stem/progenitor cells with CD19-specific chimeric antigen receptors as a novel approach for cancer immunotherapy. Hum Gene Ther. Oct. 2013;24(10):824-39. doi: 10.1089/hum.2012.202.

(56) References Cited

OTHER PUBLICATIONS

Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.

Eaton, Exonics shows CRISPR treats DMD in dogs. Biocentury. Sep. 7, 2018. 1 page.

Eaton, UC Berkley group identifies new CAS enzyme. Biocentury. Oct. 18, 2018. 1 page.

Ehninger et al., Distribution and levels of cell surface expression of CD33 and CD123 in acute myeloid leukemia. Blood Cancer J. Jun. 13, 2014;4:e218. doi: 10.1038/bcj.2014.39.

Elgundi et al., The state-of-play and future of antibody therapeutics. Adv Drug Deliv Rev. Dec. 1, 2017;122:2-19. doi: 10.1016/j.addr.2016.11.004. Epub Dec. 2, 2016.

Gardner et al., Acquisition of a CD19-negative myeloid phenotype allows immune escape of MLL-rearranged B-ALL from CD19 CAR-T-cell therapy. Blood. May 19, 2016;127(20):2406-10. doi: 10.1182/blood-2015-08-665547. Epub Feb. 23, 2016.

Gill et al., Preclinical targeting of human acute myeloid leukemia and myeloablation using chimeric antigen receptor-modified T cells. Blood. Apr. 10, 2014;123(15):2343-54. doi: 10.1182/blood-2013-09-529537. Epub Mar. 4, 2014.

Hoseini et al., Acute myeloid leukemia targets for bispecific antibodies. Blood Cancer J. Feb. 3, 2017;7(2):e522. doi: 10.1038/bcj.2017.2.

Humbert et al., Engineering resistance to CD33-targeted immunotherapy in normal hematopoiesis by CRISPR/Cas9-deletion of CD33 exon 2. Leukemia. Mar. 2019;33(3):762-808. doi: 10.1038/s41375-018-0277-8. Epub Oct. 5, 2018.

Jacoby et al., CD19 CAR immune pressure induces B-precursor acute lymphoblastic leukaemia lineage switch exposing inherent leukaemic plasticity. Nat Commun. Jul. 27, 2016;7:12320. doi: 10.1038/ncomms12320.

Jiang et al., CLT030, a leukemic stem cell-targeting CLL1 antibody-drug conjugate for treatment of acute myeloid leukemia. Blood Adv. Jul. 24, 2018;2(14):1738-1749. doi: 10.1182/bloodadvances.2018020107.

Kebriaei et al., Infusing CD19-directed T cells to augment disease control in patients undergoing autologous hematopoietic stem-cell transplantation for advanced B-lymphoid malignancies. Hum Gene Ther. May 2012;23(5):444-50. doi: 10.1089/hum.2011.167. Epub Jan. 17, 2012.

Kim et al., Genetic Inactivation of CD33 in Hematopoietic Stem Cells to Enable CAR T Cell Immunotherapy for Acute Myeloid Leukemia. Cell. May 31, 2018;173(6):1439-1453.e19. doi: 10.1016/j.cell.2018.05.013. Epub May 31, 2018.

Kim et al., Genome Editing Using CRISPR-Cas9 to Increase the Therapeutic Index of Antigen-Specific Immunotherapy in Acute Myeloid Leukemia, Molecular Therapy (2016) vol. 24, Supplement 1, p. S108, Abstract 273.

Komor et al., CRISPR-Based Technologies for the Manipulation of Eukaryotic Genomes. Cell. Jan. 12, 2017;168(1-2):20-36. doi: 10.1016/j.cell.2016.10.044. Epub Nov. 17, 2016.

Koo et al., Measuring and Reducing Off-Target Activities of Programmable Nucleases Including CRISPR-Cas9. Mol Cells. Jun. 2015;38(6):475-81. doi: 10.14348/molcells.2015.0103. Epub May 19, 2015.

Kosugi et al., Structure of the gene encoding the alpha subunit of the human interleukin 3 receptor. Biochem Biophys Res Commun. Mar. 8, 1995;208(1):360-7. doi: 10.1006/bbrc.1995.1346.

Labanieh et al., Programming CAR-T cells to kill cancer. Nat Biomed Eng. Jun. 2018;2(6):377-391. doi: 10.1038/s41551-018-0235-9. Epub Jun. 11, 2018.

Laborda et al., Development of A Chimeric Antigen Receptor Targeting C-Type Lectin-Like Molecule-1 for Human Acute Myeloid Leukemia. Int J Mol Sci. Oct. 27, 2017;18(11):2259. doi: 10.3390/ijms18112259.

Laing et al., Unlocking the potential of anti-CD33 therapy in adult and childhood acute myeloid leukemia. Exp Hematol. Oct. 2017;54:40-50. doi: 10.1016/j.exphem.2017.06.007. Epub Jun. 28, 2017.

Larson et al., Tracking the global spread of vaccine sentiments: the global response to Japan's suspension of its HPV vaccine recommendation. Hum Vaccin Immunother. 2014;10(9):2543-50. doi: 10.4161/21645515.2014.969618. Epub Nov. 13, 2014.

Lee et al., Targeted chromosomal deletions in human cells using zinc finger nucleases. Genome Res. Jan. 2010;20(1):81-9. doi: 10.1101/gr.099747.109. Epub Dec. 1, 2009.

Lee et al., Targeted chromosomal duplications and inversions in the human genome using zinc finger nucleases. Genome Res. Mar. 2012;22(3):539-48. doi: 10.1101/gr.129635.111. Epub Dec. 19, 2011.

Leong et al., An anti-CD3/anti-CLL-1 bispecific antibody for the treatment of acute myeloid leukemia. Blood. Feb. 2, 2017;129(5):609-618. doi: 10.1182/blood-2016-08-735365. Epub Dec. 1, 2016.

Liu et al., Immunotherapy in acute myeloid leukemia and myelodysplastic syndromes: The dawn of a new era? Blood Rev. Mar. 2019;34:67-83. doi: 10.1016/j.blre.2018.12.001. Epub Dec. 5, 2018.

Majzner et al., Tumor Antigen Escape from CAR T-cell Therapy. Cancer Discov. Oct. 2018;8(10):1219-1226. doi: 10.1158/2159-8290.CD-18-0442. Epub Aug. 22, 2018.

Mak et al., Eds. Chapter 20: Hematopoietic Cancers from Primer to the Immune Response. Elsevier, Inc . . . 2nd ed. 2014:-553-585.

Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.

Marin-Acevedo et al., Cancer immunotherapy beyond immune checkpoint inhibitors. J Hematol Oncol. Jan. 12, 2018;11(1):8. doi: 10.1186/s13045-017-0552-6.

Martz et al., Allogeneic CARs on the horizon. Biocentury. Oct. 18, 2018. 1 page.

Perna et al., Integrating Proteomics and Transcriptomics for Systematic Combinatorial Chimeric Antigen Receptor Therapy of AML. Cancer Cell. Oct. 9, 2017;32(4):506-519.e5. doi: 10.1016/j.ccell.2017.09.004.

Petrov et al., Compound CAR T-cells as a double-pronged approach for treating acute myeloid leukemia. Leukemia. Jun. 2018;32(6):1317-1326. doi: 10.1038/s41375-018-0075-3. Epub Feb. 25, 2018.

Rees et al., Publisher Correction: Base editing: precision chemistry on the genome and transcriptome of living cells. Nat Rev Genet. Dec. 2018;19(12):801. doi: 10.1038/s41576-018-0068-0.

Safari et al., New Developments in CRISPR Technology: Improvements in Specificity and Efficiency. Curr Pharm Biotechnol. 2017;18(13):1038-1054. doi: 10.2174/1389201019666180209120533.

Schendel et al., Limitations for TCR gene therapy by MHC-restricted fratricide and TCR-mediated hematopoietic stem cell toxicity. Oncoimmunology. Jan. 1, 2013; 2(1): e22410.

Slaney et al., CARs versus BiTEs: A Comparison between T Cell-Redirection Strategies for Cancer Treatment. Cancer Discov. Aug. 2018;8(8):924-934. doi: 10.1158/2159-8290.CD-18-0297. Epub Jul. 16, 2018.

Sotillo et al., Convergence of Acquired Mutations and Alternative Splicing of CD19 Enables Resistance to CART-19 Immunotherapy. Cancer Discov. Dec. 2015;5(12):1282-95. doi: 10.1158/2159-8290.CD-15-1020. Epub Oct. 29, 2015.

Stella et al., Class 2 CRISPR-Cas RNA-guided endonucleases: Swiss Army knives of genome editing. Nat Struct Mol Biol. Nov. 2017;24(11):882-892. doi: 10.1038/nsmb.3486. Epub Oct. 16, 2017.

Strohkendl et al., Kinetic Basis for DNA Target Specificity of CRISPR-Cas12a. Mol Cell. Sep. 6, 2018;71(5):816-824.e3. doi: 10.1016/j.molcel.2018.06.043. Epub Aug. 2, 2018.

Sulem et al., Identification of a large set of rare complete human knockouts. Nat Genet. May 2015;47(5):448-52. doi: 10.1038/ng.3243. Epub Mar. 25, 2015.

Taraseviciute et al., Advances in hematopoietic cell transplant for the treatment of hematologic malignancies. Curr Opin Pediatr. Feb. 2019;31(1):3-13. doi: 10.1097/MOP.0000000000000729.

Tashiro et al., Treatment of Acute Myeloid Leukemia with T Cells Expressing Chimeric Antigen Receptors Directed to C-type Lectin-like Molecule 1. Mol Ther. Sep. 6, 2017;25(9):2202-2213. doi: 10.1016/j.ymthe.2017.05.024. Epub Jul. 1, 2017.

(56) References Cited

OTHER PUBLICATIONS

Tasian, Acute myeloid leukemia chimeric antigen receptor T-cell immunotherapy: how far up the road have we traveled? Ther Adv Hematol. Jun. 2018;9(6):135-148. doi: 10.1177/2040620718774268. Epub May 17, 2018.
Taussig et al., Hematopoietic stem cells express multiple myeloid markers: implications for the origin and targeted therapy of acute myeloid leukemia. Blood. Dec. 15, 2005;106(13):4086-92. doi: 10.1182/blood-2005-03-1072. Epub Aug. 30, 2005.
Thurtle-Schmidt et al., Molecular biology at the cutting edge: A review on CRISPR/CAS9 gene editing for undergraduates. Biochem Mol Biol Educ. Mar. 2018;46(2):195-205. doi: 10.1002/bmb.21108. Epub Jan. 30, 2018.
Van Galen et al., Single-Cell RNA-Seq Reveals AML Hierarchies Relevant to Disease Progression and Immunity. Cell. 2019;176(6):1265-1281.e24. doi:10.1016/j.cell.2019.01.031.
Walter, Investigational CD33-targeted therapeutics for acute myeloid leukemia. Expert Opin Investig Drugs. Apr. 2018;27(4):339-348. doi: 10.1080/13543784.2018.1452911. Epub Mar. 15, 2018.
Wang et al. CAR-T cells targeting CLL-1 as an approach to treat acute myeloid leukemia. J Hematol Oncol. 2018;11(1):7. Published Jan. 10, 2018. doi:10.1186/s13045-017-0553-5.
Zhao et al., Extrathymic generation of tumor-specific T cells from genetically engineered human hematopoietic stem cells via Notch signaling. Cancer Res. Mar. 15, 2007;67(6):2425-9.
Zheng et al., An Anti-CLL-1 Antibody-Drug Conjugate for the Treatment of Acute Myeloid Leukemia. Clin Cancer Res. Feb. 15, 2019;25(4):1358-1368. doi: 10.1158/1078-0432.CCR-18-0333. Epub Jun. 29, 2018.
U.S. Appl. No. 18/023,548, filed Feb. 27, 2023, Lydeard et al.
U.S. Appl. No. 18/023,561, filed Feb. 27, 2023, Lydeard et al.
EP 18760400.4, Oct. 28, 2020, Extended European Search Report.
EP 20740954.1, May 11, 2023, Extended European Search Report.
PCT/US2020/013887, Jun. 11, 2020, International Search Report and Written Opinion.
PCT/US2020/013887, Jul. 29, 2021, International Preliminary Report on Patentability.
PCT/US2020/034391, Sep. 7, 2020, International Search Report and Written Opinion.
PCT/US2020/034391, Dec. 5, 2021, International Preliminary Report on Patentability.
PCT/US2020/048617, Nov. 19, 2020, International Search Report and Written Opinion.
PCT/US2020/048617, Mar. 10, 2022, International Preliminary Report on Patentability.
PCT/US2020/048623, Nov. 18, 2020, International Search Report and Written Opinion.
PCT/US2020/048623, Mar. 10, 2022, International Preliminary Report on Patentability.
PCT/US2021/047967, Dec. 8, 2021, International Search Report and Written Opinion.
PCT/US2021/047967, Mar. 9, 2023, International Preliminary Report on Patentability.
PCT/US2021/047964, Jul. 12, 2021, International Search Report and Written Opinion.
PCT/US2021/047964, Mar. 9, 2023, International Preliminary Report on Patentability.
PCT/US2022/074423, Jan. 18, 2023, International Search Report and Written Opinion.
[No Author Listed], Clinical Trial NCT03795779. CLL1-CD33 cCar in Patients with Relapsed and/or Refractory, High Risk Hematologic Malignancies. Access at ClincialTrials.gov on Mar. 27, 2020. 7 pages.
Anurathapan et al., Engineered T cells for cancer treatment. Cytotherapy. Jun. 2014;16(6):713-33. doi: 10.1016/j.jcyt.2013.10.002. Epub Nov. 13, 2013. Author Manuscript, 35 pages.
Baselga et al., Mechanism of action of anti-HER2 monoclonal antibodies. Ann Oncol. 2001;12 Suppl 1: S35-41. doi: 10.1093/annonc/12.suppl_1.s35.

Beck et al., Strategies and challenges for the next generation of antibody-drug conjugates. Nat Rev Drug Discov. May 2017;16(5):315-337. doi: 10.1038/nrd.2016.268. Epub Mar. 17, 2017.
Belicha-Villanueva et al., What is the role of alternate splicing in antigen presentation by major histocompatibility complex class I molecules? Immunol Res. Mar. 2010;46(1-3):32-44. doi: 10.1007/s12026-009-8123-8. Author Manuscript, 14 pages.
Bubien et al., Transfection of the CD20 cell surface molecule into ectopic cell types generates a Ca2+ conductance found constitutively in B lymphocytes. J Cell Biol. Jun. 1993;121(5):1121-32. doi: 10.1083/jcb.121.5.1121.
Buckley et al., Update on antigen-specific immunotherapy of acute myeloid leukemia. Curr Hematol Malig Rep. Jun. 2015;10(2):65-75. doi: 10.1007/s11899-015-0250-9.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Doench et al., Optimized sgRNA design to maximize activity and minimize off-target effects of CRISPR-Cas9. Nat Biotechnol. Feb. 2016;34(2):184-191. doi: 10.1038/nbt.3437. Epub Jan. 18, 2016.
Doench et al., Rational design of highly active sgRNAs for CRISPR-Cas9-mediated gene inactivation. Nat Biotechnol. Dec. 2014;32(12): Supplemental Information. 58 pages.
Eid et al., CRISPR base editors: genome editing without double-stranded breaks. Biochem J. Jun. 11, 2018;475(11):1955-1964. doi: 10.1042/BCJ20170793.
Elkins et al., FcRL5 as a target of antibody-drug conjugates for the treatment of multiple myeloma. Mol Cancer Ther. Oct. 2012;11(10):2222-32. doi: 10.1158/1535-7163.MCT-12-0087. Epub Jul. 17, 2012.
Falkenburg et al., T cell therapy in allogeneic stem cell transplantation. Biol Blood Marrow Transplant. Jan. 2008;14(1 Suppl 1):136-41. doi: 10.1016/j.bbmt.2007.10.022. Erratum in: Biol Blood Marrow Transplant. Nov. 2008;14(11):1317-8.
Fu et al., Improving CRISPR-Cas nuclease specificity using truncated guide RNAs. Nat Biotechnol. Mar. 2014;32(3):279-284. doi: 10.1038/nbt.2808. Epub Jan. 26, 2014.
Gao et al., Engineered Cpf1 variants with altered PAM specificities. Nat Biotechnol. Aug. 2017;35(8):789-792. doi: 10.1038/nbt.3900. Epub Jun. 5, 2017.
Godwin et al., Gemtuzumab ozogamicin in acute myeloid leukemia. Leukemia. Sep. 2017;31(9):1855-1868. doi: 10.1038/leu.2017.187. Epub Jun. 13, 2017.
Gratz et al., Genome Engineering of *Drosophila* with the CRISPR RNA-Guided Cas9 Nuclease. Genetics. Aug. 2013;194(4):1029-35. doi: 10.1534/genetics.113.152710. Epub May 24, 2013.
Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.
Harrington et al., Programmed Dna destruction by miniature CRISPR-Cas14 enzymes. Science. Nov. 16, 2018;362(6416):839-842. doi: 10.1126/science.aav4294. Epub Oct. 18, 2018.
Haubner et al., Coexpression profile of leukemic stem cell markers for combinatorial targeted therapy in Aml. Leukemia. Jan. 2019;33(1):64-74. doi: 10.1038/s41375-018-0180-3. Epub Jun. 26, 2018.
Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015.
Henig et al., Hematopoietic stem cell transplantation-50 years of evolution and future perspectives. Rambam Maimonides Med J. Oct. 29, 2014;5(4): e0028. doi: 10.5041/RMMJ.10162.
Hernandez-Caselles et al., A study of CD33 (SIGLEC-3) antigen expression and function on activated human T and NK cells: two isoforms of CD33 are generated by alternative splicing. J Leukoc Biol. Jan. 2006;79(1):46-58. doi: 10.1189/jlb.0205096.
Hsu et al., Development and applications of CRISPR-Cas9 for genome engineering. Cell. Jun. 5, 2014;157(6):1262-1278. doi: 10.1016/j.cell.2014.05.010.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

(56) References Cited

OTHER PUBLICATIONS

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Kenderian et al., CD33 Directed Chimeric Antigen Receptor T Cell Therapy As a Novel Preparative Regimen Prior to Allogeneic Stem Cell Transplantation in Acute Myeloid Leukemia. Biol Blood Marrow Transplant. Feb. 1, 2015;21(2): Supplement S25-S26. doi: 10.1016/j.bbmt.2014.11.013. 2 pages.

Kenderian et al., CD33-specific chimeric antigen receptor T cells exhibit potent preclinical activity against human acute myeloid leukemia. Leukemia. Aug. 2015;29(8):1637-47. doi: 10.1038/leu.2015.52. Epub Feb. 27, 2015.

Kenderian et al., Targeting CLEC12A with Chimeric Antigen Receptor T Cells Can Overcome the Chemotherapy Refractoriness of Leukemia Stem Cells. Biol Blood Marrow Transplant. 2017;23(3): S247-S248. doi: 10.1016/j.bbmt.2016.12.413.

Kim et al., 1000 Engineering Resistance to Antigen-Specific Immunotherapy in Normal Hematopoietic Stem Cells by Gene Editing to Enable Targeting of /Acute Myeloid Leukemia. Gene Therapy and Transfer Program: Oral and Poster Abstract. Session 801. Gene Therapy and Transfer: Immunogene Therapy and Genotoxicity. Dec. 5, 2016. San Diego. 3 pages.

Kim et al., Fine Mutational Analysis of 2B8 and 3H7 Tag Epitopes with Corresponding Specific Monoclonal Antibodies. Mol Cells. Jun. 30, 2016;39(6):460-7. doi: 10.14348/molcells.2016.2265. Epub May 3, 2016.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kolb, Graft-versus-leukemia effects of transplantation and donor lymphocytes. Blood. Dec. 1, 2008;112(12):4371-83. doi: 10.1182/blood-2008-03-077974.

Krupka et al., CD33 target validation and sustained depletion of AML blasts in long-term cultures by the bispecific T-cell-engaging antibody AMG 330. Blood. Jan. 16, 2014;123(3):356-65. doi: 10.1182/blood-2013-08-523548. Epub Dec. 3, 2013.

Kuijpers et al., CD20 deficiency in humans results in impaired T cell-independent antibody responses. J Clin Invest. Jan. 2010;120(1):214-22. doi: 10.1172/JCI40231. Epub Dec. 21, 2009.

Kungulovski et al., Epigenome Editing: State of the Art, Concepts, and Perspectives. Trends Genet. Feb. 2016;32(2):101-113. doi: 10.1016/j.tig.2015.12.001. Epub Dec. 28, 2015.

Lamba et al., CD33 Splicing Polymorphism Determines Gemtuzumab Ozogamicin Response in De Novo Acute Myeloid Leukemia: Report From Randomized Phase III Children's Oncology Group Trial AAML0531. J Clin Oncol. Aug. 10, 2017;35(23):2674-2682. doi: 10.1200/JCO.2016.71.2513. Epub Jun. 23, 2017.

Laszlo et al., Expression and functional characterization of CD33 transcript variants in human acute myeloid leukemia. Oncotarget. Jul. 12, 2016;7(28):43281-43294. doi: 10.18632/oncotarget.9674.

Li et al., CD33-Specific Chimeric Antigen Receptor T Cells with Different Co-Stimulators Showed Potent Anti-Leukemia Efficacy and Different Phenotype. Hum Gene Ther. May 2018;29(5):626-639. doi: 10.1089/hum.2017.241. Epub Mar. 19, 2018.

Lomova et al., Improving Gene Editing Outcomes in Human Hematopoietic Stem and Progenitor Cells by Temporal Control of DNA Repair. Stem Cells. Feb. 2019;37(2):284-294. doi: 10.1002/stem.2935. Epub Nov. 27, 2018. Author Manuscript. 27 pages.

Minagawa et al., In Vitro Pre-Clinical Validation of Suicide Gene Modified Anti-CD33 Redirected Chimeric Antigen Receptor T-Cells for Acute Myeloid Leukemia. PLoS One. Dec. 1, 2016;11(12): e0166891. doi: 10.1371/journal.pone.0166891. Erratum in: PLoS One. Feb. 15, 2017;12 (2): e0172640.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Peters et al., Antibody-drug conjugates as novel anti-cancer chemotherapeutics. Biosci Rep. Jun. 12, 2015;35(4): e00225. doi: 10.1042/BSR20150089. 20 pages.

Poirot et al., Multiplex Genome-Edited T-cell Manufacturing Platform for "Off-the-Shelf" Adoptive T-cell Immunotherapies. Cancer Res. Sep. 15, 2015;75(18):3853-64. doi: 10.1158/0008-5472.CAN-14-3321. Epub Jul. 16, 2015.

Qi et al., Repurposing CRISPR as an RNA-guided platform for sequence-specific control of gene expression. Cell. Feb. 28, 2013;152(5):1173-83. doi: 10.1016/j.cell.2013.02.022. Erratum in: Cell. Feb. 4, 2021;184(3):844.

Qin et al., Chimeric Antigen Receptors Incorporating D Domains Targeting CD123 Direct Potent Mono- and Bi-specific Antitumor Activity of T Cells. Mol Ther. Jul. 3, 2019;27(7):1262-1274 with Supplemental Info. doi: 10.1016/j.ymthe.2019.04.010. Epub Apr. 17, 2019. 31 pages.

Rahdar et al., Synthetic CRISPR RNA-Cas9-guided genome editing in human cells. Proc Natl Acad Sci U S A. Dec. 22, 2015;112(51): E7110-7. doi: 10.1073/pnas.1520883112. Epub Nov. 16, 2015. 8 pages.

Ran et al., Genome engineering using the CRISPR-Cas9 system. Nat Protoc. Nov. 2013;8(11):2281-2308. doi: 10.1038/nprot.2013.143. Epub Oct. 24, 2013.

Roberts et al., CD45-deficient severe combined immunodeficiency caused by uniparental disomy. Proc Natl Acad Sci U S A. Jun. 26, 2012;109(26):10456-61. doi: 10.1073/pnas.1202249109. Epub Jun. 11, 2012.

Saydaminova et al., Efficient genome editing in hematopoietic stem cells with helper-dependent Ad5/35 vectors expressing site-specific endonucleases under microRNA regulation. Mol Ther Methods Clin Dev. Jan. 14, 2015;1:14057. doi: 10.1038/mtm.2014.57.

Schmitt et al., T cell receptor gene therapy for cancer. Hum Gene Ther. Nov. 2009;20(11):1240-8. doi: 10.1089/hum.2009.146.

Schneider et al., A Unique Human Immunoglobulin Heavy Chain Variable Domain-Only CD33 Car for the Treatment of Acute Myeloid Leukemia. Front Oncol. Nov. 22, 2018; 8:539. doi: 10.3389/fonc.2018.00539.

Shalem et al., Genome-scale CRISPR-Cas9 knockout screening in human cells. Science. Jan. 3, 2014;343(6166):84-87. doi: 10.1126/science.1247005. Epub Dec. 12, 2013.

Shmakov et al., Discovery and Functional Characterization of Diverse Class 2 CRISPR-Cas Systems. Mol Cell. Nov. 5, 2015;60(3):385-97 and Supplemental Information. doi: 10.1016/j.molcel.2015.10.008. Epub Oct. 22, 2015.

Shono et al., Bone marrow graft-versus-host disease: early destruction of hematopoietic niche after MHC-mismatched hematopoietic stem cell transplantation. Blood. Jul. 1, 2010;115(26):5401-11. doi: 10.1182/blood-2009-11-253559. Epub Mar. 30, 2010. 36 pages.

Slaymaker et al., Rationally engineered Cas9 nucleases with improved specificity. Science. Jan. 1, 2016;351(6268):84-8. doi: 10.1126/science.aad5227. Epub Dec. 1, 2015.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Tchilian et al., Molecular cloning of two isoforms of the murine homolog of the myeloid CD33 antigen. Blood. Jun. 1, 1994;83(11):3188-98.

Ukena et al., Human regulatory T cells in allogeneic stem cell transplantation. Blood. Sep. 29, 2011;118(13): e82-92. doi: 10.1182/blood-2011-05-352708. Epub Jul. 21, 2011.

Walter et al., Engineering resistance to CD33-targeted immunotherapy in normal hematopoiesis by CRISPR/Cas9-deletion of CD33 exon 2. Gene Therapy and Transfer: Poster I. Blood. Nov. 29, 2018;132(Suppl 1):2200. doi: 10.1182/blood-2018-99-117856. 4 pages.

Wang et al., State-of-the-art human gene therapy: part I. Gene delivery technologies. Discov Med. Jul.-Aug. 2014;18(97):67-77. Author Manuscript. 17 pages.

(56) References Cited

OTHER PUBLICATIONS

Wayne et al., Immunotoxins for leukemia. Blood. Apr. 17, 2014;123(16):2470-7. doi: 10.1182/blood-2014-01-492256. Epub Feb. 27, 2014.

Wellhausen et al., Epitope base editing CD45 in hematopoietic cells enables universal blood cancer immune therapy. Sci Transl Med. Aug. 31, 2023:eadi1145. doi: 10.1126/scitranslmed.adi1145. Epub ahead of print.

Wisniewski et al., Further phenotypic characterization of the primitive lineage CD34+CD38−CD90+CD45RA− hematopoietic stem cell/progenitor cell sub-population isolated from cord blood, mobilized peripheral blood patients with chronic myelogenous leukemia. Blood Cancer J. Apr. 28, 2011;1(9):e36.

Yousef et al., Genomic organization of the siglec gene locus on chromosome 19q13.4 and cloning of two new siglec pseudogenes. Gene. Mar. 20, 2002;286(2):259-70. doi: 10.1016/s0378-1119(02)00432-8.

Zernich et al., Natural HLA class I polymorphism controls the pathway of antigen presentation and susceptibility to viral evasion. J Exp Med. Jul. 5, 2004;200(1):13-24. doi: 10.1084/jem.20031680. Epub Jun. 28, 2004.

U.S. Appl. No. 16/554,520, filed Aug. 28, 2019, Bolen et al.
U.S. Appl. No. 17/222,855, filed Apr. 5, 2021, Bolen et al.
U.S. Appl. No. 17/222,834, filed Apr. 5, 2021, Bolen et al.
U.S. Appl. No. 17/222,812, filed Apr. 5, 2021, Bolen et al.
U.S. Appl. No. 17/222,765, filed Apr. 5, 2021, Bolen et al.
PCT/US2018/020327, dated May 7, 2018, International Search Report and Written Opinion.
PCT/US2018/020327, dated Sep. 12, 2019, International Preliminary Report on Patentability.
PCT/US2019/048662, dated Dec. 5, 2019, International Search Report and Written Opinion.
PCT/US2019/048662, dated Mar. 11, 2021, International Search Report and Written Opinion.

* cited by examiner

Engineering Donor CD34+:
Modifying "Non-Essential" Epitope

TO

FIG. 1B (CONTINUED)
FROM FIG.1B (SEQ ID NO: 57)

(SEQ ID NO: 57)

FROM FIG. 3A

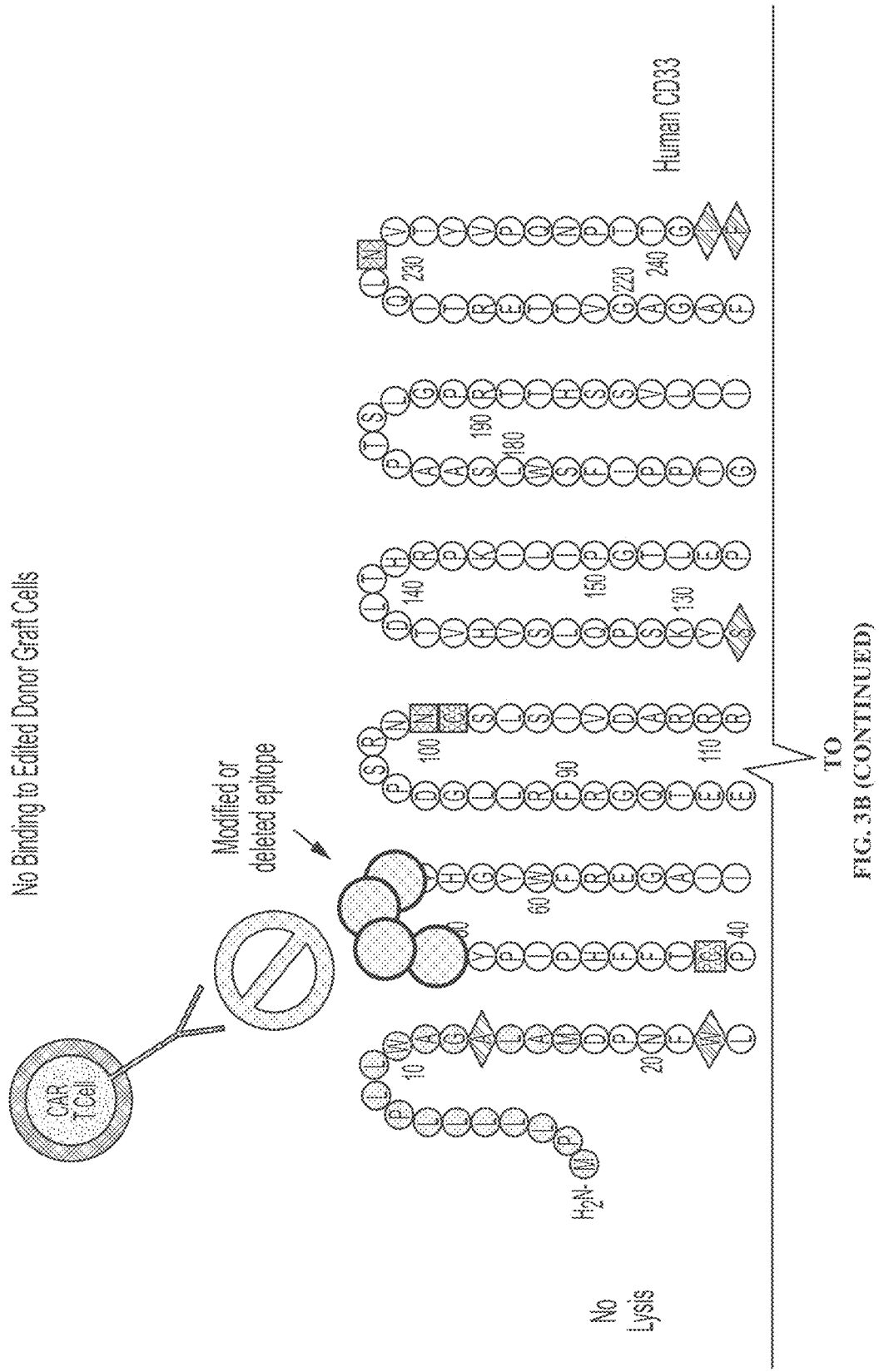

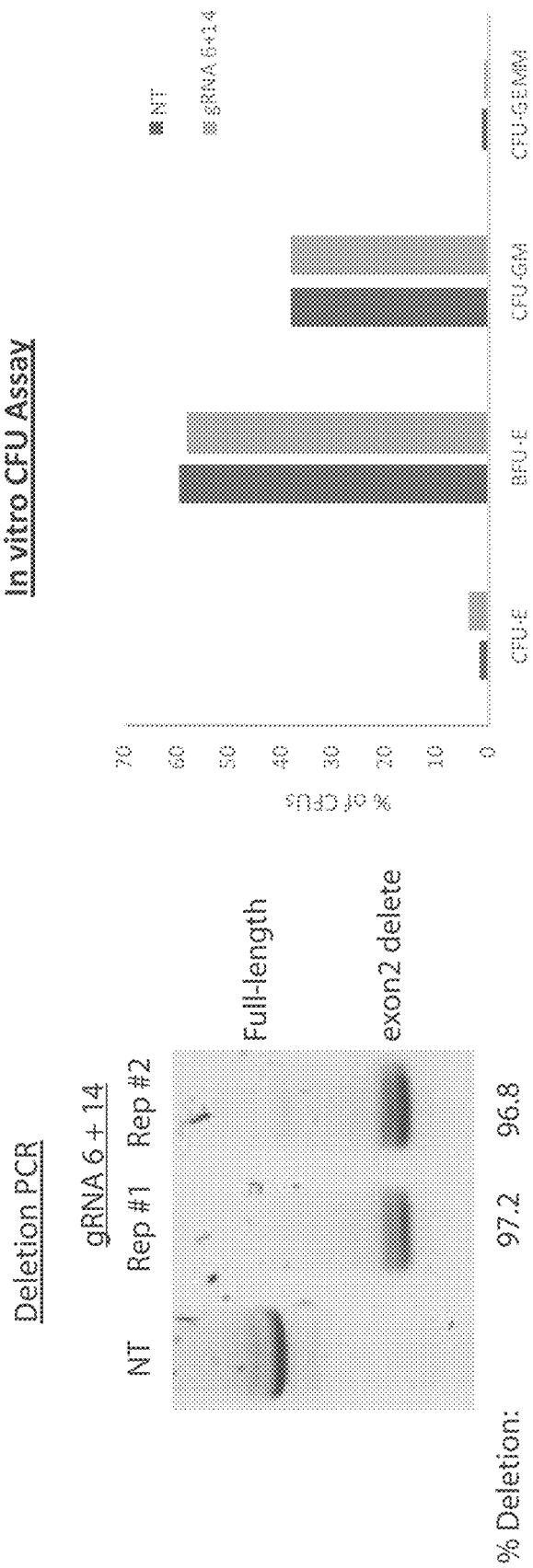

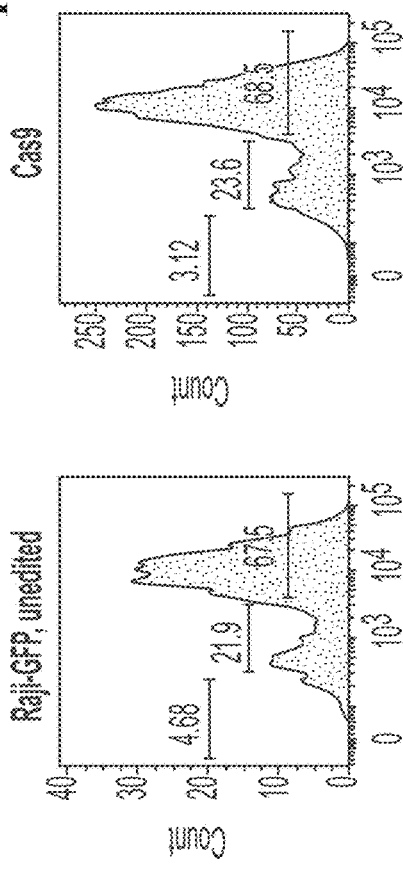
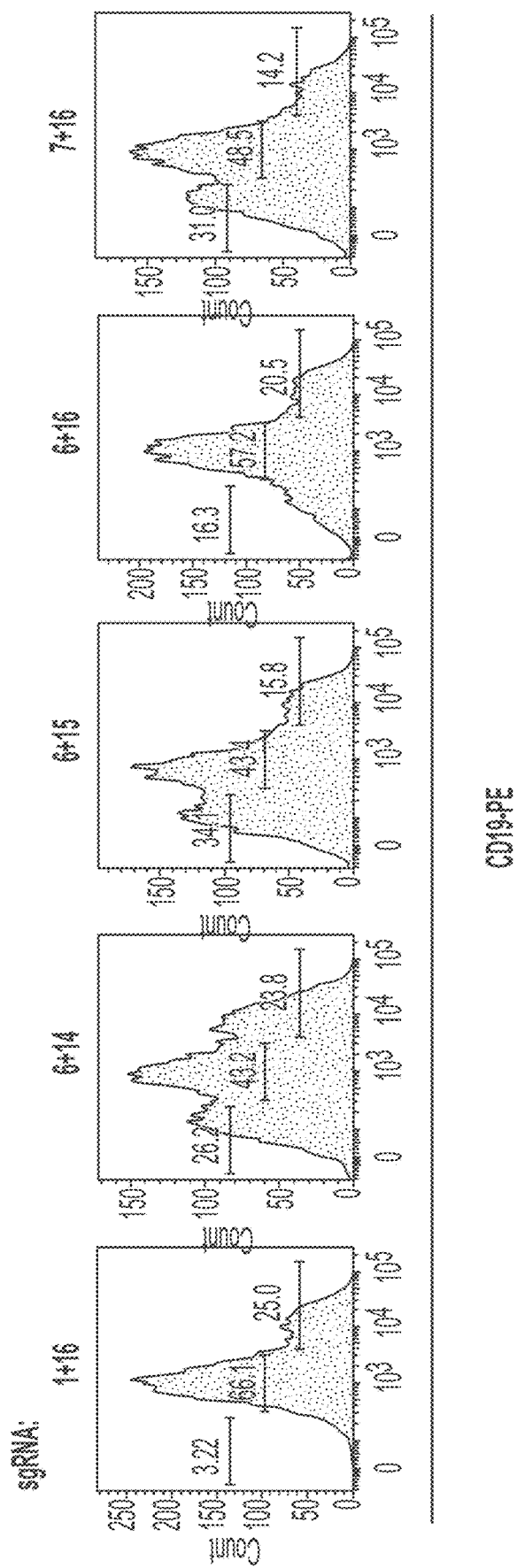
FIG. 14A

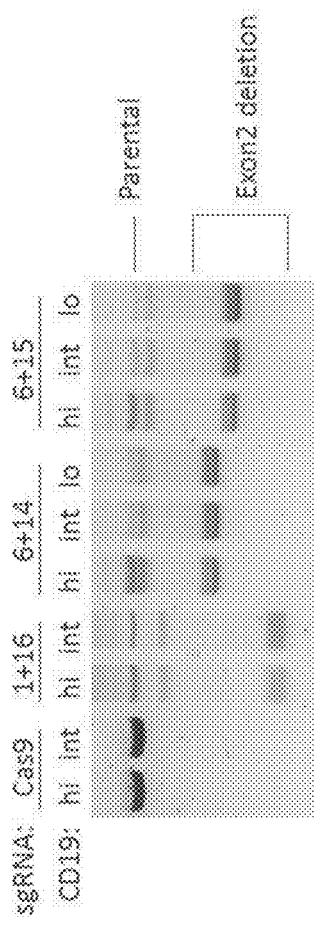
FIG. 14B
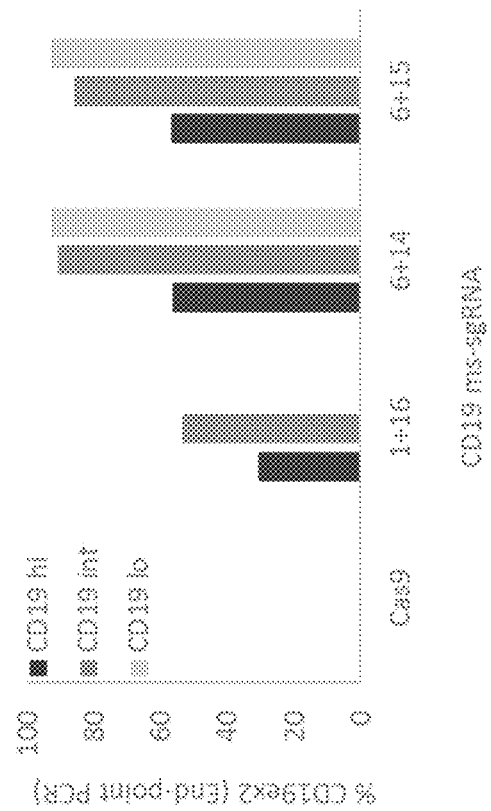
FIG. 14C
FIG. 14D
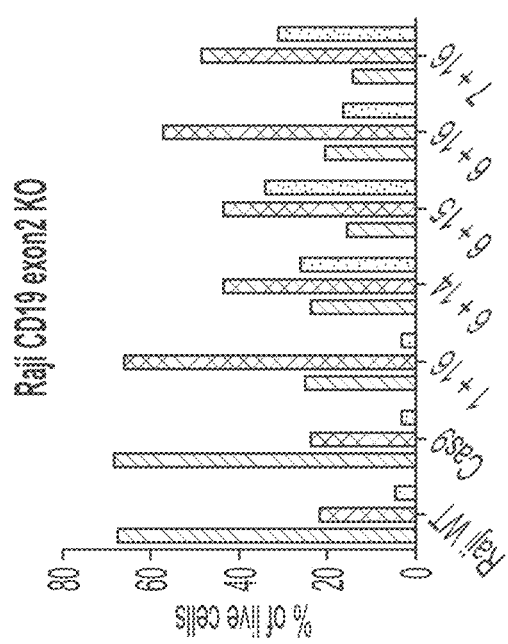

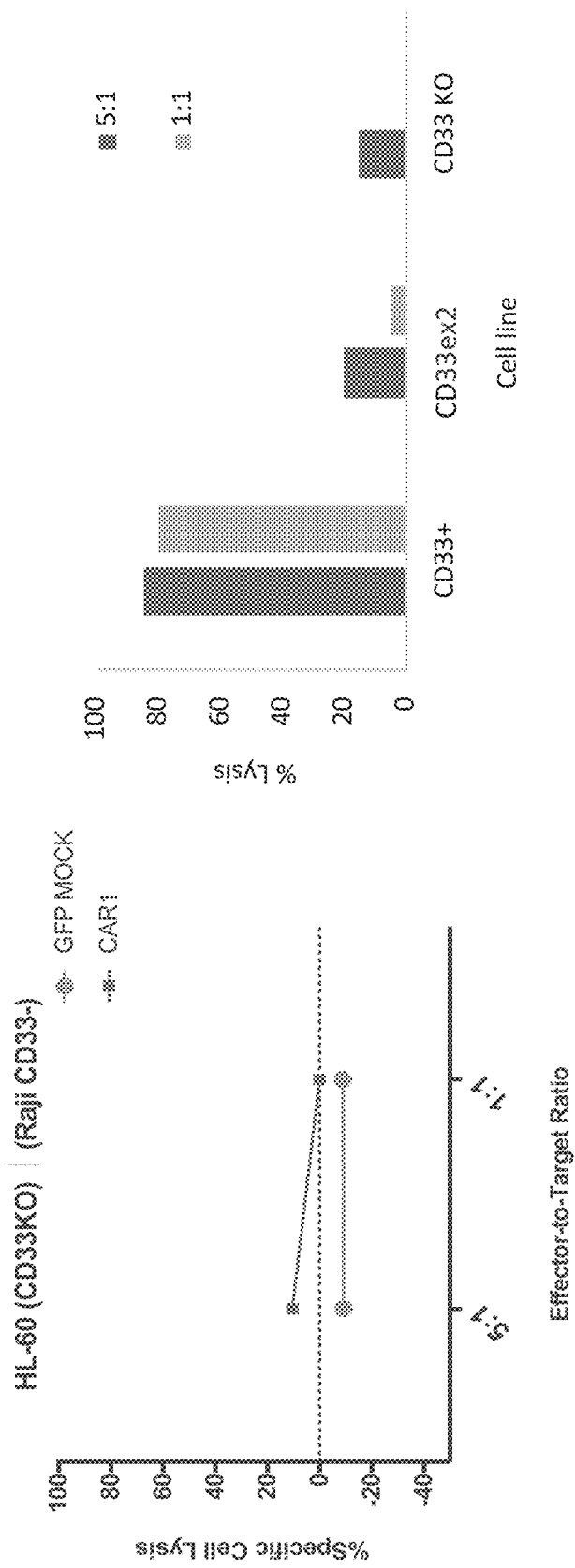

FIG. 26A

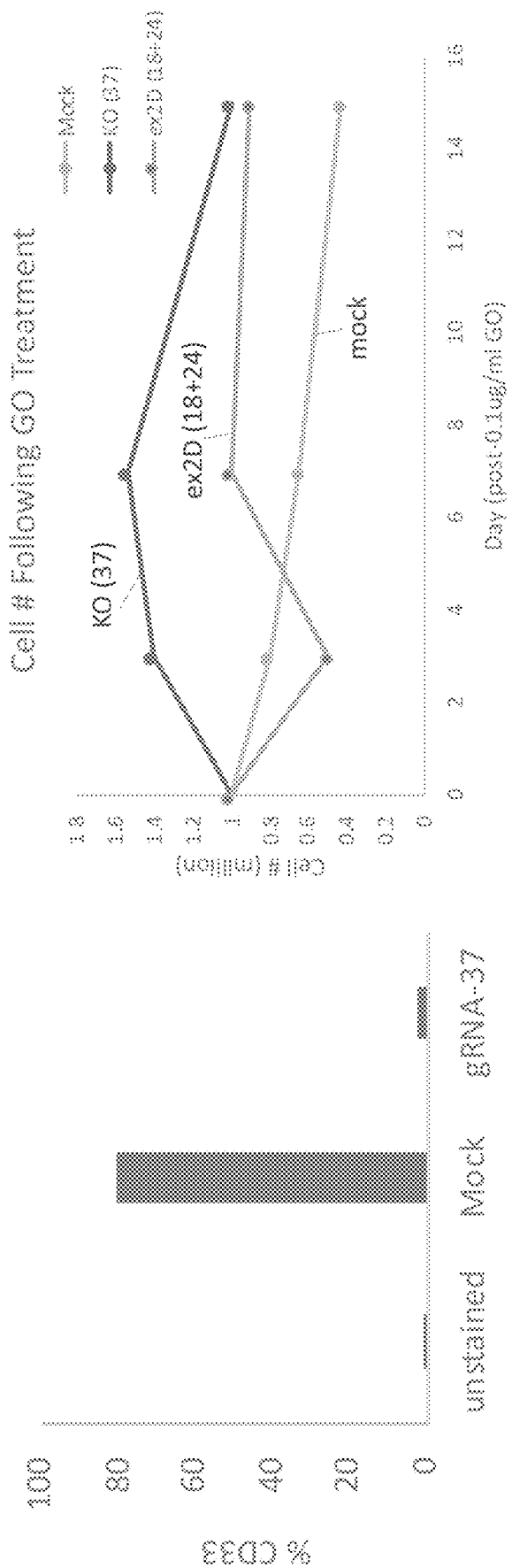

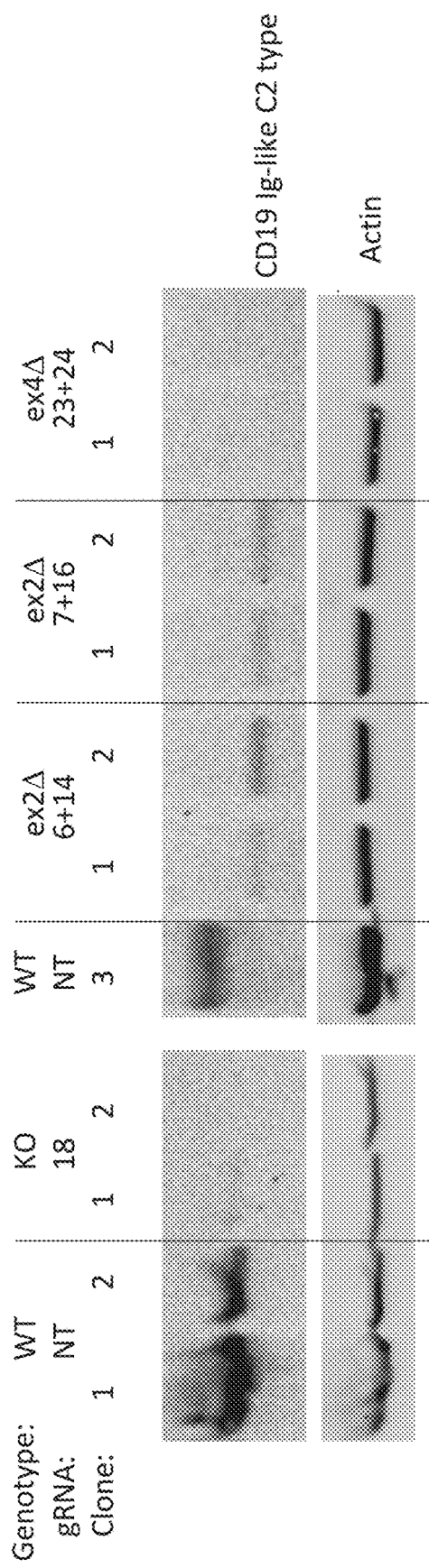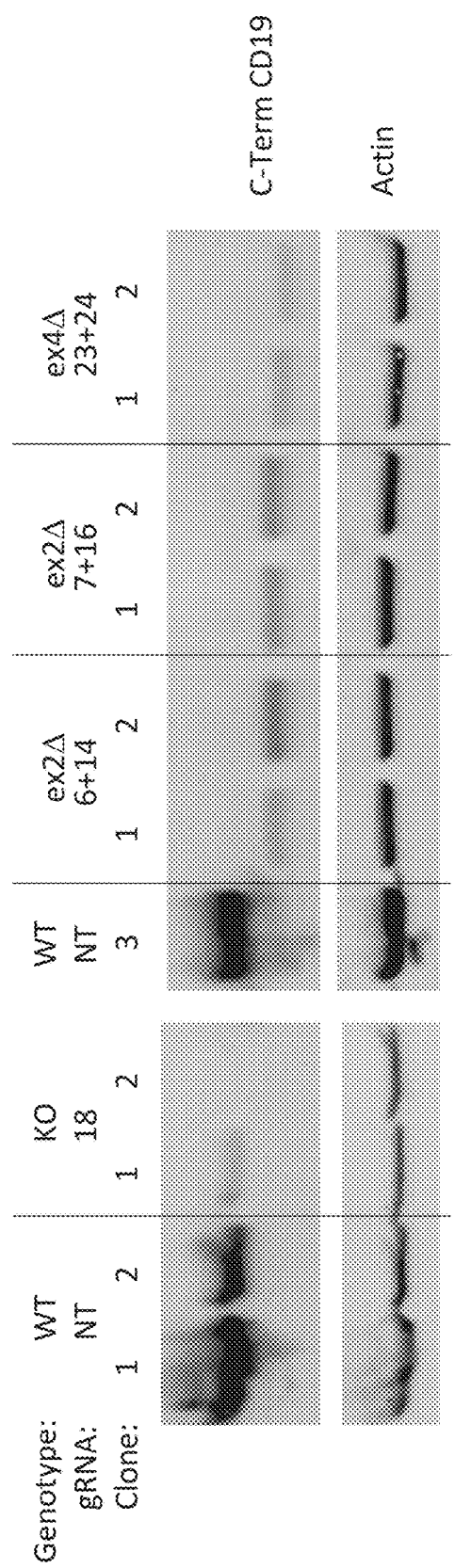

GENETICALLY ENGINEERED HEMATOPOIETIC STEM CELLS AND USES THEREOF

This application is a continuation of U.S. Ser. No. 16/701,818, filed Dec. 3, 2019, which is a continuation of U.S. Ser. No. 16/554,520, filed Aug. 28, 2019, which claims priority to U.S. Ser. No. 62/723,993 filed Aug. 28, 2018, U.S. Ser. No. 62/728,061 filed Sep. 6, 2018, U.S. Ser. No. 62/789,440 filed Jan. 7, 2019, and U.S. Ser. No. 62/809,202 filed Feb. 22, 2019, the entire contents of each of which is incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 4, 2021, is named V029170002US07-SUBSEQ-CEW and is 93,343 bytes in size.

BACKGROUND OF THE INVENTION

A major challenge in designing targeted therapies is the successful identification of proteins that are uniquely expressed on cells that would be therapeutically relevant to eliminate (e.g., abnormal, malignant, or other target cells) but not present on cells that one does not wish to eliminate (e.g., normal, healthy, or other non-target cells). For example, many cancer therapeutics struggle to effectively target cancer cells while leaving normal cells unharmed.

An alternative strategy that has emerged involves targeting an entire cell lineage, which includes targeting normal cells, cancer cells, and pre-cancerous cells. For example, CD19-targeted chimeric antigen receptor T cells (CAR T cells) and anti-CD20 monoclonal antibodies (e.g. Rituximab) each target B cell lineage proteins (CD19 and CD20, respectively). While potentially effective in treating B cell malignancies, use of such therapies is limited as elimination of B cells is detrimental. Similarly, targeting lineage-specific proteins of other cell populations, for example, myeloid lineage cells (e.g., cancers arising from myeloid blasts, monocytes, megakaryocytes, etc) is not feasible, as these cell populations are necessary for survival.

Thus, there remains an unmet need to effectively target cells of interest, e.g., cancer cells, without targeting or harming normal cell populations.

SUMMARY OF THE INVENTION

Provided herein are compositions, e.g., engineered cells, and methods that provide the ability to target one or more cells or cell populations of interest while allowing non-targeted cell populations to escape such targeting. For example, provided herein are genetically engineered hematopoietic cells such as hematopoietic stem cells (HSCs) having genetically modified or edited genes of one or more lineage-specific cell-surface antigens. In some embodiments, the modified, e.g., edited genes are able to produce the lineage-specific cell surface proteins in modified form, which retain, at least partially, the biological activity of the lineage-specific cell-surface antigens in the HSCs or in descendant cells expressing such, but can escape targeting by cytotoxic agents that are specific to the wild-type lineage-specific cell-surface antigens. In some embodiments, the modified, e.g., edited, genes do not produce the lineage-specific cell surface protein(s) or produce a truncated version of the lineage-specific cell surface protein(s) that, while able to escape targeting by cytotoxic agents that are specific to the wild-type lineage-specific cell-surface antigen(s), may not retain biological activity of the lineage-specific cell-surface antigen(s) in the HSCs or in descendant cells expressing such.

Thus, provided herein are genetically engineered hematopoietic cells, such as hematopoietic stem cells (HSCs), having one or more modified lineage-specific cell-surface antigen. In some embodiments, the one or more modified lineage-specific cell surface proteins are modified such that one or more of the lineage-specific cell surface proteins retain at least partially its biological activity of the lineage-specific cell-surface antigens in the HSCs or in descendant cells expressing such, but can escape targeting by cytotoxic agents that are specific to the corresponding wild-type lineage-specific cell-surface antigen(s). In some embodiments, the one or more modified lineage-specific cell surface proteins are modified such that all of the modified lineage-specific cell surface proteins (e.g., one, two, three, four, etc.) retain at least partial biological activity. In some embodiments, the one or more modified lineage-specific cell surface proteins are modified such that at least one, but not all, of the modified lineage-specific cell surface protein(s) retain at least partial biological activity. In some embodiments, the one or more modified lineage-specific cell surface proteins are modified such that one or more of the lineage-specific cell surface proteins do not retain at least partial biological activity of the lineage-specific cell-surface antigens in the HSCs or in descendant cells expressing such, but can escape targeting by cytotoxic agents that are specific to the corresponding wild-type lineage-specific cell-surface antigen(s). In some embodiments, the one or more modified lineage-specific cell surface proteins are modified such that none of the modified lineage-specific cell surface protein(s) retain at least partial biological activity. Thus, the genetically engineered hematopoietic cells provided herein having one or more modified lineage-specific cell-surface antigens can escape targeting by cytotoxic agents that are specific to the corresponding wild-type lineage-specific cell-surface antigen(s) and may comprise modified lineage-specific cell-surface antigen(s) that retain at least partial biological activity and/or may comprise lineage-specific cell-surface antigen(s) that do not retain biological activity (e.g., the protein may be knocked out).

The genetically engineered hematopoietic cells provided herein having genetically modified or edited genes of one or more lineage-specific cell-surface antigens are useful in therapies, e.g., immunotherapies and other cytotoxic agents, that specifically target cells expressing a lineage-specific cell-surface antigen, by virtue of the fact that the genetically engineered hematopoietic cells produce one or more modified lineage-specific cell-surface antigen(s) that are able to escape such targeting while retaining their biological activity. Accordingly, with such engineered hematopoietic cell it is possible to target or direct immunotherapies or other cytotoxic agents against a lineage-specific cell-surface antigen that is required for survival of an organism. Also, with such engineered hematopoietic cell, it is possible to target or direct immunotherapies or other cytotoxic agents against a cell type required for survival of an organism expressing a targeted lineage-specific cell-surface antigen. In other embodiments, the genetically engineered hematopoietic cells provided herein having genetically modified or edited genes of one or more lineage-specific cell-surface antigens are useful in therapies, e.g., immunotherapies and other cytotoxic agents, that specifically target cells expressing a lineage-specific cell-surface antigen, by having the ability to escape such targeting even though that do not retain biological activity. With such engineered hematopoietic cell it is possible to target or direct immunotherapies or other cytotoxic agents against a lineage-specific cell-surface antigen that is not required for survival of an organism. Also, with such engineered hematopoietic cell, it is possible to target or direct immunotherapies or other cytotoxic agents against a cell type that is not required for survival of an organism expressing a targeted lineage-specific cell-surface antigen. In some embodiments, in which the genetically engineered hematopoietic cells have one or more modified lineage-specific cell-surface antigens, wherein one or more lineage-specific cell-surface antigens retain biological activity and wherein one or more lineage-specific cell-surface antigens do not retain biological activity, it is possible to target or direct immunotherapies or other cytotoxic agents against lineage-specific cell-surface antigen(s) that may or may not be required for survival of an organism. Also, with such engineered hematopoietic cell, it is possible to target or direct immunotherapies or other cytotoxic agents against a cell type that may or may not be required for survival of an organism expressing a targeted lineage-specific cell-surface antigen.

In some aspects, the genetically engineered hematopoietic cell is genetically modified or edited such that it produces one modified or mutated lineage-specific cell-surface antigen that retains biological activity, but escapes targeting by a cytotoxic agent specific to the wild-type lineage-specific cell-surface antigen. In some aspects, the genetically engineered hematopoietic cell is genetically modified or edited such that it produces two or more (e.g., 2, 3, 4, 5, etc) modified or mutated lineage-specific cell-surface antigens that escape targeting by a cytotoxic agent specific to (or that targets) the corresponding wild-type lineage-specific cell-surface antigens. In some embodiments of these latter aspects, at least one of the modified or mutated lineage-specific cell-surface proteins retains its biological activity. In some embodiments, two or more of the modified or mutated lineage-specific cell-surface antigens retain their respective biological activities. In some embodiments, all of the modified or mutated lineage-specific cell-surface antigens expressed in the genetically engineered hematopoietic cell retain (at least partially) their respective biological activities.

Accordingly, one aspect of the present disclosure features a genetically engineered hematopoietic cell, comprising: (i) a first gene encoding a first lineage-specific cell-surface antigen, which gene has been modified or edited and (ii) a second gene encoding a second lineage-specific cell-surface antigen, which gene has been modified or edited. In some embodiments, the first gene has been modified or edited such that expression of the first lineage-specific cell-surface antigen is reduced or eliminated in the genetically engineered hematopoietic cell (e.g., as compared with expression of the corresponding endogenous or wild-type lineage-specific cell-surface antigen). In some embodiments, the first gene has been modified or edited such that the genetically engineered hematopoietic cell expresses a mutant or modified version of the first lineage-specific cell-surface antigen. In some embodiments, the mutant or modified version of the first lineage-specific cell-surface antigen escapes targeting by a cytotoxic agent that targets the corresponding wild-type lineage-specific cell-surface antigen. In some embodiments, the mutant or modified version of the first lineage-specific cell-surface antigen retains its biological activity. In some embodiments, the mutant or modified version of the first lineage-specific cell-surface antigen escapes targeting by a cytotoxic agent that targets the corresponding wild-type lineage-specific cell-surface antigen and retains its biological activity. In some embodiments, the second gene has been modified or edited such that expression of the second lineage-specific cell-surface antigen is reduced or eliminated in the genetically engineered hematopoietic cell (e.g., as compared with expression of the corresponding endogenous or wild-type lineage-specific cell-surface antigen). In some embodiments, the second gene has been modified or edited such that the genetically engineered hematopoietic cell expresses a mutant or modified version of the second lineage-specific cell-surface antigen. In some embodiments, the mutant or modified version of the second lineage-specific cell-surface antigen escapes targeting by a cytotoxic agent that targets the corresponding wild-type lineage-specific cell-surface antigen. In some embodiments, the mutant or modified version of the second lineage-specific cell-surface antigen retains its biological activity. In some embodiments, the mutant or modified version of the second lineage-specific cell-surface antigen escapes targeting by a cytotoxic agent that targets the corresponding wild-type lineage-specific cell-surface antigen and retains its biological activity. In some embodiments, the mutant or modified versions of the first and second lineage-specific cell-surface antigens retain their respective biological activities. In some embodiments, the mutant or modified version of the first lineage-specific cell-surface antigen retains its biological activity and the mutant or modified version of the second lineage-specific cell-surface antigen does not retain its biological activity. In some embodiments, neither the mutant or modified version of the first lineage-specific cell-surface antigen retains its biological activity nor the mutant or modified version of the second lineage-specific cell-surface antigen retains its biological activity.

Another aspect of the present disclosure features a genetically engineered hematopoietic cell, comprising: (i) a first gene encoding a first lineage-specific cell-surface antigen, which gene has been modified or edited; (ii) a second gene encoding a second lineage-specific cell-surface antigen, which gene has been modified or edited; and (iii) a third gene encoding a third lineage-specific cell-surface antigen, which gene has been modified or edited. In some embodiments, the genetically engineered hematopoietic cell further comprises (iv) a fourth gene encoding a fourth lineage-specific cell-surface antigen, which gene has been modified or edited. In some embodiments, the genetically engineered hematopoietic cell further comprises (v) a fifth gene encoding a fifth lineage-specific cell-surface antigen, which gene has been modified or edited.

In some embodiments, any one or more of the gene(s) encoding a lineage-specific cell-surface antigen has been modified or edited such that expression of the respective lineage-specific cell-surface antigen(s) is reduced or eliminated in the genetically engineered hematopoietic cell (e.g., as compared with expression of the corresponding endogenous or wild-type lineage-specific cell-surface antigen). In some embodiments, any one or more of the gene(s) encoding a lineage-specific cell-surface antigen has been modified or edited such that the genetically engineered hematopoietic cell expresses a mutant or modified version of the respective lineage-specific cell-surface antigen(s).

In some embodiments, any one or more of the mutant lineage-specific cell-surface antigen(s) escapes targeting by a cytotoxic agent that targets the corresponding wild-type lineage-specific cell-surface antigen. In some embodiments, any one or more of the mutant lineage-specific cell-surface antigen(s) retains its biological activity. In some embodiments, any one or more of the mutant lineage-specific cell-surface antigen(s) escapes targeting by a cytotoxic agent that targets the corresponding wild-type lineage-specific cell-surface antigen and retains its biological activity.

Another aspect of the present disclosure features a population of genetically engineered hematopoietic cells, wherein the genetically engineered hematopoietic cells in the population comprise: (i) a first gene encoding a first lineage-specific cell-surface antigen, which gene has been modified or edited and (ii) a second gene encoding a second lineage-specific cell-surface antigen, which gene has been modified or edited. In some embodiments, the first gene has been modified or edited such that expression of the first lineage-specific cell-surface antigen is reduced or eliminated in the genetically engineered hematopoietic cell (e.g., as compared with expression of the corresponding endogenous or wild-type lineage-specific cell-surface antigen). In some embodiments, the first gene has been modified or edited such that the genetically engineered hematopoietic cell expresses a mutant or modified version of the first lineage-specific cell-surface antigen. In some embodiments, the mutant or modified version of the first lineage-specific cell-surface antigen escapes targeting by a cytotoxic agent that targets the corresponding wild-type lineage-specific cell-surface antigen. In some embodiments, the mutant or modified version of the first lineage-specific cell-surface antigen retains its biological activity. In some embodiments, the mutant or modified version of the first lineage-specific cell-surface antigen escapes targeting by a cytotoxic agent that targets the corresponding wild-type lineage-specific cell-surface antigen and retains its biological activity. In some embodiments, the second gene has been modified or edited such that expression of the second lineage-specific cell-surface antigen is reduced or eliminated in the genetically engineered hematopoietic cell (e.g., as compared with expression of the corresponding endogenous or wild-type lineage-specific cell-surface antigen). In some embodiments, the second gene has been modified or edited such that the genetically engineered hematopoietic cell expresses a mutant or modified version of the second lineage-specific cell-surface antigen. In some embodiments, the mutant or modified version of the second lineage-specific cell-surface antigen escapes targeting by a cytotoxic agent that targets the corresponding wild-type lineage-specific cell-surface antigen. In some embodiments, the mutant or modified version of the second lineage-specific cell-surface antigen retains its biological activity. In some embodiments, the mutant or modified version of the second lineage-specific cell-surface antigen escapes targeting by a cytotoxic agent that targets the corresponding wild-type lineage-specific cell-surface antigen and retains its biological activity.

Another aspect of the present disclosure features a population of genetically engineered hematopoietic cells, wherein the genetically engineered hematopoietic cells of the population further comprise: (iii) a third gene encoding a third lineage-specific cell-surface antigen, which gene has been modified or edited. In some embodiments, the genetically engineered hematopoietic cells of the population further comprise: (iv) a fourth gene encoding a fourth lineage-specific cell-surface antigen, which gene has been modified or edited. In some embodiments, the genetically engineered hematopoietic cells of the population further comprise (v) a fifth gene encoding a fifth lineage-specific cell-surface antigen, which gene has been modified or edited. In some embodiments, any one or more of the gene(s) encoding a lineage-specific cell-surface antigen has been modified or edited such that expression of the respective lineage-specific cell-surface antigen(s) is reduced or eliminated in the genetically engineered hematopoietic cell (e.g., as compared with expression of the corresponding endogenous or wild-type lineage-specific cell-surface antigen). In some embodiments, any one or more of the gene(s) encoding a lineage-specific cell-surface antigen has been modified or edited such that the genetically engineered hematopoietic cell expresses a mutant or modified version of the respective lineage-specific cell-surface antigen(s). In some embodiments, any one or more of the mutant lineage-specific cell-surface antigen(s) escapes targeting by a cytotoxic agent that targets the corresponding wild-type lineage-specific cell-surface antigen. In some embodiments, any one or more of the mutant or modified version lineage-specific cell-surface antigen(s) retains its biological activity. In some embodiments, any one or more of the mutant lineage-specific cell-surface antigen(s) escapes targeting by a cytotoxic agent that targets the corresponding wild-type lineage-specific cell-surface antigen and retains its biological activity. One aspect of the present disclosure features a population of genetically engineered hematopoietic cells, comprising: (i) a first group of genetically engineered hematopoietic cells, which have genetic modification or editing in a first gene encoding a first lineage-specific cell-surface antigen, wherein the first group of genetically engineered hematopoietic cells (a) have reduced or eliminated expression of the first lineage-specific cell-surface antigen or (b) express a mutant of the first lineage-specific cell-surface antigen; and (ii) a second group of genetically engineered hematopoietic cells, which have genetic modification or editing in a second gene encoding a second lineage-specific cell-surface antigen, wherein the second group of genetically engineered hematopoietic cells (a) have reduced or eliminated expression of the second lineage-specific cell-surface antigen or (b) express a mutant of the second lineage-specific cell-surface antigen. In some embodiments, the first group of genetically engineered hematopoietic cells may overlap with the second group of genetically engineered hematopoietic cells, completely or partially.

In some embodiments, the present disclosure provides a genetically engineered hematopoietic cell, comprising: (i) a gene encoding a CD19, which gene has been modified or edited and (ii) a gene encoding a CD33, which gene has been modified or edited. In some embodiments, the CD19 gene has been modified or edited such that expression of the CD19 antigen is reduced or eliminated in the genetically engineered hematopoietic cell (e.g., as compared with expression of the corresponding endogenous or wild-type CD19 antigen). In some embodiments, the CD19 gene has been modified or edited such that the genetically engineered hematopoietic cell expresses a mutant or modified version of the CD19 antigen. In some embodiments, the mutant or modified version of the CD19 antigen escapes targeting by a cytotoxic agent that targets the corresponding wild-type CD19 antigen. In some embodiments, the mutant or modified version of the CD19 antigen retains its biological activity. In some embodiments, the mutant or modified version of the CD19 antigen escapes targeting by a cytotoxic agent that targets the corresponding wild-type CD19 antigen and retains its biological activity. In some embodiments, the CD33 gene has been modified or edited such that expression of the CD33 antigen is reduced or eliminated in the genetically engineered hematopoietic cell (e.g., as compared with expression of the corresponding endogenous or wild-type CD33 antigen). In some embodiments, the CD33 gene has been modified or edited such that the genetically engineered hematopoietic cell expresses a mutant or modified version of the CD33 antigen. In some embodiments, the mutant or modified version of the CD33 antigen escapes targeting by a cytotoxic agent that targets the corresponding wild-type CD33 antigen. In some embodiments, the mutant or modified version of the CD33 antigen retains its biological activity. In some embodiments, the mutant or modified version of the CD33 antigen escapes targeting by a cytotoxic agent that targets the corresponding wild-type CD33 antigen and retains its biological activity. In some embodiments of the genetically engineered hematopoietic cell comprising: (i) a modified or edited gene encoding a CD19 and (ii) a modified or edited gene encoding a CD33, the gene encoding CD19 has been modified or edited such that the entire exon 2 is deleted or a portion of exon 2 is deleted. In some embodiments of the genetically engineered hematopoietic cell comprising: (i) a modified or edited gene encoding a CD19 and (ii) a modified or edited gene encoding a CD33, the gene encoding CD33 has been modified or edited such that the entire exon 2 is deleted or a portion of exon 2 is deleted. In some embodiments of the genetically engineered hematopoietic cell comprising: (i) a modified or edited gene encoding a CD19 and (ii) a modified or edited gene encoding a CD33, the gene encoding CD19 has been modified or edited such that the gene is truncated, has inserted and/or deleted sequences (e.g., resulting in scrambled, frameshift, or nonsense sequence), or the entire gene is deleted (e.g., effectively a knock-out gene). In some embodiments of the genetically engineered hematopoietic cell comprising: (i) a modified or edited gene encoding a CD19 and (ii) a modified or edited gene encoding a CD33, the gene encoding CD33 has been modified or edited such that the gene is truncated, has inserted and/or deleted sequences (e.g., resulting in scrambled, frameshift, or nonsense sequence), or the entire gene is deleted (e.g., effectively a knock-out gene). In some embodiments of the genetically engineered hematopoietic cell comprising: (i) a modified or edited gene encoding a CD19 and (ii) a modified or edited gene encoding a CD33, the gene encoding CD19 has been modified or edited such that the entire exon 2 of CD19 is deleted or a portion of exon 2 od CD19 is deleted and the gene encoding CD33 has been modified or edited such that the CD33 gene is truncated, has inserted and/or deleted sequences (e.g., resulting in scrambled, frameshift, or nonsense sequence), or the entire CD33 gene is deleted. In some embodiments of the genetically engineered hematopoietic cell comprising: (i) a modified or edited gene encoding a CD19 and (ii) a modified or edited gene encoding a CD33, the gene encoding CD33 has been modified or edited such that the entire exon 2 of CD33 is deleted or a portion of exon 2 of CD33 is deleted and the gene encoding CD19 has been modified or edited such that the CD19 gene is truncated, has inserted and/or deleted sequences (e.g., resulting in scrambled, frameshift, or nonsense sequence), or the entire gene is deleted.

In some embodiments, the present disclosure provides a genetically engineered hematopoietic cell, comprising: (i) a gene encoding a CD19, which gene has been modified or edited such that the entire exon 2 is deleted or a portion of exon 2 is deleted and (ii) a gene encoding a CD33, which gene has been modified or edited such that the entire exon 2 is deleted or a portion of exon 2 is deleted. In some embodiments, the mutant of the CD19 antigen with exon 2 deleted or a portion of exon 2 deleted retains its biological activity. In some embodiments, the mutant of the CD19 antigen with exon 2 deleted or a portion of exon 2 deleted escapes targeting by a cytotoxic agent that targets the corresponding wild-type CD19 antigen and retains its biological activity. In some embodiments, the mutant of the CD33 antigen with exon 2 deleted or a portion of exon 2 deleted retains its biological activity. In some embodiments, the mutant of the CD33 antigen with exon 2 deleted or a portion of exon 2 deleted escapes targeting by a cytotoxic agent that targets the corresponding wild-type CD33 antigen and retains its biological activity. In some embodiments, the present disclosure provides a genetically engineered hematopoietic cell, comprising: (i) a gene encoding a CD19, which gene has been modified or edited such that the entire exon 2 is deleted or a portion of exon 2 is deleted and (ii) a gene encoding a CD33, which gene has been modified or edited such that the entire exon 2 is deleted or a portion of exon 2 is deleted. In some embodiments, the present disclosure provides a genetically engineered hematopoietic cell, comprising a gene encoding a CD19, which gene has been modified or edited such that intron 1 and/or intron 2 in CD19 has been modified or edited. In some embodiments, the genetically engineered hematopoietic cell has a sequence deletion in intron 1 and/or intron 2 of CD19 gene, e.g., either a portion of intron 1 and/or intron 2 of CD19 is deleted or the entire intron 1 and/or intron 2 of CD19 is deleted. In some embodiments, the present disclosure provides a genetically engineered hematopoietic cell, comprising a gene encoding a CD33, which gene has been modified or edited such that intron 1 and/or intron 2 in CD33 has been modified or edited. In some embodiments, the genetically engineered hematopoietic cell has a sequence deletion in intron 1 and/or intron 2 of CD33 gene, e.g., either a portion of intron 1 and/or intron 2 of CD33 is deleted or the entire intron 1 and/or intron 2 of CD33 is deleted. In some embodiments, the present disclosure provides a genetically engineered hematopoietic cell, comprising: (i) a gene encoding a CD19, which gene has been modified or edited such that intron 1 and/or intron 2 in CD19 has been modified or edited and (ii) a gene encoding a CD33, which gene has been modified or edited such that intron 1 and/or intron 2 in CD33 has been modified or edited. In some embodiments, the mutant of the CD19 antigen with intron 1 and/or intron 2 deleted or a portion of intron 1 and/or intron 2 deleted retains its biological activity. In some embodiments, the mutant of the CD19 antigen with intron 1 and/or intron 2 deleted or a portion of intron 1 and/or intron 2 deleted escapes targeting by a cytotoxic agent that targets the corresponding wild-type CD19 antigen and retains its biological activity. In some embodiments, the mutant of the CD33 antigen with intron 1 and/or intron 2 deleted or a portion of intron 1 and/or intron 2 deleted retains its biological activity. In some embodiments, the mutant of the CD33 antigen with intron 1 and/or intron 2 deleted or a portion of intron 1 and/or intron 2 deleted escapes targeting by a cytotoxic agent that targets the corresponding wild-type CD33 antigen and retains its biological activity.

Any of the genetically engineered hematopoietic cells or populations of genetically engineered hematopoietic cells described herein may be hematopoietic stem cells (HSCs). In some instances, the HSCs are CD34+/CD33− cells. Any of the hematopoietic cells described herein can be from bone marrow cells, cord blood cells, or peripheral blood mononuclear cells (PBMCs). In some embodiments, the genetically engineered hematopoietic cell is a human hematopoietic cell. In some embodiments, any of the hematopoietic cells described herein are bone marrow cells, cord blood cells, or peripheral blood mononuclear cells (PBMCs) derived from a human.

In some embodiments, the mutant of the first lineage-specific cell-surface antigen and/or the mutant of the second lineage-specific cell-surface antigen (and/or the mutant of a third, and/or fourth, and/or fifth lineage-specific cell-surface antigen) includes a mutated or deleted non-essential epitope. Such a non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) has at least 3 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-10 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-200 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-175 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-150 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-125 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-100 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-75 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-50 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is 6-25 amino acids. In some examples, the non-essential epitope in the first lineage-specific cell surface antigen and/or the non-essential epitope in the second lineage-specific cell surface antigen (and/or the non-essential epitope in the third, and/or fourth, and/or fifth lineage-specific cell-surface antigen) is an entire exon or a portion of an exon.

In some embodiments at least one of the first and second lineage-specific cell-surface antigens is associated with a hematopoietic malignancy. In some embodiments at least one of any of the modified or mutant lineage-specific cell-surface antigens is associated with a hematopoietic malignancy. Non-limiting examples include CD7, CD13, CD19, CD22, CD25, CD32, CD33, CD38, CD44, CD47, CD56, 96, CD117, CD123, CD135, CD174, CLL-1, folate receptor b, IL1RAP, MUC1, NKG2D/NKG2DL, TIM-3, and WT1. In some examples, the first and second lineage-specific cell-surface antigens are selected from (a) CD19+ CD33, (b) CD19+CD13, (c) CD19+CD123, (d) CD33+ CD13, (e) CD33+CD123, (f) CD13+CD123.

In some embodiments, the modified lineage-specific cell-surface antigen is a type 1 lineage-specific cell-surface antigen. In some embodiments, at least one of the lineage-specific cell-surface antigens is a type 1 lineage-specific cell-surface antigen. In some embodiments, the lineage-specific cell-surface antigen is CD19. In some embodiments, at least one of the lineage-specific cell-surface antigens is CD19. In some embodiments, at least one of the first and second lineage-specific cell-surface antigens is a type 1 lineage-specific cell-surface antigen, for example, CD19. In some embodiments at least one of any of the modified or mutant lineage-specific cell-surface antigens is a type 1 lineage-specific cell-surface antigen, for example, CD19. In some embodiments, both of the first and second lineage-specific cell-surface antigens are type 1 lineage-specific cell-surface antigens. In some embodiments, the genetic modification or editing of a CD19 gene (e.g., an endogenous CD19 gene) occurs in an exon of the CD19 gene. In some embodiments, the genetic modification or editing of a CD19 gene (e.g., an endogenous CD19 gene) occurs in exon 2 of the CD19 gene. In some embodiments, the genetic modification or editing of a CD19 gene (e.g., an endogenous CD19 gene) occurs in one or more introns of the CD19 gene, e.g., including modification or editing of one or more introns that result in modification(s) in exon 2 of CD19. In some embodiments, the genetic modification or editing of a CD19 gene (e.g., an endogenous CD19 gene) results in mutation or deletion of exon 2 of a CD19 gene. In some embodiments, the genetic modification or editing of a CD19 gene (e.g., an endogenous CD19 gene) results in deletion of the entire exon 2 of a CD19 gene or deletion of a portion of exon 2 of a CD19 gene. In some instances, the mutated CD19 comprises the amino acid sequence of SEQ ID NO: 52.

In some embodiments, the genetic modification or editing of a CD19 gene (e.g., an endogenous CD19 gene) occurs in one or more introns of the CD19 gene, e.g., including modification or editing of one or more introns that result in modification(s) in exon 4 of CD19. In some embodiments, the genetic modification or editing of a CD19 gene (e.g., an endogenous CD19 gene) results in mutation or deletion of exon 4 of a CD19 gene. In some embodiments, the genetic modification or editing of a CD19 gene (e.g., an endogenous CD19 gene) results in deletion of the entire exon 4 of a CD19 gene or deletion of a portion of exon 2 of a CD19 gene. In some instances, the mutated CD19 comprises the amino acid sequence of SEQ ID NO: 73.

In some embodiments, the modified lineage-specific cell-surface antigen is a type 2 lineage-specific cell-surface antigen. In some embodiments, at least one of the lineage-specific cell-surface antigens is a type 2 lineage-specific cell-surface antigen. In some embodiments, the lineage-specific cell-surface antigen is CD33. In some embodiments, at least one of the lineage-specific cell-surface antigens is CD33. In some embodiments, at least one of the first and second lineage-specific cell-surface antigens is a type 2 lineage-specific cell-surface antigen, for example, CD33. In some embodiments at least one of any of the modified or mutant lineage-specific cell-surface antigens is a type 2 lineage-specific cell-surface antigen, for example, CD33. In some embodiments, both of the first and second lineage-specific cell-surface antigens are type 2 lineage-specific cell-surface antigens. In some embodiments, the genetic modification or editing of a CD33 gene (e.g., an endogenous CD33 gene) occurs in an exon of the CD33 gene. In some embodiments, the genetic modification or editing of a CD33 gene (e.g., an endogenous CD33 gene) occurs in exon 2 of the CD33 gene. In some embodiments, the genetic modification or editing of a CD33 gene (e.g., an endogenous CD33 gene) occurs in one or more introns of the CD33 gene, e.g., including modification or editing of one or more introns that result in modification(s) in exon 2 of CD33. In some embodiments, the genetic modification or editing of a CD33 gene (e.g., an endogenous CD33 gene) occurs in intron 1 and intron 2 of the CD33 gene. In some embodiments, the genetic modification or editing of a CD33 gene (e.g., an endogenous CD33 gene) results in mutation or deletion of exon 2 of the CD33 gene. In some embodiments, the genetic modification or editing of a CD33 gene (e.g., an endogenous CD33 gene) results in deletion of the entire exon 2 of the CD33 gene or deletion of a portion of exon 2 of the CD33 gene. In some embodiments, the genetic modification or editing of a CD33 gene (e.g., an endogenous CD33 gene) occurs in exon 3 of the CD33 gene. In some embodiments, the genetic modification or editing of a CD33 gene (e.g., an endogenous CD33 gene) occurs in one or more introns of the CD33 gene, e.g., including modification or editing of one or more introns that result in modification(s) in exon 3 of CD33. In some embodiments, the genetic modification or editing of a CD33 gene (e.g., an endogenous CD33 gene) results in mutation or deletion of exon 3 of the CD33 gene. In some embodiments, the genetic modification or editing of a CD33 gene (e.g., an endogenous CD33 gene) results in deletion of the entire exon 3 of the CD33 gene or deletion of a portion of exon 3 of the CD33 gene. In some examples, the second group of genetically engineered hematopoietic cells may contain genetic editing in exon 2 or exon 3 of a CD33 gene (e.g., including genetic modifications at one or more introns that result in modifications in exon 2 or exon 3). In some examples, the CD33 gene is an endogenous CD33 gene. Example CD33 mutants include SEQ ID NO: 56 or SEQ ID NO: 58.

In some embodiments, the second lineage-specific cell surface antigen is a type 0 protein. In some embodiments, at least one of the first and second lineage-specific cell surface antigens is a type 0 protein. In some embodiments at least one of any of the modified or mutant lineage-specific cell-surface antigens is a type 0 lineage-specific cell-surface antigen. In some embodiments, both of the first and second lineage-specific cell-surface antigens are type 0 lineage-specific cell-surface antigens. In some embodiments, the genetic modification or editing of a Type 0 antigen gene occurs in an exon of the Type 0 gene. In some embodiments, the genetic modification or editing of a Type 0 antigen occurs in exon 2 of the Type 0 antigen gene. In some embodiments, the genetic modification or editing of a Type 0 antigen gene occurs in one or more introns of the Type 0 antigen gene, e.g., including modification or editing of one or more introns that result in modification(s) in exon 2 of the Type 0 antigen gene. In some embodiments, the genetic modification or editing of a Type 0 antigen gene occurs in intron 1 and intron 2 of the Type 0 antigen gene.

Any of the genetically engineered hematopoietic cells described herein can be produced by genomic editing. In some embodiments, the genomic editing does not involve an exogenous nuclease. In some embodiments, the genomic editing involves adeno-associated virus vector mediated homologous recombination. In some embodiments, the genomic editing involves an exogenous nuclease. Exemplary approaches include the method that involve the use of a zinc finger nuclease (ZFN), a transcription activator-like effector-based nuclease (TALEN), or a CRISPR-Cas system. In some embodiments, the CRISPR-Cas system comprises a Cas endonuclease. In some embodiments, the Cas endonuclease is a Cas9 endonuclease.

In another aspect, provided herein are methods for producing any of the genetically engineered hematopoietic cells or populations of genetically engineered hematopoietic cells. In one aspect, provided herein is a method for producing a population of genetically engineered hematopoietic cells, the method comprising: (i) providing a population of hematopoietic cells, and (ii) genetically modifying or editing at least one lineage-specific cell surface antigen. In some embodiments, the at least one lineage-specific cell surface antigen is genetically modified via CRISPR to produce the population of genetically engineered hematopoietic cells. In one aspect, provided herein is a method for producing a population of genetically engineered hematopoietic cells, the method comprising: (i) providing a population of hematopoietic cells, and (ii) genetically modifying or editing a first lineage-specific cell surface antigen, or genetically modifying or editing a second lineage-specific cell surface antigen, or genetically modifying or editing a first lineage-specific cell surface antigen and a second lineage-specific cell surface antigen in the population of hematopoietic cells via CRISPR to produce the population of genetically engineered hematopoietic cells. In one aspect, provided herein is a method for producing a population of genetically engineered hematopoietic cells, the method comprising: (i) providing a population of hematopoietic cells, and (ii) genetically modifying or editing a first lineage-specific cell surface antigen and genetically modifying or editing a second lineage-specific cell surface antigen in the population of hematopoietic cells to produce the population of genetically engineered hematopoietic cells. In some embodiments, the method for producing a population of genetically engineered hematopoietic cells further comprises (iii) genetically modifying or editing one or more other lineage-specific cell surface antigen(s) in the population of hematopoietic cells to produce the population of genetically engineered hematopoietic cells. In any of these methods, the genetically engineered hematopoietic cell is a human cell.

In one aspect, provided herein is a method for producing a genetically engineered hematopoietic cell, the method comprising: (i) providing a hematopoietic cell, and (ii) genetically modifying or editing a first lineage-specific cell surface antigen, or genetically modifying or editing a second lineage-specific cell surface antigen, or genetically modifying or editing a first lineage-specific cell surface antigen and a second lineage-specific cell surface antigen in the hematopoietic cell via CRISPR to produce the genetically engineered hematopoietic cell. In one aspect, provided herein is a method for producing a genetically engineered hematopoietic cell, the method comprising: (i) providing a hematopoietic cell, and (ii) genetically modifying or editing a first lineage-specific cell surface antigen and genetically modifying or editing a second lineage-specific cell surface antigen to produce the genetically engineered hematopoietic cell. In some embodiments, the method for producing a genetically engineered hematopoietic cell further comprises (iii) genetically modifying or editing one or more other lineage-specific cell surface antigen(s) to produce the genetically engineered hematopoietic cell. In any of these methods, the genetically engineered hematopoietic cell is a human cell.

In one aspect, provided herein is a method for producing a population of genetically engineered hematopoietic cells, the method comprising: (i) providing a population of hematopoietic cells, and (ii) genetically modifying or editing a CD19 gene, or genetically modifying or editing a CD33 gene, or genetically modifying or editing a CD19 gene and a CD33 gene in the population of hematopoietic cells via CRISPR to produce the genetically engineered hematopoietic cells. In one aspect, provided herein is a method for producing a population of genetically engineered hematopoietic cells, the method comprising: (i) providing a population of hematopoietic cells, and (ii) genetically modifying or editing a CD19 gene and genetically modifying or editing a CD33 gene in the population of hematopoietic cells to produce the population of genetically engineered hematopoietic cells. In one aspect, provided herein is a method for producing a genetically engineered hematopoietic cell, the method comprising: (i) providing a hematopoietic cell, and (ii) genetically modifying or editing a CD19 gene, or genetically modifying or editing a CD33 gene, or genetically modifying or editing a CD19 gene and genetically modifying or editing a CD33 gene in the hematopoietic cell via CRISPR to produce the genetically engineered hematopoietic cell. In one aspect, provided herein is a method for producing a genetically engineered hematopoietic cell, the method comprising: (i) providing a hematopoietic cell, and (ii) genetically modifying or editing a CD19 gene and genetically modifying or editing a CD33 gene to produce the genetically engineered hematopoietic cell. In some embodiments, the method for producing a genetically engineered hematopoietic cell or population of genetically engineered hematopoietic cells further comprises (iii) genetically modifying or editing one or more other lineage-specific cell surface antigen(s) to produce the genetically engineered hematopoietic cell. In any of these methods, the genetically engineered hematopoietic cell is a human cell.

In some embodiments, the genetic editing of the CD19 gene involves one or more guide nucleic acid molecules that target one or more introns of CD19. In some embodiments, the genetic editing of the CD33 gene involves one or more guide nucleic acid molecules that target one or more introns of CD33. In some embodiments, the genetic editing of the CD33 gene involves one or more guide nucleic acid molecules that do not target the CD33 pseudogene upstream of the CD33 gene. In some embodiments, the genetic editing of the CD33 gene involves one or more guide nucleic acid molecules that (a) target one or more introns of CD33 and (b) do not target the CD33 pseudogene upstream of the CD33 gene. In some embodiments, the introns of the CD19 gene comprise intron 1 and intron 2. In some embodiments, the introns of the CD33 gene comprise intron 1 and intron 2. In some embodiments, the genetic editing of CD19 results in exclusion of exon 2 of the CD19 gene. In some embodiments, the genetic editing of CD19 results in exclusion of exon 4 of the CD19 gene. In some embodiments, the genetic editing of CD33 results in exclusion of exon 2 of the CD33 gene. In some embodiments, the genetic editing of the CD33 gene involves one or more guide nucleic acid molecules that target exon 3 of CD33. In some embodiments, the genetic editing of the CD33 gene involves at least one guide nucleic acid molecule comprising the nucleotide sequence of SEQ ID NO: 67.

Further, provided herein is a method for producing genetically engineered hematopoietic cells, the method comprising: (i) providing a population of hematopoietic cells, and (ii) genetically editing a CD19 gene, a CD33 gene, or both a CD19 and a CD33 gene in the population of hematopoietic cells via CRISPR to produce the genetically engineered hematopoietic cells, wherein the genetic editing of the CD19 gene involves at least one guide nucleic acid molecule comprising the nucleotide sequence of SEQ ID NOs: 14-26, 67, and 69-72, and/or wherein the genetic editing of the CD33 gene involves at least one guide nucleic acid molecule comprising the nucleotide sequence of SEQ ID NOs: 27-50 and 68. In some embodiments, the method for producing genetically engineered hematopoietic cells comprises genetically editing a CD33 gene in the population of hematopoietic cells via CRISPR to produce the genetically engineered hematopoietic cells, wherein the genetic editing of the CD33 gene involves at least one guide nucleic acid molecule comprising the nucleotide sequence of SEQ ID NO: 67.

In some embodiments, step (ii) is performed by genetic editing of both a CD19 gene and a CD33 gene in the population of hematopoietic cells via CRISPR to produce the genetically engineered hematopoietic cells. The genetic editing of the CD19 gene involves a guide nucleic acid comprising the nucleotide sequence of SEQ ID NO: 67, and/or the genetic editing of the CD33 gene involves a guide nucleic acid comprising the nucleotide sequence of SEQ ID NO: 68.

In any of the methods described herein, the hematopoietic cells can be HSCs, for example, CD34+/CD33− cells. The hematopoietic cells can be from bone marrow cells, cord blood cells, or peripheral blood mononuclear cells (PBMCs). In some embodiments, the hematopoietic cells are from human bone marrow cells, human cord blood cells, or human peripheral blood mononuclear cells (PBMCs). Also provided herein are genetically engineered hematopoietic cells having one of more of the following features:

(a) carry a genetically edited CD19 gene capable of expressing a mutant CD19 comprising the amino acid sequence of SEQ ID NO: 52 or 73 and/or a genetically edited CD33 gene capable of expressing a mutant CD33 comprising the amino acid sequence of SEQ ID NO: 56 or SEQ ID NO: 58;
  (b) carry a genetically edited CD19 gene capable of expressing a mutant CD19 comprising the amino acid sequence of SEQ ID NO: 52 or 73 and a genetically edited CD33 gene capable of expressing a mutant CD33 comprising the amino acid sequence of SEQ ID NO: 56;
  (c) exon 2 of CD33 gene in the hematopoietic cell is modified and wherein one or more portions of the CD33 pseudogene are not modified;
  (d) exon 2 of CD33 gene in the hematopoietic cell is deleted and wherein one or more portions of the CD33 pseudogene are not modified;
  (e) exon 2 of CD33 gene in the hematopoietic cell is modified and wherein one or more portions of the CD33 pseudogene are not modified by deletion or mutation that causes a frameshift.
  (f) exon 2 of CD33 gene in the hematopoietic cell is modified and wherein the one or more portion(s) of the CD33 pseudogene that is not modified by deletion or mutation that causes a frameshift is selected from Exon 1, intron1, Exon 2, and combinations thereof;
  (g) exon 2 of CD33 gene in the hematopoietic cell is modified and wherein the one or more portion(s) of the CD33 pseudogene that is not modified by deletion or mutation that causes a frameshift is selected from sequence(s) in Exon 1, intron 1, and/or Exon 2, that share sequence homology, respectively, with sequence(s) in Exon 1, intron 1, and/or Exon 2 of CD33.

Further, genetically engineered hematopoietic cells produced by any method disclosed herein are also within the scope of the present disclosure.

Also provided herein is a population of genetically engineered hematopoietic stem cells, wherein at least 50% (e.g., at least 60%, 70%, 75%, 80%, 85%, 90%, or 95%) of the hematopoietic stem cells therein carry both a genetically edited CD19 gene and a genetically edited CD33 gene. In some instances, the genetically edited CD19 gene is capable of expressing a CD19 mutant comprising the amino acid sequence of SEQ ID NO: 52 or 73. Alternatively or in addition, the genetically edited CD33 gene is capable of expressing a CD33 mutant comprising the amino acid sequence of SEQ ID NO: 56 or SEQ ID NO: 58.

Moreover, provided herein is a method of treating a hematopoietic malignancy (e.g., AML), comprising administering to a subject in need thereof a population of genetically engineered hematopoietic cells as disclosed herein. The method may further comprise administering to the subject an effective amount of a first immunotherapeutic agent. In some instances, the first immunotherapeutic agent is a cytotoxic agent that targets cells expressing either the first lineage-specific cell-surface antigen or the second lineage-specific cell-surface antigen.

In some examples, the first immunotherapeutic agent is a cytotoxic agent that targets cells expressing the first lineage-specific cell-surface antigen, and the method further comprises administering to the subject a second immunotherapeutic agent when the hematopoietic malignancy relapses in the subject. The second immunotherapeutic agent may be a cytotoxic agent that targets cells expressing the second lineage-specific cell-surface antigen. In one example, the first immunotherapeutic agent, the second immunotherapeutic agent, or both are CAR-T cells. In one example, the first immunotherapeutic agent, the second immunotherapeutic agent, or both are antibody drug conjugates.

The disclosure also provides methods of protecting hematopoietic stem cells from immunotherapy in a subject in need thereof, wherein the therapy targets one or more lineage-specific antigen(s). In some embodiments, the methods comprise administering a modified hematopoietic stem cell to a subject, wherein the stem cell comprises one or more gene(s) encoding the lineage-specific antigen(s) being targeted by the immunotherapy, and wherein the gene(s) are modified, mutated or edited. In some embodiments of the methods, the gene(s) are modified such that expression of the gene(s) results in modified, mutated protein(s) or complete knockout(s) of the protein or combinations thereof. In some embodiments of the method, modified, mutated protein(s) or complete knockout(s) prevent the immunotherapy from targeting the hematopoietic stem cells comprising the mutated gene(s). In some embodiments of the methods, the editing results in expression of one or more lineage-specific antigen(s), which contain a partial deletion. In some embodiments of the methods, the partial deletion compasses an entire exon or a portion of an exon. In some embodiments of the methods, the immunotherapy administered includes one or more antibody-drug conjugate(s), which can be administered concurrently or sequentially. In some embodiments of the methods, the immunotherapy administered includes cells expressing one or more chimeric antigen receptors or a pool of 2 or more cells, each expressing a different chimeric antigen receptor, which can be administered concurrently or sequentially. In one embodiment, the disclosure provides a method of protecting hematopoietic stem cells from one or more chimeric antigen receptor T cell therapies targeting one or more lineage specific antigen(s) in a subject in need thereof, wherein the hematopoietic stem cells are administered, and wherein the hematopoietic stem cells are modified such that expression of the gene(s) encoding one or more lineage specific antigen(s) result in modified, mutated forms or complete knockout(s) of the lineage specific antigen(s) targeted by the CART(s). In one embodiment of this method, the mutated form(s) of the one or more lineage specific antigen(s) lack an exon, e.g., an exon which comprises the CART or antibody-drug conjugate epitope. In any of these methods, the modified hematopoietic cell can be any of the modified hematopoietic cells described here and elsewhere herein.

Such modified hematopoietic stems cells can be generated using gene editing technologies, e.g. CRISPR, as described herein. As described elsewhere, CRISPR methodology can be used to delete a portion or an entire gene of interest. In some embodiments, CRISPR methodology can be used to delete one or more exons comprising a targeted epitope. In some instances, it is beneficial to target one or more flanking intron sequences to excise an exon. In some instances, the exon sequence itself may be targeted by CRISPR, however, current conventional CRISPR therapies may lead to small insertions and deletions, which can lead to frameshift and truncated non-functional proteins. To avoid unintentional knockouts, the intron sequences may be beneficial to target so as to more precisely edit the exon sequence of interest.

Accordingly, the disclosure also provides methods for generating modified hematopoietic stem cells, comprising introducing one or more guide RNAs capable of editing one or more gene(s) encoding one or more lineage specific antigen(s) targeted by one or more chimeric antigen receptor(s). In some embodiments of the methods, the editing results in expression of lineage specific antigen(s) lacking an exon. In some embodiments, the editing results complete knockout of lineage specific antigen(s). In some embodiments of the methods, the editing results in a combination of expression of lineage specific antigen(s) lacking an exon and complete knockout of lineage specific antigen(s) in one cell or a cell population. In some embodiments, the one or more guide RNAs are selected to target one or more introns. In some embodiments of the method, targeting of adjacent introns results in excision of the gene sequence encoding the exon between the two introns.

Targeting one intron may result in the generation of a new splice site, resulting in excision of the gene sequence encoding the adjacent exon. Exon skipping using a single guide RNA has been described (e.g., Mou et al., Genome Biology 201718:108). Accordingly, in some embodiments, one intron may be targeted according to the methods described herein.

In some embodiments, a method of protecting hematopoietic stem cells from immunotherapy may be used in a subject in need thereof, wherein the therapy targets one or more lineage-specific antigen(s). In some embodiments, the methods comprise administering a modified hematopoietic stem cell to a subject, wherein the stem cell comprises one or more gene(s) encoding the lineage-specific antigen(s) CD19 and/or CD33 being targeted by the immunotherapy, and wherein the CD19 and/or CD33 gene(s) are modified, mutated or edited. In some embodiments of the methods, the CD19 and/or CD33 gene(s) are modified such that expression result in modified, mutated CD19 and/or CD33 or complete knockout(s) of the CD19 and/or CD33 or combinations thereof. In some embodiments of the method, modified, mutated CD19 and/or CD33 protein(s) or complete CD19 and/or CD33 knockout(s) prevent the immunotherapy from targeting the hematopoietic stem cells comprising the mutated gene(s). In some embodiments of the methods, the editing results in expression CD19 and/or CD33, which contain a partial deletion. In some embodiments of the methods, the partial deletion compasses an entire exon or a portion of an exon, e.g., exon2 of CD33 and/or CD19. In some embodiments of the methods, the immunotherapy administered includes one or more antibody-drug conjugate(s) directed against CD19 and/or CD33, which can be administered concurrently or sequentially. In some embodiments of the methods, the immunotherapy administered includes cells expressing one or more chimeric antigen receptors directed against CD19 and/or CD33 or a pool of 2 cell populations, one expressing chimeric antigen receptor directed against CD19 and the other expressing a chimeric antigen receptor directed against CD33. The cells expressing chimeric antigen receptor directed against CD19 can be administered concurrently or sequentially with the cells expressing chimeric antigen receptor directed against CD33. In one embodiment, the disclosure provides a method of protecting hematopoietic stem cells from one or more chimeric antigen receptor T cell therapies targeting CD19 and/or CD33 in a subject in need thereof, wherein the hematopoietic stem cells are administered, and wherein the hematopoietic stem cells are modified such that expression of the gene(s) encoding CD19 and/or CD33 result in modified, mutated forms or complete knockout(s) of the CD19 and/or CD33. In one embodiment of this method, the mutated form(s) of CD19 and/or CD33 lack an exon, e.g., an exon which comprises the CART epitope.

Accordingly, the disclosure also provides methods for generating modified hematopoietic stem cells, comprising introducing one or more guide RNAs capable of editing one or more gene(s) encoding CD19 and/or CD33, wherein CD19 and/or CD33 are targeted by one or more chimeric antigen receptor(s) or antibody-drug conjugates. In some embodiments of the methods, the editing results in expression of CD19 and/or CD33 lacking an exon. In some embodiments, the editing results complete knockout of CD19 and/or CD33. In some embodiments of the methods, the editing results in a combination of expression of lineage specific antigen(s) lacking an exon and complete knockout of CD19 and/or CD33 in one cell or a cell population. In some embodiments, the one or more guide RNAs are selected to target one or more introns. In some embodiments of the method, targeting of adjacent introns results in excision of the gene sequence encoding the exon between the two introns.

ENUMERATED EMBODIMENTS

1. A population of genetically engineered hematopoietic cells, comprising:
   (i) a first group of genetically engineered hematopoietic cells, which have genetic editing in a first gene encoding a first lineage-specific cell-surface antigen, wherein the first group of genetically engineered hematopoietic cells (a) have reduced or eliminated expression of the first lineage-specific cell-surface antigen or (b) express a mutant of the first lineage-specific cell-surface antigen; and
   (ii) a second group of genetically engineered hematopoietic cells, which have genetic editing in a second gene encoding a second lineage-specific cell-surface antigen, wherein the second group of genetically engineered hematopoietic cells (a) have reduced or eliminated expression of the second lineage-specific cell-surface antigen or (b) express a mutant of the second lineage-specific cell-surface antigen.

2. The population of genetically engineered hematopoietic cells of embodiment 1, wherein the first group of genetically engineered hematopoietic cells overlaps with the second group of genetically engineered hematopoietic cells.

3. A population of genetically engineered hematopoietic cells, wherein one or more cells of the population:
   (i) have reduced or eliminated expression of a first lineage-specific cell-surface antigen relative to a wild-type counterpart cell, or express a mutant of the first lineage-specific cell-surface antigen; and
   (ii) have reduced or eliminated expression of a second lineage-specific cell-surface antigen relative to a wild-type counterpart cell, or express a mutant of the second lineage-specific cell-surface antigen.

4. The population of embodiment 3, wherein the reduction in expression of the first lineage-specific cell-surface antigen, second first lineage-specific cell-surface antigen, or both, is to less than or equal to 50%, 40%, 30%, 20%, 10%, 5%, 2%, or 1% of the level in a wild-type counterpart cell.

5. The population of genetically engineered hematopoietic cells of any of the preceding embodiments, wherein the first lineage-specific cell-surface antigen (e.g., CD19) is expressed in a primary cancer in a subject and the second lineage-specific cell-surface antigen (e.g., CD33) is expressed in a relapsed cancer in the subject.

6. The population of genetically engineered hematopoietic cells of embodiment 1 or 2, wherein the first lineage-specific cell-surface antigen (e.g., CD33) is expressed in a first sub-population of cancer cells in a subject, and the second lineage-specific cell-surface antigen (e.g., CD123 or CLL-1) is expressed in a second sub-population of cancer cells in the subject.

7. The population of genetically engineered hematopoietic cells of any of the preceding embodiments, wherein at least 40%, 50%, 60%, 70%, 75%, 80%, 85%, 90%, or 95% of cells in the population have genetic editing (e.g., comprise an indel or comprise a deletion) at both alleles encoding the first lineage-specific cell-surface antigen.

8. The population of genetically engineered hematopoietic cells of any of the preceding embodiments, wherein at least 40%, 50%, 60%, 70%, 75%, 80%, 85%, 90%, or 95% of cells in the population have genetic editing (e.g., comprise an indel or comprise a deletion) at both alleles encoding the second lineage-specific cell-surface antigen.

9. The population of genetically engineered hematopoietic cells of any of the preceding embodiments, wherein at least 40%, 50%, 60%, 70%, 75%, 80%, 85%, 90%, or 95% of cells in the population have genetic editing (e.g., comprise an indel or comprise a deletion) at both alleles encoding the first lineage-specific cell-surface antigen and at both alleles encoding the second lineage-specific cell-surface antigen.

10. The population of genetically engineered hematopoietic cells of any of the preceding embodiments, wherein at least 40%, 50%, 60%, 70%, 75%, 80%, 85%, 90%, or 95% of copies of the first gene (encoding the lineage-specific cell-surface antigen) in the population of cells have genetic editing, e.g., as measured using PCR, e.g., according to an assay of Example 1.

11. The population of genetically engineered hematopoietic cells of any of the preceding embodiments, wherein at least 40%, 50%, 60%, 70%, 75%, 80%, 85%, 90%, or 95% of copies of the second gene (encoding the lineage-specific cell-surface antigen) in the population of cells have genetic editing, e.g., as measured using PCR, e.g., according to an assay of Example 1.

12. The population of genetically engineered hematopoietic cells of any of the preceding embodiments, wherein at least 40%, 50%, 60%, 70%, 75%, 80%, 85%, 90%, or 95% of copies of the first and second genes (encoding the first and second lineage-specific cell-surface antigens, respectively) in the population of cells have genetic editing, e.g., as measured using PCR, e.g., according to an assay of Example 1.

13. The population of genetically engineered hematopoietic cells of any of the preceding embodiments, wherein at least 60%, 70%, 75%, 80%, 85%, 90%, or 95% of cells in the population (or cells differentiated from cells in the population) are negative for the first lineage-specific cell-surface antigen.

14. The population of genetically engineered hematopoietic cells of any of the preceding embodiments, wherein at least 60%, 70%, 75%, 80%, 85%, 90%, or 95% of cells in the population (or cells differentiated from cells in the population) are negative for the second lineage-specific cell-surface antigen.

15. The population of genetically engineered hematopoietic cells of any of the preceding embodiments, wherein at least 60%, 70%, 75%, 80%, 85%, 90%, or 95% of cells in the population (or cells differentiated from cells in the population) are negative for both of the first lineage-specific cell-surface antigen and the second lineage-specific cell-surface antigen.

16. The population of genetically engineered hematopoietic cells of any of the preceding embodiments, wherein surface levels of the first lineage-specific cell-surface antigen in the population (or cells differentiated from cells in the population) are less than 50%, 40%, 30%, 20%, 10%, 5%, 2%, or 1% of surface levels of the first lineage-specific cell-surface antigen in wild-type counterpart cells.

17. The population of genetically engineered hematopoietic cells of any of the preceding embodiments, wherein surface levels of the second lineage-specific cell-surface antigen in the population (or cells differentiated from cells in the population) are less than 50%, 40%, 30%, 20%, 10%, 5%, 2%, or 1% of surface levels of the second lineage-specific cell-surface antigen in wild-type counterpart cells.

18. The population of genetically engineered hematopoietic cells of any of the preceding embodiments, wherein intracellular levels of the first lineage-specific antigen in the population (or cells differentiated from cells in the population) are less than 50%, 40%, 30%, 20%, 10%, 5%, 2%, or 1% of intracellular levels of the first lineage-specific cell-surface antigen in wild-type counterpart cells.

19. The population of genetically engineered hematopoietic cells of any of the preceding embodiments, wherein intracellular levels of the second lineage-specific antigen in the population (or cells differentiated from cells in the population) are less than 50%, 40%, 30%, 20%, 10%, 5%, 2%, or 1% of intracellular levels of the second lineage-specific cell-surface antigen in wild-type counterpart cells.

20. The population of genetically engineered hematopoietic cells of any of the preceding embodiments, wherein the first and second genes are chosen from Table 1A.

21. The population of genetically engineered hematopoietic cells of any of the preceding embodiments, wherein the first and second lineage-specific cell-surface antigens are chosen from Table 1A.

22. The population of genetically engineered hematopoietic cells of any of the preceding embodiments, which comprises a plurality of HSCs and/or HPCs.

23. The population of genetically engineered hematopoietic cells of embodiment 22, which retains differentiation potential, e.g., in an in vitro CFU assay, e.g., as described in Example 1 herein.

24. The population of genetically engineered hematopoietic cells of embodiment 23, wherein the cells form at least 1, 2, 3, 4, 5, 10, 20, 30, 40, 50, 60, 70, 80, 90, 100, or 200 total colonies per 250 cells in a CFU assay, e.g., an assay of Example 1 herein.

25. The population of genetically engineered hematopoietic cells of embodiment 23 or 24, wherein the cells form at least 1, 2, 3, 4, 5, 10, or 20 CFU-GEMM colonies per 250 cells in a CFU assay, e.g., an assay of Example 1 herein.

26. The population of genetically engineered hematopoietic cells of any of embodiments 23-25, wherein the cells form at least 1, 2, 3, 4, 5, 10, 20, 30, 40, 50, 60, 70, 80, 90, or 100 CFU-GM colonies per 250 cells in a CFU assay, e.g., an assay of Example 1 herein.

27. The population of genetically engineered hematopoietic cells of any of embodiments 23-26, wherein the cells form at least 1, 2, 3, 4, 5, 10, 20, 30, 40, 50, 60, 70, 80, 90, or 100 BFU-E colonies per 250 cells in a CFU assay, e.g., an assay of Example 1 herein.

28. The population of genetically engineered hematopoietic cells of any of embodiments 23-27, wherein the number of BFU-E colonies is about 30%-150%, 35-135%, 40-120%, or 50%-100% of the number of CFU-GM colonies when assayed in a CFU assay (e.g., an assay of Example 1 herein).

29. The population of genetically engineered hematopoietic cells of any of embodiments 23-28, wherein the number of CFU-GEMM colonies is about 1-15%, 1-10%, or 1.5-5.0% of the number of CFU-GM colonies when assayed in a CFU assay (e.g., an assay of Example 1 herein).

30. The population of genetically engineered hematopoietic cells of any of embodiments 23-29, wherein the number of CFU-GEMM colonies is about 1-30%, 2-20%, or 3-10% of the number of BFU-E colonies when assayed in a CFU assay (e.g., an assay of Example 1 herein).

31. The population of genetically engineered hematopoietic cells of any of embodiments 23-30, wherein one, two, three, or all of:

a) the number of BFU-E colonies formed by the cells in a CFU assay is within about 5%, 10%, 20%, or 30% of the number of BFU-E colonies formed by otherwise similar, unmodified cells;

b) the number of CFU-GM colonies formed by the cells in a CFU assay is within about 5%, 10%, 20%, or 30% of the number of CFU-GM colonies formed by otherwise similar, unmodified cells;

c) the number of CFU-GEMM colonies formed by the cells in a CFU assay is within about 5%, 10%, 20%, or 30% of the number of CFU-GEMM colonies formed by otherwise similar, unmodified cells; and d) the total number of colonies formed by the cells in a CFU assay is within about 5%, 10%, 20%, or 30% of the total number of colonies formed by otherwise similar, unmodified cells.

32. The population of genetically engineered hematopoietic cells of any of embodiments 23-31, wherein the cells can give rise to differentiated myeloid cells.

33. The population of genetically engineered hematopoietic cells of any of the preceding embodiments, which are capable of growing in culture, e.g., of increasing by at least 2, 3, 4, 5, or 10-fold (e.g., over 8 days, e.g., in conditions according to Example 1).

34. The population of genetically engineered hematopoietic cells of any of the preceding embodiments, which have a viability of at least 50%, 60%, 70%, 75%, 80%, 85%, or 90% (e.g., after 2, 4, 6, 8, or 10 days), e.g., in conditions according to Example 1 or Example 4.

35. The population of genetically engineered hematopoietic cells of any of the preceding embodiments, which are capable of engraftment, e.g., to produce at least 0.1%, 0.2%, 0.5%, 1%, 2%, 5%, or 10% of CD45+ cells in peripheral blood of a subject, e.g., according to an assay of Example 1.

36. The population of genetically engineered hematopoietic cells of any of the preceding embodiments, which can produce at least 0.1%, 0.2%, 0.5%, 1%, 2%, 5%, 10%, 20%, 40%, 60%, or 80% of B cells in peripheral blood of a subject, e.g., according to an assay of Example 1.

37. The population of genetically engineered hematopoietic cells of any of the preceding embodiments, which are resistant to a first immunotherapeutic agent that targets the first lineage-specific cell-surface antigen, e.g., wherein the $IC_{50}$ the first immunotherapeutic agent for the population of cells is greater than the $IC_{50}$ of the first immunotherapeutic agent for control cells (e.g., wherein the control cells are wild-type counterpart cells), e.g., by at least 2, 3, 4, 5, 10, 20, 50, or 100-fold, e.g., in an assay of Example 2.

38. The population of genetically engineered hematopoietic cells of any of the preceding embodiments, which are resistant to a second immunotherapeutic agent that targets the second lineage-specific cell-surface antigen, e.g., wherein the $IC_{50}$ the second immunotherapeutic agent for the population of cells is greater than the $IC_{50}$ of the second immunotherapeutic agent for control cells (e.g., wherein the control cells are wild-type counterpart cells), e.g., by at least 2, 3, 4, 5, 10, 20, 50, or 100-fold, e.g., in an assay of Example 2.

39. The population of genetically engineered hematopoietic cells of any of the preceding embodiments, which are resistant to a first immunotherapeutic agent that targets the first lineage-specific cell-surface antigen and a second immunotherapeutic agent that targets the second lineage-specific cell-surface antigen, e.g., wherein the cells show a specific killing of less than 50%, 40%, 35%, 30%, 25%, 20%, or 15%, e.g., in an in vitro cytotoxicity assay, e.g., in an assay of Example 9.

40. The population of genetically engineered hematopoietic cells of any of the preceding embodiments, wherein about 5-10%, 10-20%, 20-30%, 30-40%, 40-50%, 50-60%, 60-70%, 70-80%, or 80-90% of cells in the population substantially lack cell surface expression of both of the first lineage-specific cell-surface antigen and the second lineage-specific cell-surface antigen.

41. The population of genetically engineered hematopoietic cells of any of the preceding embodiments, wherein about 5-10%, 10-20%, 20-30%, 30-40%, 40-50%, 50-60%, 60-70%, 70-80%, or 80-90% of cells in the population comprise a mutation of at least one allele of the first lineage-specific cell-surface antigen and a mutation of at least one allele of the second lineage-specific cell-surface antigen.

42. The population of genetically engineered hematopoietic cells of any of the preceding embodiments, wherein about 5-10%, 10-20%, 20-30%, 30-40%, 40-50%, 50-60%, 60-70%, 70-80%, or 80-90% of cells in the population comprise mutations at two alleles of the first lineage-specific cell-surface antigen and mutations at two alleles of the second lineage-specific cell-surface antigen.

43. The population of genetically engineered hematopoietic cells of any of embodiments 1-42, wherein:
(a) the first lineage-specific cell-surface antigen is CD33 and the second lineage-specific cell-surface antigen is CD123;
(b) the population of cells comprises HSCs; and
(c) at least 20%, 30%, 40%, 50%, or 60% of cells in the population substantially lack cell surface expression of both of CD123 and CD33.

44. The population of genetically engineered hematopoietic cells of any of embodiments 1-42, wherein:
(a) the first lineage-specific cell-surface antigen is CD33 and the second lineage-specific cell-surface antigen is CLL-1;
(b) the population of cells comprises HSCs; and
(c) at least 20%, 30%, 40%, 50%, or 60% of cells in the population substantially lack cell surface expression of both of CLL1 and CD33.

45. The population of genetically engineered hematopoietic cells of any of embodiments 1-42, wherein:
(a) the first lineage-specific cell-surface antigen is CD123 and the second lineage-specific cell-surface antigen is CLL-1;
(b) the population of cells comprises HSCs; and
(c) at least 20%, 30%, 40%, 50%, or 60% of cells in the population substantially lack cell surface expression of both of CLL1 and CD123.

46. The population of genetically engineered hematopoietic cells of any of embodiments 1-42, wherein:
(a) the first lineage-specific cell-surface antigen is CD19 and the second lineage-specific cell-surface antigen is CD33;
(b) the population of cells comprises HSCs; and
(c) at least 20%, 30%, 40%, 50%, or 60% of cells in the population substantially lack cell surface expression of both of CD19 and CD33.

47. The population of any of embodiments 43-46, wherein (d) the genetic editing of the first gene comprises a frameshift mutation and the genetic editing of the second gene comprises a frameshift mutation.

48. The population of genetically engineered hematopoietic cells of any of the preceding embodiments, wherein the hematopoietic cells are hematopoietic stem cells (HSCs).

49. The population of genetically engineered hematopoietic cells of embodiment 48, wherein the HSCs are CD34+/CD33− cells.

50. The population of genetically engineered hematopoietic cells of any one of embodiments 1-49, which the hematopoietic cells are from bone marrow cells, cord blood cells, or peripheral blood mononuclear cells (PBMCs).

51. The population of genetically engineered hematopoietic cells of any one of embodiments 1-40, wherein the mutant of the first lineage-specific cell-surface antigen and/or the mutant of the second lineage-specific cell-surface antigen includes a mutated non-essential epitope.

52. The population of genetically engineered hematopoietic cells of any of embodiments 1-51, wherein one or both of: the genetic editing of the gene encoding the first lineage-specific cell surface antigen comprises a frameshift mutation, and the genetic editing of the second gene comprises a frameshift mutation.

53. The population of genetically engineered hematopoietic cells of embodiment 52, wherein the frameshift mutation comprises an insertion or deletion of less than 20, 15, 10, 5, 4, 3, or 2 nucleotides.

54. The population genetically engineered hematopoietic cells of any of the preceding embodiments, wherein the genetic editing comprises genome editing.

55. The population of genetically engineered hematopoietic cells of any of embodiments 1-54, wherein one or more cells in the population are negative for one or both of the first lineage-specific cell-surface antigen and the second first lineage-specific cell-surface antigen.

56. The population of genetically engineered hematopoietic cells of any of embodiments 1-55, wherein the CD33 pseudogene is not modified in one or more (e.g., at least 50%, 60%, 70%, 80%, 85%, 90%, 95%, 98%, 99%, or all) of the cells of the population.

57. The population of genetically engineered hematopoietic cells of any of embodiments 1-56, wherein the average number of off-target genetic edits in the cell population is less than 3, 2, or 1 per cell.

58. The population of genetically engineered hematopoietic cells of embodiment 57, wherein the non-essential epitope in the first lineage-specific cell surface antigen and/or the non-essential epitope in the second lineage-specific cell surface antigen has at least 3 amino acids.

59. The population of genetically engineered hematopoietic cells of embodiment 58, wherein the non-essential epitope in the first lineage-specific cell surface antigen and/or the non-essential epitope in the second lineage-specific cell surface antigen is 6-10 amino acids.

60. The population of genetically engineered hematopoietic cells of any one of embodiments 1-59, wherein at least one of the first and second lineage-specific cell-surface antigens is a type 1 lineage-specific cell-surface antigen.

61. The population of genetically engineered hematopoietic cells of embodiment 60, wherein the type 1 lineage-specific cell-surface antigen is CD19.

62. The population of genetically engineered hematopoietic cells of embodiment 61, wherein the first group of genetically engineered hematopoietic cells contain genetic editing in exon 2 or exon 4 of a CD19 gene.

63. The population of genetically engineered hematopoietic cells of embodiment 62, wherein the CD19 gene is an endogenous CD19 gene.

64. The population of genetically engineered hematopoietic cells of embodiment 62 or 63, wherein the first group of genetically engineered hematopoietic cells express a mutated CD19 comprising the amino acid sequence of SEQ ID NO: 52 or SEQ ID NO: 73.

65. The population of genetically engineered hematopoietic cells of any one of embodiments 1-64, wherein at least one of the first and second lineage-specific cell-surface antigens is a type 2 lineage-specific cell-surface antigen.

66. The population of genetically engineered hematopoietic cells of embodiment 65, wherein the type 2 lineage-specific cell-surface antigen is CD33.

67. The population of genetically engineered hematopoietic cells of embodiment 66, wherein the second group of genetically engineered hematopoietic cells contain genetic editing in exon 2 or exon 3 of a CD33 gene.

68. The population of genetically engineered hematopoietic cells of embodiment 67, wherein the CD33 gene is an endogenous CD33 gene.

69. The population of genetically engineered hematopoietic cells of embodiment 67 or 68, wherein the second group of genetically engineered hematopoietic cells express a mutated CD33 comprising the amino acid sequence of SEQ ID NO: 56 or SEQ ID NO: 58.

70. The population of genetically engineered hematopoietic cells of any one of embodiments 1-69, which are produced by genomic editing.

71. The population of genetically engineered hematopoietic cells of embodiment 70, wherein the genome editing involves a zinc finger nuclease (ZFN), a transcription activator-like effector-based nuclease (TALEN), or a CRISPR-Cas system.

72. The population of genetically engineered hematopoietic cells of embodiment 71, wherein the CRISPR-Cas system comprises a Cas endonuclease.

73. The population of genetically engineered hematopoietic cells of embodiment 72, wherein the Cas endonuclease is a Cas9 endonuclease.

74. The population of genetically engineered hematopoietic cells of any one of embodiments 1-73, wherein at least one of the first and second lineage-specific cell-surface antigens is associated with a hematopoietic malignancy.

75. The population of genetically engineered hematopoietic cells of any one of embodiments 1-74, wherein at least one of the first and second lineage-specific cell surface antigens is a type 0 protein.

76. The population of genetically engineered hematopoietic cells of any one of embodiments 1-75, wherein the first and second lineage-specific cell surface antigens are selected from the group consisting of CD7, CD13, CD19, CD20, CD22, CD25, CD32, CD33, CD38, CD44, CD45, CD47, CD56, 96, CD117, CD123, CD135, CD174, CLL-1, folate receptor b, IL1RAP, MUC1, NKG2D/NKG2DL, TIM-3, and WT1.

77. The population of genetically engineered hematopoietic cells of embodiment 76, wherein the first and second lineage-specific cell surface antigens are selected from the group consisting of:
  (i) CD19 and CD33;
  (ii) CD19 and CD13;
  (iii) CD19 and CD123;
  (iv) CD19 and CLL-1;
  (v) CD33 and CD13;
  (vi) CD33 and CD123;
  (vii) CD33 and CLL-1;
  (viii) CD13 and CD123;
  (ix) CD123 and CLL-1;
  (x) CD19, CD33, and CD13;
  (xi) CD19, CD33, and CD123;
  (xii) CD33, CD13, and CD123;
  (xiii) CD19, CD13, and CD123;
  (xiv) CLL-1, CD123, and CD33; or
  (xv) CD19, CD33, CD13, and CD123.

78. A method for producing genetically engineered hematopoietic cells, the method comprising:
  (i) providing a population of hematopoietic cells, and
  (ii) genetically editing a first gene encoding a first lineage-specific cell-surface antigen and a second gene encoding a second lineage-specific cell-surface antigen in the population of hematopoietic to produce the genetically engineered hematopoietic cells.

79. The method of embodiment 78, wherein the first gene and the second gene are:
  (i) CD19 and CD33;
  (ii) CD19 and CD13;
  (iii) CD19 and CD123;
  (iv) CD19 and CLL-1;
  (v) CD33 and CD13;
  (vi) CD33 and CD123;

(vii) CD33 and CLL-1;
(viii) CD13 and CD123; or
(ix) CD123 and CLL-1.

80. A method for producing genetically engineered hematopoietic cells, the method comprising:
(i) providing a population of hematopoietic cells, and
(ii) genetically editing a CD19 gene, a CD33 gene, or both genes in the population of hematopoietic cells via CRISPR to produce the genetically engineered hematopoietic cells,
wherein the genetic editing of the CD19 gene involves one or more guide nucleic acid molecules that target one or more introns of CD19; and
wherein the genetic editing of the CD33 gene involves one or more guide nucleic acid molecules that (a) target one or more introns of CD33; and/or (b) do not target the CD33 pseudogene upstream of the CD33 gene.

81. The method of embodiment 80, wherein the introns of the CD19 gene comprise intron 1 and intron 2, and/or the introns of the CD33 gene comprise intron 1 and intron 2.

82. The method of embodiment 80 or 81, wherein the genetic editing of CD19 results in exclusion of exon 2 of the CD19 gene; and/or the genetic editing of CD33 results in exclusion of exon 2 of the CD33 gene.

83. A method for producing genetically engineered hematopoietic cells, the method comprising:
(i) providing a population of hematopoietic cells, and
(ii) genetic editing a CD19 gene, a CD33 gene, or both in the population of hematopoietic cells via CRISPR to produce the genetically engineered hematopoietic cells, wherein the genetic editing of the CD19 gene involves at least one guide nucleic acid molecule comprising the nucleotide sequence of SEQ ID NOs: 14-26, 67, and 69-72, and/or wherein the genetic editing of the CD33 gene involves at least one guide nucleic acid molecule comprising the nucleotide sequence of SEQ ID NOs: 27-50 and 68.

84. The method of embodiment 83, wherein step (ii) is performed by genetic editing both a CD19 gene and a CD33 gene in the population of hematopoietic cells via CRISPR to produce the genetically engineered hematopoietic cells,
wherein the genetic editing of the CD19 gene involves a guide nucleic acid comprising the nucleotide sequence of SEQ ID NO: 67, and
wherein the genetic editing of the CD33 gene involves a guide nucleic acid comprising the nucleotide sequence of SEQ ID NO: 68.

85. The method of any one of embodiments 80-84, wherein the hematopoietic cells are HSCs.

86. The method of embodiment 85, wherein the HSCs are CD34+/CD33− cells.

87. The method of any one of embodiment 80-86, wherein the hematopoietic cells are from bone marrow cells, cord blood cells, or peripheral blood mononuclear cells (PBMCs).

88. Genetically engineered hematopoietic cells produced by any one of embodiments 80-87.

89. A genetically engineered hematopoietic cell, which carries a genetically edited CD19 gene capable of expressing a mutant CD19 comprising the amino acid sequence of SEQ ID NO: 52 or 73, and/or a genetically edited CD33 gene capable of expressing a mutant CD33 comprising the amino acid sequence of SEQ ID NO: 56 or SEQ ID NO: 58.

90. The genetically engineered hematopoietic cell of embodiment 89, which carries a genetically edited CD19 gene capable of expressing a mutant CD19 comprising the amino acid sequence of SEQ ID NO: 52 or 73, and a genetically edited CD33 gene capable of expressing a mutant CD33 comprising the amino acid sequence of SEQ ID NO: 56.

91. A population of genetically engineered hematopoietic stem cells, wherein at least 50% of the hematopoietic stem cells therein carry both a genetically edited CD19 gene and a genetically edited CD33 gene.

92. The population of genetically engineered hematopoietic stem cells of embodiment 91, wherein the genetically edited CD19 gene is capable of expressing a CD19 mutant comprising the amino acid sequence of SEQ ID NO: 52 or 73, and/or the genetically edited CD33 gene is capable of expressing a CD33 mutant comprising the amino acid sequence of SEQ ID NO: 56 or SEQ ID NO:58.

93. A genetically engineered hematopoietic cell, wherein exon 2 of CD33 gene in the hematopoietic cell is modified and wherein the CD33 pseudogene is not modified.

94. The genetically engineered hematopoietic cell of embodiment 93, wherein exon 2 of CD33 gene in the hematopoietic cell is deleted.

95. The genetically engineered hematopoietic cell of embodiment 93 or 94, wherein the CD33 pseudogene is not modified by deletion or mutation that causes a frameshift.

96. The genetically engineered hematopoietic cell of embodiment 93 or 94, wherein the CD33 pseudogene is not modified by deletion or mutation that causes a frameshift in exon 1, intron 1, exon 2, or a combination thereof.

97. The genetically engineered hematopoietic cell of embodiment 93, wherein the frameshift is in sequence(s) in exon 1, intron 1, and/or exon 2 of the CD33 pseudogene that share sequence homology, respectively, with sequence(s) in exon 1, intron 1, and/or exon 2 of CD33.

98. A method of supplying hematopoietic cells to a subject (e.g., a subject having a hematopoietic malignancy), comprising:
(a) providing a population of genetically engineered hematopoietic cells of any one of embodiments 1-77 and 88-97, wherein optionally the genetically engineered hematopoietic cells comprise HSCs and/or HPCs; and
(b) administering the population of genetically engineered hematopoietic cells to the subject, e.g., under conditions that allow for engraftment of at least a portion of the population,
thereby supplying the hematopoietic cells to the subject.

99. A method of treating a hematopoietic malignancy, comprising administering to a subject in need thereof a population of genetically engineered hematopoietic cells of any one of embodiments 1-77 and 88-97.

100. The method of embodiment 99, which further comprises:
(a) administering to the subject an effective amount of a first immunotherapeutic agent that targets the first lineage-specific cell-surface antigen, and
(b) administering to the subject an effective amount of a second immunotherapeutic agent that targets the second lineage-specific cell-surface antigen.

101. The method of embodiment 100, wherein the first immunotherapeutic agent and the second immunotherapeutic agent are administered simultaneously or sequentially (e.g., sequentially with or without overlap, e.g., wherein the first and second immunotherapeutic agent are not present in the subject at the same time).

102. The method of embodiment 100 or 101, wherein the first immunotherapeutic agent is administered when the subject has a primary cancer, and the second immunotherapeutic is administered when the subject has a relapsed cancer or cancer that is resistant to the first immunotherapeutic agent.

103. The method of embodiment 102, wherein the primary cancer is AML and the relapsed cancer is relapsed AML.

104. The method of embodiment 102, wherein the primary cancer is AML and the relapsed cancer is ALL.

105. The method of any of embodiments 102 or 104, wherein the relapsed cancer underwent a lineage switch relative to the primary cancer.

106. The method of any of embodiments 102-105, wherein the first lineage-specific cell surface antigen is absent in the relapsed cancer, or is expressed at a lower level in the relapsed cancer compared to the primary cancer (e.g., at less than 50%, 40%, 30%, 20%, or 10% of the protein level in the primary cancer), or is expressed in fewer cancer cells in the relapsed cancer compared to the primary cancer (e.g., less than 50%, 40%, 30%, 20%, or 10% the relapsed cancer cells detectably express the protein).

107. The method of any of embodiments 102-106, wherein the primary cancer comprises one or more resistant cells, e.g., cells that lack the first lineage-specific cell surface antigen or express it at a lower level than in sensitive cells.

108. The method of any of embodiments 89-107, which further comprises: administering to the subject an effective amount of a first immunotherapeutic agent that targets expressing the first lineage-specific cell-surface antigen.

109. The method of embodiment 108, wherein, if the subject experiences relapse (e.g., a relapse wherein the cancer is negative for the first lineage-specific cell surface antigen), then administering to the subject an effective amount of a second immunotherapeutic agent that targets the second lineage-specific cell-surface antigen.

110. The method of any of embodiments 100-109, wherein the first lineage-specific cell-surface antigen is CD19 and the second lineage-specific cell-surface antigen is CD33.

111. The method of any of embodiments 100-110, wherein the subject has a cancer (e.g., a primary cancer) that comprises a first sub-population of cancer cells and a second sub-population of cancer cells.

112. The method of embodiment 111, wherein the first sub-population of cancer cells expresses the first lineage-specific cell-surface antigen and the second sub-population of cancer cells expresses the second lineage-specific cell-surface antigen.

113. The method of embodiment 112, wherein the first sub-population of cancer cells is targeted by the first immunotherapeutic agent and the second sub-population of cancer cells is targeted by the second immunotherapeutic agent.

114. The method of embodiment 113, wherein the first sub-population of cancer cells is resistant to the second immunotherapeutic agent, or wherein the second immunotherapeutic agent is less effective against the first sub-population of cancer cells than against the second sub-population of cancer cells, e.g., by about 10%, 20%, 30%, 40%, 50%, 60%, 70%, 80%, or 90%.

115. The method of embodiment 113 or 114, wherein the second sub-population of cancer cells is resistant to the first immunotherapeutic agent, or wherein the first immunotherapeutic agent is less effective against the second sub-population of cancer cells than against the first sub-population of cancer cells, e.g., by about 10%, 20%, 30%, 40%, 50%, 60%, 70%, 80%, or 90%.

116. The method of any of embodiments 113-115, wherein the first sub-population of cancer cells does not express the second lineage-specific cell surface antigen, or the second lineage-specific cell surface antigen is expressed at a lower level in the first sub-population compared to the second sub-population (e.g., at less than 50%, 40%, 30%, 20%, or 10% of the protein level).

117. The method of any of embodiments 113-116, wherein the second sub-population of cancer cells does not express the first lineage-specific cell surface antigen, or the first lineage-specific cell surface antigen is expressed at a lower level in the second sub-population compared to the first sub-population (e.g., at less than 50%, 40%, 30%, 20%, or 10% of the protein level).

118. The method of any of embodiments 113-117, wherein the first sub-population of cancer cells expresses CD33 and the second sub-population of cancer cells expresses CD123 or CLL-1.

119. The method of any of embodiments 113-118, wherein the first sub-population of cancer cells is about 50-99%, 60-90%, 70-90%, or about 80% of cancer cells in the subject.

120. The method of any of embodiments 113-119, wherein the second sub-population of cancer cells is about 1-50%, 10-40%, 10-30%, or about 20% of cancer cells in the subject.

121. The method of any of embodiments 113-120, wherein the first sub-population of cancer cells are bulk cancer cells and/or the second sub-population of cancer cells are cancer stem cells.

122. The method of any of embodiments 113-121, wherein the first sub-population of cancer cells have one or more markers of differentiated hematopoietic cells and/or the second sub-population of cancer cells have one or more markers of HSCs or HPCs.

123. The method of any of embodiments 113-122, wherein the first immunotherapeutic agent and the second immunotherapeutic agent are administered simultaneously.

124. The method of any of embodiments 113-123, wherein the first immunotherapeutic agent and the second immunotherapeutic agent are administered such that both of the first immunotherapeutic agent and the second immunotherapeutic agent are present in the subject at the same time.

125. The method of any of embodiments 113-124, further comprising administering to the subject an effective amount of a first immunotherapeutic agent.

126. The method of embodiment 125, wherein the first immunotherapeutic agent is a cytotoxic agent that targets cells expressing either the first lineage-specific cell-surface antigen or the second lineage-specific cell-surface antigen.

127. The method of embodiment 126, wherein the first immunotherapeutic agent is a cytotoxic agent that targets cells expressing the first lineage-specific cell-surface antigen, and the method further comprises administering to the subject a second immunotherapeutic agent when the hematopoietic malignancy relapses in the subject.

128. The method of embodiment 127, wherein the second immunotherapeutic agent is a cytotoxic agent that targets cells expressing the second lineage-specific cell-surface antigen.

129. The method of any one of embodiments 126-128, wherein the first immunotherapeutic agent, the second immunotherapeutic agent, or both are CAR-T cells.

130. The method of any one of embodiments 126-128, wherein the first immunotherapeutic agent, the second immunotherapeutic agent, or both are antibodies.

131. The method of any one of embodiments 126-128, wherein the first immunotherapeutic agent, the second immunotherapeutic agent, or both are antibody-drug conjugates.

132. The method of any one of embodiments 113-131, wherein the hematopoietic malignancy is AML.

133. The method of embodiment 132, wherein the AML is relapsed AML.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A: The process includes the steps of obtaining CD34+ cells (obtained from a donor or autologously), genetically engineering the CD34+ cells, engrafting the engineered cells into a patient, performing CAR T cell therapy on the patient, resulting in cleared or reduced cancer burden and retained hematopoiesis. The sequence corresponds to SEQ ID NO: 57. FIG. 1B: An engineered donor CD34+ cell in which the non-essential epitope of a lineage-specific cell-surface antigen is modified such that it does not bind a CAR T cell that is specific for an epitope of the lineage-specific cell-surface antigen. The sequence corresponds to SEQ ID NO: 57.

FIG. 3A: CAR T cells targeting CD33+ acute myeloid leukemia cells leading to cell lysis. The sequence corresponds to SEQ ID NO: 57. FIG. 3B: CAR T cells are not able to bind to genetically engineered donor graft cells in which an epitope of CD33 has been modified or deleted. As a result, these cells do not undergo lysis. The sequence corresponds to SEQ ID NO: 57.

FIG. 5A: photos showing PCR amplicons derived from the region spanning introns 1 and 2 of the CD19 gene as determined by T7E1 assays. Samples were either treated (+) or untreated (−) with T7E1. The percentage cleavage efficiency is indicated under each lane. C=New England Biolabs™ (NEB™) Sample Control, WT=wild-type untransfected cells, Cas9=Cas9 only. FIG. 5B: a chart showing the percent INDEL determined by T7E1 assays and TIDE analysis.

FIG. 6A: a schematic showing a PCR-based assay to detect CRISPR/Cas9-mediated genomic deletion of exon 2 of CD19 via dual ms-sgRNA-mediated CRISPR/Cas9. FIG. 6B: a photo showing deletion of the region between exon 1 and exon 3 after treating K562 cells with indicated pairs of ms-sgRNAs by an end-point PCR assay of genomic DNA. FIG. 6C: a chart showing the percentage deletion quantitated by end-point PCR.

FIG. 7A: a photo showing PCR amplicons derived from the region spanning introns 1 and 2 of the CD19 gene as determined by T7E1 assays. Samples were either treated (+) or untreated (−) with T7E1. The percent insertion/deletion (INDEL) and cleavage efficiency are indicated under each lane. C=NEB™ Sample Control, Cas9=Cas9 only. FIG. 7B: PCR amplicons derived from the region spanning introns 1 and 2 of the CD19 gene were analyzed by T7E1 Assay or TIDE analysis, and the percent INDEL was determined. Cas9=cas9 only control.

FIG. 8A: a photo showing the smaller deletion PCR product compared to the larger parental band as determined by PCR across the genomic deletion region. FIG. 8B: a chart showing the percent deletion quantified by end-point PCR.

FIG. 9A: a photo showing PCR amplicons derived from the region spanning introns 1 and 2 of the CD19 gene as determined by T7E1 assays. The percent cleavage efficiency is indicated under each lane. FIG. 9B: a chart showing PCR amplicons derived from the region spanning introns 1 and 2 of the CD19 gene as analyzed by T7E1 assay, and the percent INDEL. Cas9=cas9 only control.

FIGS. 10A-10D include diagrams showing efficient dual ms-sgRNA-mediated deletion of exon 2 of CD19 in CD34+ HSCs. FIG. 10A: a photo showing the smaller deletion PCR product compared to the larger parental band as determined by PCR across the genomic deletion region. The percent deletion is indicated under each lane. FIG. 10B: a chart showing the percent deletion quantified by end-point PCR. FIG. 10C: is a photo showing PCR products of full-length CD19 or CD19 with deletion of exon 2 when edited using the pair of gRNA6/gRNA14. FIG. 10D: a chart showing percentage of CFUs of cells edited by the gRNA6/gRNA14 pair. BFU-E: burst forming unit-erythroid; CFU-GM: colony forming unit-granulocyte/macrophage; CFU-GEMM: colony forming unit of multipotential myeloid progenitor cells (generate granulocytes, erythrocytes, monocytes, and megakaryocytes.

FIG. 11A: photos showing PCR products of genomic DNA of full-length CD19 and CD19 with exon 2 deletion (left panel) and cDNA of full-length CD19 and CD19 with exon 2 deletion. FIG. 11B: charts showing quantification of editing efficiency by end-point PCR. FIG. 11C: a photo showing expressing of full-length CD19 and CD19 mutant with deletion of fragment encoded by exon 2 using an antibody specific to the C-terminus of CD19. FIG. 11D: charts showing surface and intracellular staining of CD19-expressing in edited cells as measured by flow cytometry. FIG. 11E: charts showing cell number (left panel) and cell viability (right panel) of Raji B-cells expressing CD19exon2.

FIG. 12A: a schematic work flow to assess differentiation potential of edited CD34+ HSCs. d=days, w=weeks, w/o=week old, RNP=ribonucleoprotein. FIG. 12B: a chart showing percentage of CD45+ cells in peripheral blood collected from mice engrafted with HSCs expressing CD19ex2. FIG. 12C: a chart showing percentage of CD19 B cells in peripheral blood collected from mice engrafted with HSCs expressing CD19ex2.

FIGS. 14A-14D include diagrams showing the generation of Raji-fluc-GFP cells in which exon 2 of CD19 has been deleted. FIG. 14A: diagrams showing expression of CD19 in Raji-fluc-GFP cell lines transfected with the indicated combinations of ms-sgRNAs as determined by FACS. Parental Raji cells and Raj-fluc-GFP nucleofected with Cas9 only are included as controls. FIG. 14B: is a chart showing the percentage of live cells in each population of cells (CD19 "hi," CD19 "int," and CD19 "lo"). FIG. 14C: is a photo showing the smaller PCR product for the exon 2 deletion compared to the larger parental band as determined by PCR across the genomic deletion region. FIG. 14D: is a chart showing the percentage of cells having a deleted exon 2 of CD19 in the bulk population of cells as determined by end-point PCR.

FIG. 15A: a line graph showing that cells in which exon 2 of CD19 has been deleted are resistant to CART19 cytotoxicity. FIG. 15B: a bar graph showing that cells in which exon 2 of CD19 has been deleted are resistant to CART19 cytotoxicity.

FIG. 18A: guide RNAs 1-19. FIG. 18B: guide RNAs 10-24.

FIG. 19A: a diagram showing flow cytometric analysis of CD34+ HSCs, either unedited (left panel) or mock ("NT")) or edited producing a full CD33 knockout (middle panel, "CD33 gRNA KO"), or edited with the CD33 gRNA-18/gRNA-24 pair resulting in the expression of a mutated CD33 with exon 2-encoded fragment deleted (CD33ex2) or producing a full knock out (right panel, "CD33 gRNA 18+24"). FIG. 19B: a chart showing the percentage of HSCs having CD33 knocked out ("KO") and CD33 with exon 2 deletion ("ex2 Del") obtained in cells edited by knock-out gRNA or the CD33 gRNA18/gRNA24 pair.

FIG. 20A: a chart showing that CD33ex2 cells and CD33KO cells retained differentiation potential in vitro, as determined by a CFU assay. FIG. 20B: a photo showing that both CD33ex2 and knock-out alleles were observed in differentiated myeloid cells treated with the CD33 gRNA18/gRNA24 pair.

FIG. 21A: a photo showing genomic PCR results of selected HL60 clones resulting from gene editing with the CD33 gRNA18/gRNA24 pair. FIG. 21B: a diagram illustrating Taqman™ assays of total CD33 (Full-length+ex2del, including both full-length and exon 2 deletion) and CD33 (with exon 2 deletion). FIG. 21C: charts showing the expression level of total CD33 (full-length and exon 2 deletion; left panel) and the expression level of CD33ex2del in Jurkat cells, parent HL60 cells, and a number of edited HL60 clones.

FIG. 22A: chart showing viability of cancer cell lines (Jurkat, THP-1, and HL-60) treated with GO at the indicated concentrations. FIG. 22B: chart showing viability of THP-1 cells, CD33ex2 THP-1 cells (generated using CD33 gRNA18/gRNA24 pair), HL-60 cells, and CD33ex2 HL-60 cells (generated using CD33 gRNA18/gRNA24 pair) treated with GO at the indicated concentrations. FIG. 22C: chart showing viability of wild-type HSCs, CD33KO HSCs, and CD33ex2 HSCs (generated using CD33 gRNA18/gRNA24 pair) post-GO treatment ("GO") as compared to PBS control ("PBS").

FIGS. 23A-23D include diagrams showing that CD33ex2 cells are resistant to CART33-mediated cytotoxicity. FIG. 23A: a chart showing the level of cell lysis of wild-type HL-60 cells (CD33$^+$) in the presence of CART33 (expressing anti-CD33 CAR1). FIG. 23B: a chart showing the level of cell lysis of CD33ex2 HL-60 cells in the presence of CART33. FIG. 23C: a chart showing the level of cell lysis of CD33KO HL-60 cells in the presence of CART33. FIG. 23D: a chart comparing the percentage of cell lysis of CD33$^+$ cells, CD33ex2 cells, and CD33KO cells in the presence of CART33, at the indicated cell ratios.

FIG. 24A: a chart showing genomic editing of CD19, CD33, and CD19+CD33 in NALM-6 cells. FIG. 24B: a chart showing genomic editing of CD19, CD33, and CD19+CD33 in HSCs. FIG. 24C: a chart showing genomic editing of CD19, CD33, and CD19+CD33 in HL-60 cells. FIG. 24D: a chart showing genomic editing of CD19, CD33, and both CD19 and CD33 in NALM-6 cells.

FIG. 25A: a chart showing percent viability of HSC cells following genome editing. FIG. 25B: a chart showing percent viability of Nalm-6 cells following genome editing. From left to right, each set of three bars corresponds to zero, 24 h, and 48 h. FIG. 25C: a chart showing percent viability of HL-60 cells following genome editing. From left to right, each set of four bars corresponds to zero, 48 h, 96 h, and 7 d.

Figure 26A:
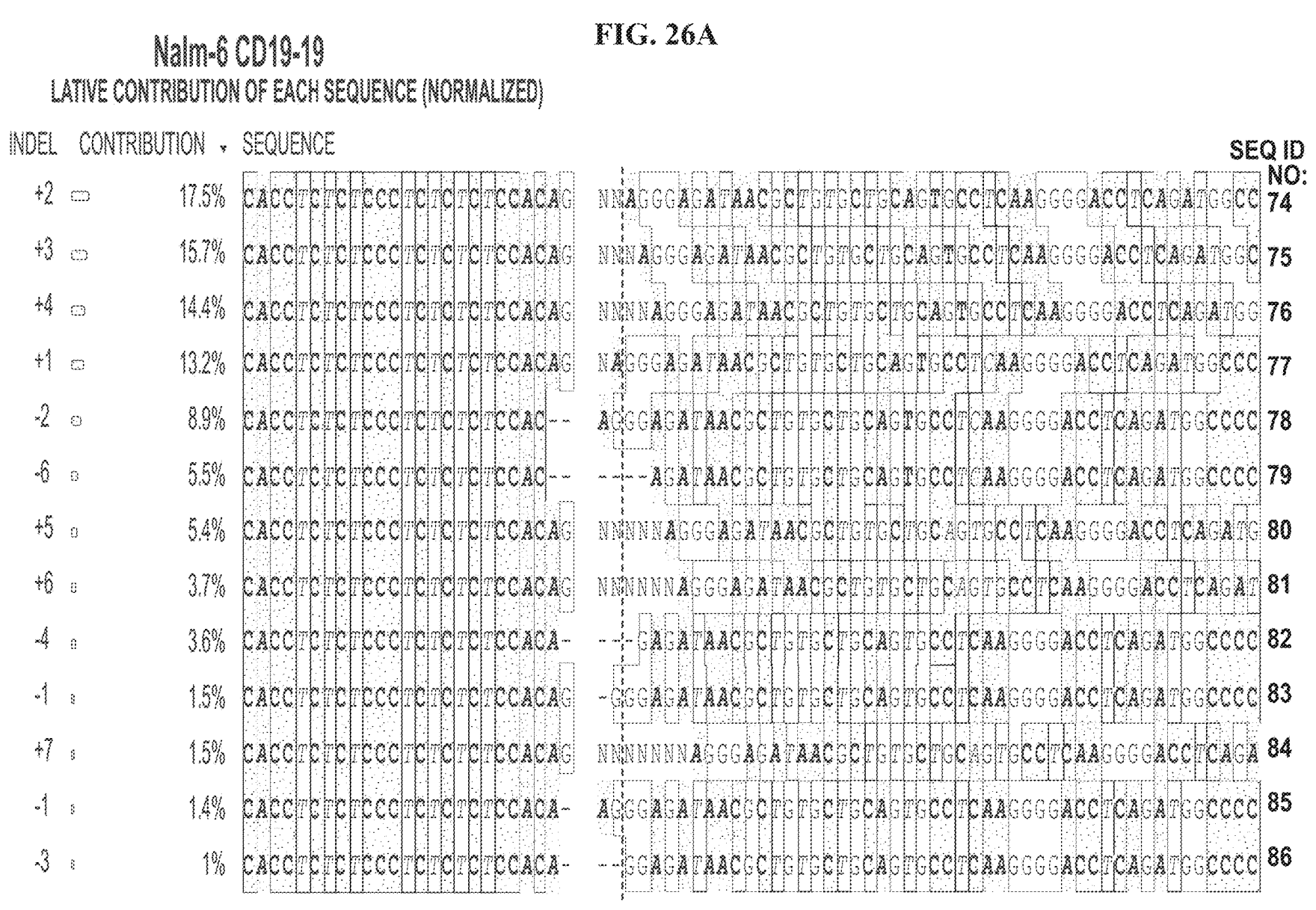

FIGS. 26A-26C include diagrams showing sequences and bar graphs of a TIDE analysis of NALM-6 cells transfected with CD19-19 gRNA/RNP and CD33-37 gRNA/RNP complexes. FIG. 26A: a schematic of sequences identified and the relative contribution of each sequence for the CD19 edited Nalm-6 cells. The sequences from top to bottom correspond to SEQ ID NOs: 74-86. FIG. 26B: a schematic of sequences identified and the relative contribution of each sequence for the CD33 edited Nalm-6 cells. The sequences from top to bottom correspond to SEQ ID NOs: 87-101. FIG. 26C: a chart showing the frequency of INDELS that are +/−1 and +/−2 (left columns and right columns, respectively, for each gene). The TIDE analysis indicates most INDELS are small insertions.

FIG. 30 includes a diagram showing the results of flow cytometric analysis of unstained cells, unedited ("Mock"), and HSCs edited using CD33 gRNA-37.

FIGS. 31A-31E include diagrams and a table showing analysis of populations of CD34+ HSCs edited with either CD33 gRNA-37 or the CD33 gRNA-18 and gRNA-24 pair, at various times following treatment with gemtuzumab ozogamicin (GO). FIG. 31A: a line graph showing the number of cells in each of the indicated populations following GO treatment over time. FIG. 31B: a table showing results corresponding to the graph shown in FIG. 31A. FIG. 31C: a photograph showing analysis of CD33 editing following treatment with gemtuzumab ozogamicin. Percentage of edited cells in the sample edited using CD33 gRNA37 ("KO") was assessed by TIDE analysis, and the percentage of edited cells in the sample edited using CD333 gRNA-18 and gRNA-24 ("CD33ex2del") was assessed by deletion PCR. FIG. 31D: a chart showing the percent CD14+ cells (myeloid differentiation) in the indicated cell populations in the absence of gemtuzumab ozogamicin over time as indicated. FIG. 31E: a chart showing the percent CD14+ cells (myeloid differentiation) in the indicated cell populations following treatment gemtuzumab ozogamicin over time as indicated.

FIGS. 32A-32B include photographs showing genomic editing of CD19 in the NAM6 cell line transfected with control ("WT," wildtype/unmodified), CD19 sgRNA 6 and sgRNA-14 pair ("Ex2del-1"), CD19 sgRNA-7 and sgRNA-16 pair ("Ex2del-2"), CD19 sgRNA-23 and sgRNA-24 pair (CD19 knock out; "CD19KO"). FIG. 32A: a photograph of a Western blot with an antibody recognizing the Ig-like C2-type domain encoded by CD19 exon 4 in the indicated cell populations. FIG. 32B: a photograph of a Western blot with an antibody recognizing the C-terminus of CD19 in the indicated cell populations.

DETAILED DESCRIPTION OF THE INVENTION

Figure 1A:
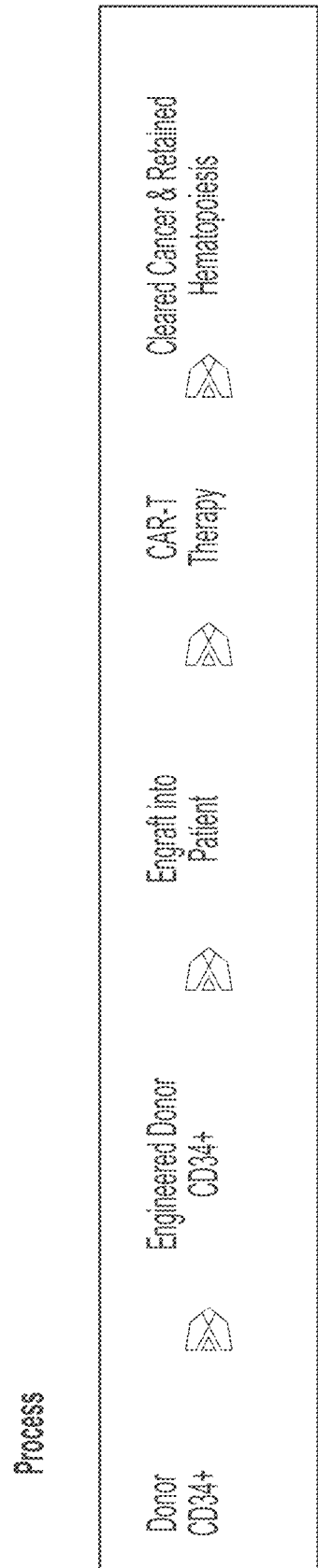
FIGS. 1A-1B are schematic illustrations showing an example therapeutic process involving the methods described herein.
Figure 1B:
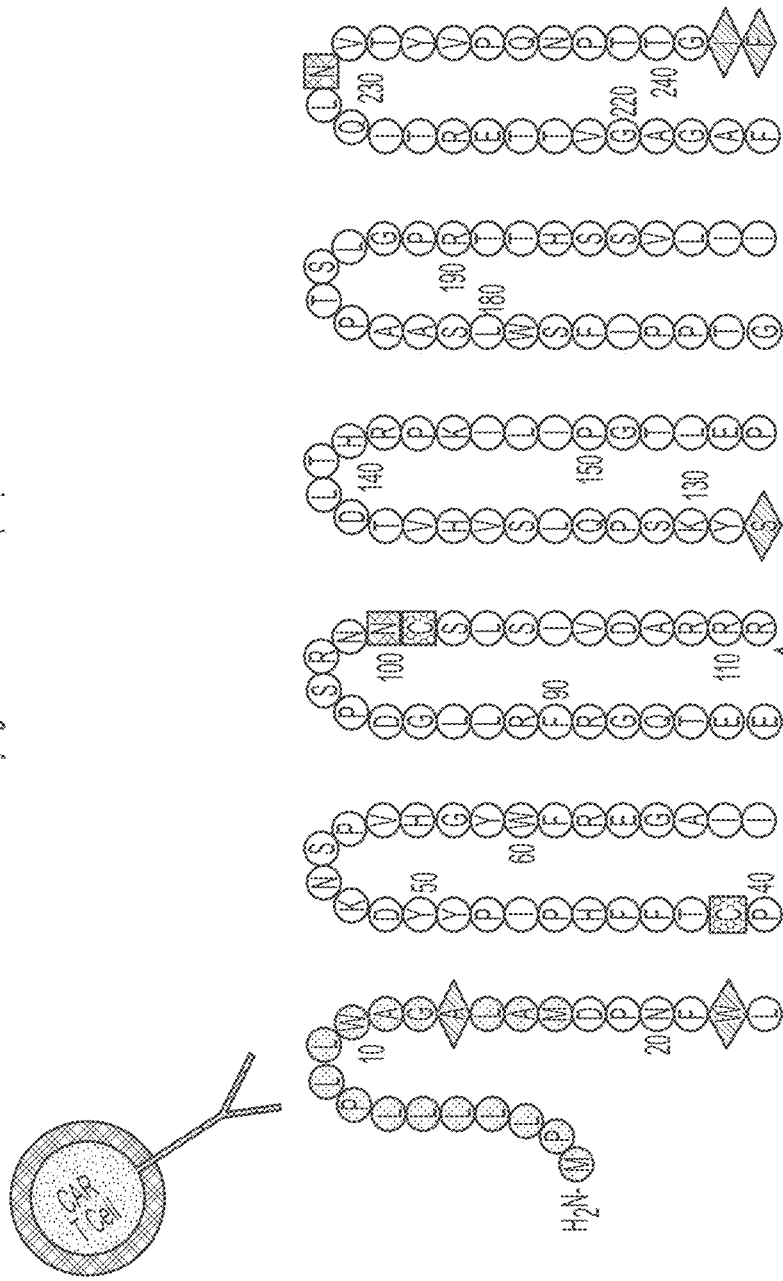
Figure 1B:
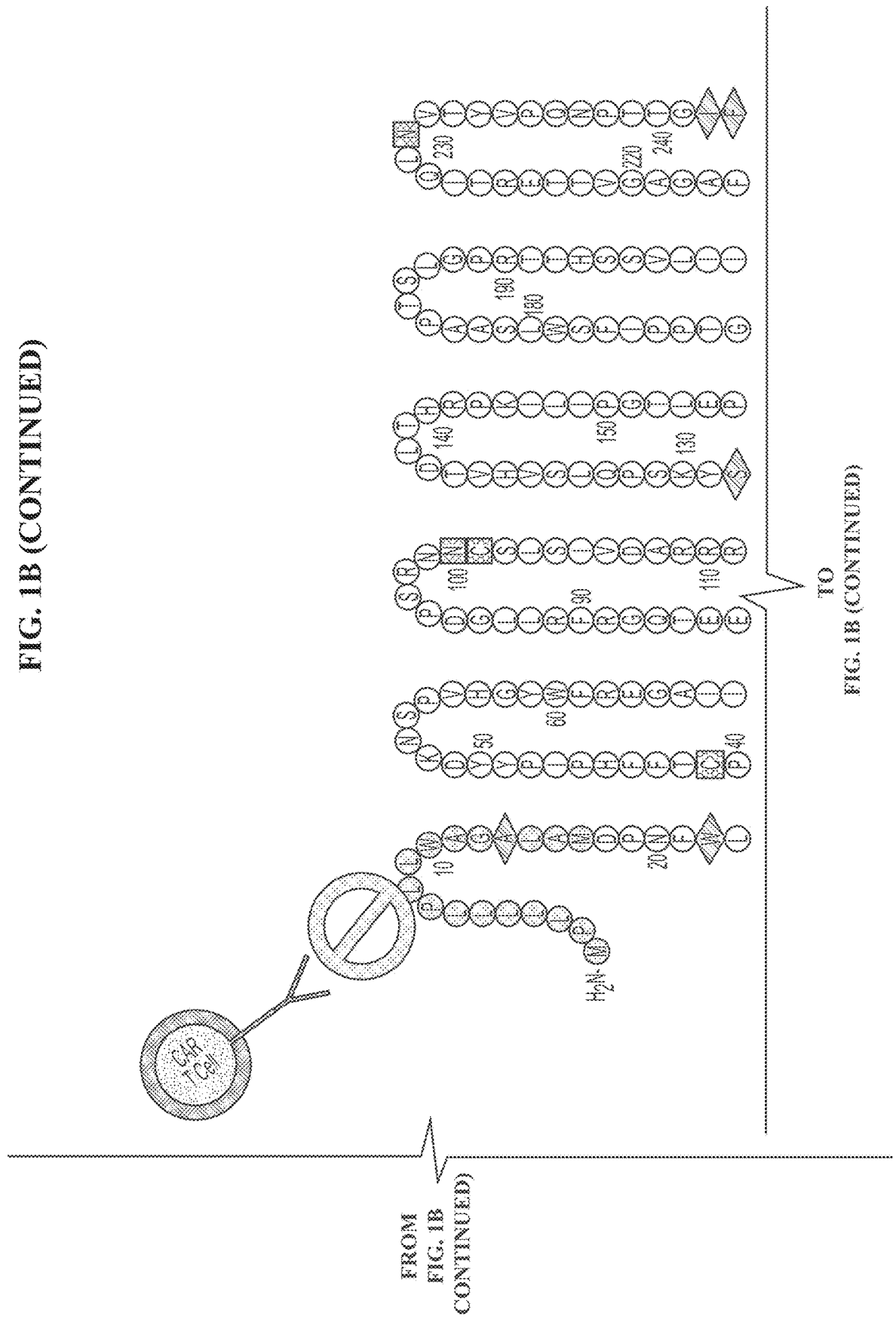
Figure 1B:
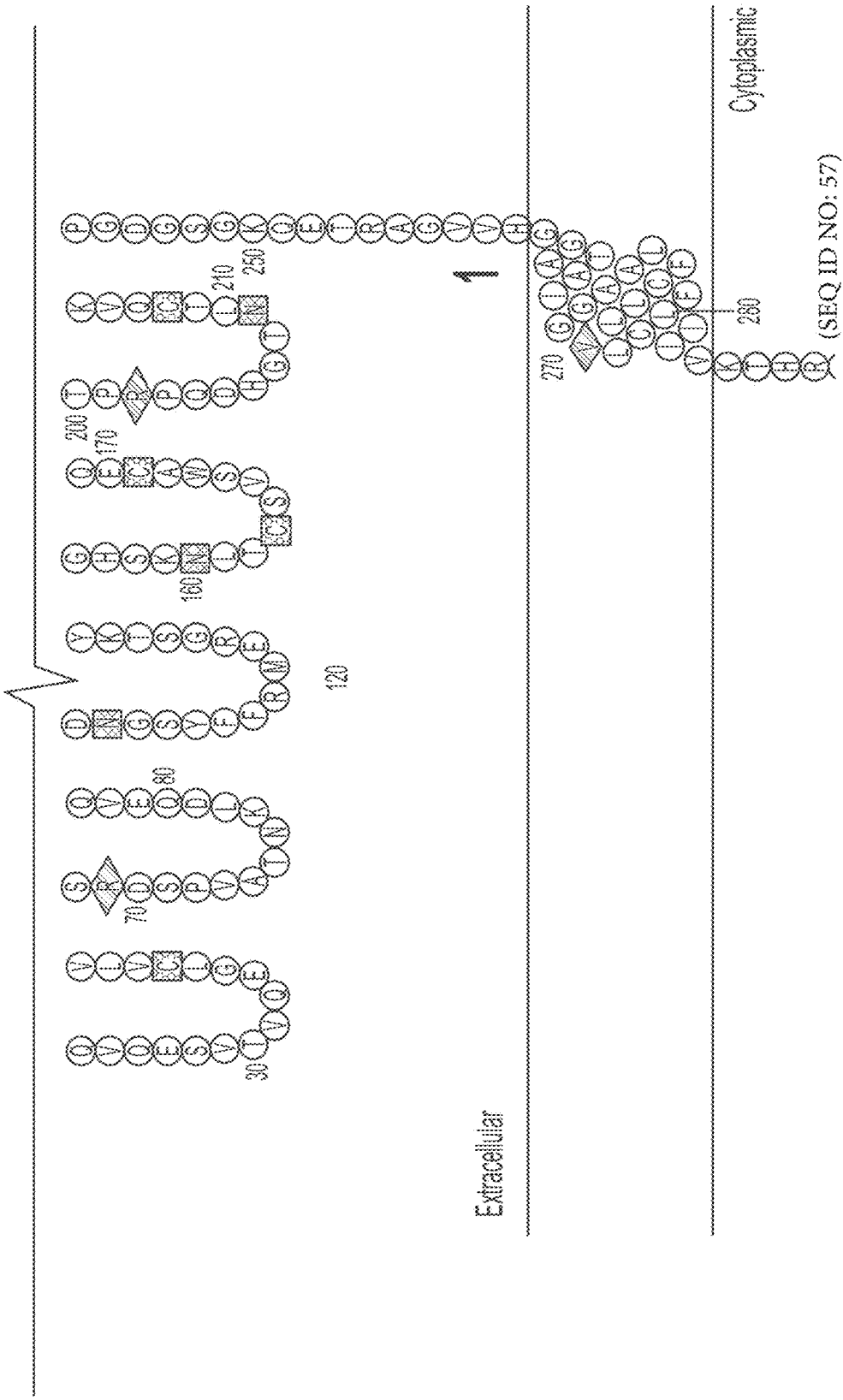
Figure 2:
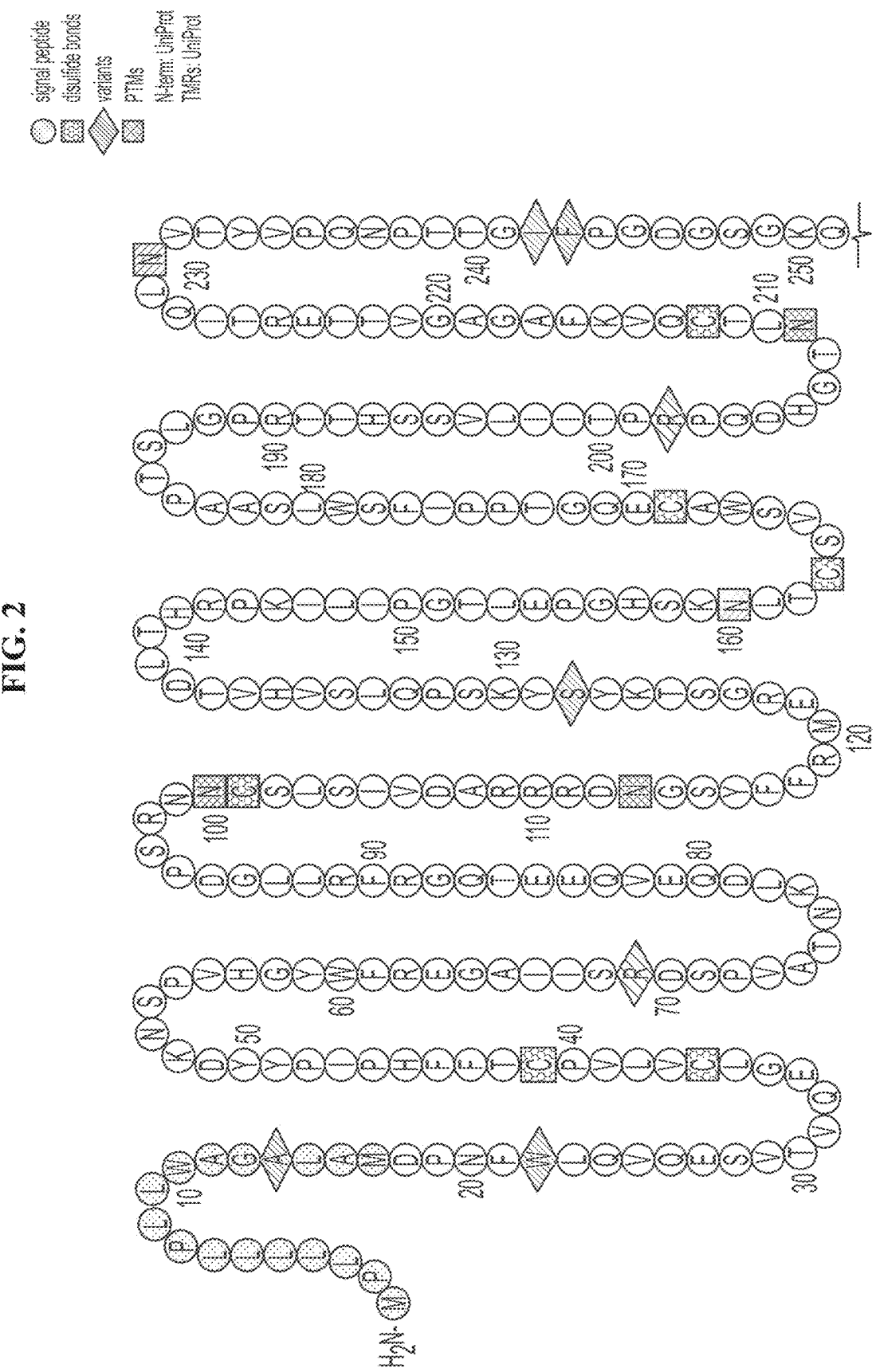
FIG. 2 is a schematic of the extracellular and transmembrane portions of the lineage-specific cell-surface protein human CD33. Regions of CD33 that are predicted to be less deleterious when modified are indicated by the boxes. The sequence corresponds to SEQ ID NO: 57.
Figure 2:
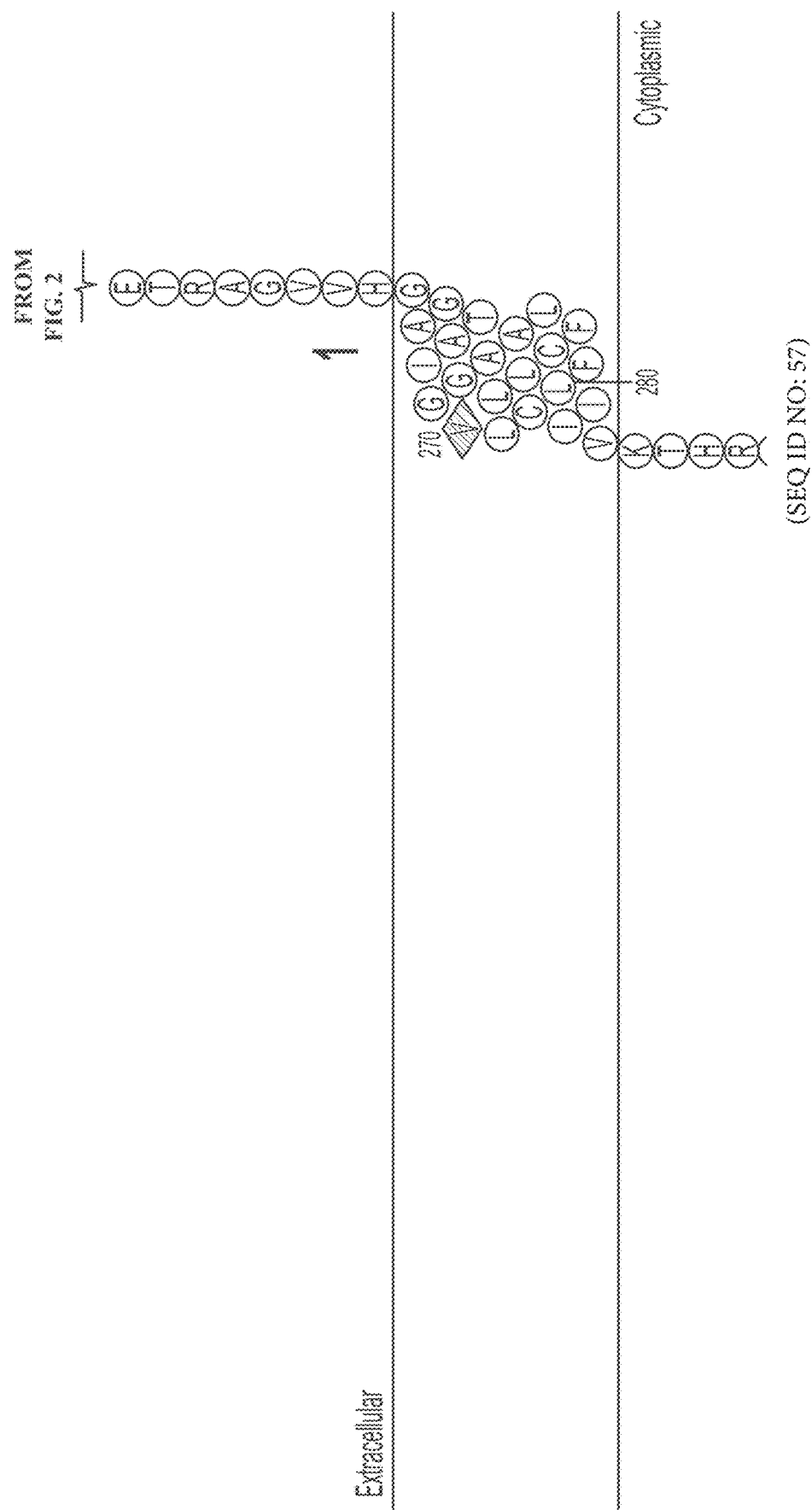

Successfully identifying suitable proteins for targeted cancer therapies presents a significant challenge. Many potential target proteins are present on both the cell surface of a cancer cell and on the cell surface of normal, non-cancer cells, which may be required or critically involved in the development and/or survival of the subject. Many of the target proteins contribute to the functionality of such essential cells. Thus, therapies targeting these proteins may lead to deleterious effects in the subject, such as significant toxicity and/or other side effects. Further, resistance to CAR-T therapy remains a challenge in treatment of hematopoietic malignance, such as acute myeloid leukemia (AML) due to switch of cancer antigens on cancer cells, thereby escaping CAR-T therapy. For example, patients having B-cell acute lymphoblastic leukemia (B-ALL) were found to develop acute myeloid leukemia (AML) with CD19⁻ cancer cells after CAR-T therapy.

The present disclosure provides methods, cells, compositions, and kits aimed at addressing at least the above-stated problems. The methods, cells, compositions, and kits described herein provide a safe and effective treatment for hematological malignancies, allowing for targeting of one or more lineage-specific cell surface proteins (e.g., type 0, type 1, or type 2 proteins) that are present not only on cancer cells but also on cells critical for the development and/or survival of the subject.

More specifically, hematopoietic cells as described herein can be used (for example) in the treatment of a subject that receives two or more different therapies for cancer. Many therapies deplete the subject's endogenous, non-cancerous hematopoietic cells. Replacement or rescue hematopoietic cells described herein can replace the subject's depleted immune cells. Two particular examples of this method are described below.

First, in some cases, a subject receives the first therapy (e.g., against CD19), and then the cancer relapses, and then the subject receives the second therapy (e.g., against CD33). The present application provides, e.g., rescue cells that are resistant to both therapies. Thus, the rescue cells can be administered to the subject at or near the time of the first therapy, and if relapse occurs, the subject can then receive the second therapy without depleting the rescue cells.

Second, in some cases, a subject may need to receive two therapies at once, e.g., because the cancer comprises two sub-populations of cells (e.g., one expressing CD33 and the second expressing CD123 and/or CLL-1), and each therapy only attacks one of the sub-populations. As described herein, rescue cells resistant to both therapies can replace the subject's depleted immune cells even in the presence of both therapies.

Experimental evidence provided in the working Examples herein demonstrates the production, viability, differentiation potential, and resistance to therapy of various cells edited at two antigens. For instance, Examples 3 and 4 show a high frequency of multiplex editing of CD19 and CD33 HSC cells, without impairing viability. Example 9 shows a high frequency of editing of other pairs of cell surface antigens, e.g., CD33 and CD123, CD33 and CLL1, and CD123 and CLL1. Example 9 also shows that doubly edited cells show resistance to CART targeting the antigens.

The present disclosure also provides a population of rescue hematopoietic cells that comprises a first sub-population of cells that is (and/or gives rise to) cells resistant to a first therapy and a second sub-population of cells that is (and/or gives rise to) cells resistant to a second therapy. (Optionally, the population can comprise cells that are (and/or give rise to) cells resistant to both therapies; however this is not required in this embodiment). The cell populations can be useful, e.g., when subjects are treated with two therapies sequentially. For instance, in some embodiments, the edited cell-surface antigens are antigens that are typically not expressed in normal HSCs, but become expressed in later lineages, so the transplanted HSCs are resistant to both therapies regardless of whether any HSCs are edited for both antigens. This population of HSCs will continue to produce differentiated cells, some of which are deficient for the first antigen, and some of which are deficient for the second antigen. When the subject is treated with the first therapy, differentiated cells deficient for the first antigen will survive, and when the subject is treated with the second therapy, differentiated cells deficient for the second antigen will survive. Thus, such heterogeneous populations of cells can be useful as rescue cells.

Accordingly, described herein are genetically engineered hematopoietic cells such as hematopoietic stem cells (HSCs) having genetic editing in one or more genes coding for lineage-specific cell-surface proteins, for example, CD33 and/or CD19; methods of producing such, for examples, via the CRISPR approach using specific guide RNAs; and methods of treating a hematopoietic malignancy using the engineered hematopoietic cells, either taken alone, or in combination with one or more cytotoxic agents (e.g., CAR-T cells) that can target the wild-type lineage-specific cell-surface antigens but not those encoded by the edited genes in the engineered hematopoietic cells.

I. Genetically Engineered Hematopoietic Cells

The present disclosure provides genetically engineered hematopoietic cells such as hematopoietic stem cells that carry genetically edited genes for reducing or eliminating expression of one or more lineage-specific cell-surface antigens, or for expressing the one or more lineage-specific cell-surface antigens in mutated form. The mutated antigens would retain at least partial bioactivity of the antigens but can escape targeting by cytotoxic agents such as CAR-T cells specific to the antigens. In some embodiments, the lineage-specific cell-surface antigens of interest may not be expressed on hematopoietic cells such as HSCs in nature. However, such antigens may be expressed on cells differentiated from the HSCs (e.g., descendants thereof). "Expressing a lineage-specific cell-surface protein" or "expressing a lineage-specific cell-surface antigen" means that at least a portion of the lineage-specific cell-surface protein, or antigen thereof, can be detected on the surface of the hematopoietic cells or descendants thereof. As used herein, "descendants" of hematopoietic cells include any cell type or lineage of cells that arise from the hematopoietic cells. In some embodiments, the descendants of the hematopoietic cells are a cell type or lineage of cells that have differentiated from the hematopoietic cells.

The genetically engineered hematopoietic cells may be used alone for treating hematopoietic malignancies, or in combination with one or more cytotoxic agents that target the wild-type lineage-specific cell-surface antigens but not the mutant encoded by the edited genes in the genetically engineered hematopoietic cells. Such hematopoietic cells, upon differentiation, could compensate the loss of function caused by elimination of functional non-cancerous cells due to immunotherapy that targets lineage-specific cell-surface antigen(s), which may also expressed on normal cells. This approach would also broaden the choice of target proteins for immunotherapy such as CART therapy. For example, certain lineage-specific cell-surface proteins (e.g., Type 0 antigen) are essential to the development and/or survival of essential cells/tissue and thus are poor target in conventional immunotherapy. Being compensated by the genetically engineered hematopoietic stem cells described herein, such lineage-specific cell-surface proteins (e.g., Type 0 antigen) could also be suitable targets of immunotherapy, when it is combined with the engineered HSCs.

(A) Genetically Engineered Hematopoietic Cells Expressing Multiple Lineage-Specific Cell Surface Antigens in Mutated Form In some embodiments, provided herein are a population of genetically engineered hematopoietic cells such as HSCs, which collectively carry genetically edited genes of at least two lineage-specific cell-surface proteins. The genetically edited genes express the antigens in mutated form, e.g., having one or more non-essential epitopes deleted or mutated so as to escape recognition (e.g., have a reduced binding activity) by cytotoxic agents specific to the antigens. Deletion or mutation of a non-essential epitope in a lineage-specific cell-surface protein is not expected to dramatically affect the biological activity of such an antigen.

In some instances, the hematopoietic cell population (e.g., HSCs) described herein can be homogenous, including cells each carrying multiple genetically edited genes (e.g., 2, 3, or 4) of lineage-specific cell-surface antigens. In other instances, the hematopoietic cell population is heterogeneous, comprising (a) cells that carry a genetically edited gene encoding a first lineage-specific cell-surface antigen, (b) cells that carry a genetically edited gene encoding a second lineage-specific cell-surface antigen (which is different from the first antigen), and/or (c) cells that carrying genetically edited genes of both the first and second lineage-specific cell-surface antigens.

In some embodiments, the population of cells obtained post editing comprises cells that have one or more of the target genes partially or completely deleted or both. In some embodiments, the population of cells obtained post editing comprise cells which have gene(s) encoding one or more lineage-specific antigen(s) which are edited such that expression results in a lineage-specific antigen(s) having a partial sequence deletion, e.g., lacking one or more exon(s) of the lineage-specific antigen, and cells comprising edited gene(s) which result in a complete KO of the lineage-specific antigen. In some embodiments, the population of cells obtained post editing comprise cells which have gene(s) encoding one or more lineage-specific antigen(s) which are edited such that expression results in a lineage-specific antigen(s) having a partial sequence deletion, e.g., lacking one or more exon(s) of the lineage-specific antigen, and also have edited gene(s) which result in a complete KO of the lineage-specific antigen.

In some embodiments, the population of cells obtained post editing comprise cells which have gene(s) encoding CD19 and/or CD33 which are edited such that expression results in a CD19 and/or CD33 having a partial sequence deletion, e.g., lacking one or more exon(s) of CD19 and/or CD33, and cells comprising edited CD19 and/or CD33 gene(s) which result in a complete KO of the lineage-specific antigen. In some embodiments, the population of cells obtained post editing comprise cells which have gene(s) encoding CD19 and/or CD33 which are edited such that expression results in a CD19 and/or CD33 polypeptide having a partial sequence deletion, e.g., lacking one or more exon(s) of CD19 and/or CD33, and also have edited gene(s) which result in a complete KO of CD19 and/or CD33.

Lineage-Specific Cell-Surface Proteins

As used herein, the terms "protein," "peptide," and "polypeptide" may be used interchangeably and refer to a polymer of amino acid residues linked together by peptide bonds. In general, a protein may be naturally occurring, recombinant, synthetic, or any combination of these. Also within the scope of the term are variant proteins, which comprise a mutation (e.g., substitution, insertion, or deletion) of one or more amino acid residues relative to the wild-type counterpart.

As used herein, the terms "lineage-specific cell-surface protein" and "cell-surface lineage-specific protein" may be used interchangeably and refer to any protein that is sufficiently present on the surface of a cell and is associated with one or more populations of cell lineage(s). For example, the protein may be present on one or more populations of cell lineage(s) and absent (or at reduced levels) on the cell-surface of other cell populations. In some embodiments, the terms lineage-specific cell-surface antigen" and "cell-surface lineage-specific antigen" maybe used interchangeably and refer to any antigen of a lineage-specific cell-surface protein.

In general, lineage-specific cell-surface proteins can be classified based on a number of factors, such as whether the protein and/or the populations of cells that present the protein are required for survival and/or development of the host organism. A summary of exemplary types of lineage-specific proteins is provide in Table 1 below.

TABLE 1

Classification of Lineage Specific Proteins

| Type of Lineage Specific Protein | Characteristics of the Lineage Specific Protein |
| --- | --- |
| Type 0 | a) protein is required for survival of an organism, and<br>b) cell type carrying type 0 protein is required for survival of an organism and is not unique to a tumor, or tumor-associated virus |
| Type 1 | a) protein is not required for survival of an organism, and<br>b) cell type carrying type 1 protein is not required for survival of an organism |
| Type 2 | a) protein is not required for survival of an organism, and<br>b) cell type carrying type 2 protein is required for the survival of an organism |
| Type 3 | a) protein is not required for the survival of an organism;<br>b) cell type carrying protein is not required for survival of an organism; and<br>c) The protein is unique to a tumor, or a tumor associated virus<br>An example is the LMP-2 protein in EBV infected cells, including EBV infected tumor cells (Nasopharyngeal carcinoma and Burkitts Lymphoma) |

As shown in Table 1, type 0 lineage-specific cell-surface proteins are necessary for the tissue homeostasis and survival, and cell types carrying type 0 lineage-specific cell-surface protein may be also necessary for survival of the subject. Thus, given the importance of type 0 lineage-specific cell-surface proteins, or cells carrying type 0 lineage-specific cell-surface proteins, in homeostasis and survival, targeting this category of proteins may be challenging using conventional CAR T cell immunotherapies, as the inhibition or removal of such proteins and cell carrying such proteins may be detrimental to the survival of the subject. Consequently, lineage-specific cell-surface proteins (such as type 0 lineage-specific proteins) and/or the cell types that carry such proteins may be required for the survival, for example because it performs a vital non-redundant function in the subject, then this type of lineage specific protein may be a poor target for conventional CAR T cell based immunotherapies.

However, by combining the genetically engineered hematopoietic stem cells described herein and cytotoxic agent such as CAR-T cell-based therapy, the selection of target antigen can be expanded to essential antigens such as type 0 lineage-specific cell-surface proteins. In some embodiments, the engineered hematopoietic cells (e.g., HSCs) have one or more genes of type 0 antigens edited for expression of these type 0 antigens in mutated form, which retain (at least partially) bioactivity of the type 0 antigens but can escape targeting by type 0 antigen-specific cytotoxic agents such as CAR-T cells so as to remedy the loss of normal cells expressing the type 0 antigens due to the therapy.

In contrast to type 0 proteins, type 1 cell-surface lineage-specific proteins and cells carrying type 1 cell-surface lineage-specific proteins are not required for tissue homeostasis or survival of the subject. Targeting type 1 cell-surface lineage-specific proteins is not likely to lead to acute toxicity and/or death of the subject. For example, as described in Elkins et al. (*Mol. Cancer Ther*. (2012) 10:2222-32) a CAR T cell engineered to target CD307, a type 1 protein expressed uniquely on both normal plasma cells and multiple myeloma (MM) cells would lead to elimination of both cell types. However, since the plasma cell lineage is expendable for the survival of the organism, CD307 and other type 1 lineage specific proteins are proteins that are suitable for CAR T cell based immunotherapy. Lineage specific proteins of type 1 class may be expressed in a wide variety of different tissues, including, ovaries, testes, prostate, breast, endometrium, and pancreas.

In some embodiments, the genetically engineered hematopoietic cells (e.g., HSCs) have one or more genes of type 1 antigens for expression of the type 1 proteins in mutated forms, which retain (at least partially) bioactivity of the type 1 antigens but can escape targeting by type 1 antigen-specific cytotoxic agents such as CAR-T cells. Use of such engineered HSCs (either alone or in combination with cytotoxic agents such as CAR-T cells targeting the type 1 antigens) may improve the longer-term survival and quality of life of the patient. For example, targeting all plasma cells, while not expected to lead to acute toxicity and/or death, could have longer-term consequences such as reduced function of the humoral immune system leading to increased risk of infection.

Targeting type 2 proteins presents a significant difficulty as compared to type 1 proteins. Type 2 proteins are those characterized where: (1) the protein is dispensable for the survival of an organism (i.e., is not required for the survival), and (2) the cell lineage carrying the protein is indispensable for the survival of an organism (i.e., the particular cell lineage is required for the survival). For example, CD33 is a type 2 protein expressed in both normal myeloid cells as well as in Acute Myeloid Leukemia (AML) cells (Dohner et al., *NEJM* 373:1136 (2015)). As a result, a CART cell engineered to target CD33 protein could lead to the killing of both normal myeloid cells as well as AML cells, which may be incompatible with survival of the subject.

In some embodiments, the genetically engineered hematopoietic cells (e.g., HSCs) have one or more genes of type 2 antigens for expression of the type 2 antigens in mutated form, which retain (at least partially) bioactivity of the type 2 antigens but can escape targeting by type 1 antigen-specific cytotoxic agents such as CAR-T cells. Use of such engineered HSCs (either alone or in combination with cytotoxic agents such as CAR-T cells targeting the type 2 antigens) may improve the longer-term survival and quality of life of the patient. For example, targeting all plasma cells, while not expected to lead to acute toxicity and/or death, could have longer-term consequences such as reduced function of the humoral immune system leading to increased risk of infection.

In some embodiments, the cell-surface lineage-specific protein is BCMA, CD19, CD20, CD30, ROR1, B7H6, B7H3, CD23, CD38, C-type lectin like molecule-1, CS1, IL-5, L1-CAM, PSCA, PSMA, CD138, CD133, CD70, CD7, CD13, NKG2D, NKG2D ligand, CLEC12A, CD11, CD123, CD56, CD34, CD14, CD33, CD66b, CD41, CD61, CD62, CD235a, CD146, CD326, LMP2, CD22, CD52, CD10, CD3/TCR, CD79/BCR, and CD26. In some embodiments, the cell-surface lineage-specific protein is CD33 or CD19.

Alternatively or in addition, the cell-surface lineage-specific protein may be a cancer protein, for example a cell-surface lineage-specific protein that is differentially present on cancer cells. In some embodiments, the cancer protein is a protein that is specific to a tissue or cell lineage. Examples of cell-surface lineage-specific protein that are associated with a specific type of cancer include, without limitation, CD20, CD22 (Non-Hodgkin's lymphoma, B-cell lymphoma, chronic lymphocytic leukemia (CLL)), CD52 (B-cell CLL), CD33 (Acute myelogenous leukemia (AML)), CD10 (gp100) (Common (pre-B) acute lymphocytic leukemia and malignant melanoma), CD3/T-cell receptor (TCR) (T-cell lymphoma and leukemia), CD79/B-cell receptor (BCR) (B-cell lymphoma and leukemia), CD26 (epithelial and lymphoid malignancies), human leukocyte antigen (HLA)-DR, HLA-DP, and HLA-DQ (lymphoid malignancies), RCAS1 (gynecological carcinomas, biliary adenocarcinomas and ductal adenocarcinomas of the pancreas) as well as prostate specific membrane antigen. In some embodiments, the cell-surface protein CD33 and is associated with AML cells.

In some embodiments, the genetically engineered HSCs may have edited genes which encode at least two (e.g., two, three, or four) lineage-specific cell-surface proteins, which can be selected from CD7, CD13, CD19, CD22, CD20, CD25, CD32, CD33, CD38, CD44, CD45, CD47, CD56, 96, CD117, CD123, CD135, CD174, CLL-1, folate receptor β, IL1RAP, MUC1, NKG2D/NKG2DL, TIM-3, and WT1. In specific examples, the genetically engineered HSCs may have edited genes of the following combinations: (a) CD19+CD33, (b) CD19+CD13, (c) CD19+CD123, (d) CD33+CD13, (e) CD33+CD123, (f) CD13+CD123, (g) CD19+CD33+CD13, (h) CD19+CD33+CD123, (i) CD19+CD13+CD123, (j) CD33+CD13+CD123, or (k) CD19+CD33+CD13+CD123. In some embodiments, the genetically engineered HSCs may have edited genes which encode CD33 and one or more lineage-specific cell-surface proteins selected from CD7, CD13, CD19, CD22, CD20, CD25, CD32, CD33, CD38, CD44, CD45, CD47, CD56, 96, CD117, CD123, CD135, CD174, CLL-1, folate receptor β, IL1RAP, MUC1, NKG2D/NKG2DL, TIM-3, and WT1.

In some embodiments, one or both of the lineage-specific cell surface proteins are chosen from CD1a, CD1b, CD1c, CD1d, CD1e, CD2, CD3, CD3d, CD3e, CD3g, CD4, CD5, CD6, CD7, CD8a, CD8b, CD9, CD10, CD11a, CD11b, CD11c, CD11d, CDw12, CD13, CD14, CD15, CD16, CD16b, CD17, CD18, CD19, CD20, CD21, CD22, CD23, CD24, CD25, CD26, CD27, CD28, CD29, CD30, CD31, CD32a, CD32b, CD32c, CD33, CD34, CD35, CD36, CD37, CD38, CD39, CD40, CD41, CD42a, CD42b, CD42c, CD42d, CD43, CD44, CD45, CD45RA, CD45RB, CD45RC, CD45RO, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD61, CD62E, CD62L, CD62P, CD63, CD64a, CD65, CD65s, CD66a, CD66b, CD66c, CD66F, CD68, CD69, CD70, CD71, CD72, CD73, CD74, CD75, CD75S, CD77, CD79a, CD79b, CD80, CD81, CD82, CD83, CD84, CD85A, CD85C, CD85D, CD85E, CD85F, CD85G, CD85H, CD85I, CD85J, CD85K, CD86, CD87, CD88, CD89, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD121a, CD121b, CD122, CD123, CD124, CD125, CD126, CD127, CD129, CD130, CD131, CD132, CD133, CD134, CD135, CD136, CD137, CD138, CD139, CD140a, CD140b, CD141, CD142, CD143, CD14, CDw145, CD146, CD147, CD148, CD150, CD152, CD152, CD153, CD154, CD155, CD156a, CD156b, CD156c, CD157, CD158b1, CD158b2, CD158d, CD158e1/e2, CD158f, CD158g, CD158h, CD158i, CD158j, CD158k, CD159a, CD159c, CD160, CD161, CD163, CD164, CD165, CD166, CD167a, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CDw198, CDw199, CD200, CD201, CD202b, CD203c, CD204, CD205, CD206, CD207, CD208, CD209, CD210a, CDw210b, CD212, CD213a1, CD213a2, CD215, CD217, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240, CD241, CD242, CD243, CD244, CD245, CD246, CD247, CD248, CD249, CD252, CD253, CD254, CD256, CD257, CD258, CD261, CD262, CD263, CD264, CD265, CD266, CD267, CD268, CD269, CD270, CD272, CD272, CD273, CD274, CD275, CD276, CD277, CD278, CD279, CD280, CD281, CD282, CD283, CD284, CD286, CD288, CD289, CD290, CD292, CDw293, CD294, CD295, CD296, CD297, CD298, CD299, CD300a, CD300c, CD300e, CD301, CD302, CD303, CD304, CD305, CD306, CD307a, CD307b, CD307c, CD307d, CD307e, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD359, CD360, CD361, CD362 and CD363.

In some embodiments, one or both of the lineage-specific cell surface proteins are chosen from CD19; CD123; CD22; CD30; CD171; CS-1 (also referred to as CD2 subset 1, CRACC, SLAMF7, CD319, and 19A24); C-type lectin-like molecule-1 (CLECL1); CD33; epidermal growth factor receptor variant III (EGFRvIII); ganglioside G2 (CD2); ganglioside GD3 (aNeu5Ac(2-8)aNeu5Ac(2-3)bDGalp(1-4) bDGlep(1-1)Cer); TNF receptor family member B cell maturation (BCMA); Tn antigen ((Tn Ag) or (GalNAc.alpha.-Ser/Thr)); prostate-specific membrane antigen (PSMA); Receptor tyrosine kinase-like orphan receptor 1 (ROR1); Fms-Like tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor I receptor (IGF-I receptor), carbonic anhydrase IX (CAIX), Proteasome (Prosome, Macropain) Subunit, Beta Type 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDG1cp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex; locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1), ETS translocation-variant gene 6, located on chromosome 12p (ETV6-AML); sperm protein 17 (SPA17); X Antigen Family, member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-1AP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxy esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2), lymphocyte antigen 75 (LY75); Glypican-3 (GPC3); Fc receptor-like 5 (FCRL5); and immunoglobulin lambda-like polypeptide 1 (IGLL1).

In some embodiments, one or both of the lineage-specific cell surface proteins are chosen from CD11a, CD18, CD19, CD20, CD31, CD34, CD44, CD45, CD47, CD51, CD58, CD59, CD63, CD97, CD99, CD100, CD102, CD123, CD127, CD133, CD135, CD157, CD172b, CD217, CD300a, CD305, CD317, CD321, CD33, and CLL1.

In some embodiments, one or both of the lineage-specific cell surface proteins are chosen from CD33, CD123, CLL1, CD38, CD135 (FLT3), CD56 (NCAM1), CD117 (c-KIT), FRβ (FOLR2), CD47, CD82, TNFRSF1B (CD120B), CD191, CD96, PTPRJ (CD148), CD70, LILRB2 (CD85D), CD25 (IL2Ralpha), CD44, CD96, NKG2D Ligand, CD45, CD7, CD15, CD19, CD20, CD22, CD37, and CD82.

In some embodiments, one or both of the lineage-specific cell surface proteins are chosen from CD7, CD11a, CD15, CD18, CD19, CD20, CD22, CD25, CD31, CD33, CD34, CD37, CD38, CD44, CD45, CD47, CD51, CD56, CD58, CD59, CD63, CD70, CD82, CD85D, CD96, CD97, CD99, CD100, CD102, CD117, CD120B, CD123, CD127, CD133, CD135, CD148, CD157, CD172b, CD191, CD217, CD300a, CD305, CD317, CD321, CLL1, FRβ (FOLR2), NKG2D Ligand.

Table 1A lists exemplary pairs of first and second lineage-specific cell surface proteins that can be used in accordance with the compositions and methods described herein.

| — | CD11a, CD7 | CD15, CD7 | CD18, CD7 | CD19, CD7 |
|---|---|---|---|---|
| CD7, CD11a | — | CD15, CD11a | CD18, CD11a | CD19, CD11a |
| CD7, CD15 | CD11a, CD15 | — | CD18, CD15 | CD19, CD15 |
| CD7, CD18 | CD11a, CD18 | CD15, CD18 | — | CD19, CD18 |
| CD7, CD19 | CD11a, CD19 | CD15, CD19 | CD18, CD19 | — |
| CD7, CD20 | CD11a, CD20 | CD15, CD20 | CD18, CD20 | CD19, CD20 |
| CD7, CD22 | CD11a, CD22 | CD15, CD22 | CD18, CD22 | CD19, CD22 |
| CD7, CD25 | CD11a, CD25 | CD15, CD25 | CD18, CD25 | CD19, CD25 |
| CD7, CD31 | CD11a, CD31 | CD15, CD31 | CD18, CD31 | CD19, CD31 |
| CD7, CD33 | CD11a, CD33 | CD15, CD33 | CD18, CD33 | CD19, CD33 |
| CD7, CD34 | CD11a, CD34 | CD15, CD34 | CD18, CD34 | CD19, CD34 |
| CD7, CD37 | CD11a, CD37 | CD15, CD37 | CD18, CD37 | CD19, CD37 |
| CD7, CD38 | CD11a, CD38 | CD15, CD38 | CD18, CD38 | CD19, CD38 |
| CD7, CD44 | CD11a, CD44 | CD15, CD44 | CD18, CD44 | CD19, CD44 |
| CD7, CD45 | CD11a, CD45 | CD15, CD45 | CD18, CD45 | CD19, CD45 |
| CD7, CD47 | CD11a, CD47 | CD15, CD47 | CD18, CD47 | CD19, CD47 |
| CD7, CD51 | CD11a, CD51 | CD15, CD51 | CD18, CD51 | CD19, CD51 |
| CD7, CD56 | CD11a, CD56 | CD15, CD56 | CD18, CD56 | CD19, CD56 |
| CD7, CD58 | CD11a, CD58 | CD15, CD58 | CD18, CD58 | CD19, CD58 |
| CD7, CD59 | CD11a, CD59 | CD15, CD59 | CD18, CD59 | CD19, CD59 |
| CD7, CD63 | CD11a, CD63 | CD15, CD63 | CD18, CD63 | CD19, CD63 |
| CD7, CD70 | CD11a, CD70 | CD15, CD70 | CD18, CD70 | CD19, CD70 |
| CD7, CD82 | CD11a, CD82 | CD15, CD82 | CD18, CD82 | CD19, CD82 |
| CD7, CD85D | CD11a, CD85D | CD15, CD85D | CD18, CD85D | CD19, CD85D |
| CD7, CD96 | CD11a, CD96 | CD15, CD96 | CD18, CD96 | CD19, CD96 |
| CD7, CD97 | CD11a, CD97 | CD15, CD97 | CD18, CD97 | CD19, CD97 |
| CD7, CD99 | CD11a, CD99 | CD15, CD99 | CD18, CD99 | CD19, CD99 |
| CD7, CD100 | CD11a, CD100 | CD15, CD100 | CD18, CD100 | CD19, CD100 |
| CD7, CD102 | CD11a, CD102 | CD15, CD102 | CD18, CD102 | CD19, CD102 |
| CD7, CD117 | CD11a, CD117 | CD15, CD117 | CD18, CD117 | CD19, CD117 |
| CD7, CD120B | CD11a, CD120B | CD15, CD120B | CD18, CD120B | CD19, CD120B |
| CD7, CD123 | CD11a, CD123 | CD15, CD123 | CD18, CD123 | CD19, CD123 |
| CD7, CD127 | CD11a, CD127 | CD15, CD127 | CD18, CD127 | CD19, CD127 |
| CD7, CD133 | CD11a, CD133 | CD15, CD133 | CD18, CD133 | CD19, CD133 |
| CD7, CD135 | CD11a, CD135 | CD15, CD135 | CD18, CD135 | CD19, CD135 |
| CD7, CD148 | CD11a, CD148 | CD15, CD148 | CD18, CD148 | CD19, CD148 |
| CD7, CD157 | CD11a, CD157 | CD15, CD157 | CD18, CD157 | CD19, CD157 |
| CD7, CD172b | CD11a, CD172b | CD15, CD172b | CD18, CD172b | CD19, CD172b |
| CD7, CD191 | CD11a, CD191 | CD15, CD191 | CD18, CD191 | CD19, CD191 |
| CD7, CD217 | CD11a, CD217 | CD15, CD217 | CD18, CD217 | CD19, CD217 |
| CD7, CD300a | CD11a, CD300a | CD15, CD300a | CD18, CD300a | CD19, CD300a |
| CD7, CD305 | CD11a, CD305 | CD15, CD305 | CD18, CD305 | CD19, CD305 |
| CD7, CD317 | CD11a, CD317 | CD15, CD317 | CD18, CD317 | CD19, CD317 |
| CD7, CD321 | CD11a, CD321 | CD15, CD321 | CD18, CD321 | CD19, CD321 |
| CD7, CLL1 | CD11a, CLL1 | CD15, CLL1 | CD18, CLL1 | CD19, CLL1 |
| CD7, FOLR2 | CD11a, FOLR2 | CD15, FOLR2 | CD18, FOLR2 | CD19, FOLR2 |
| CD7, NKG2D Ligand | CD11a, NKG2D Ligand | CD15, NKG2D Ligand | CD18, NKG2D Ligand | CD19, NKG2D Ligand |
| CD7, EMR2 | CD11a, EMR2 | CD15, EMR2 | CD18, EMR2 | CD19, EMR2 |
| CD20, CD7 | CD22, CD7 | CD25, CD7 | CD31, CD7 | CD33, CD7 |
| CD20, CD11a | CD22, CD11a | CD25, CD11a | CD31, CD11a | CD33, CD11a |
| CD20, CD15 | CD22, CD15 | CD25, CD15 | CD31, CD15 | CD33, CD15 |
| CD20, CD18 | CD22, CD18 | CD25, CD18 | CD31, CD18 | CD33, CD18 |

-continued

| | | | | |
|---|---|---|---|---|
| CD20, CD19 | CD22, CD19 | CD25, CD19 | CD31, CD19 | CD33, CD19 |
| — | CD22, CD20 | CD25, CD20 | CD31, CD20 | CD33, CD20 |
| CD20, CD22 | — | CD25, CD22 | CD31, CD22 | CD33, CD22 |
| CD20, CD25 | CD22, CD25 | — | CD31, CD25 | CD33, CD25 |
| CD20, CD31 | CD22, CD31 | CD25, CD31 | — | CD33, CD31 |
| CD20, CD33 | CD22, CD33 | CD25, CD33 | CD31, CD33 | — |
| CD20, CD34 | CD22, CD34 | CD25, CD34 | CD31, CD34 | CD33, CD34 |
| CD20, CD37 | CD22, CD37 | CD25, CD37 | CD31, CD37 | CD33, CD37 |
| CD20, CD38 | CD22, CD38 | CD25, CD38 | CD31, CD38 | CD33, CD38 |
| CD20, CD44 | CD22, CD44 | CD25, CD44 | CD31, CD44 | CD33, CD44 |
| CD20, CD45 | CD22, CD45 | CD25, CD45 | CD31, CD45 | CD33, CD45 |
| CD20, CD47 | CD22, CD47 | CD25, CD47 | CD31, CD47 | CD33, CD47 |
| CD20, CD51 | CD22, CD51 | CD25, CD51 | CD31, CD51 | CD33, CD51 |
| CD20, CD56 | CD22, CD56 | CD25, CD56 | CD31, CD56 | CD33, CD56 |
| CD20, CD58 | CD22, CD58 | CD25, CD58 | CD31, CD58 | CD33, CD58 |
| CD20, CD59 | CD22, CD59 | CD25, CD59 | CD31, CD59 | CD33, CD59 |
| CD20, CD63 | CD22, CD63 | CD25, CD63 | CD31, CD63 | CD33, CD63 |
| CD20, CD70 | CD22, CD70 | CD25, CD70 | CD31, CD70 | CD33, CD70 |
| CD20, CD82 | CD22, CD82 | CD25, CD82 | CD31, CD82 | CD33, CD82 |
| CD20, CD85D | CD22, CD85D | CD25, CD85D | CD31, CD85D | CD33, CD85D |
| CD20, CD96 | CD22, CD96 | CD25, CD96 | CD31, CD96 | CD33, CD96 |
| CD20, CD97 | CD22, CD97 | CD25, CD97 | CD31, CD97 | CD33, CD97 |
| CD20, CD99 | CD22, CD99 | CD25, CD99 | CD31, CD99 | CD33, CD99 |
| CD20, CD100 | CD22, CD100 | CD25, CD100 | CD31, CD100 | CD33, CD100 |
| CD20, CD102 | CD22, CD102 | CD25, CD102 | CD31, CD102 | CD33, CD102 |
| CD20, CD117 | CD22, CD117 | CD25, CD117 | CD31, CD117 | CD33, CD117 |
| CD20, CD120B | CD22, CD120B | CD25, CD120B | CD31, CD120B | CD33, CD120B |
| CD20, CD123 | CD22, CD123 | CD25, CD123 | CD31, CD123 | CD33, CD123 |
| CD20, CD127 | CD22, CD127 | CD25, CD127 | CD31, CD127 | CD33, CD127 |
| CD20, CD133 | CD22, CD133 | CD25, CD133 | CD31, CD133 | CD33, CD133 |
| CD20, CD135 | CD22, CD135 | CD25, CD135 | CD31, CD135 | CD33, CD135 |
| CD20, CD148 | CD22, CD148 | CD25, CD148 | CD31, CD148 | CD33, CD148 |
| CD20, CD157 | CD22, CD157 | CD25, CD157 | CD31, CD157 | CD33, CD157 |
| CD20, CD172b | CD22, CD172b | CD25, CD172b | CD31, CD172b | CD33, CD172b |
| CD20, CD191 | CD22, CD191 | CD25, CD191 | CD31, CD191 | CD33, CD191 |
| CD20, CD217 | CD22, CD217 | CD25, CD217 | CD31, CD217 | CD33, CD217 |
| CD20, CD300a | CD22, CD300a | CD25, CD300a | CD31, CD300a | CD33, CD300a |
| CD20, CD305 | CD22, CD305 | CD25, CD305 | CD31, CD305 | CD33, CD305 |
| CD20, CD317 | CD22, CD317 | CD25, CD317 | CD31, CD317 | CD33, CD317 |
| CD20, CD321 | CD22, CD321 | CD25, CD321 | CD31, CD321 | CD33, CD321 |
| CD20, CLL1 | CD22, CLL1 | CD25, CLL1 | CD31, CLL1 | CD33, CLL1 |
| CD20, FOLR2 | CD22, FOLR2 | CD25, FOLR2 | CD31, FOLR2 | CD33, FOLR2 |
| CD20, NKG2D Ligand | CD22, NKG2D Ligand | CD25, NKG2D Ligand | CD31, NKG2D Ligand | CD33, NKG2D Ligand |
| CD20, EMR2 | CD22, EMR2 | CD25, EMR2 | CD31, EMR2 | CD33, EMR2 |
| CD34, CD7 | CD37, CD7 | CD38, CD7 | CD44, CD7 | CD45, CD7 |
| CD34, CD11a | CD37, CD11a | CD38, CD11a | CD44, CD11a | CD45, CD11a |
| CD34, CD15 | CD37, CD15 | CD38, CD15 | CD44, CD15 | CD45, CD15 |
| CD34, CD18 | CD37, CD18 | CD38, CD18 | CD44, CD18 | CD45, CD18 |
| CD34, CD19 | CD37, CD19 | CD38, CD19 | CD44, CD19 | CD45, CD19 |
| CD34, CD20 | CD37, CD20 | CD38, CD20 | CD44, CD20 | CD45, CD20 |
| CD34, CD22 | CD37, CD22 | CD38, CD22 | CD44, CD22 | CD45, CD22 |
| CD34, CD25 | CD37, CD25 | CD38, CD25 | CD44, CD25 | CD45, CD25 |
| CD34, CD31 | CD37, CD31 | CD38, CD31 | CD44, CD31 | CD45, CD31 |
| CD34, CD33 | CD37, CD33 | CD38, CD33 | CD44, CD33 | CD45, CD33 |
| — | CD37, CD34 | CD38, CD34 | CD44, CD34 | CD45, CD34 |
| CD34, CD37 | — | CD38, CD37 | CD44, CD37 | CD45, CD37 |
| CD34, CD38 | CD37, CD38 | — | CD44, CD38 | CD45, CD38 |
| CD34, CD44 | CD37, CD44 | CD38, CD44 | — | CD45, CD44 |
| CD34, CD45 | CD37, CD45 | CD38, CD45 | CD44, CD45 | — |
| CD34, CD47 | CD37, CD47 | CD38, CD47 | CD44, CD47 | CD45, CD47 |
| CD34, CD51 | CD37, CD51 | CD38, CD51 | CD44, CD51 | CD45, CD51 |
| CD34, CD56 | CD37, CD56 | CD38, CD56 | CD44, CD56 | CD45, CD56 |
| CD34, CD58 | CD37, CD58 | CD38, CD58 | CD44, CD58 | CD45, CD58 |
| CD34, CD59 | CD37, CD59 | CD38, CD59 | CD44, CD59 | CD45, CD59 |
| CD34, CD63 | CD37, CD63 | CD38, CD63 | CD44, CD63 | CD45, CD63 |
| CD34, CD70 | CD37, CD70 | CD38, CD70 | CD44, CD70 | CD45, CD70 |
| CD34, CD82 | CD37, CD82 | CD38, CD82 | CD44, CD82 | CD45, CD82 |
| CD34, CD85D | CD37, CD85D | CD38, CD85D | CD44, CD85D | CD45, CD85D |
| CD34, CD96 | CD37, CD96 | CD38, CD96 | CD44, CD96 | CD45, CD96 |
| CD34, CD97 | CD37, CD97 | CD38, CD97 | CD44, CD97 | CD45, CD97 |
| CD34, CD99 | CD37, CD99 | CD38, CD99 | CD44, CD99 | CD45, CD99 |
| CD34, CD100 | CD37, CD100 | CD38, CD100 | CD44, CD100 | CD45, CD100 |
| CD34, CD102 | CD37, CD102 | CD38, CD102 | CD44, CD102 | CD45, CD102 |
| CD34, CD117 | CD37, CD117 | CD38, CD117 | CD44, CD117 | CD45, CD117 |
| CD34, CD120B | CD37, CD120B | CD38, CD120B | CD44, CD120B | CD45, CD120B |
| CD34, CD123 | CD37, CD123 | CD38, CD123 | CD44, CD123 | CD45, CD123 |
| CD34, CD127 | CD37, CD127 | CD38, CD127 | CD44, CD127 | CD45, CD127 |
| CD34, CD133 | CD37, CD133 | CD38, CD133 | CD44, CD133 | CD45, CD133 |

-continued

| | | | | |
|---|---|---|---|---|
| CD34, CD135 | CD37, CD135 | CD38, CD135 | CD44, CD135 | CD45, CD135 |
| CD34, CD148 | CD37, CD148 | CD38, CD148 | CD44, CD148 | CD45, CD148 |
| CD34, CD157 | CD37, CD157 | CD38, CD157 | CD44, CD157 | CD45, CD157 |
| CD34, CD172b | CD37, CD172b | CD38, CD172b | CD44, CD172b | CD45, CD172b |
| CD34, CD191 | CD37, CD191 | CD38, CD191 | CD44, CD191 | CD45, CD191 |
| CD34, CD217 | CD37, CD217 | CD38, CD217 | CD44, CD217 | CD45, CD217 |
| CD34, CD300a | CD37, CD300a | CD38, CD300a | CD44, CD300a | CD45, CD300a |
| CD34, CD305 | CD37, CD305 | CD38, CD305 | CD44, CD305 | CD45, CD305 |
| CD34, CD317 | CD37, CD317 | CD38, CD317 | CD44, CD317 | CD45, CD317 |
| CD34, CD321 | CD37, CD321 | CD38, CD321 | CD44, CD321 | CD45, CD321 |
| CD34, CLL1 | CD37, CLL1 | CD38, CLL1 | CD44, CLL1 | CD45, CLL1 |
| CD34, FOLR2 | CD37, FOLR2 | CD38, FOLR2 | CD44, FOLR2 | CD45, FOLR2 |
| CD34, NKG2D Ligand | CD37, NKG2D Ligand | CD38, NKG2D Ligand | CD44, NKG2D Ligand | CD45, NKG2D Ligand |
| CD34, EMR2 | CD37, EMR2 | CD38, EMR2 | CD44, EMR2 | CD45, EMR2 |
| CD47, CD7 | CD51, CD7 | CD56, CD7 | CD58, CD7 | CD59, CD7 |
| CD47, CD11a | CD51, CD11a | CD56, CD11a | CD58, CD11a | CD59, CD11a |
| CD47, CD15 | CD51, CD15 | CD56, CD15 | CD58, CD15 | CD59, CD15 |
| CD47, CD18 | CD51, CD18 | CD56, CD18 | CD58, CD18 | CD59, CD18 |
| CD47, CD19 | CD51, CD19 | CD56, CD19 | CD58, CD19 | CD59, CD19 |
| CD47, CD20 | CD51, CD20 | CD56, CD20 | CD58, CD20 | CD59, CD20 |
| CD47, CD22 | CD51, CD22 | CD56, CD22 | CD58, CD22 | CD59, CD22 |
| CD47, CD25 | CD51, CD25 | CD56, CD25 | CD58, CD25 | CD59, CD25 |
| CD47, CD31 | CD51, CD31 | CD56, CD31 | CD58, CD31 | CD59, CD31 |
| CD47, CD33 | CD51, CD33 | CD56, CD33 | CD58, CD33 | CD59, CD33 |
| CD47, CD34 | CD51, CD34 | CD56, CD34 | CD58, CD34 | CD59, CD34 |
| CD47, CD37 | CD51, CD37 | CD56, CD37 | CD58, CD37 | CD59, CD37 |
| CD47, CD38 | CD51, CD38 | CD56, CD38 | CD58, CD38 | CD59, CD38 |
| CD47, CD44 | CD51, CD44 | CD56, CD44 | CD58, CD44 | CD59, CD44 |
| CD47, CD45 | CD51, CD45 | CD56, CD45 | CD58, CD45 | CD59, CD45 |
| — | CD51, CD47 | CD56, CD47 | CD58, CD47 | CD59, CD47 |
| CD47, CD51 | — | CD56, CD51 | CD58, CD51 | CD59, CD51 |
| CD47, CD56 | CD51, CD56 | — | CD58, CD56 | CD59, CD56 |
| CD47, CD58 | CD51, CD58 | CD56, CD58 | — | CD59, CD58 |
| CD47, CD59 | CD51, CD59 | CD56, CD59 | CD58, CD59 | — |
| CD47, CD63 | CD51, CD63 | CD56, CD63 | CD58, CD63 | CD59, CD63 |
| CD47, CD70 | CD51, CD70 | CD56, CD70 | CD58, CD70 | CD59, CD70 |
| CD47, CD82 | CD51, CD82 | CD56, CD82 | CD58, CD82 | CD59, CD82 |
| CD47, CD85D | CD51, CD85D | CD56, CD85D | CD58, CD85D | CD59, CD85D |
| CD47, CD96 | CD51, CD96 | CD56, CD96 | CD58, CD96 | CD59, CD96 |
| CD47, CD97 | CD51, CD97 | CD56, CD97 | CD58, CD97 | CD59, CD97 |
| CD47, CD99 | CD51, CD99 | CD56, CD99 | CD58, CD99 | CD59, CD99 |
| CD47, CD100 | CD51, CD100 | CD56, CD100 | CD58, CD100 | CD59, CD100 |
| CD47, CD102 | CD51, CD102 | CD56, CD102 | CD58, CD102 | CD59, CD102 |
| CD47, CD117 | CD51, CD117 | CD56, CD117 | CD58, CD117 | CD59, CD117 |
| CD47, CD120B | CD51, CD120B | CD56, CD120B | CD58, CD120B | CD59, CD120B |
| CD47, CD123 | CD51, CD123 | CD56, CD123 | CD58, CD123 | CD59, CD123 |
| CD47, CD127 | CD51, CD127 | CD56, CD127 | CD58, CD127 | CD59, CD127 |
| CD47, CD133 | CD51, CD133 | CD56, CD133 | CD58, CD133 | CD59, CD133 |
| CD47, CD135 | CD51, CD135 | CD56, CD135 | CD58, CD135 | CD59, CD135 |
| CD47, CD148 | CD51, CD148 | CD56, CD148 | CD58, CD148 | CD59, CD148 |
| CD47, CD157 | CD51, CD157 | CD56, CD157 | CD58, CD157 | CD59, CD157 |
| CD47, CD172b | CD51, CD172b | CD56, CD172b | CD58, CD172b | CD59, CD172b |
| CD47, CD191 | CD51, CD191 | CD56, CD191 | CD58, CD191 | CD59, CD191 |
| CD47, CD217 | CD51, CD217 | CD56, CD217 | CD58, CD217 | CD59, CD217 |
| CD47, CD300a | CD51, CD300a | CD56, CD300a | CD58, CD300a | CD59, CD300a |
| CD47, CD305 | CD51, CD305 | CD56, CD305 | CD58, CD305 | CD59, CD305 |
| CD47, CD317 | CD51, CD317 | CD56, CD317 | CD58, CD317 | CD59, CD317 |
| CD47, CD321 | CD51, CD321 | CD56, CD321 | CD58, CD321 | CD59, CD321 |
| CD47, CLL1 | CD51, CLL1 | CD56, CLL1 | CD58, CLL1 | CD59, CLL1 |
| CD47, FOLR2 | CD51, FOLR2 | CD56, FOLR2 | CD58, FOLR2 | CD59, FOLR2 |
| CD47, NKG2D Ligand | CD51, NKG2D Ligand | CD56, NKG2D Ligand | CD58, NKG2D Ligand | CD59, NKG2D Ligand |
| CD47, EMR2 | CD51, EMR2 | CD56, EMR2 | CD58, EMR2 | CD59, EMR2 |
| CD63, CD7 | CD70, CD7 | CD82, CD7 | CD85D, CD7 | CD96, CD7 |
| CD63, CD11a | CD70, CD11a | CD82, CD11a | CD85D, CD11a | CD96, CD11a |
| CD63, CD15 | CD70, CD15 | CD82, CD15 | CD85D, CD15 | CD96, CD15 |
| CD63, CD18 | CD70, CD18 | CD82, CD18 | CD85D, CD18 | CD96, CD18 |
| CD63, CD19 | CD70, CD19 | CD82, CD19 | CD85D, CD19 | CD96, CD19 |
| CD63, CD20 | CD70, CD20 | CD82, CD20 | CD85D, CD20 | CD96, CD20 |
| CD63, CD22 | CD70, CD22 | CD82, CD22 | CD85D, CD22 | CD96, CD22 |
| CD63, CD25 | CD70, CD25 | CD82, CD25 | CD85D, CD25 | CD96, CD25 |
| CD63, CD31 | CD70, CD31 | CD82, CD31 | CD85D, CD31 | CD96, CD31 |
| CD63, CD33 | CD70, CD33 | CD82, CD33 | CD85D, CD33 | CD96, CD33 |
| CD63, CD34 | CD70, CD34 | CD82, CD34 | CD85D, CD34 | CD96, CD34 |
| CD63, CD37 | CD70, CD37 | CD82, CD37 | CD85D, CD37 | CD96, CD37 |
| CD63, CD38 | CD70, CD38 | CD82, CD38 | CD85D, CD38 | CD96, CD38 |
| CD63, CD44 | CD70, CD44 | CD82, CD44 | CD85D, CD44 | CD96, CD44 |
| CD63, CD45 | CD70, CD45 | CD82, CD45 | CD85D, CD45 | CD96, CD45 |

-continued

| | | | | |
|---|---|---|---|---|
| CD63, CD47 | CD70, CD47 | CD82, CD47 | CD85D, CD47 | CD96, CD47 |
| CD63, CD51 | CD70, CD51 | CD82, CD51 | CD85D, CD51 | CD96, CD51 |
| CD63, CD56 | CD70, CD56 | CD82, CD56 | CD85D, CD56 | CD96, CD56 |
| CD63, CD58 | CD70, CD58 | CD82, CD58 | CD85D, CD58 | CD96, CD58 |
| CD63, CD59 | CD70, CD59 | CD82, CD59 | CD85D, CD59 | CD96, CD59 |
| — | CD70, CD63 | CD82, CD63 | CD85D, CD63 | CD96, CD63 |
| CD63, CD70 | — | CD82, CD70 | CD85D, CD70 | CD96, CD70 |
| CD63, CD82 | CD70, CD82 | — | CD85D, CD82 | CD96, CD82 |
| CD63, CD85D | CD70, CD85D | CD82, CD85D | — | CD96, CD85D |
| CD63, CD96 | CD70, CD96 | CD82, CD96 | CD85D, CD96 | — |
| CD63, CD97 | CD70, CD97 | CD82, CD97 | CD85D, CD97 | CD96, CD97 |
| CD63, CD99 | CD70, CD99 | CD82, CD99 | CD85D, CD99 | CD96, CD99 |
| CD63, CD100 | CD70, CD100 | CD82, CD100 | CD85D, CD100 | CD96, CD100 |
| CD63, CD102 | CD70, CD102 | CD82, CD102 | CD85D, CD102 | CD96, CD102 |
| CD63, CD117 | CD70, CD117 | CD82, CD117 | CD85D, CD117 | CD96, CD117 |
| CD63, CD120B | CD70, CD120B | CD82, CD120B | CD85D, CD120B | CD96, CD120B |
| CD63, CD123 | CD70, CD123 | CD82, CD123 | CD85D, CD123 | CD96, CD123 |
| CD63, CD127 | CD70, CD127 | CD82, CD127 | CD85D, CD127 | CD96, CD127 |
| CD63, CD133 | CD70, CD133 | CD82, CD133 | CD85D, CD133 | CD96, CD133 |
| CD63, CD135 | CD70, CD135 | CD82, CD135 | CD85D, CD135 | CD96, CD135 |
| CD63, CD148 | CD70, CD148 | CD82, CD148 | CD85D, CD148 | CD96, CD148 |
| CD63, CD157 | CD70, CD157 | CD82, CD157 | CD85D, CD157 | CD96, CD157 |
| CD63, CD172b | CD70, CD172b | CD82, CD172b | CD85D, CD172b | CD96, CD172b |
| CD63, CD191 | CD70, CD191 | CD82, CD191 | CD85D, CD191 | CD96, CD191 |
| CD63, CD217 | CD70, CD217 | CD82, CD217 | CD85D, CD217 | CD96, CD217 |
| CD63, CD300a | CD70, CD300a | CD82, CD300a | CD85D, CD300a | CD96, CD300a |
| CD63, CD305 | CD70, CD305 | CD82, CD305 | CD85D, CD305 | CD96, CD305 |
| CD63, CD317 | CD70, CD317 | CD82, CD317 | CD85D, CD317 | CD96, CD317 |
| CD63, CD321 | CD70, CD321 | CD82, CD321 | CD85D, CD321 | CD96, CD321 |
| CD63, CLL1 | CD70, CLL1 | CD82, CLL1 | CD85D, CLL1 | CD96, CLL1 |
| CD63, FOLR2 | CD70, FOLR2 | CD82, FOLR2 | CD85D, FOLR2 | CD96, FOLR2 |
| CD63, NKG2D Ligand | CD70, NKG2D Ligand | CD82, NKG2D Ligand | CD85D, NKG2D Ligand | CD96, NKG2D Ligand |
| CD63, EMR2 | CD70, EMR2 | CD82, EMR2 | CD85D, EMR2 | CD96, EMR2 |
| CD97, CD7 | CD99, CD7 | CD100, CD7 | CD102, CD7 | CD117, CD7 |
| CD97, CD11a | CD99, CD11a | CD100, CD11a | CD102, CD11a | CD117, CD11a |
| CD97, CD15 | CD99, CD15 | CD100, CD15 | CD102, CD15 | CD117, CD15 |
| CD97, CD18 | CD99, CD18 | CD100, CD18 | CD102, CD18 | CD117, CD18 |
| CD97, CD19 | CD99, CD19 | CD100, CD19 | CD102, CD19 | CD117, CD19 |
| CD97, CD20 | CD99, CD20 | CD100, CD20 | CD102, CD20 | CD117, CD20 |
| CD97, CD22 | CD99, CD22 | CD100, CD22 | CD102, CD22 | CD117, CD22 |
| CD97, CD25 | CD99, CD25 | CD100, CD25 | CD102, CD25 | CD117, CD25 |
| CD97, CD31 | CD99, CD31 | CD100, CD31 | CD102, CD31 | CD117, CD31 |
| CD97, CD33 | CD99, CD33 | CD100, CD33 | CD102, CD33 | CD117, CD33 |
| CD97, CD34 | CD99, CD34 | CD100, CD34 | CD102, CD34 | CD117, CD34 |
| CD97, CD37 | CD99, CD37 | CD100, CD37 | CD102, CD37 | CD117, CD37 |
| CD97, CD38 | CD99, CD38 | CD100, CD38 | CD102, CD38 | CD117, CD38 |
| CD97, CD44 | CD99, CD44 | CD100, CD44 | CD102, CD44 | CD117, CD44 |
| CD97, CD45 | CD99, CD45 | CD100, CD45 | CD102, CD45 | CD117, CD45 |
| CD97, CD47 | CD99, CD47 | CD100, CD47 | CD102, CD47 | CD117, CD47 |
| CD97, CD51 | CD99, CD51 | CD100, CD51 | CD102, CD51 | CD117, CD51 |
| CD97, CD56 | CD99, CD56 | CD100, CD56 | CD102, CD56 | CD117, CD56 |
| CD97, CD58 | CD99, CD58 | CD100, CD58 | CD102, CD58 | CD117, CD58 |
| CD97, CD59 | CD99, CD59 | CD100, CD59 | CD102, CD59 | CD117, CD59 |
| CD97, CD63 | CD99, CD63 | CD100, CD63 | CD102, CD63 | CD117, CD63 |
| CD97, CD70 | CD99, CD70 | CD100, CD70 | CD102, CD70 | CD117, CD70 |
| CD97, CD82 | CD99, CD82 | CD100, CD82 | CD102, CD82 | CD117, CD82 |
| CD97, CD85D | CD99, CD85D | CD100, CD85D | CD102, CD85D | CD117, CD85D |
| CD97, CD96 | CD99, CD96 | CD100, CD96 | CD102, CD96 | CD117, CD96 |
| — | CD99, CD97 | CD100, CD97 | CD102, CD97 | CD117, CD97 |
| CD97, CD99 | — | CD100, CD99 | CD102, CD99 | CD117, CD99 |
| CD97, CD100 | CD99, CD100 | — | CD102, CD100 | CD117, CD100 |
| CD97, CD102 | CD99, CD102 | CD100, CD102 | — | CD117, CD102 |
| CD97, CD117 | CD99, CD117 | CD100, CD117 | CD102, CD117 | — |
| CD97, CD120B | CD99, CD120B | CD100, CD120B | CD102, CD120B | CD117, CD120B |
| CD97, CD123 | CD99, CD123 | CD100, CD123 | CD102, CD123 | CD117, CD123 |
| CD97, CD127 | CD99, CD127 | CD100, CD127 | CD102, CD127 | CD117, CD127 |
| CD97, CD133 | CD99, CD133 | CD100, CD133 | CD102, CD133 | CD117, CD133 |
| CD97, CD135 | CD99, CD135 | CD100, CD135 | CD102, CD135 | CD117, CD135 |
| CD97, CD148 | CD99, CD148 | CD100, CD148 | CD102, CD148 | CD117, CD148 |
| CD97, CD157 | CD99, CD157 | CD100, CD157 | CD102, CD157 | CD117, CD157 |
| CD97, CD172b | CD99, CD172b | CD100, CD172b | CD102, CD172b | CD117, CD172b |
| CD97, CD191 | CD99, CD191 | CD100, CD191 | CD102, CD191 | CD117, CD191 |
| CD97, CD217 | CD99, CD217 | CD100, CD217 | CD102, CD217 | CD117, CD217 |
| CD97, CD300a | CD99, CD300a | CD100, CD300a | CD102, CD300a | CD117, CD300a |
| CD97, CD305 | CD99, CD305 | CD100, CD305 | CD102, CD305 | CD117, CD305 |
| CD97, CD317 | CD99, CD317 | CD100, CD317 | CD102, CD317 | CD117, CD317 |
| CD97, CD321 | CD99, CD321 | CD100, CD321 | CD102, CD321 | CD117, CD321 |
| CD97, CLL1 | CD99, CLL1 | CD100, CLL1 | CD102, CLL1 | CD117, CLL1 |

| | | | | |
|---|---|---|---|---|
| CD97, FOLR2 | CD99, FOLR2 | CD100, FOLR2 | CD102, FOLR2 | CD117, FOLR2 |
| CD97, NKG2D Ligand | CD99, NKG2D Ligand | CD100, NKG2D Ligand | CD102, NKG2D Ligand | CD117, NKG2D Ligand |
| CD97, EMR2 | CD99, EMR2 | CD100, EMR2 | CD102, EMR2 | CD117, EMR2 |
| CD120B, CD7 | CD123, CD7 | CD127, CD7 | CD133, CD7 | CD135, CD7 |
| CD120B, CD11a | CD123, CD11a | CD127, CD11a | CD133, CD11a | CD135, CD11a |
| CD120B, CD15 | CD123, CD15 | CD127, CD15 | CD133, CD15 | CD135, CD15 |
| CD120B, CD18 | CD123, CD18 | CD127, CD18 | CD133, CD18 | CD135, CD18 |
| CD120B, CD19 | CD123, CD19 | CD127, CD19 | CD133, CD19 | CD135, CD19 |
| CD120B, CD20 | CD123, CD20 | CD127, CD20 | CD133, CD20 | CD135, CD20 |
| CD120B, CD22 | CD123, CD22 | CD127, CD22 | CD133, CD22 | CD135, CD22 |
| CD120B, CD25 | CD123, CD25 | CD127, CD25 | CD133, CD25 | CD135, CD25 |
| CD120B, CD31 | CD123, CD31 | CD127, CD31 | CD133, CD31 | CD135, CD31 |
| CD120B, CD33 | CD123, CD33 | CD127, CD33 | CD133, CD33 | CD135, CD33 |
| CD120B, CD34 | CD123, CD34 | CD127, CD34 | CD133, CD34 | CD135, CD34 |
| CD120B, CD37 | CD123, CD37 | CD127, CD37 | CD133, CD37 | CD135, CD37 |
| CD120B, CD38 | CD123, CD38 | CD127, CD38 | CD133, CD38 | CD135, CD38 |
| CD120B, CD44 | CD123, CD44 | CD127, CD44 | CD133, CD44 | CD135, CD44 |
| CD120B, CD45 | CD123, CD45 | CD127, CD45 | CD133, CD45 | CD135, CD45 |
| CD120B, CD47 | CD123, CD47 | CD127, CD47 | CD133, CD47 | CD135, CD47 |
| CD120B, CD51 | CD123, CD51 | CD127, CD51 | CD133, CD51 | CD135, CD51 |
| CD120B, CD56 | CD123, CD56 | CD127, CD56 | CD133, CD56 | CD135, CD56 |
| CD120B, CD58 | CD123, CD58 | CD127, CD58 | CD133, CD58 | CD135, CD58 |
| CD120B, CD59 | CD123, CD59 | CD127, CD59 | CD133, CD59 | CD135, CD59 |
| CD120B, CD63 | CD123, CD63 | CD127, CD63 | CD133, CD63 | CD135, CD63 |
| CD120B, CD70 | CD123, CD70 | CD127, CD70 | CD133, CD70 | CD135, CD70 |
| CD120B, CD82 | CD123, CD82 | CD127, CD82 | CD133, CD82 | CD135, CD82 |
| CD120B, CD85D | CD123, CD85D | CD127, CD85D | CD133, CD85D | CD135, CD85D |
| CD120B, CD96 | CD123, CD96 | CD127, CD96 | CD133, CD96 | CD135, CD96 |
| CD120B, CD97 | CD123, CD97 | CD127, CD97 | CD133, CD97 | CD135, CD97 |
| CD120B, CD99 | CD123, CD99 | CD127, CD99 | CD133, CD99 | CD135, CD99 |
| CD120B, CD100 | CD123, CD100 | CD127, CD100 | CD133, CD100 | CD135, CD100 |
| CD120B, CD102 | CD123, CD102 | CD127, CD102 | CD133, CD102 | CD135, CD102 |
| CD120B, CD117 | CD123, CD117 | CD127, CD117 | CD133, CD117 | CD135, CD117 |
| — | CD123, CD120B | CD127, CD120B | CD133, CD120B | CD135, CD120B |
| CD120B, CD123 | — | CD127, CD123 | CD133, CD123 | CD135, CD123 |
| CD120B, CD127 | CD123, CD127 | — | CD133, CD127 | CD135, CD127 |
| CD120B, CD133 | CD123, CD133 | CD127, CD133 | — | CD135, CD133 |
| CD120B, CD135 | CD123, CD135 | CD127, CD135 | CD133, CD135 | — |
| CD120B, CD148 | CD123, CD148 | CD127, CD148 | CD133, CD148 | CD135, CD148 |
| CD120B, CD157 | CD123, CD157 | CD127, CD157 | CD133, CD157 | CD135, CD157 |
| CD120B, CD172b | CD123, CD172b | CD127, CD172b | CD133, CD172b | CD135, CD172b |
| CD120B, CD191 | CD123, CD191 | CD127, CD191 | CD133, CD191 | CD135, CD191 |
| CD120B, CD217 | CD123, CD217 | CD127, CD217 | CD133, CD217 | CD135, CD217 |
| CD120B, CD300a | CD123, CD300a | CD127, CD300a | CD133, CD300a | CD135, CD300a |
| CD120B, CD305 | CD123, CD305 | CD127, CD305 | CD133, CD305 | CD135, CD305 |
| CD120B, CD317 | CD123, CD317 | CD127, CD317 | CD133, CD317 | CD135, CD317 |
| CD120B, CD321 | CD123, CD321 | CD127, CD321 | CD133, CD321 | CD135, CD321 |
| CD120B, CLL1 | CD123, CLL1 | CD127, CLL1 | CD133, CLL1 | CD135, CLL1 |
| CD120B, FOLR2 | CD123, FOLR2 | CD127, FOLR2 | CD133, FOLR2 | CD135, FOLR2 |
| CD120B, NKG2D Ligand | CD123, NKG2D Ligand | CD127, NKG2D Ligand | CD133, NKG2D Ligand | CD135, NKG2D Ligand |
| CD120B, EMR2 | CD123, EMR2 | CD127, EMR2 | CD133, EMR2 | CD135, EMR2 |
| CD148, CD7 | CD157, CD7 | CD172b, CD7 | CD191, CD7 | CD217, CD7 |
| CD148, CD11a | CD157, CD11a | CD172b, CD11a | CD191, CD11a | CD217, CD11a |
| CD148, CD15 | CD157, CD15 | CD172b, CD15 | CD191, CD15 | CD217, CD15 |
| CD148, CD18 | CD157, CD18 | CD172b, CD18 | CD191, CD18 | CD217, CD18 |
| CD148, CD19 | CD157, CD19 | CD172b, CD19 | CD191, CD19 | CD217, CD19 |
| CD148, CD20 | CD157, CD20 | CD172b, CD20 | CD191, CD20 | CD217, CD20 |
| CD148, CD22 | CD157, CD22 | CD172b, CD22 | CD191, CD22 | CD217, CD22 |
| CD148, CD25 | CD157, CD25 | CD172b, CD25 | CD191, CD25 | CD217, CD25 |
| CD148, CD31 | CD157, CD31 | CD172b, CD31 | CD191, CD31 | CD217, CD31 |
| CD148, CD33 | CD157, CD33 | CD172b, CD33 | CD191, CD33 | CD217, CD33 |
| CD148, CD34 | CD157, CD34 | CD172b, CD34 | CD191, CD34 | CD217, CD34 |
| CD148, CD37 | CD157, CD37 | CD172b, CD37 | CD191, CD37 | CD217, CD37 |
| CD148, CD38 | CD157, CD38 | CD172b, CD38 | CD191, CD38 | CD217, CD38 |
| CD148, CD44 | CD157, CD44 | CD172b, CD44 | CD191, CD44 | CD217, CD44 |
| CD148, CD45 | CD157, CD45 | CD172b, CD45 | CD191, CD45 | CD217, CD45 |
| CD148, CD47 | CD157, CD47 | CD172b, CD47 | CD191, CD47 | CD217, CD47 |
| CD148, CD51 | CD157, CD51 | CD172b, CD51 | CD191, CD51 | CD217, CD51 |
| CD148, CD56 | CD157, CD56 | CD172b, CD56 | CD191, CD56 | CD217, CD56 |
| CD148, CD58 | CD157, CD58 | CD172b, CD58 | CD191, CD58 | CD217, CD58 |
| CD148, CD59 | CD157, CD59 | CD172b, CD59 | CD191, CD59 | CD217, CD59 |
| CD148, CD63 | CD157, CD63 | CD172b, CD63 | CD191, CD63 | CD217, CD63 |
| CD148, CD70 | CD157, CD70 | CD172b, CD70 | CD191, CD70 | CD217, CD70 |
| CD148, CD82 | CD157, CD82 | CD172b, CD82 | CD191, CD82 | CD217, CD82 |
| CD148, CD85D | CD157, CD85D | CD172b, CD85D | CD191, CD85D | CD217, CD85D |
| CD148, CD96 | CD157, CD96 | CD172b, CD96 | CD191, CD96 | CD217, CD96 |
| CD148, CD97 | CD157, CD97 | CD172b, CD97 | CD191, CD97 | CD217, CD97 |

-continued

| | | | | |
|---|---|---|---|---|
| CD148, CD99 | CD157, CD99 | CD172b, CD99 | CD191, CD99 | CD217, CD99 |
| CD148, CD100 | CD157, CD100 | CD172b, CD100 | CD191, CD100 | CD217, CD100 |
| CD148, CD102 | CD157, CD102 | CD172b, CD102 | CD191, CD102 | CD217, CD102 |
| CD148, CD117 | CD157, CD117 | CD172b, CD117 | CD191, CD117 | CD217, CD117 |
| CD148, CD120B | CD157, CD120B | CD172b, CD120B | CD191, CD120B | CD217, CD120B |
| CD148, CD123 | CD157, CD123 | CD172b, CD123 | CD191, CD123 | CD217, CD123 |
| CD148, CD127 | CD157, CD127 | CD172b, CD127 | CD191, CD127 | CD217, CD127 |
| CD148, CD133 | CD157, CD133 | CD172b, CD133 | CD191, CD133 | CD217, CD133 |
| CD148, CD135 | CD157, CD135 | CD172b, CD135 | CD191, CD135 | CD217, CD135 |
| — | CD157, CD148 | CD172b, CD148 | CD191, CD148 | CD217, CD148 |
| CD148, CD157 | — | CD172b, CD157 | CD191, CD157 | CD217, CD157 |
| CD148, CD172b | CD157, CD172b | — | CD191, CD172b | CD217, CD172b |
| CD148, CD191 | CD157, CD191 | CD172b, CD191 | — | CD217, CD191 |
| CD148, CD217 | CD157, CD217 | CD172b, CD217 | CD191, CD217 | — |
| CD148, CD300a | CD157, CD300a | CD172b, CD300a | CD191, CD300a | CD217, CD300a |
| CD148, CD305 | CD157, CD305 | CD172b, CD305 | CD191, CD305 | CD217, CD305 |
| CD148, CD317 | CD157, CD317 | CD172b, CD317 | CD191, CD317 | CD217, CD317 |
| CD148, CD321 | CD157, CD321 | CD172b, CD321 | CD191, CD321 | CD217, CD321 |
| CD148, CLL1 | CD157, CLL1 | CD172b, CLL1 | CD191, CLL1 | CD217, CLL1 |
| CD148, FOLR2 | CD157, FOLR2 | CD172b, FOLR2 | CD191, FOLR2 | CD217, FOLR2 |
| CD148, NKG2D Ligand | CD157, NKG2D Ligand | CD172b, NKG2D Ligand | CD191, NKG2D Ligand | CD217, NKG2D Ligand |
| CD148, EMR2 | CD157, EMR2 | CD172b, EMR2 | CD191, EMR2 | CD217, EMR2 |

(i) Mutated Lineage-Specific Cell-Surface Antigens

In some embodiments, the hematopoietic cells (HSCs) described herein may contain an edited gene encoding one or more lineage-specific cell-surface proteins of interest in mutated form (mutants or variants, which are used herein interchangeably), which has reduced binding or no binding to a cytotoxic agent as described herein. The variants may lack the epitope to which the cytotoxic agent binds. Alternatively, the mutants may carry one or more mutations of the epitope to which the cytotoxic agent binds, such that binding to the cytotoxic agent is reduced or abolished as compared to the natural or wild-type lineage-specific cell-surface protein counterpart. Such a variant is preferred to maintain substantially similar biological activity as the wild-type counterpart.

As used herein, the term "reduced binding" refers to binding that is reduced by at least 25%. The level of binding may refer to the amount of binding of the cytotoxic agent to a hematopoietic cell or descendant thereof or the amount of binding of the cytotoxic agent to the lineage-specific cell-surface protein. The level of binding of a hematopoietic cell or descendant thereof that has been manipulated to a cytotoxic agent may be relative to the level of binding of the cytotoxic agent to a hematopoietic cell or descendant thereof that has not been manipulated as determined by the same assay under the same conditions. Alternatively, the level of binding of a lineage-specific cell-surface protein that lacks an epitope to a cytotoxic agent may be relative to the level of binding of the cytotoxic agent to a lineage-specific cell-surface protein that contains the epitope (e.g., a wild-type protein) as determined by the same assay under the same conditions. In some embodiments, the binding is reduced by at least 25%, 30%, 40%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, the binding is reduced such that there is substantially no detectable binding in a conventional assay.

As used herein, "no binding" refers to substantially no binding, e.g., no detectable binding or only baseline binding as determined in a conventional binding assay. In some embodiments, there is no binding between the hematopoietic cells or descendants thereof that have been manipulated and the cytotoxic agent. In some embodiments, there is no detectable binding between the hematopoietic cells or descendants thereof that have been manipulated and the cytotoxic agent. In some embodiments, no binding of the hematopoietic cells or descendant thereof to the cytotoxic agent refers to a baseline level of binding, as shown using any conventional binding assay known in the art. In some embodiments, the level of binding of the hematopoietic cells or descendants thereof that have been manipulated and the cytotoxic agent is not biologically significant. The term "no binding" is not intended to require the absolute absence of binding.

A cell that is "negative" for a given lineage-specific cell-surface antigen has a substantially reduced expression level of the lineage-specific antigen as compared with its naturally-occurring counterpart (e.g., otherwise similar, unmodified cells), e.g., not detectable or not distinguishable from background levels, e.g., using a flow cytometry assay, e.g., an assay of Example 1. In some instances, a cell that is negative for the lineage-specific cell-surface antigen has a level of less than 10%, 5%, 2%, or 1% of as compared with its naturally-occurring counterpart. The variant may share a sequence homology of at least 80% (e.g., 85%, 90%, 95%, 97%, 98%, 99%, or above) as the wild-type counterpart and, in some embodiments, may contain no other mutations in addition to those for mutating or deleting the epitope of interest. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST™ and XBLAST™ programs (version 2.0) of Altschul, et al. *J. Mol. Biol.* 215:403-10, 1990. BLAST™ protein searches can be performed with the XBLAST™ program, score=50, wordlength=3 to obtain amino acid sequences homologous to the protein molecules of the invention. Where gaps exist between two sequences, Gapped BLAST™ can be utilized as described in Altschul et al., *Nucleic Acids Res.* 25(17):3389-3402, 1997. When utilizing BLAST™ and Gapped BLAST™ programs, the default parameters of the respective programs (e.g., XBLAST™ and NBLAST™) can be used.

In some instances, the variant contains one or more amino acid residue substitutions (e.g., 2, 3, 4, 5, or more) within the epitope of interest such that the cytotoxic agent does not bind or has reduced binding to the mutated epitope. Such a variant may have substantially reduced binding affinity to the cytotoxic agent (e.g., having a binding affinity that is at least 40%, 50%, 60%, 70%, 80% or 90% lower than its wild-type counterpart). In some examples, such a variant may have abolished binding activity to the cytotoxic agent. In other instances, the variant contains a deletion of a region that comprises the epitope of interest. Such a region may be encoded by an exon. In some embodiments, the region is a domain of the lineage-specific cell-surface protein of interest that encodes the epitope. In one example, the variant has just the epitope deleted. The length of the deleted region may range from 3-60 amino acids, e.g., 5-50, 5-40, 10-30, 10-20, etc.

The mutation(s) or deletions in a mutant of a lineage-specific cell-surface antigen may be within or surround a non-essential epitope such that the mutation(s) or deletion(s) do not substantially affect the bioactivity of the protein.

As used herein, the term "epitope" refers to an amino acid sequence (linear or conformational) of a protein, such as a lineage-specific cell-surface antigens, that is bound by the CDRs of an antibody. In some embodiments, the cytotoxic agent binds to one or more (e.g., at least 2, 3, 4, 5 or more) epitopes of a lineage-specific cell-surface antigens. In some embodiments, the cytotoxic agent binds to more than one epitope of the lineage-specific cell-surface antigen and the hematopoietic cells are manipulated such that each of the epitopes is absent and/or unavailable for binding by the cytotoxic agent.

In some embodiments, the genetically engineered HSCs described herein have one or more edited genes of lineage-specific cell-surface antigens such that the edited genes express mutated lineage-specific cell-surface antigens with mutations in one or more non-essential epitopes. A non-essential epitope (or a fragment comprising such) refers to a domain within the lineage-specific protein, the mutation in which (e.g., deletion) is less likely to substantially affect the bioactivity of the lineage-specific protein and thus the bioactivity of the cells expressing such. For example, when hematopoietic cells comprising a deletion or mutation of a non-essential epitope of a lineage-specific cell-surface antigen, such hematopoietic cells are able to proliferate and/or undergo erythropoietic differentiation to a similar level as hematopoietic cells that express a wild-type lineage-specific cell-surface antigen.

Non-essential epitopes of a lineage-specific cell-surface antigen can be identified by the methods described herein or by conventional methods relating to protein structure-function prediction. For example, a non-essential epitope of a protein can be predicted based on comparing the amino acid sequence of a protein from one species with the sequence of the protein from other species. Non-conserved domains are usually not essential to the functionality of the protein. As will be evident to one of ordinary skill in the art, non-essential epitope of a protein is predicted using an algorithm or software, such as the PROVEAN software (see, e.g., see: provean.jcvi.org; Choi et al. *PLoS ONE* (2012) 7(10): e46688), to predict potential non-essential epitopes in a lineage-specific protein of interest ("candidate non-essential epitope"). Mutations, including substitution and/or deletion, many be made in any one or more amino acid residues of a candidate non-essential epitope using convention nucleic acid modification technologies. The protein variants thus prepared may be introduced into a suitable type of cells, such as hematopoietic cells, and the functionality of the protein variant can be investigated to confirm that the candidate non-essential epitope is indeed a non-essential epitope.

Alternatively, a non-essential epitope of a lineage-specific cell-surface antigen may be identified by introducing a mutation into a candidate region in a lineage-specific protein of interest in a suitable type of host cells (e.g., hematopoietic cells) and examining the functionality of the mutated lineage-specific protein in the host cells. If the mutated lineage-specific protein maintains substantially the biological activity of the native counterpart, this indicates that the region where the mutation is introduced is non-essential to the function of the lineage-specific protein.

Methods for assessing the functionality of the lineage-specific cell-surface antigen and the hematopoietic cells or descendants thereof will be known in the art and include, for example, proliferation assays, differentiation assays, colony formation, expression analysis (e.g., gene and/or protein), protein localization, intracellular signaling, functional assays, and in vivo humanized mouse models.

Any of the methods for identifying and/or verifying non-essential epitopes in lineage-specific cell-surface antigens is also within the scope of the present disclosure.

(ii) Hematopoietic Stem Cells

In some embodiments, the hematopoietic cells described herein are hematopoietic stem cells. Hematopoietic stem cells (HSCs) are capable of giving rise to both myeloid and lymphoid progenitor cells that further give rise to myeloid cells (e.g., monocytes, macrophages, neutrophils, basophils, dendritic cells, erythrocytes, platelets, etc) and lymphoid cells (e.g., T cells, B cells, NK cells), respectively. HSCs are characterized by the expression of the cell surface marker CD34 (e.g., CD34$^+$), which can be used for the identification and/or isolation of HSCs, and absence of cell surface markers associated with commitment to a cell lineage.

In some embodiments, the HSCs are obtained from a subject, such as a mammalian subject. In some embodiments, the mammalian subject is a non-human primate, a rodent (e.g., mouse or rat), a bovine, a porcine, an equine, or a domestic animal. In some embodiments, the HSCs are obtained from a human patient, such as a human patient having a hematopoietic malignancy. In some embodiments, the HSCs are obtained from a healthy donor. In some embodiments, the HSCs are obtained from the subject to whom the immune cells expressing the chimeric receptors will be subsequently administered. HSCs that are administered to the same subject from which the cells were obtained are referred to as autologous cells, whereas HSCs that are obtained from a subject who is not the subject to whom the cells will be administered are referred to as allogeneic cells.

In some embodiments, the HSCs that are administered to the subject are allogeneic cells. In some embodiments, the HSCs are obtained from a donor having a HLA haplotype that is matched with the HLA haplotype of the subject. Human Leukocyte Antigen (HLA) encodes major histocompatibility complex (MHC) proteins in humans. MHC molecules are present on the surface of antigen-presenting cells as well as many other cell types and present peptides of self and non-self (e.g., foreign) antigens for immunosurveillance. However, HLA are highly polymorphic, which results in many distinct alleles. Different (foreign, non-self) alleles may be antigenic and stimulate robust adverse immune responses, particularly in organ and cell transplantation. HLA molecules that are recognized as foreign (non-self) can result in transplant rejection. In some embodiments, it is desirable to administer HSCs from donor that has the same HLA type as the patient to reduce the incidence of rejection.

The HLA loci of a donor subject may be typed to identify an individual as a HLA-matched donor for the subject. Methods for typing the HLA loci will be evident to one of ordinary skill in the art and include, for example, serology (serotyping), cellular typing, gene sequencing, phenotyping, and PCR methods. A HLA from a donor is considered "matched" with the HLA of the subject if the HLA loci of the donor and the subject are identical or sufficiently similar such that an adverse immune response is not expected.

In some embodiments, the HLA from the donor is not matched with the HLA of the subject. In some embodiments, the subject is administered HSCs that are not HLA matched with the HLA of the subject. In some embodiments, the subject is further administered one or more immunosuppressive agents to reduce or prevent rejection of the donor HSC cells. In some embodiments, the HSCs do not comprise a CART.

HSCs may be obtained from any suitable source using convention means known in the art. In some embodiments, HSCs are obtained from a sample from a subject (or donor), such as bone marrow sample or from a blood sample. Alternatively or in addition, HSCs may be obtained from an umbilical cord. In some embodiments, the HSCs are from bone marrow, cord blood cells, or peripheral blood mononuclear cells (PBMCs). In general, bone marrow cells may be obtained from iliac crest, femora, tibiae, spine, rib or other medullary spaces of a subject (or donor). Bone marrow may be taken out of the patient and isolated through various separations and washing procedures known in the art. An exemplary procedure for isolation of bone marrow cells comprises the following steps: a) extraction of a bone marrow sample; b) centrifugal separation of bone marrow suspension in three fractions and collecting the intermediate fraction, or buffycoat; c) the buffycoat fraction from step (b) is centrifuged one more time in a separation fluid, commonly Ficoll™, and an intermediate fraction which contains the bone marrow cells is collected; and d) washing of the collected fraction from step (c) for recovery of re-transfusable bone marrow cells.

HSCs typically reside in the bone marrow but can be mobilized into the circulating blood by administering a mobilizing agent in order to harvest HSCs from the peripheral blood. In some embodiments, the subject (or donor) from which the HSCs are obtained is administered a mobilizing agent, such as granulocyte colony-stimulating factor (G-CSF). The number of the HSCs collected following mobilization using a mobilizing agent is typically greater than the number of cells obtained without use of a mobilizing agent.

The HSCs for use in the methods described herein may express the lineage-specific cell-surface antigen of interest. Upon any of the modifications described herein (e.g., genetic modification or incubation with a blocking agent), the HSCs would not be targeted by the cytotoxicity agent also described herein. Alternatively, the HSCs for use in the methods described herein may not express the lineage-specific cell surface protein of interest (e.g., CD19); however, descendant cells differentiated from the HSCs (e.g., B cells) express the lineage-specific cell surface protein. Upon genetic modification, an endogenous gene of the HSCs coding for the lineage-specific cell surface protein may be disrupted at a region encoding a non-essential epitope of the lineage-specific cell surface protein. Descendant cells differentiated from such modified HSCs (e.g., in vivo) would express a modified lineage-specific cell surface protein having the non-essential epitope mutated such that they would not be targeted by the cytotoxicity agent capable of binding the non-essential epitope.

In some embodiments, a sample is obtained from a subject (or donor) and is then enriched for a desired cell type (e.g. $CD34^+/CD33^-$ cells). For example, PBMCs and/or $CD34^+$ hematopoietic cells can be isolated from blood as described herein. Cells can also be isolated from other cells, for example by isolation and/or activation with an antibody binding to an epitope on the cell surface of the desired cell type. Another method that can be used includes negative selection using antibodies to cell surface markers to selectively enrich for a specific cell type without activating the cell by receptor engagement.

Populations of HSC can be expanded prior to or after manipulating the HSC such that they don't bind the cytotoxic agent or have reduced binding to the cytotoxic agent. The cells may be cultured under conditions that comprise an expansion medium comprising one or more cytokines, such as stem cell factor (SCF), Flt-3 ligand (Flt3L), thrombopoietin (TPO), Interleukin 3 (IL-3), or Interleukin 6 (IL-6). The cell may be expanded for about 1, 2, 3, 4, 5, 6, 7, 8, 9, 10, 11, 12, 13, 14, 15, 16, 17, 18, 19, 20, 21, 22, 23, 24, 25 days or any range necessary. In some embodiments, the HSC are expanded after isolation of a desired cell population (e.g., $CD34^+/CD33^-$) from a sample obtained from a subject (or donor) and prior to manipulation (e.g., genetic engineering, contact with a blocking agent). In some embodiments, the HSC are expanded after genetic engineering, thereby selectively expanding cells that have undergone the genetic modification and lack the epitope (e.g., have a deletion or substitution of at least a portion of the epitope) of the lineage-specific cell-surface antigen to which the cytotoxic agent binds. In some embodiments, a cell ("a clone") or several cells having a desired characteristic (e.g., phenotype or genotype) following genetic modification may be selected and independently expanded. In some embodiments, the HSC are expanded prior to contacting the HSC with a blocking agent that binds the epitope of the lineage-specific cell-surface antigens, thereby providing a population of HSC expressing the lineage-specific cell-surface antigens that cannot be bound by the cytotoxic agent due to blocking of the corresponding epitope by the blocking agent.

(iii) Preparation of Genetically Engineered Hematopoietic Cells

Any of the genetically engineering hematopoietic cells, such as HSCs, that carry edited genes of one or more lineage-specific cell-surface antigens can be prepared by a routine method or by a method described herein. In some embodiments, the genetic engineering is performed using genome editing. As used herein, "genome editing" refers to a method of modifying the genome, including any protein-coding or non-coding nucleotide sequence, of an organism to knock out the expression of a target gene. In general, genome editing methods involve use of an endonuclease that is capable of cleaving the nucleic acid of the genome, for example at a targeted nucleotide sequence. Repair of the double-stranded breaks in the genome may be repaired introducing mutations and/or exogenous nucleic acid may be inserted into the targeted site.

Genome editing methods are generally classified based on the type of endonuclease that is involved in generating double stranded breaks in the target nucleic acid. These methods include use of zinc finger nucleases (ZFN), transcription activator-like effector-based nuclease (TALEN), meganucleases, and CRISPR/Cas systems.

In some embodiments, the modified cells are manipulated as described herein using the TALEN technology known in the art. In general, TALENs are engineered restriction enzymes that can specifically bind and cleave a desired target DNA molecule. A TALEN typically contains a Transcriptional Activator-Like Effector (TALE) DNA-binding domain fused to a DNA cleavage domain. The DNA binding domain may contain a highly conserved 33-34 amino acid sequence with a divergent 2 amino acid RVD (repeat variable dipeptide motif) at positions 12 and 13. The RVD motif determines binding specificity to a nucleic acid sequence and can be engineered according to methods known to those of skill in the art to specifically bind a desired DNA sequence. In one example, the DNA cleavage domain may be derived from the FokI endonuclease. The FokI domain functions as a dimer, requiring two constructs with unique DNA binding domains for sites in the target genome with proper orientation and spacing. TALENs specific to sequences in a target gene of interest (e.g., CD19, CD33) can be constructed using any method known in the art.

A TALEN specific to a target gene of interest can be used inside a cell to produce a double-stranded break (DSB). A mutation can be introduced at the break site if the repair mechanisms improperly repair the break via non-homologous end joining. For example, improper repair may introduce a frame shift mutation. Alternatively, a foreign DNA molecule having a desired sequence can be introduced into the cell along with the TALEN. Depending on the sequence of the foreign DNA and chromosomal sequence, this process can be used to correct a defect or introduce a DNA fragment into a target gene of interest, or introduce such a defect into the endogenous gene, thus decreasing expression of the target gene.

In some embodiments, one or more population of hematopoietic cells is generated by genetic engineering of a lineage-specific cell-surface antigen (e.g., those described herein) using a TALEN. The genetically engineered hematopoietic cells may not express the lineage-specific cell-surface antigen. Alternatively, the hematopoietic cells may be engineered to express an altered version of the lineage-specific cell-surface antigen, e.g., having a deletion or mutation relative to the wild-type counterpart. Such a mutated lineage-specific cell-surface antigen may preserve a certain level of the bioactivity as the wild-type counterpart. In some embodiments, a population of hematopoietic cells containing a mutated CD33 is generated by genetic engineering using a TALEN. In some embodiments, exon 2 or exon 3 of CD33 is mutated using a TALEN. In some examples, a population of hematopoietic cells containing a mutated CD19 is generated by genetic engineering using a TALEN. In some embodiments, exon 2 or exon 4 of CD19 is mutated using a TALEN.

In some embodiments, the cells can be genetically manipulated using zinc finger (ZFN) technology known in the art. In general, zinc finger mediated genomic editing involves use of a zinc finger nuclease, which typically comprises a DNA binding domain (i.e., zinc finger) and a cleavage domain (i.e., nuclease). The zinc finger binding domain may be engineered to recognize and bind to any target gene of interest (e.g., CD19, CD33) using methods known in the art and in particular, may be designed to recognize a DNA sequence ranging from about 3 nucleotides to about 21 nucleotides in length, or from about 8 to about 19 nucleotides in length. Zinc finger binding domains typically comprise at least three zinc finger recognition regions (e.g., zinc fingers).

Restriction endonucleases (restriction enzymes) capable of sequence-specific binding to DNA (at a recognition site) and cleaving DNA at or near the site of binding are known in the art and may be used to form ZFN for use in genomic editing. For example, Type IIS restriction endonucleases cleave DNA at sites removed from the recognition site and have separable binding and cleavage domains. In one example, the DNA cleavage domain may be derived from the FokI endonuclease.

In some embodiments, one or more population of hematopoietic cells is generated by genetic engineering of a lineage-specific cell-surface antigen (e.g., those described herein) using a ZFN. The genetically engineered hematopoietic cells may not express the lineage-specific cell-surface antigen. Alternatively, the hematopoietic cells may be engineered to express an altered version of the lineage-specific cell-surface antigen, e.g., having a deletion or mutation relative to the wild-type counterpart. Such a mutated lineage-specific cell-surface antigen may preserve a certain level of the bioactivity as the wild-type counterpart.

In some examples, a population of hematopoietic cells containing a mutated CD33 is generated by genetic engineering using a ZFN. In some embodiments, exon 2 or exon 3 of CD33 is mutated using a ZFN. In some examples, a population of hematopoietic cells containing a mutated CD19 is generated by genetic engineering using a ZFN. In some embodiments, exon 2 or exon 4 of CD19 is mutated using a ZFN.

In one aspect of the present disclosure, the replacement of cancer cells by a modified population of normal cells is performed using normal cells that have been manipulated such that the cells do not bind the cytotoxic agent. Such modification may include the deletion or mutation of an epitope of the lineage specific protein using a CRISPR-Cas system, where the Clustered Regularly Interspaced Short Palindromic Repeats (CRISPR)-Cas system is an engineered, non-naturally occurring CRISPR-Cas system.

The present disclosure utilizes the CRISPR/Cas system that hybridizes with a target sequence in a lineage specific protein polynucleotide, where the CRISPR/Cas system comprises a Cas endonuclease and an engineered crRNA/tracrRNA (or single guide RNA). In some embodiments, the CRISPR/Cas system includes a crRNA and does not include a tracrRNA sequence. CRISPR/Cas complex can bind to the lineage specific protein polynucleotide and allow the cleavage of the protein polynucleotide, thereby modifying the polynucleotide.

The CRISPR/Cas system of the present disclosure may bind to and/or cleave the region of interest within a cell-surface lineage-specific protein in a coding or non-coding region, within or adjacent to the gene, such as, for example, a leader sequence, trailer sequence or intron, or within a non-transcribed region, either upstream or downstream of the coding region. The guide RNAs (gRNAs) used in the present disclosure may be designed such that the gRNA directs binding of the Cas enzyme-gRNA complexes to a pre-determined cleavage sites (target site) in a genome. The cleavage sites may be chosen so as to release a fragment that contains a region of unknown sequence, or a region containing a SNP, nucleotide insertion, nucleotide deletion, rearrangement, etc.

Cleavage of a gene region may comprise cleaving one or two strands at the location of the target sequence by the Cas enzyme. In one embodiment, such, cleavage can result in decreased transcription of a target gene. In another embodiment, the cleavage can further comprise repairing the cleaved target polynucleotide by homologous recombination with an exogenous template polynucleotide, wherein the repair results in an insertion, deletion, or substitution of one or more nucleotides of the target polynucleotide.

The terms "gRNA," "guide RNA" and "CRISPR guide sequence" may be used interchangeably throughout and refer to a nucleic acid comprising a sequence that determines the specificity of a Cas DNA binding protein of a CRISPR/Cas system. A gRNA hybridizes to (complementary to, partially or completely) a target nucleic acid sequence in the genome of a host cell. The gRNA or portion thereof that hybridizes to the target nucleic acid may be between 15-25 nucleotides, 18-22 nucleotides, or 19-21 nucleotides in length. In some embodiments, the gRNA sequence that hybridizes to the target nucleic acid is 15, 16, 17, 18, 19, 20, 21, 22, 23, 24, or 25 nucleotides in length. In some embodiments, the gRNA sequence that hybridizes to the target nucleic acid is between 10-30, or between 15-25, nucleotides in length.

In addition to a sequence that binds to a target nucleic acid, in some embodiments, the gRNA also comprises a scaffold sequence. Expression of a gRNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gRNA may be referred to as a single guide RNA (sgRNA).

As used herein, a "scaffold sequence," also referred to as a tracrRNA, refers to a nucleic acid sequence that recruits a Cas endonuclease to a target nucleic acid bound (hybridized) to a complementary gRNA sequence. Any scaffold sequence that comprises at least one stem loop structure and recruits an endonuclease may be used in the genetic elements and vectors described herein. Exemplary scaffold sequences will be evident to one of skill in the art and can be found, for example, in Jinek, et al. *Science* (2012) 337(6096):816-821, Ran, et al. *Nature Protocols* (2013) 8:2281-2308, PCT Application No. WO2014/093694, and PCT Application No. WO2013/176772. In some embodiments, the CRISPR-Cas system does not include a tracrRNA sequence.

In some embodiments, the gRNA sequence does not comprise a scaffold sequence and a scaffold sequence is expressed as a separate transcript. In such embodiments, the gRNA sequence further comprises an additional sequence that is complementary to a portion of the scaffold sequence and functions to bind (hybridize) the scaffold sequence and recruit the endonuclease to the target nucleic acid.

In some embodiments, the gRNA sequence is at least 50%, 55%, 60%, 65%, 70%, 75%, 80%, 85%, 90%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (Upadhyay, et al. *Genes Genome Genetics* (2013) 3(12):2233-2238). In some embodiments, the gRNA sequence is at least 50%, 55%, 60%, 65%, 70%, 75%, 80%, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

Example sgRNA sequences targeting intron 1, intron 2 or intron 4 of CD19 are provided in Table 3. Example sgRNA sequence targeting introns 1 and 2 of CD33 are provided in Table 4. Additional guide RNAs for editing CD19 and CD33 are provide below. As will be evident to one of ordinary skill in the art, selection of sgRNA sequences may depend on factors such as the number of predicted on-target and/or off-target binding sites. In some embodiments, the sgRNA sequence is selected to maximize potential on-target and minimize potential off-target sites.

As would be evident to one of ordinary skill in the art, various tools may be used to design and/or optimize the sequence of a sgRNA, for example to increase the specificity and/or precision of genomic editing. In general, candidate sgRNAs may be designed by identifying a sequence within the target region that has a high predicted On-target efficiency and low Off-target efficiency based on any of the available web-based tools. Candidate sgRNAs may be further assessed by manual inspection and/or experimental screening. Examples of web-based tools include, without limitation, CRISPR seek, CRISPR Design Tool, Cas-OFFinder, E-CRISP, ChopChop, CasOT, CRISPR direct, CRISPOR, BREAKING-CAS, CrispRGold, and CCTop. See, e.g., Safari, et al. *Current Pharma. Biotechol.* (2017) 18(13).

In some embodiments, the Cas endonuclease is a Cas9 nuclease (or variant thereof) or a Cpf1 nuclease (or variant thereof). Cas9 endonucleases cleave double stranded DNA of a target nucleic acid resulting in blunt ends, whereas cleavage with Cpf1 nucleases results in staggered ends of the nucleic acid.

In general, the target nucleic acid is flanked on the 3' side or 5' side by a protospacer adjacent motif (PAM) that may interact with the endonuclease and be further involved in targeting the endonuclease activity to the target nucleic acid. It is generally thought that the PAM sequence flanking the target nucleic acid depends on the endonuclease and the source from which the endonuclease is derived. For example, for Cas9 endonucleases that are derived from *Streptococcus pyogenes*, the PAM sequence is NGG, although the PAM sequences NAG and NGA may be recognized with lower efficiency. For Cas9 endonucleases derived from *Staphylococcus aureus*, the PAM sequence is NNGRRT (SEQ ID NO: 104). For Cas9 endonucleases that are derived from *Neisseria meningitidis*, the PAM sequence is NNNNGATT (SEQ ID NO: 105) or the degenerate PAM sequence NNNNGHTT (SEQ ID NO: 106). See, e.g., Adli *Nature Communications* (2018)9:1191. Cas9 endonucleases derived from *Streptococcus thermophilus*, St1Cas9 and St3Cas9, the PAM sequences are NNAGAAW (SEQ ID NO: 107) and NGGNG (SEQ ID NO: 108), respectively. For Cas9 endonuclease derived from *Treponema denticola*, the PAM sequence is NAAAAC (SEQ ID NO: 109). For Cas9 endonuclease derived from *Streptococcus canis* the PAM sequence is NNG (SEQ ID NO: 110). See, Chatterjee, et al. *Sci. Adv.* (2018) 4: eaau0766. For Cas9 endonuclease derived from *Campylobacter jejuni*, the PAM sequence is NNNNACAC (SEQ ID NO: 111). See, e.g., Adli *Nature Communications* (2018)9:1191.

In some embodiments, the Cas endonuclease is a Cpf1 nuclease. In contrast to Cas9 endonucleases, Cpf1 endonuclease generally do not require a tracrRNA sequence and recognize a PAM sequence located at the 5' end of the target nucleic acid. For a Cpf1 nuclease, the PAM sequence is TTTN (SEQ ID NO: 112). In some embodiments, the Cas endonuclease is MAD7 (also referred to as Cpf1 nuclease from *Eubacterium rectale*) and the PAM sequence is YTTTN (SEQ ID NO: 113).

In some embodiments, genetically engineering a cell also comprises introducing a Cas endonuclease into the cell. In some embodiments, the Cas endonuclease and the nucleic acid encoding the gRNA are provided on the same nucleic acid (e.g., a vector). In some embodiments, the Cas endonuclease and the nucleic acid encoding the gRNA are provided on different nucleic acids (e.g., different vectors). Alternatively or in addition, the Cas endonuclease may be provided or introduced into the cell in protein form.

In some embodiments, the Cas endonuclease is a Cas9 enzyme or variant thereof. In some embodiments, the Cas9 endonuclease is derived from *Streptococcus pyogenes* (SpCas9), *Staphylococcus aureus* (SaCas9), *Streptococcus canis* (ScCas9), *Neisseria meningitidis* (NmCas9), *Streptococcus thermophilus, Campylobacter jejuni* (CjCas9), or *Treponema denticola*. In some embodiments, the nucleotide sequence encoding the Cas endonuclease may be codon optimized for expression in a host cell. In some embodiments, the endonuclease is a Cas9 homolog or ortholog.

In some embodiments, the nucleotide sequence encoding the Cas9 endonuclease is further modified to alter the activity of the protein. In some embodiments, the Cas9 endonuclease has been modified to inactivate one or more catalytic residues of the endonuclease. In some embodiments, the Cas9 endonuclease has been modified to inactivate one of the catalytic residues of the endonuclease, referred to as a "nickase" or "Cas9n". Cas9 nickase endonucleases cleave one DNA strand of the target nucleic acid. See, e.g., Dabrowska et al. *Frontiers in Neuroscience* (2018) 12(75). It has been shown that one or more mutations in the RuvC and HNH catalytic domains of the enzyme may improve Cas9 efficiency. See, e.g., Sarai et al. *Currently Pharma. Biotechnol.* (2017) 18(13). In some embodiments, the Cas9 nickase comprises a mutation at amino acid position D10 and/or H840. In some examples, the Cas9 nickase comprises the substitution mutation D10A and/or H840A.

In some embodiments, the methods described herein involve two distinct cleavage reactions, in which one Cas9 nickase is directed to cleave one DNA strand of the target nucleic acid and a Cas9 nickase is directed to cleave the second DNA strand of the target nucleic acid.

In some embodiments, the Cas9 endonuclease is a catalytically inactive Cas9. For example, dCas9 contains mutations of catalytically active residues (D10 and H840) and does not have nuclease activity. Alternatively or in addition, the Cas9 endonuclease may be fused to another protein or portion thereof. In some embodiments, dCas9 is fused to a repressor domain, such as a KRAB domain. In some embodiments, such dCas9 fusion proteins are used with the constructs described herein for multiplexed gene repression (e.g., CRISPR interference (CRISPRi)). In some embodiments, dCas9 is fused to an activator domain, such as VP64 or VPR. In some embodiments, such dCas9 fusion proteins are used with the constructs described herein for gene activation (e.g., CRISPR activation (CRISPRa)). In some embodiments, dCas9 is fused to an epigenetic modulating domain, such as a histone demethylase domain or a histone acetyltransferase domain. In some embodiments, dCas9 is fused to a LSD1 or p300, or a portion thereof. In some embodiments, the dCas9 fusion is used for CRISPR-based epigenetic modulation. In some embodiments, dCas9 or Cas9 is fused to a FokI nuclease domain (referred to as "FokI-dCas9"). In some embodiments, Cas9 or dCas9 fused to a FokI nuclease domain is used for genome editing. See, e.g., Safari et al. *Current Pharma. Biotechnol.* (2017):18. In some embodiments, Cas9 or dCas9 is fused to a fluorescent protein (e.g., GFP, RFP, mCherry, etc.). In some embodiments, Cas9/dCas9 proteins fused to fluorescent proteins are used for labeling and/or visualization of genomic loci or identifying cells expressing the Cas endonuclease.

In some embodiments, the Cas endonuclease is modified to enhance specificity of the enzyme (e.g., reduce off-target effects, maintain robust on-target cleavage). In some embodiments, the Cas endonuclease is an enhanced specificity Cas9 variant (e.g., eSPCas9). See, e.g., Slaymaker et al. *Science* (2016) 351 (6268): 84-88. In some embodiments, the Cas endonuclease is a high fidelity Cas9 variant (e.g., SpCas9-HF1). See, e.g., Kleinstiver et al. *Nature* (2016) 529: 490-495.

Cas enzymes, such as Cas endonucleases, are known in the art and may be obtained from various sources and/or engineered/modified to modulate one or more activities or specificities of the enzymes. In some embodiments, the Cas enzyme has been engineered/modified to recognize one or more PAM sequence. In some embodiments, the Cas enzyme has been engineered/modified to recognize one or more PAM sequence that is different than the PAM sequence the Cas enzyme recognizes without engineering/modification. In some embodiments, the Cas enzyme has been engineered/modified to reduce off-target activity of the enzyme.

In some embodiments, the nucleotide sequence encoding the Cas endonuclease is modified further to alter the specificity of the endonuclease activity (e.g., reduce off-target cleavage, decrease the Cas endonuclease activity or lifetime in cells, increase homology-directed recombination and reduce non-homologous end joining). See, e.g., Komor et al. *Cell* (2017) 168: 20-36. In some embodiments, the nucleotide sequence encoding the Cas endonuclease is modified to alter the PAM recognition of the endonuclease. For example, the Cas endonuclease SpCas9 recognizes PAM sequence NGG, whereas relaxed variants of the SpCas9 comprising one or more modifications of the endonuclease (e.g., VQR SpCas9, EQR SpCas9, VRER SpCas9) may recognize the PAM sequences NGA, NGAG (SEQ ID NO: 114), NGCG (SEQ ID NO: 115). PAM recognition of a modified Cas endonuclease is considered "relaxed" if the Cas endonuclease recognizes more potential PAM sequences as compared to the Cas endonuclease that has not been modified. For example, the Cas endonuclease SaCas9 recognizes PAM sequence NNGRRT (SEQ ID NO: 104), whereas a relaxed variant of the SaCas9 comprising one or more modifications of the endonuclease (e.g., KKH SaCas9) may recognize the PAM sequence NNNRRT (SEQ ID NO: 116). In one example, the Cas endonuclease FnCas9 recognizes PAM sequence NNG, whereas a relaxed variant of the FnCas9 comprising one or more modifications of the endonuclease (e.g., RHA FnCas9) may recognize the PAM sequence YG. In one example, the Cas endonuclease is a Cpf1 endonuclease comprising substitution mutations S542R and K607R and recognize the PAM sequence TYCV. In one example, the Cas endonuclease is a Cpf1 endonuclease comprising substitution mutations S542R, K607R, and N552R and recognize the PAM sequence TATV. See, e.g., Gao et al. *Nat. Biotechnol.* (2017) 35(8): 789-792.

In some embodiments, the methods described herein involve genetically engineering a population of hematopoietic cells using a Cas9 nuclease (or variant thereof). In some embodiments, the methods described herein involve genetically engineering a gene encoding a type 1 lineage-specific cell-surface antigen in a population of hematopoietic cells using a Cas9 nuclease (or variant thereof). In some embodiments, the methods described herein involve genetically modifying or editing a CD19 gene, or genetically modifying or editing a CD33 gene, or genetically modifying or editing a CD19 gene and a CD33 gene in the population of hematopoietic cells using a Cas9 nuclease (or variant thereof). In some embodiments, the methods described herein involve genetically engineering a mutant CD19 gene in a population of hematopoietic cells using a Cas9 nuclease (or variant thereof). In some embodiments, the methods described herein involve genetically engineering a mutation in exon 2 or exon 4 of CD19 in a population of hematopoietic cells using a Cas9 nuclease (or variant thereof). In some embodiments, the methods described herein involve genetically engineering a mutant CD19 gene in a population of hematopoietic cells using a Cas9 nuclease (or variant thereof) and a guide sequence provided by any one of SEQ ID NOs: 14-26, 67, and 69-72. In some embodiments, the methods described herein involve genetically engineering a mutant CD19 gene in a population of hematopoietic cells using a Cas9 nuclease (or variant thereof) and a guide sequence provided by SEQ ID NO: 67.

In some embodiments, the methods described herein involve genetically engineering a gene encoding a type 2 lineage-specific cell-surface antigen in a population of hematopoietic cells using a Cas9 nuclease (or variant thereof). In some embodiments, the methods described herein involve genetically engineering a mutant CD33 gene in a population of hematopoietic cells using a Cas9 nuclease (or variant thereof). In some embodiments, the methods described herein involve genetically engineering a mutation in exon 2 or exon 3 of CD33 in a population of hematopoietic cells using a Cas9 nuclease (or variant thereof). In some embodiments, the methods described herein involve genetically engineering a mutant CD33 gene in a population of hematopoietic cells using a Cas9 nuclease (or variant thereof) and a guide sequence provided by any one of SEQ ID NOs: 27-50 and 68. In some embodiments, the methods described herein involve genetically engineering a mutant CD33 gene in a population of hematopoietic cells using a Cas9 nuclease (or variant thereof) and a guide sequence provided by SEQ ID NO: 68.

In some embodiments, the endonuclease is a base editor. Base editor endonuclease generally comprises a catalytically inactive Cas endonuclease fused to a function domain. See, e.g., Eid et al. *Biochem. J.* (2018) 475(11): 1955-1964; Rees et al. *Nature Reviews Genetics* (2018) 19:770-788. In some embodiments, the catalytically inactive Cas endonuclease is dCas9. In some embodiments, the endonuclease comprises a dCas9 fused to one or more uracil glycosylase inhibitor (UGI) domains. In some embodiments, the endonuclease comprises a dCas9 fused to an adenine base editor (ABE), for example an ABE evolved from the RNA adenine deaminase TadA. In some embodiments, the endonuclease comprises a dCas9 fused to cytodine deaminase enzyme (e.g., APOBEC deaminase, pmCDA1, activation-induced cytidine deaminase (AID)). In some embodiments, the catalytically inactive Cas endonuclease has reduced activity and is nCas9. In some embodiments, the endonuclease comprises a nCas9 fused to one or more uracil glycosylase inhibitor (UGI) domains. In some embodiments, the endonuclease comprises a nCas9 fused to an adenine base editor (ABE), for example an ABE evolved from the RNA adenine deaminase TadA. In some embodiments, the endonuclease comprises a nCas9 fused to cytodine deaminase enzyme (e.g., APOBEC deaminase, pmCDA1, activation-induced cytidine deaminase (AID)).

Examples of base editors include, without limitation, BE1, BE2, BE3, HF-BE3, BE4, BE4max, BE4-Gam, YE1-BE3, EE-BE3, YE2-BE3, YEE-CE3, VQR-BE3, VRER-BE3, SaBE3, SaBE4, SaBE4-Gam, Sa(KKH)-BE3, Target-AID, Target-AID-NG, xBE3, eA3A-BE3, BE-PLUS, TAM, CRISPR-X, ABE7.9, ABE7.10, ABE7.10*, xABE, ABESa, VQR-ABE, VRER-ABE, Sa(KKH)-ABE, and CRISPR-SKIP. Additional examples of base editors can be found, for example, in US Publication No. 2018/0312825A1, US Publication No. 2018/0312828A1, and PCT Publication No. WO 2018/165629A1, which are incorporated by reference herein in their entireties.

In some embodiments, the base editor has been further modified to inhibit base excision repair at the target site and induce cellular mismatch repair. Any of the Cas endonucleases described herein may be fused to a Gam domain (bacteriophage Mu protein) to protect the Cas endonuclease from degradation and exonuclease activity. See, e.g., Eid et al. *Biochem. J.* (2018) 475(11): 1955-1964.

In some embodiments, the methods described herein involve genetically engineering a population of hematopoietic cells using a base editor (or variant thereof). In some embodiments, the methods described herein involve genetically engineering a gene encoding a type 1 lineage-specific cell-surface antigen in a population of hematopoietic cells using a base editor (or variant thereof). In some embodiments, the methods described herein involve genetically modifying or editing a CD19 gene, or genetically modifying or editing a CD33 gene, or genetically modifying or editing a CD19 gene and a CD33 gene in the population of hematopoietic cells using a base editor (or variant thereof). In some embodiments, the methods described herein involve genetically engineering a mutant CD19 gene in a population of hematopoietic cells using a base editor (or variant thereof). In some embodiments, the methods described herein involve genetically engineering a mutation in exon 2 or exon 4 of CD19 in a population of hematopoietic cells using a base editor (or variant thereof). In some embodiments, the methods described herein involve genetically engineering a mutant CD19 gene in a population of hematopoietic cells using a base editor (or variant thereof) and a guide sequence provided by any one of SEQ ID NOs: 14-26, 67, and 69-72. In some embodiments, the methods described herein involve genetically engineering a mutant CD19 gene in a population of hematopoietic cells using a base editor (or variant thereof) and a guide sequence provided by SEQ ID NO: 67.

In some embodiments, the methods described herein involve genetically engineering a gene encoding a type 2 lineage-specific cell-surface antigen in a population of hematopoietic cells using a base editor (or variant thereof). In some embodiments, the methods described herein involve genetically engineering a mutant CD33 gene in a population of hematopoietic cells using a base editor (or variant thereof). In some embodiments, the methods described herein involve genetically engineering a mutation in exon 2 or exon 3 of CD33 in a population of hematopoietic cells using a base editor nuclease (or variant thereof). In some embodiments, the methods described herein involve genetically engineering a mutant CD33 gene in a population of hematopoietic cells using a base editor nuclease (or variant thereof) and a guide sequence provided by any one of SEQ ID NOs: 27-50 and 68. In some embodiments, the methods described herein involve genetically engineering a mutant CD33 gene in a population of hematopoietic cells using a base editor (or variant thereof) and a guide sequence provided by SEQ ID NO: 68.

In some embodiments, the Cas endonuclease belongs to class 2 type V of Cas endonuclease. Class 2 type V Cas endonucleases can be further categorized as type V-A, type V-B, type V-C, and type V-U. See, e.g., Stella et al. *Nature Structural & Molecular Biology* (2017). In some embodiments, the Cas endonuclease is a type V-A Cas endonuclease, such as a Cpf1 nuclease. In some embodiments, the Cas endonuclease is a type V-B Cas endonuclease, such as a C2c1 endonuclease. See, e.g., Shmakov et al. *Mol Cell* (2015) 60: 385-397. In some embodiments, the Cas endonuclease is Mad7.

In some embodiments, the Cas endonuclease is a Cpf1 nuclease or variant thereof. As will be appreciated by one of skill in the art, the Cas endonuclease Cpf1 nuclease may also be referred to as Cas12a. See, e.g., Strohkendl et al. *Mol. Cell* (2018) 71: 1-9. In some embodiments, the host cell expresses a Cpf1 nuclease derived from *Provetella* spp., *Francisella* spp, *Acidaminococcus* sp. (AsCpf1), *Lachnospiraceae bacterium* (LpCpf1), or *Eubacterium rectale*. In some embodiments, the nucleotide sequence encoding the Cpf1 nuclease may be codon optimized for expression in a host cell. In some embodiments, the nucleotide sequence encoding the Cpf1 endonuclease is further modified to alter the activity of the protein.

A catalytically inactive variant of Cpf1 (Cas12a) may be referred to as dCas12a. As described herein, catalytically inactive variants of Cpf1 maybe fused to a function domain to form a base editor. See, e.g., Rees et al. *Nature Reviews Genetics* (2018) 19:770-788. In some embodiments, the catalytically inactive Cas endonuclease is dCas9. In some embodiments, the endonuclease comprises a dCas12a fused to one or more uracil glycosylase inhibitor (UGI) domains. In some embodiments, the endonuclease comprises a dCas12a fused to an adenine base editor (ABE), for example an ABE evolved from the RNA adenine deaminase TadA. In some embodiments, the endonuclease comprises a dCas12a fused to cytidine deaminase enzyme (e.g., APOBEC deaminase, pmCDA1, activation-induced cytidine deaminase (AID)).

In some embodiments, the methods described herein involve genetically engineering a population of hematopoietic cells using a Cpf1 nuclease (or variant thereof. In some embodiments, the methods described herein involve genetically engineering a gene encoding a type 1 lineage-specific cell-surface antigen in a population of hematopoietic cells using a Cpf1 nuclease (or variant thereof. In some embodiments, the methods described herein involve genetically modifying or editing a CD19 gene, or genetically modifying or editing a CD33 gene, or genetically modifying or editing a CD19 gene and a CD33 gene in the population of hematopoietic cells using a Cpf1 nuclease (or variant thereof. In some embodiments, the methods described herein involve genetically engineering a mutant CD19 gene in a population of hematopoietic cells using a Cpf1 nuclease (or variant thereof. In some embodiments, the methods described herein involve genetically engineering a mutation in exon 2 or exon 4 of CD19 in a population of hematopoietic cells using a Cpf1 nuclease (or variant thereof). In some embodiments, the methods described herein involve genetically engineering a mutant CD19 gene in a population of hematopoietic cells using a Cpf1 nuclease (or variant thereof) and a guide sequence provided by any one of SEQ ID NOs: 14-26, 67, and 69-72. In some embodiments, the methods described herein involve genetically engineering a mutant CD19 gene in a population of hematopoietic cells using a Cpf1 nuclease (or variant thereof) and a guide sequence provided by SEQ ID NO: 67.

In some embodiments, the methods described herein involve genetically engineering a gene encoding a type 2 lineage-specific cell-surface antigen in a population of hematopoietic cells using a Cpf1 nuclease (or variant thereof). In some embodiments, the methods described herein involve genetically engineering a mutant CD33 gene in a population of hematopoietic cells using a Cpf1 nuclease (or variant thereof). In some embodiments, the methods described herein involve genetically engineering a mutation in exon 2 or exon 3 of CD33 in a population of hematopoietic cells using a Cpf1 nuclease (or variant thereof). In some embodiments, the methods described herein involve genetically engineering a mutant CD33 gene in a population of hematopoietic cells using a Cpf1 nuclease (or variant thereof) and a guide sequence provided by any one of SEQ ID NOs: 27-50 and 68. In some embodiments, the methods described herein involve genetically engineering a mutant CD33 gene in a population of hematopoietic cells using a Cpf1 nuclease (or variant thereof) and a guide sequence provided by SEQ ID NO: 68.

Alternatively or in addition, the Cas endonuclease may be a Cas14 endonuclease or variant thereof. In contrast to Cas9 endonucleases, Cas14 endonucleases are derived from archaea and tend to be smaller in size (e.g., 400-700 amino acids). Additionally Cas14 endonucleases do not require a PAM sequence. See, e.g., Harrington et al. *Science* (2018).

In some embodiments, the methods described herein involve genetically engineering a population of hematopoietic cells using a Cas14 endonuclease (or variant thereof. In some embodiments, the methods described herein involve genetically engineering a gene encoding a type 1 lineage-specific cell-surface antigen in a population of hematopoietic cells using a Cas14 endonuclease (or variant thereof. In some embodiments, the methods described herein involve genetically modifying or editing a CD19 gene, or genetically modifying or editing a CD33 gene, or genetically modifying or editing a CD19 gene and a CD33 gene in the population of hematopoietic cells using a Cas14 endonuclease (or variant thereof). In some embodiments, the methods described herein involve genetically engineering a mutant CD19 gene in a population of hematopoietic cells using a Cas14 endonuclease (or variant thereof). In some embodiments, the methods described herein involve genetically engineering a mutation in exon 2 or exon 4 of CD19 in a population of hematopoietic cells using a Cas14 endonuclease (or variant thereof). In some embodiments, the methods described herein involve genetically engineering a mutant CD19 gene in a population of hematopoietic cells using a Cas14 endonuclease (or variant thereof) and a guide sequence provided by any one of SEQ ID NOs: 14-26, 67, and 69-72. In some embodiments, the methods described herein involve genetically engineering a mutant CD19 gene in a population of hematopoietic cells using a Cas14 endonuclease (or variant thereof) and a guide sequence provided by SEQ ID NO: 67.

In some embodiments, the methods described herein involve genetically engineering a gene encoding a type 2 lineage-specific cell-surface antigen in a population of hematopoietic cells using a Cas14 endonuclease (or variant thereof. In some embodiments, the methods described herein involve genetically engineering a mutant CD33 gene in a population of hematopoietic cells using a Cas14 endonuclease (or variant thereof). In some embodiments, the methods described herein involve genetically engineering a mutation in exon 2 or exon 3 of CD33 in a population of hematopoietic cells using a Cas14 endonuclease (or variant thereof). In some embodiments, the methods described herein involve genetically engineering a mutant CD33 gene in a population of hematopoietic cells using a Cas14 endonuclease (or variant thereof) and a guide sequence provided by any one of SEQ ID NOs: 27-50 and 68. In some embodiments, the methods described herein involve genetically engineering a mutant CD33 gene in a population of hematopoietic cells using a Cas14 endonuclease (or variant thereof) and a guide sequence provided by SEQ ID NO: 68.

Any of the Cas endonucleases described herein may be modulated to regulate levels of expression and/or activity of the Cas endonuclease at a desired time. For example, it may be advantageous to increase levels of expression and/or activity of the Cas endonuclease during particular phase(s) of the cell cycle. It has been demonstrated that levels of homology-directed repair are reduced during the G1 phase of the cell cycle, therefore increasing levels of expression and/or activity of the Cas endonuclease during the S phase, G2 phase, and/or M phase may increase homology-directed repair following the Cas endonuclease editing. In some embodiments, levels of expression and/or activity of the Cas endonuclease are increased during the S phase, G2 phase, and/or M phase of the cell cycle. In one example, the Cas endonuclease fused to a the N-terminal region of human Geminin. See, e.g., Gutschner et al. *Cell Rep.* (2016) 14(6): 1555-1566. In some embodiments, levels of expression and/or activity of the Cas endonuclease are reduced during the G1 phase. In one example, the Cas endonuclease is modified such that it has reduced activity during the G1 phase. See, e.g., Lomova et al. *Stem Cells* (2018).

Alternatively or in addition, any of the Cas endonucleases described herein may be fused to an epigenetic modifier (e.g., a chromatin-modifying enzyme, e.g., DNA methylase, histone deacetylase). See, e.g., Kungulovski et al. *Trends Genet.* (2016) 32(2):101-113. Cas endonucleases fused to an epigenetic modifier may be referred to as "epieffectors" and may allow for temporal and/or transient endonuclease activity. In some embodiments, the Cas endonuclease is a dCas9 fused to a chromatin-modifying enzyme.

In some embodiments, the present disclosure provides compositions and methods for modifying or deleting a cell-surface lineage-specific protein in hematopoietic cells using a CRISPR/Cas9 system, wherein guide RNA sequence hybridizes to the nucleotide sequence encoding an epitope of the lineage-specific cell-surface antigen. In some embodiments, the present disclosure provides compositions and methods for modifying or deleting two or more cell-surface lineage-specific protein in hematopoietic cells using a CRISPR/Cas9 system, wherein guide RNA sequence hybridizes to the nucleotide sequence encoding an epitope of the lineage-specific cell-surface antigen. In some embodiments, the guide RNA sequence(s) hybridize to the nucleotide sequence encoding an exon of the lineage-specific cell-surface antigen. In some embodiments, one or more guide RNA sequences may hybridize to one or more intron sequences, leading to skipping of an adjacent exon. For example, two guide RNA sequence may be used to target regions in two nearby introns (e.g., intron 1 and intron 2 or intron 2 and intron 3), leading to skipping of the exon between the two introns. In some embodiments, the cell-surface lineage-specific protein is CD33 or CD19 and the gRNA hybridizes to a portion of the nucleotide sequence that encodes an epitope of CD33 or CD19. In some embodiments, the cell-surface lineage-specific protein is CD33 and the gRNA hybridizes to a portion of intron 1 or intron 2 of the nucleotide sequence encoding CD19. In some embodiments, the cell-surface lineage-specific protein is CD19 and the gRNA hybridizes to a portion of intron 1 or intron 2 of the nucleotide sequence encoding CD19.

In some embodiments, the cell-surface lineage-specific protein is CD33 and the gRNA hybridizes to a portion of the gene encoding exon2. In some embodiments, the cell-surface lineage-specific protein is CD18 and the gRNA hybridizes to a portion of the gene encoding exon3. In some embodiments, a first cell-surface lineage-specific protein is CD33 (wherein the gRNA hybridizes to a portion of the gene encoding exon2 and a second cell-surface lineage-specific protein is CD19 and the gRNA hybridizes to a portion of exon3. In some embodiments, the CD33 and/or CD19 gene is knocked out. In some embodiments, a portion of the CD33 and/or CD19 gene is knocked out.

In some embodiments, it may be desired to further genetically engineer the HSC, particularly allogeneic HSCs, to reduce the graft-versus-host effects. For example, the standard therapy for relapsed AML is hematopoietic stem cell transplantation (HSCT). However, at least one of the limiting factors for successful HSCT is graft-versus-host disease (GVHD), in which expression of the cell surface molecule CD45 has been implicated. See, e.g., Van Besie, *Hematology Am. Soc. Hematol Educ Program* (2013)56; Mawad, *Curr. Hematol. Malig. Rep.* (2013) 8(2):132. CD45RA and CD45RO are isoforms of CD45 (found on all hematopoietic cells except erythrocytes). In T lymphocytes, CD45RA is expressed on naive cells, while CD45RO is expressed on memory cells. CD45RA T cells have a high potential for reactivity against recipient-specific proteins following HSCT, resulting in GVHD. CD45 is a type 1 lineage protein, as CD45-bearing cells are required for survival; however, the antigenic portion of CD45 may be deleted from stem cells using CRISPR to prevent and/or reduce the incidence or extent of GvHD.

Also provided herein are methods of producing the genetically engineered hematopoietic cells as described herein, which carry edited genes for expressing one or more lineage-specific cell-surface antigens in mutated form. Such methods may involve providing a cell and introducing into the cell components of a CRISPR Cas system for genome editing. In some embodiments, a nucleic acid that comprises a CRISPR-Cas guide RNA (gRNA) that hybridizes or is predicted to hybridize to a portion of the nucleotide sequence that encodes the lineage-specific cell-surface antigen is introduced into the cell. In some embodiments, the gRNA is introduced into the cell on a vector. In some embodiments, a Cas endonuclease is introduced into the cell. In some embodiments, the Cas endonuclease is introduced into the cell as a nucleic acid encoding a Cas endonuclease. In some embodiments, the gRNA and a nucleotide sequence encoding a Cas endonuclease are introduced into the cell on the same nucleic acid (e.g., the same vector). In some embodiments, the Cas endonuclease is introduced into the cell in the form of a protein. In some embodiments, the Cas endonuclease and the gRNA are pre-formed in vitro and are introduced to the cell in as a ribonucleoprotein complex.

In some embodiments, multiple gRNAs are introduced into the cell. In some embodiments, the two or more guide RNAs are transfected into cells in equimolar amounts. In some embodiments, the two or more guide RNAs are provided in amounts that are not equimolar. In some embodiments, the two or more guide RNAs are provided in amounts that are optimized so that editing of each target occurs at equal frequency. In some embodiments, the two or more guide RNAs are provided in amounts that are optimized so that editing of each target occurs at optimal frequency.

In some embodiments, multiple gRNAs are allowed to form gRNA-RNP complexes in the same reaction. In some embodiments, two or more gRNA-RNP complexes are formed in separate reactions. The RNP complexes with the two or more guide RNAs can be transfected together or separately. For example, Cas9-CD19_gRNA-19 RNPs and Cas9-CD33_gRNA-37 RNPs can be formed separately in two isolated incubations or together in one incubation and can be transfected together or separately, e.g., concurrently.

In some embodiments, the two or more guides are transfected concurrently with each other. In some embodiments, the two or more guides are provided sequentially or consecutively, i.e., in two or more separate transfections. For example, Cas9-CD19_gRNA-RNPs and Cas9-CD33 gRNA RNPs can be transfected together, e.g., in equimolar amounts or another optimal ratio. In some examples, RNPs comprising Cas9 and any one of the CD19 gRNAs provided by SEQ ID NOs: 14-26, 67, 69-72 are transfected with RNPs comprising Cas9 and any one of the CD33 gRNAs provided by SEQ ID NOs: 22-50 and 68. Alternatively, Cas9-CD19_gRNA-RNPs and Cas9-CD33 gRNA RNPs can be transfected sequentially, e.g., either first Cas9-CD19_gRNA-RNPs and then Cas9-CD33 gRNA RNPs or first Cas9-CD33_gRNA-RNPs and then Cas9-CD19 gRNA RNPs. In some examples, RNPs comprising Cas9 and any one of the CD19 gRNAs provided by SEQ ID NOs: 14-26, 67, 69-72 are transfected sequentially (e.g., prior to or after) RNPs comprising Cas9 and any one of the CD33 gRNAs provided by SEQ ID NOs: 22-50 and 68.

Vectors of the present disclosure can drive the expression of one or more sequences in mammalian cells using a mammalian expression vector. Examples of mammalian expression vectors include pCDM8 (Seed, *Nature* (1987) 329: 840) and pMT2PC (Kaufman, et al., *EMBO J.* (1987) 6: 187). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd eds., Cold Spring Harbor Laboratory, Cold Spring Harbor Laboratory Press, Cold Spring Harbor, N.Y., 1989.

The vectors of the present disclosure are capable of directing expression of the nucleic acid preferentially in a particular cell type (e.g., tissue-specific regulatory elements are used to express the nucleic acid). Such regulatory elements include promoters that may be tissue specific or cell specific. The term "tissue-specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining.

Conventional viral and non-viral based gene transfer methods can be used to introduce nucleic acids encoding CRISPR/Cas9 in mammalian cells or target tissues. Such methods can be used to administer nucleic acids encoding components of a CRISPR-Cas system to cells in culture, or in a host organism. Non-viral vector delivery systems include DNA plasmids, RNA (e.g., a transcript of a vector described herein), naked nucleic acid, and nucleic acid complexed with a delivery vehicle. In some embodiments, nucleic acids encoding CRISPR/Cas9 are introduced by transfection (e.g., electroporation, microinjection. In some embodiments, nucleic acids encoding CRISPR/Cas9 are introduced by nanoparticle delivery, e.g., cationic nanocarriers.

Viral vector delivery systems include DNA and RNA viruses, which have either episomal or integrated genomes after delivery to the cell.

Viral vectors can be administered directly to patients (in vivo) or they can be used to manipulate cells in vitro or ex vivo, where the modified cells may be administered to patients. In one embodiment, the present disclosure utilizes viral based systems including, but not limited to retroviral, lentivirus, adenoviral, adeno-associated and herpes simplex virus vectors for gene transfer. Furthermore, the present disclosure provides vectors capable of integration in the host genome, such as retrovirus or lentivirus. Preferably, the vector used for the expression of a CRISPR-Cas system of the present disclosure is a lentiviral vector.

In one embodiment, the disclosure provides for introducing one or more vectors encoding CRISPR-Cas into eukaryotic cell. The cell can be a cancer cell. Alternatively, the cell is a hematopoietic cell, such as a hematopoietic stem cell. Examples of stem cells include pluripotent, multipotent and unipotent stem cells. Examples of pluripotent stem cells include embryonic stem cells, embryonic germ cells, embryonic carcinoma cells and induced pluripotent stem cells (iPSCs). In a preferred embodiment, the disclosure provides introducing CRISPR-Cas9 into a hematopoietic stem cell.

The vectors of the present disclosure are delivered to the eukaryotic cell in a subject. Modification of the eukaryotic cells via CRISPR/Cas9 system can takes place in a cell culture, where the method comprises isolating the eukaryotic cell from a subject prior to the modification. In some embodiments, the method further comprises returning said eukaryotic cell and/or cells derived therefrom to the subject.

In some embodiments, the gRNA is introduced into the cell in the form of a vector. In some embodiments, the gRNA and a nucleotide sequence encoding a Cas endonuclease are introduced into the cell on the same nucleic acid (e.g., the same vector). In some embodiments, the gRNA is introduced into the cell in the form of an RNA. In some embodiments, the gRNA may comprise one or more modifications, for example, to enhance stability of the gRNA, reduce off-target activity, increase editing efficiency. Examples of modifications include, without limitation, base modifications, backbone modifications, and modifications to the length of the gRNA. For example, it has been demonstrated that extending the length of a gRNA at the 5'end and/or introducing one or more chemical modification may increase editing efficiency. See, e.g., Park et al. *Nature Communications* (2018) 9:3313; Moon et al. *Nature Communications* (2018) 9: 3651. Additionally, incorporation of nucleic acids or locked nucleic acids have been found to increase specificity of genomic editing. See, e.g., Cromwell, et al. *Nature Communications* (2018) 9: 1448. See, e.g., Safari et al. *Current Pharm. Biotechnol.* (2017) 18:13. In some embodiments, the gRNA may comprise one or more modification chosen from phosphorothioate backbone modification, 2'-O-Me-modified sugars (e.g., at one or both of the 3' and 5' termini), 2'F-modified sugar, replacement of the ribose sugar with the bicyclic nucleotide-cEt, 3'thioPACE (MSP), or any combination thereof. Suitable gRNA modifications are described, e.g., in Randar et al. PNAS Dec. 22, 2015 112 (51) E7110-E7117 and Hendel et al., Nat Biotechnol. 2015 September; 33(9): 985-989, each of which is incorporated herein by reference in its entirety. In some embodiments, a gRNA described herein comprises one or more 2'-O-methyl-3'-phosphorothioate nucleotides, e.g., at least 2, 3, 4, 5, or 6 2'-O-methyl-3'-phosphorothioate nucleotides. In some embodiments, a gRNA described herein comprises modified nucleotides (e.g., 2'-O-methyl-3¹-phosphorothioate nucleotides) at the three terminal positions and the 5' end and/or at the three terminal positions and the 3' end.

In some embodiments, the gRNA comprises one or more modified bases (e.g. 2' O-methyl nucleotides). In some embodiments, the gRNA comprises one or more modified uracil base. In some embodiments, the gRNA comprises one or more modified adenine base. In some embodiments, the gRNA comprises one or more modified guanine base. In some embodiments, the gRNA comprises one or more modified cytosine base.

In some embodiments, the gRNA comprises one or more modified internucleotide linkages such as, for example, phosphorothioate, phosphoramidate, and O'methyl ribose or deoxyribose residue.

In some embodiments, the gRNA comprises an extension of about 10 nucleotides to 100 nucleotides at the 3' end and/or 5'end of the gRNA. In some embodiments, the gRNA comprises an extension of about 10 nucleotides to 100 nucleotides, about 20 nucleotides to 90 nucleotides, about 30 nucleotides to 80 nucleotides, about 40 nucleotides to 70 nucleotides, about 40 nucleotides to 60 nucleotides, about 50 nucleotides to 60 nucleotides.

In some embodiments, the Cas endonuclease and the gRNA are pre-formed in vitro and are introduced to the cell in as a ribonucleoprotein complex. Examples of mechanisms to introduce a ribonucleoprotein complex comprising the Cas endonuclease and the gRNA include, without limitation, electroporation, cationic lipids, DNA nanoclew, and cell penetrating peptides. See, e.g., Safari et al. *Current Pharma. Biotechnol.* (2017) 18(13); Yin et al. *Nature Review Drug Discovery* (2017) 16: 387-399.

Any of the CRISPR/Cas systems described herein may be further optimized to increase selectivity of genomic editing, for example by enhancing homologous recombination. See, e.g., Komor et al. Cell (2017) 168: 20-36. For example, in some embodiments, CRISPR/Cas system is optimized to inhibit nonhomologous end joining and/or promote homologous directed recombination.

A number of small molecules have been identified to modulate Cas endonuclease genome editing. In some embodiments, the cells are contacted with one or more small molecule to enhance Cas endonuclease genome editing. In some embodiments, a subject is administered one or more small molecule to enhance Cas endonuclease genome editing. In some embodiments, the cells are contacted with one or more small molecule to inhibit nonhomologous end joining and/or promote homologous directed recombination. Examples of small molecules that may modulate Cas endonuclease genome editing include, without limitation L755507, Brefeldin A, ligase IV inhibitor SCR7, VE-822, AZD-7762. See, e.g., Hu et al. *Cell Chem. Biol.* (2016) 23: 57-73; Yu et al. *Cell Stem Cell* (2015) 16: 142-147; Chu et al. *Nat. Biotechnol.* (2015) 33: 543-548; Maruyama et al. *Nat. Biotechnol.* (2015) 33: 538-542; and Ma et al. *Nature Communications* (2018) 9:1303.

In some embodiments, any of the Cas endonucleases may be used with a donor single stranded DNA designed to anneal with the DNA strand initially released from the Cas endonucleases.

In some embodiments, it is desirable to temporally regulate genomic editing. For example, in some embodiments, the expression and/or activity of a Cas endonuclease may be regulated to induce genomic editing at a desired time. In some embodiments, cells containing any of the CRISPR/Cas systems described herein may be allowed to engraft into a subject and then expression and/or activity the Cas endonuclease may be induced. Alternatively or in addition, as described herein, the Cas endonuclease may be fused to an epigenetic modifier (e.g., a chromatin-modifying enzyme, e.g., DNA methylase, histone deacetylase).

(B) Genetically Engineered Hematopoietic Cells Expressing CD19 Mutants and/or CD33 Mutants In some embodiments, the genetically engineered hematopoietic cells may have edited CD19 gene, CD33 gene, or both, which are designed to express mutated CD19, CD33, or both. In some instances, the mutated CD19 and/or CD33 include mutations or deletions in one or more non-essential epitopes so as to retain (at least partially) the bioactivity of CD19 and/or CD33.

(i) Genetically Engineered Hematopoietic Cells Expressing CD19 Mutants

In some examples, provided herein are variants of CD19, which may comprise a deletion or mutation of a fragment of the protein that is encoded by any one of the exons of CD19, or deletion or mutation in a non-essential epitope of CD19. The whole sequence of the CD19 gene, containing fifteen exons, is known in the art. See, e.g., GenBank accession no. NC_000016. For example, one or more epitopes located in the region encoded by exon 2 the CD19 gene may be deleted or mutated. Certain modifications to the region of the CD19 gene encoding exon 2 have been shown to result in successful CD19 protein expression, membrane localization, and partial maintenance of protein function (Sotillo et al. *Cancer Discovery.* (2015) 5: 1282-1295). For example, missense or frameshift mutations in exon 2 of the CD19 gene, or alternatively, modifications that permanently or transiently reduce expression of the splicing factor SRSF3, which is involved in retention of CD19 exon 2, may reduce CD19 expression in vivo. In some embodiments, one or more epitopes located in the region encoded by exon 2 of the CD19 gene are mutated or deleted. For example, the FMC63 epitope of CD19, which is a known target of CD19-targeted CAR therapies may be mutated or deleted (Sotillo et al. *Cancer Discovery.* (2015) 5: 1282-129; Nicholson et al. *Mol Immunol.* (1997) 34:1157-1165; Zola et al. *Immunol Cell Biol.* (1991) 69:411-422).

In some examples, one or more epitopes located in the region encoded by exon 4 of the CD19 gene may be deleted or mutated.

In some embodiments, exon 2 of CD19 is mutated or deleted. In some embodiments, exon 4 of CD19 is mutated or deleted. The amino acid sequence of an exemplary human CD19 is provided below with the fragment encoded by exon 2 underlined and the fragment encoded by exon 4 in italics (SEQ ID NO:51).

(SEQ ID NO: 51)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQ*DLTMAPGSTLWLSC*

*GVPPDSVSRGPLSWTHVHPKGPKSLLSLELKDDRPARDMWVMETGLLL*

*PRATAQDAGKYYCHRGNLTMSFHLEI*TARPVLWHWLLRTGGWKVSAVT

LAYLIFCLCSLVGILHLQRALVLRRKRKRMTDPTRRFFKVTPPPGSGP

QNQYGNVLSLPTPTSGLGRAQRWAAGLGGTAPSYGNPSSDVQADGALG

SRSPPGVGPEEEEGEGYEEPDSEEDSEFYENDSNLGQDQLSQDGSYE

NPEDEPLGPEDEDSFSNAESYENEDEELTQPVARTMDFLSPHGSAWDP

SREATSLGSQSYEDMRGILYAAPQLRSIRGQPGPNHEEDADSYENMDN

PDGPDPAWGGGGRMGTWSTR

CD19 Full-length
mRNA (underlined = exon 2; italics = exon 4)
(SEQ ID NO: 117)
AUGCCACCUCCUCGCCUCCUCUUCUUCCUCCUCUUCCUCACCCCAUGGA

AGUCAGGCCCGAGGAACCUCUAGUGGUGAAGGUGGAAGAGGGAGAUAACG

CUGUGCUGCAGUGCCUCAAGGGGACCUCAGAUGGCCCCACUCAGCAGCUG

ACCUGGUCUCGGGAGUCCCCGCUUAAACCCUUCUUAAAACUCAGCCUGGG

GCUGCCAGGCCUGGGAAUCCACAUGAGGCCCCUGGCCAUCUGGCUUUUCA

UCUUCAACGUCUCUCAACAGAUGGGGGGCUUCUACCUGUGCCAGCCGGGG

CCCCCCUCGAGAAGGCCUGGCAGCCUGGCUGGACAGUCAAUGUGGAGGG

CAGCGGGGAGCUGUUCCGGUGGAAUGUUUCGGACCUAGGUGGCCUGGGCU

GUGGCCUGAAGAACAGGUCCUCAGAGGGCCCCAGCUCCCCUUCCGGGAAG

CUCAUGAGCCCCAAGCUGUAUGUGUGGGCCAAAGACCGCCCUGAGAUCUG

GGAGGGAGAGCCUCCGUGUCUCCCACCGAGGGACAGCCUGAACCAGAGCC

UCAGCCAG

*GACCUCACCAUGGCCCCUGGCUCCACACUCUGGCUGUCCUGU*

*GGGGUACCCCCUGACUCUGUGUCCAGGGGCCCCCUCUCCUGGAC*

*CCAUGUGCACCCCAAGGGGCCUAAGUCAUUGCUGAGCCUAGAGC*

*UGAAGGACGAUCGCCCGGCCAGAGAUAUGUGGGUAAUGGAGACG*

*GGUCUGUUGUUGCCCCGGGCCACAGCUCAAGACGCUGGAAAGUA*

*UUAUUGUCACCGUGGCAACCUGACCAUGUCAUUCCACC*

UGGAGAUCACUGCUCGGCCAGUACUAUGGCACUGGC

UGCUGAGGACUGGUGGCUGGAAGGUCUCAGCUGUGACUUUGGCUUAUCUG

AUCUUCUGCCUGUGUUCCCUUGUGGGCAUUCUUCAUCUUCAAAGAGCCCU

GGUCCUGAGGAGAAAAGAAAGCGAAUGACUGACCCCACCAGGAGAUUCU

UCAAAGUGACGCCUCCCCCAGGAAGCGGGCCCCAGAACCAGUACGGGAAC

GUGCUGUCUCUCCCCACACCCACCUCAGGCCUCGGACGCGCCCAGCGUUG

GGCCGCAGGCCUGGGGGGCACUGCCCCGUCUUAUGGAAACCCGAGCAGCG

ACGUCCAGGCGGAUGGAGCCUUGGGGUCCCGGAGCCCGCCGGGAGUGGGC

CCAGAAGAAGAGGAAGGGGAGGGCUAUGAGGAACCUGACAGUGAGGAGGA

CUCCGAGUUCUAUGAGAACGACUCCAACCUUGGGCAGGACCAGCUCUCCC

AGGAUGGCAGCGGCUACGAGAACCCUGAGGAUGAGCCCCUGGGUCCUGAG

GAUGAAGACUCCUUCUCCAACGCUGAGUCUUAUGAGAACGAGGAUGAAGA

GCUGACCCAGCCGGUCGCCAGGACAAUGGACUUCCUGAGCCCUCAUGGGU

CAGCCUGGGACCCCAGCCGGGAAGCAACCUCCUGGCAGGGUCCCAGUCC

UAUGAGGAUAUGAGAGGAAUCCUGUAUGCAGCCCCCCAGCUCCGCUCCAU

UCGGGGCCAGCCUGGACCCAAUCAUGAGGAAGAUGCAGACUCUUAUGAGA

ACAUGGAUAAUCCCGAUGGGCCAGACCCAGCCUGGGGAGGAGGGGCCGC

AUGGGCACCUGGAGCACCAGGUGA

In some examples, the genetically engineered hematopoietic cells have a genetically engineered CD19 gene (e.g., a genetically engineered endogenous CD19 gene), which expresses a CD19 mutant having the fragment encoded by exon 2 deleted (CD19ex2). An exemplary amino acid sequence of such a CD19 mutant is provided below (the junction of exon 1-encoded fragment and exon-3 encoded fragment is shown in boldface):

(SEQ ID NO: 52)
MPPPRLLFFLLFLTPMEVRPEEPLVVKVEGELFRWNVSDLGGLGCGLKNR

SSEGPSSPSGKLMSPKLYVWAKDRPEIWEGEPPCLPPRDSLNQSLSQDLT

MAPGSTLWLSCGVPPDSVSRGPLSWTHVHPKGPKSLLSLELKDDRPARDM

WVMETGLLLPRATAQDAGKYYCHRGNLTMSFHLEITARPVLWHWLLRTGG

WKVSAVTLAYLIFCLCSLVGILHLQRALVLRRKRKRMTDPTRRFFKVTPP

PGSGPQNQYGNVLSLPTPTSGLGRAQRWAAGLGGTAPSYGNPSSDVQADG

ALGSRSPPGVGPEEEEGEGYEEPDSEEDSEFYENDSNLGQDQLSQDGSGY

ENPEDEPLGPEDEDSFSNAESYENEDEELTQPVARTMDFLSPHGSAWDPS

REATSLGSQSYEDMRGILYAAPQLRSIRGQPGPNHEEDADSYENMDNPD

GPDPAWGGGGRMGTWSTR mRNA ex2 delete
(SEQ ID NO: 118)
AUGCCACCUCCUCGCCUCCUCUUCUUCCUCCUCUUCCUCACCCCAUGGA

AGUCAGGCCCGAGGAACCUCUAGUGGUGAAGGUGGAAGGGGAGCUGUUCC

GGUGGAAUGUUUCGGACCUAGGUGGCCUGGGCUGUGGCCUGAAGAACAGG

UCCUCAGAGGGCCCCAGCUCCCCUUCCGGGAAGCUCAUGAGCCCCAAGCU

GUAUGUGUGGGCCAAAGACCGCCCUGAGAUCUGGGAGGGAGAGCCUCCGU

GUCUCCCACCGAGGGACAGCCUGAACCAGAGCCUCAGCCAGGACCUCACC

AUGGCCCCUGGCUCCACACUCUGGCUGUCCUGUGGGGUACCCCCUGACUC

UGUGUCCAGGGGCCCCCUCUCCUGGACCCAUGUGCACCCCAAGGGGCCUA

AGUCAUUGCUGAGCCUAGAGCUGAAGGACGAUCGCCCGGCCAGAGAUAUG

UGGGUAAUGGAGACGGGUCUGUUGUUGCCCCGGGCCACAGCUCAAGACGC

UGGAAAGUAUUAUUGUCACCGUGGCAACCUGACCAUGUCAUUCCACCUGG

AGAUCACUGCUCGGCCAGUACUAUGGCACUGGCUGCUGAGGACUGGUGGC

UGGAAGGUCUCAGCUGUGACUUUGGCUUAUCUGAUCUUCUGCCUGUGUUC

CCUUGUGGGCAUUCUUCAUCUUCAAAGAGCCCUGGUCCUGAGGAGGAAAA

GAAAGCGAAUGACUGACCCCACCAGGAGAUUCUUCAAAGUGACGCCUCCC

CCAGGAAGCGGGCCCCAGAACCAGUACGGGAACGUGCUGUCUCUCCCCAC

ACCCACCUCAGGCCUCGGACGCGCCCAGCGUUGGGCCGCAGGCCUGGGGG

GCACUGCCCCGUCUUAUGGAAACCCGAGCAGCGACGUCCAGGCGGAUGGA

GCCUUGGGGUCCCGGAGCCCGCCGGGAGUGGGCCCAGAAGAAGAGGAAGG

GGAGGGCUAUGAGGAACCUGACAGUGAGGAGGACUCCGAGUUCUAUGAGA

```
ACGACUCCAACCUUGGGCAGGACCAGCUCUCCCAGGAUGGCAGCGGCUAC

GAGAACCCUGAGGAUGAGCCCCUGGGUCCUGAGGAUGAAGACUCCUUCUC

CAACGCUGAGUCUUAUGAGAACGAGGAUGAAGAGCUGACCCAGCCGGUCG

CCAGGACAAUGGACUUCCUGAGCCCUCAUGGGUCAGCCUGGGACCCCAGC

CGGGAAGCAACCUCCCUGGCAGGGUCCCAGUCCUAUGAGGAUAUGAGAGG

AAUCCUGUAUGCAGCCCCCCAGCUCCGCUCCAUUCGGGGCCAGCCUGGAC

CCAAUCAUGAGGAAGAUGCAGACUCUUAUGAGAACAUGGAUAAUCCCGAU

GGGCCAGACCCAGCCUGGGGAGGAGGGGGCCGCAUGGGCACCUGGAGCAC

CAGGUGA
```

In some embodiments, exon 4 of CD19 is mutated or deleted. In some examples, the genetically engineered hematopoietic cells have a genetically engineered CD19 gene (e.g., a genetically engineered endogenous CD19 gene), which expresses a CD19 mutant having the fragment encoded by exon 4 deleted (CD19ex4). An exemplary amino acid sequence of such a CD19 mutant is provided below:

```
                                         (SEQ ID NO: 73)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQVLWHWLLRTGGWKV

SAVTLAYLIFCLCSLVGILHLQRALVLRRKRKRMTDPTRRFFKVTPPPGS

GPQNQYGNVLSLPTPTSGLGRAQRWAAGLGGTAPSYGNPSSDVQADGALG

SRSPPGVGPEEEEGEGYEEPDSEEDSEFYENDSNLGQDQLSQDGSGYENP

EDEPLGPEDEDSFSNAESYENEDEELTQPVARTMDFLSPHGSAWDPSREA

TSLAGSQSYEDMRGILYAAPQLRSIRGQPGPNHEEDADSYENMDNPDGPD

PAWGGGGRMGTWSTR mRNA ex4 delete
                                         (SEQ ID NO: 119)
ATGCCACCTCCTCGCCTCCTCTTCTTCCTCCTCTTCCTCACCCCCATGGA

AGTCAGGCCCGAGGAACCTCTAGTGGTGAAGGTGGAAGAGGGAGATAACG

CTGTGCTGCAGTGCCTCAAGGGGACCTCAGATGGCCCCACTCAGCAGCTG

ACCTGGTCTCGGGAGTCCCCGCTTAAACCCTTCTTAAAACTCAGCCTGGG

GCTGCCAGGCCTGGGAATCCACATGAGGCCCCTGGCCATCTGGCTTTTCA

TCTTCAACGTCTCTCAACAGATGGGGGGCTTCTACCTGTGCCAGCCGGGG

CCCCCCTCTGAGAAGGCCTGGCAGCCTGGCTGGACAGTCAATGTGGAGGG

CAGCGGGGAGCTGTTCCGGTGGAATGTTTCGGACCTAGGTGGCCTGGGCT

GTGGCCTGAAGAACAGGTCCTCAGAGGGCCCCAGCTCCCCTTCCGGGAAG

CTCATGAGCCCCAAGCTGTATGTGTGGGCCAAAGACCGCCCTGAGATCTG

GGAGGGAGAGCCTCCGTGTCTCCCACCGAGGGACAGCCTGAACCAGAGCC

TCAGCCAGGTACTATGGCACTGGCTGCTGAGGACTGGTGGCTGGAAGGTC

TCAGCTGTGACTTTGGCTTATCTGATCTTCTGCCTGTGTTCCCTTGTGGG

CATTCTTCATCTTCAAAGAGCCCTGGTCCTGAGGAGGAAAAGAAAGCGAA
```
```
TGACTGACCCCACCAGGAGATTCTTCAAAGTGACGCCTCCCCCAGGAAGC

GGGCCCCAGAACCAGTACGGGAACGTGCTGTCTCTCCCCACACCCACCTC

AGGCCTCGGACGCGCCCAGCGTTGGGCCGCAGGCCTGGGGGGCACTGCCC

CGTCTTATGGAAACCCGAGCAGCGACGTCCAGGCGGATGGAGCCTTGGGG

TCCCGGAGCCCGCCGGGAGTGGGCCCAGAAGAAGAGGAAGGGGAGGGCTA

TGAGGAACCTGACAGTGAGGAGGACTCCGAGTTCTATGAGAACGACTCCA

ACCTTGGGCAGGACCAGCTCTCCCAGGATGGCAGCGGCTACGAGAACCCT

GAGGATGAGCCCCTGGGTCCTGAGGATGAAGACTCCTTCTCCAACGCTGA

GTCTTATGAGAACGAGGATGAAGAGCTGACCCAGCCGGTCGCCAGGACAA

TGGACTTCCTGAGCCCTCATGGGTCAGCCTGGGACCCCAGCCGGGAAGCA

ACCTCCCTGGCAGGGTCCCAGTCCTATGAGGATATGAGAGGAATCCTGTA

TGCAGCCCCCCAGCTCCGCTCCATTCGGGGCCAGCCTGGACCCAATCATG

AGGAAGATGCAGACTCTTATGAGAACATGGATAATCCCGATGGGCCAGAC

CCAGCCTGGGGAGGAGGGGCCGCATGGGCACCTGGAGCACCAGGTGA
```

Genetically engineered hematopoietic stem cells carrying an edited CD19 gene that expresses this CD19 mutant are also within the scope of the present disclosure.

Genetically engineered hematopoietic stem cells carrying an edited CD19 gene that expresses this CD19 mutant are also within the scope of the present disclosure. Such cells may be a homogenous population containing cells expressing the same CD19 mutant (e.g., CD19ex2, CD19ex4). Alternatively, the cells may be a heterogeneous population containing cells expressing different CD19 mutants (which may due to heterogeneous editing/repairing events inside cells) or cells that do not express CD19 (CD19KO). In specific examples, the genetically engineered HSCs may be a heterogeneous population containing cells expressing CD19ex2 and cells that do not express CD19 (CD19KO). In some specific examples, the genetically engineered HSCs may be a heterogeneous population containing cells expressing CD19ex4 and cells that do not express CD19 (CD19KO).

Genetically engineered hematopoietic stem cells having edited a CD19 gene can be prepared by a suitable genome editing method, such as those known in the art or disclosed herein. In some embodiments, the genetically engineered hematopoietic stem cells described herein can be generated using the CRISPR approach. See discussions herein. In certain examples, specific guide RNAs targeting a fragment of the CD19 gene (an exon sequence or an intron sequence) can be used in the CRISPR method. Exemplary gRNAs for editing the CD19 gene (e.g., deletion of exon 2, exon 4) are provided in Example 1, Table 3, and Example 3 below.

In some examples, multiple gRNAs can be used for editing the CD19 gene via CRISPR. Different combinations of gRNAs, e.g., selected from those listed in Table 3, can be used in the multiplex approach. In one example, the pair of

```
gRNA6
(AGCAGAGGACTCCAAAAGCT; SEQ ID NO: 18)
and gRNA 14
(CCATGGACAGAAGAGGTCCG; SEQ ID NO: 24)
are used for editing CD19 via CRISPR.
```

Also provided herein are methods of genetically editing CD19 in hematopoietic cells (e.g., HSCs) via CRISPR, using one or more of the gRNAs described herein, for example, the pair of gRNA6+gRNA14 or the pair of gRNA 23+gRNA 24.

Because of the mechanism of Cas9 cutting and DNA repair, there will be a spectrum of repair events including small insertions on 1-2 nucleotides and occasionally longer deletions. Representative sequences of repaired CD19exon 2 deletion products (intron 1-intron 2 displayed) are shown below (SEQ ID Nos:53-55):

| Example | Repair | Sequence | Com-Length | ments |
|---|---|---|---|---|
| #1 | Ligation: | CCGGCTCCTCCACTCCCagccc gCGGCCACAATGGAGCTGGAG | 0 | |
| #2 | Insertion: | CCGGCTCCTCCACTCCCagcTc cgCGGCCACAATGGAGCTGGAG | +1 | |
| #3 | Deletion: | ---------------------- ------------------gCGGC CACAATGGAGCTGGAG | -133 | Partial loss Exon 1 |

Despite the heterogeneity at the genomic DNA level, the RNA transcripts provided from the edited CD19 gene all encode a CD19 mutant having the fragment encoded by exon 2 deleted.

(ii) Genetically Engineered Hematopoietic Cells Expressing CD33 Mutants

Figure 17:
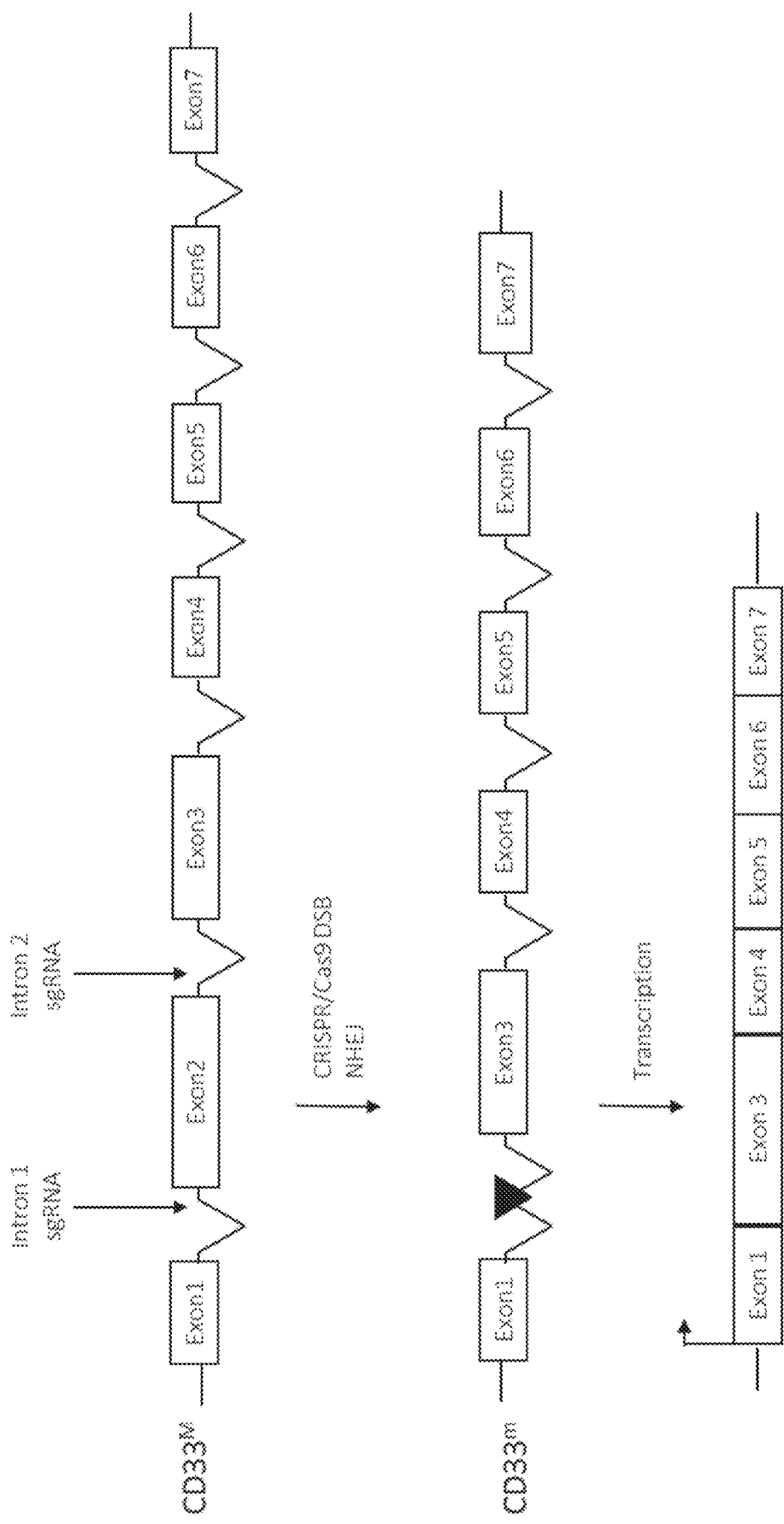
FIG. 17 is a schematic showing CD33 exon 2 editing, resulting in expression of the CD33m variant.

In some embodiments, the lineage-specific cell-surface protein is CD33. As will be known to one of ordinary skill in the art, CD33 is encoded by seven exons, including the alternatively spliced exons 7A and 7B (Brinkman-Van der Linden et al. *Mol Cell. Biol*. (2003) 23: 4199-4206). Further, the CD33 gene encodes two isoforms, one of which retains exon 2, referred to as CD33M, and one that excludes exon 2, referred to as CD33m (FIG. 17).

Exemplary amino acid sequences of the 7A and 7B splicing isoforms are provided below:

CD33M-7A: Amino Acid (underlined = exon 2; italicized = exon 7A)

(SEQ ID NO: 1)

MPLLLLLPLLWAGALAMDPNFWLQVQESVTVQEGLCVLVPCTFFHPIPYYDKNSPVHGYWF

REGAIISRDSPVATNKLDQEVQEETQGRFRLLGDPSRNNCSLSIVDARRRDNGSYFFRMERGS

TKYSYKSPQLSVHVTDLTHRPKILIPGTLEPGHSKNLTCSVSWACEQGTPPIFSWLSAAPTSLG

PRTTHSSVLIITPRPQDHGTNLTCQVKFAGAGVTTERTIQLNVTYVPQNPTTGIFPGDGSGKQE

TRAGVVHGAIGGAGVTALLALCLCLIFFIVKTHRRKAARTAVGRNDTHPTTGSAS*PKHQKKS*

*KLHGPTETSSCSGAAPTVEMDEELHYASLNFHGMNPSKDTSTEYSEVRTQ*

CD33-M; transcript variant 1
mRNA. NM_001772 (underlined = exon 2; italicized = exon 7A)

(SEQ ID NO: 120)

AUGCCGCUGCUGCUACUGCUGCCCCUGCUGUGGGCAGGGGCCCUGGCUAUGGAUCCAA

AUUUCUGGCUGCAAGUGCAGGAGUCAGUGACGGUACAGGAGGGUUUGUGCGUCCUCG

UGCCCUGCACUUUCUUCCAUCCCAUACCCUACUACGACAAGAACUCCCCAGUUCAUGG

UUACUGGUUCCGGGAAGGAGCCAUUAUAUCCAGGGACUCUCCAGUGGCCACAAACAA

GCUAGAUCAAGAAGUACAGGAGGAGACUCAGGGCAGAUUCCGCCUCCUUGGGGAUCC

CAGUAGGAACAACUGCUCCCUGAGCAUCGUAGACGCCAGGAGGAGGGAUAAUGGUUC

AUACUUCUUUCGGAUGGAGAGAGGAAGUACCAAAUACAGUUACAAAUCUCCCCAGCU

CUCUGUGCAUGUGACAGACUUGACCCACAGGCCCAAAAUCCUCAUCCCUGGCACUCUA

GAACCCGGCCACUCCAAAAACCUGACCUGCUCUGUGUCCUGGGCCUGUGAGCAGGGAA

CACCCCCGAUCUUCUCCUGGUUGUCAGCUGCCCCCACCUCCCUGGGCCCCAGGACUAC

UCACUCCUCGGUGCUCAUAAUCACCCCACGGCCCCAGGACCACGGCACCAACCUGACC

UGUCAGGUGAAGUUCGCUGGAGCUGGUGUGACUACGGAGAGAACCAUCCAGCUCAAC

GUCACCUAUGUUCCACAGAACCCAACAACUGGUAUCUUUCCAGGAGAUGGCUCAGGGA

AACAAGAGACCAGAGCAGGAGUGGUUCAUGGGGCCAUUGGAGGAGCUGGUGUUACAG

CCCUGCUCGCUCUUUGUCUCUGCCUCAUCUUCUUCAUAGUGAAGACCCACAGGAGGAA

AGCAGCCAGGACAGCAGUGGGCAGGAAUGACACCCACCCUACCACAGGGUCAGCCUCC

CCGAAACACCAGAAGAAGUCCAAGUUACAUGGCCCCACUGAAACCUCAAGCUGUUCAGGUG

-continued

*CCGCCCCUACUGUGGAGAUGGAUGAGGAGCUGCAUUAUGCUUCCCUCAACUUUCAUGGG*

*AUGAAUCCUUCCAAGGACACCUCCACCGAAUACUCAGAGGUCAGGACCCAGUGA*

CD33m-7A: Amino Acid (italicized = exon 7A; SEQ ID NO: 56)
MPLLLLLPLLWADLTHRPKILIPGTLEPGHSKNLTCSVSWACEQGTPPIFSWLSAAPTSLGPRT

THSSVLIITPRPQDHGTNLTCQVKFAGAGVTTERTIQLNVTYVPQNPTTGIFPGDGSGKQETRA

GVVHGAIGGAGVTALLALCLCLIFFIVKTHRRKAARTAVGRNDTHPTTGSASPKHQKKSKLH

GPTETSSCSGAAPT*VEMDEELHYASLNFHGMNPSKDTSTEYSEVRTQ*

CD33-m transcript variant 2; no exon 2, exon 7A
mRNA. NM_001082618 (italicized = exon 7A))

(SEQ ID NO: 121)

AUGCCGCUGCUGCUACUGCUGCCCCUGCUGUGGGCAGACUUGACCCACAGGCCCAAAA

UCCUCAUCCCUGGCACUCUAGAACCCGGCCACUCCAAAAACCUGACCUGCUCUGUGUC

CUGGGCCUGUGAGCAGGGAACACCCCCGAUCUUCUCCUGGUUGUCAGCUGCCCCCACC

UCCCUGGGCCCCAGGACUACUCACUCCUCGGUGCUCAUAAUCACCCCACGGCCCCAGG

ACCACGGCACCAACCUGACCUGUCAGGUGAAGUUCGCUGGAGCUGGUGUGACUACGGA

GAGAACCAUCCAGCUCAACGUCACCUAUGUUCCACAGAACCCAACAACUGGUAUCUUU

CCAGGAGAUGGCUCAGGGAAACAAGAGACCAGAGCAGGAGUGGUUCAUGGGGCCAUU

GGAGGAGCUGGUGUUACAGCCCUGCUCGCUCUUUGUCUCUGCCUCAUCUUCUUCAUAG

UGAAGACCCACAGGAGGAAAGCAGCCAGGACAGCAGUGGGCAGGAAUGACACCCACCC

*UACCACAGGGUCAGCCUCCCCGAAACACCAGAAGAAGUCCAAGUUACAUGGCCCCACUGA*

*AACCUCAAGCUGUUCAGGUGCCGCCCCUACUGUGGAGAUGGAUGAGGAGCUGCAUUAUG*

*CUUCCCUCAACUUUCAUGGGAUGAAUCCUUCCAAGGACACCUCCACCGAAUACUCAGAGG*

*UCAGGACCCAGUGA*

CD33M-7B: Amino Acid (underlined = exon 2; italicized = exon 7B; SEQ ID NO: 57)
MPLLLLLPLLWA<u>GALAMDPNFWLQVQESVTVQEGLCVLVPCTFFHPIPYYDKNSPVHGYWF</u>

<u>REGAIISRDSPVATNKLDQEVQEETQGRFRLLGDPSRNNCSLSIVDARRRDNGSYFFRMERGS</u>

<u>TKYSYKSPQLSVHVTDL</u>THRPKILIPGTLEPGHSKNLTCSVSWACEQGTPPIFSWLSAAPTSLG

PRTTHSSVLIITPRPQDHGTNLTCQVKFAGAGVTTERTIQLNVTYVPQNPTTGIFPGDGSGKQE

TRAGVVHGAIGGAGVTALLALCLCLIFFIVKTHRRKAARTAVGRNDTHPTTGSASP*VR*

CD33 transcript variant 3; exon 7B
mRNA. NM_001177608 (underlined = exon 2; italicized = exon 7B))

(SEQ ID NO: 122)

AUGCCGCUGCUGCUACUGCUGCCCCUGCUGUGGGCA<u>GGGGCCCUGGCUAUGGAUCCAA</u>

<u>AUUUCUGGCUGCAAGUGCAGGAGUCAGUGACGGUACAGGAGGGUUUGUGCGUCCUCG</u>

<u>UGCCCUGCACUUUCUUCCAUCCCAUACCCUACUACGACAAGAACUCCCCAGUUCAUGG</u>

<u>UUACUGGUUCCGGGAAGGAGCCAUUAUAUCCAGGGACUCUCCAGUGGCCACAAACAA</u>

<u>GCUAGAUCAAGAAGUACAGGAGGAGACUCAGGGCAGAUUCCGCCUCCUUGGGGAUCC</u>

<u>CAGUAGGAACAACUGCUCCCUGAGCAUCGUAGACGCCAGGAGGAGGGAUAAUGGUUC</u>

AUACUUCUUUCGGAUGGAGAGAGGAAGUACCAAAUACAGUUACAAAUCUCCCCAGCU

CUCUGUGCAUGUGACAGACUUGACCCACAGGCCCAAAAUCCUCAUCCCUGGCACUCUA

GAACCCGGCCACUCCAAAAACCUGACCUGCUCUGUGUCCUGGCCUGUGAGCAGGGAAC

ACCCCCGAUCUUCUCCGGUUGUCAGCUGCCCCCACCUCCCUGGGCCCCAGGACUACUC

ACUCCUCGGUGCUCAUAAUCACCCCACGGCCCCAGGACCACGGCACCAACCUGACCUG

UCAGGUGAAGUUCGCUGGAGCUGGUGUGACUACGGAGAGAACCAUCCAGCUCAACGU

CACCUAUGUUCCACAGAACCCAACAACUGGUAUCUUUCCGGAGAUGGCUCAGGGAAAC

-continued

AAGAGACCAGAGCAGGAGUGGUUCAUGGGGCCAUUGGAGGAGCUGGUGUUACAGCCC

UGCUCGCUCUUUGUCUCUGCCUCAUCUUCUUCAUAGUGAAGACCCACAGGAGGAAAGC

AGCCAGGACAGCAGUGGGCAGGAAUGACACCCACCCUACCACAGGGUCAGCCUCCCCG

*GUACGUUGA*

CD33m-7B Amino Acid (italicized = exon 7B; SEQ ID NO: 58)

MPLLLLLPLLWADLTHRPKILIPGTLEPGHSKNLTCSVSWACEQGTPPIFSWLSAAPTSLGPRT

THSSVLIITPRPQDHGTNLTCQVKFAGAGVTTERTIQLNVTYVPQNPTTGIFPGDGSGKQETRA

GVVHGAIGGAGVTALLALCLCLIFFIVKTHRRKAARTAVGRNDTHPTTGSASP*VR*

CD33 transcript variant 4; no exon 2, exon 7B.
mRNA (italicized = exon 7B)

(SEQ ID NO: 123)

AUGCCGCUGCUGCUACUGCUGCCCCUGCUGUGGGCAAGGAACAACUGCUCCCUGAGCA

UCGUAGACGCCAGGAGGAGGGAUAAUGGUUCAUACUUCUUUCGGAUGGAGAGAGGAA

GUACCAAAUACAGUUACAAAUCUCCCCAGCUCUCUGUGCAUGUGACAGACUUGACCCA

CAGGCCCAAAAUCCUCAUCCCUGGCACUCUAGAACCCGGCCACUCCAAAAACCUGACC

UGCUCUGUGUCCUGGCCUGUGAGCAGGGAACACCCCCGAUCUUCUCCGGUUGUCAGCU

GCCCCCACCUCCCUGGGCCCCAGGACUACUCACUCCUCGGUGCUCAUAAUCACCCCACG

GCCCCAGGACCACGGCACCAACCUGACCUGUCAGGUGAAGUUCGCUGGAGCUGGUGUG

ACUACGGAGAGAACCAUCCAGCUCAACGUCACCUAUGUUCCACAGAACCCAACAACUG

GUAUCUUUCCGGAGAUGGCUCAGGGAAACAAGAGACCAGAGCAGGAGUGGUUCAUGG

GGCCAUUGGAGGAGCUGGUGUUACAGCCCUGCUCGCUCUUUGUCUCUGCCUCAUCUUC

UUCAUAGUGAAGACCCACAGGAGGAAAGCAGCCAGGACAGCAGUGGGCAGGAAUGAC

ACCCACCCUACCACAGGGUCAGCCUCCCCG*GUACGUUGA*

Using human CD33 as an exemplary lineage-specific cell-surface protein, regions of the protein in which mutation and/or deletion of amino acids are less likely to result in deleterious effects (e.g., a reduction or abrogation of function) were predicted using PROVEAN software (see: provean.jcvi.org; Choi et al. PLoS ONE (2012) 7(10): e46688). Examples of the predicted regions are shown in boxes in FIG. 2 and exemplary deletions in the predicated regions are presented in Table 2. Numbering of the amino acid residues is based on the amino acid sequence of human CD33 provided by SEQ ID NO: 1 (CD33M-7A).

TABLE 2

| Exemplary deletions in CD33 | | |
|---|---|---|
| Deletion | PROVEAN Score | Epitope targeted by cytotoxic agent |
| S248-E252 | -5.508 | SGKQE (SEQ ID NO: 8) |
| I47-D51 | -5.661 | IPYYD (SEQ ID NO: 9) |
| G249-T253 | -7.078 | GKQET (SEQ ID NO: 10) |

TABLE 2-continued

| Exemplary deletions in CD33 | | |
|---|---|---|
| Deletion | PROVEAN Score | Epitope targeted by cytotoxic agent |
| K250-R254 | -7.184 | KQETR (SEQ ID NO: 11) |
| P48-K52 | -7.239 | PYYDK (SEQ ID NO: 12) |
| Q251-A255 | -7.888 | QETRA (SEQ ID NO: 13) |

The nucleotide sequence encoding CD33 are genetically manipulated to delete any epitope of the protein (of the extracellular portion of CD33), or a fragment containing such, using conventional methods of nucleic acid manipulation. The amino acid sequences provided below are exemplary sequences of CD33 mutants that have been manipulated to lack each of the epitopes in Table 2.

The amino acid sequence of the extracellular portion of CD33 is provided by SEQ ID NO: 1. The signal peptide is shown in italics and sites for manipulation are shown in underline and boldface. The transmembrane domain is shown in italics with underline.

(SEQ ID NO: 1)

*MPLLLLLPLL WAGALAM*DPN FWLQVQESVT VQEGLCVLVP CTFFHPIPYY DKNSPVHGYW

FREGAIISRD SPVATNKLDQ EVQEETQGRF RLLGDPSRNN CSLSIVDARR RDNGSYFFRM

```
ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT

GIFPGDGSGK QETRAGVVH*G AIGGAGVTAL LALCLCLIFF IV*KTHRRKAA RTAVGRNDTH

PTTGSASPKH QKKSKLHGPT ETSSCSGAAP TVEMDEELHY ASLNFHGMNP SKDTSTEYSE

VRTQ
```

The amino acid sequence of the extracellular portion of CD33 comprising a deletion of residues S248 through E252 is provided by SEQ ID NO: 2. The signal peptide is shown in italics and the transmembrane domain is shown in italics with underline.

```
S248_E252insdelTARND; PRO VEAN score = -1.916
                                                          (SEQ ID NO: 2)
*MPLLLLLPLL WAGALAMDPN* FWLQVQESVT VQEGLCVLVP CTFFHPIPYY DKNSPVHGYW

FREGAIISRD SPVATNKLDQ EVQEETQGRF RLLGDPSRNN CSLSIVDARR RDNGSYFFRM

ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT

GIFPGDGTAR NDTRAGVVH*G AIGGAGVTAL LALCLCLIFF IV*KTHRRKAA RTAVGRNDTH

PTTGSASPKH QKKSKLHGPT ETSSCSGAAP TVEMDEELHY ASLNFHGMNP SKDTSTEYSE

VRTQ
```

The amino acid sequence of the extracellular portion of CD33 comprising a deletion of residues I47 through D51 is provided by SEQ ID NO: 3. The signal peptide is shown in italics and the transmembrane domain is shown in italics with underline.

```
I47_D51insdelVPFFE; PRO VEAN score = -1.672
                                                          (SEQ ID NO: 3)
*MPLLLLLPLL WAGALAMDPN* FWLQVQESVT VQEGLCVLVP CTFFHPVPFF EKNSPVHGYW

FREGAIISRD SPVATNKLDQ EVQEETQGRF RLLGDPSRNN CSLSIVDARR RDNGSYFFRM

ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT

GIFPGDGTAR NDTRAGVVH*G AIGGAGVTAL LALCLCLIFF IV*KTHRRKAA RTAVGRNDTH

PTTGSASPKH QKKSKLHGPT ETSSCSGAAP TVEMDEELHY ASLNFHGMNP SKDTSTEYSE

VRTQ
```

The amino acid sequence of the extracellular portion of CD33 comprising a deletion of residues G249 through T253 is provided by SEQ ID NO: 4. The signal peptide is shown in italics and the transmembrane domain is shown in italics with underline.

```
                                                          (SEQ ID NO: 4)
*MPLLLLLPLL WAGALAMDPN* FWLQVQESVT VQEGLCVLVP CTFFHPIPYY DKNSPVHGYW

FREGAIISRD SPVATNKLDQ EVQEETQGRF RLLGDPSRNN CSLSIVDARR RDNGSYFFRM

ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT
```

```
-continued
GIFPGDGSRA GVVHGAIGGA GVTALLALCL CLIFFIVKTH RRKAARTAVG RNDTHPTTGS

ASPKHQKKSK LHGPTETSSC SGAAPTVEMD EELHYASLNF HGMNPSKDTS TEYSEVRTQ
```

The amino acid sequence of the extracellular portion of CD33 comprising a deletion of residues K250 through R254 is provided by SEQ ID NO: 5. The signal peptide is shown in italics and the transmembrane domain is shown in italics with underline.

```
                                                           (SEQ ID NO: 5)
MPLLLLLPLL WAGALAMDPN FWLQVQESVT VQEGLCVLVP CTFFHPIPYY DKNSPVHGYW

FREGAIISRD SPVATNKLDQ EVQEETQGRF RLLGDPSRNN CSLSIVDARR RDNGSYFFRM

ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT

GIFPGDGSGA GVVHGAIGGA GVTALLALCL CLIFFIVKTH RRKAARTAVG RNDTHPTTGS

ASPKHQKKSK LHGPTETSSC SGAAPTVEMD EELHYASLNF HGMNPSKDTS TEYSEVRTQ
```

The amino acid sequence of the extracellular portion of CD33 comprising a deletion of residues P48 through K52 is provided by SEQ ID NO: 6. The signal peptide is shown in italics and the transmembrane domain is shown in italics with underline.

```
                                                           (SEQ ID NO: 6)
MPLLLLLPLL WAGALAMDPN FWLQVQESVT VQEGLCVLVP CTFFHPINSP VHGYWFREGA

IISRDSPVAT NKLDQEVQEE TQGRFRLLGD PSRNNCSLSI VDARRRDNGS YFFRMERGST

KYSYKSPQLS VHVTDLTHRP KILIPGTLEP GHSKNLTCSV SWACEQGTPP IFSWLSAAPT

SLGPRTTHSS VLIITPRPQD HGTNLTCQVK FAGAGVTTER TIQLNVTYVP QNPTTGIFPG

DGSGKQETRA GVVHGAIGGA GVTALLALCL CLIFFIVKTH RRKAARTAVG RNDTHPTTGS

ASPKHQKKSK LHGPTETSSC SGAAPTVEMD EELHYASLNF HGMNPSKDTS TEYSEVRTQ
```

The amino acid sequence of the extracellular portion of CD33 comprising a deletion of residues Q251 through A255 is provided by SEQ ID NO: 7. The signal peptide is shown in italics and the transmembrane domain is shown in italics with underline.

```
                                                           (SEQ ID NO: 7)
MPLLLLLPLL WAGALAMDPN FWLQVQESVT VQEGLCVLVP CTFFHPIPYY DKNSPVHGYW

FREGAIISRD SPVATNKLDQ EVQEETQGRF RLLGDPSRNN CSLSIVDARR RDNGSYFFRM

ERGSTKYSYK SPQLSVHVTD LTHRPKILIP GTLEPGHSKN LTCSVSWACE QGTPPIFSWL

SAAPTSLGPR TTHSSVLIIT PRPQDHGTNL TCQVKFAGAG VTTERTIQLN VTYVPQNPTT

GIFPGDGSGK GVVHGAIGGA GVTALLALCL CLIFFIVKTH RRKAARTAVG RNDTHPTTGS

ASPKHQKKSK LHGPTETSSC SGAAPTVEMD EELHYASLNF HGMNPSKDTS TEYSEVRTQ
```

In some examples, provided herein are variants of CD33, which may comprise a deletion or mutation of a fragment of the protein that is encoded by any one of the exons of CD33, or a deletion or mutation in a non-essential epitope. The predicted structure of CD33 includes two immunoglobulin domains, an IgV domain and an IgC2 domain. In some embodiments, a portion of the immunoglobulin V domain of CD33 is deleted or mutated. In some embodiments, a portion of the immunoglobulin C domain of CD33 is deleted or mutated. In some embodiments, exon 2 of CD33 is deleted or mutated. In some embodiments, the CD33 variant lacks amino acid residues W11 to T139 of SEQ ID NO: 1. In some embodiments, the CD33 variant lacks amino acid residues G13 to T139 of SEQ ID NO: 1. In some embodiments, the deleted or mutated fragment overlaps or encompasses the epitope to which the cytotoxic agent binds. As described in Example 1, in some embodiments, the epitope comprises amino acids 47-51 or 248-252 of the extracellular portion of CD33 (SEQ ID NO: 1). In some embodiments, the epitope comprises amino acids 248-252 (SEQ ID NO: 8), 47-51 (SEQ ID NO: 9), 249-253 (SEQ ID NO: 10), 250-254 (SEQ ID NO: 11), 48-52 (SEQ ID NO: 12), or 251-255 (SEQ ID NO: 13) of the extracellular portion of CD33 (SEQ ID NO: 1).

In some embodiments, the genetically engineered hematopoietic stem cells have genetic edits in a CD33 gene, wherein exon2 of CD33 is mutated or deleted. In some embodiments, exon 2 of CD33 is mutated or deleted (see the amino acid sequence of the exon 2-encoded fragment above). In some embodiments, the genetically engineered hematopoietic stem cells have genetic edits in a CD33 gene resulting in expression of CD33 with deleted or mutated exon 2 of CD33. In some embodiments, genetically engineered hematopoietic stem cells express CD33, in which exon 2 of CD33 is mutated or deleted. In some examples, the genetically engineered hematopoietic cells have a genetically engineered CD33 gene (e.g., a genetically engineered endogenous CD33 gene), wherein the engineering results in expression of a CD33 variant having the fragment encoded by exon 2 deleted (CD33ex2).

In some embodiments, the CD33 genes edited HSCs expressing CD33 variant having the fragment encoded by exon 2 deleted also comprise a partial or complete deletion in the adjacent introns (intron 1 and intron 2) in addition to the deletion of exon 2.

Exemplary amino acid sequence of CD33 mutants, with fragments G13-T139 deleted, is provided below (the junction of exon 1-encoded fragment and exon-3 encoded fragment is shown in boldface):

(SEQ ID NO: 56)
MPLLLLLPLLWADLTHRPKILIPGTLEPGHSKNLTCSVSWACEQGTPPI

FSWLSAAPTSLGPRTTHSSVLIITPRPQDHGTNLTCQVKFAGAGVTTER

TIQLNVTYVPQNPTTGIFPGDGSGKQETRAGVVHGAIGGAGVTALLALC

LCLIFFIVKTHRRKAARTAVGRNDTHPTTGSASPKHQKKSKLHGPTETS

SCSGAAPTVEMDEELHYASLNFHGMNPSKDTSTEYSEVRTQ (SEQ ID NO: 58)
MPLLLLLPLLWADLTHRPKILIPGTLEPGHSKNLTCSVSWACEQGTPPI

FSWLSAAPTSLGPRTTHSSVLIITPRPQDHGTNLTCQVKFAGAGVTTER

TIQLNVTYVPQNPTTGIFPGDGSGKQETRAGVVHGAIGGAGVTALLALC

LCLIFFIVKTHRRKAARTAVGRNDTHPTTGSASPVR

While certain cells may express CD33 proteins lacking the fragment encoded by exon 2, the genetically engineered hematopoietic cells are different from such native cells in at least the aspect that these cells have undergone genome editing to modify a CD33 gene such as an endogenous CD33 gene. In other words, the parent hematopoietic stem cells for producing the genetically engineered HSCs carry a CD33 gene that produces exon 2-containing transcripts.

Genetically engineered hematopoietic stem cells carrying an edited CD33 gene that expresses this CD33 mutant are also within the scope of the present disclosure. Such cells may be a homogenous population containing cells expressing the same CD33 mutant (e.g., CD33ex2). Alternatively, the cells may be a heterogeneous population containing cells expressing different CD33 mutants (which may due to heterogeneous editing/repairing events inside cells) or cells that do not express CD33 (CD33KO). In specific examples, the genetically engineered HSCs may be a heterogeneous population containing cells expressing CD33ex2 and cells that do not express CD33 (CD33KO).

Genetically engineered hematopoietic stem cells having edited a CD33 gene can be prepared by a suitable genome editing method, such as those known in the art or disclosed herein. In some embodiments, the genetically engineered hematopoietic stem cells described herein can be generated using the CRISPR approach. See discussions herein. In certain examples, specific guide RNAs targeting a fragment of the CD33 gene (an exon sequence or an intron sequence) can be used in the CRISPR method. Exemplary gRNAs for editing the CD33 gene (e.g., deletion of exon 2) are provided in Example 2, Table 4, and Example 3 below.

In some examples, multiple gRNAs can be used for editing the CD33 gene via CRISPR. Different combinations of gRNAs, e.g., selected from those listed in Table 4, can be used in the multiplex approach.

A CD33 pseudogene, known as SIGLEC22P (Gene ID 114195), is located upstream of the CD33 gene and shares a certain degree of sequence homology with the CD33 gene. gRNAs that cross-target regions in the pseudogene and regions in the CD33 gene may lead to production of aberrant gene products. Thus, in some embodiments, the gRNAs used in methods of editing CD33 via CRISPR preferably have low or no cross-reactivity with regions inside the pseudogene. In some instances, the gRNAs used in methods of editing CD33 via CRISPR preferably have low or no cross-reactivity with region(s) in Exon 1, intron 1 or Exon 2 of CD33 that are homologous to the pseudogene. Such gRNAs can be designed by comparing the sequences of the pseudogene and the CD33 gene to choose targeting sites inside the CD33 gene that have less or no homology to regions of the pseudogene.

In one example, the pair of gRNA 18 (TTCATGGGTACTGCAGGGCA; SEQ ID NO: 44)) and gRNA 24 (GTGAGTGGCTGTGGGGAGAG; SEQ ID NO: 50) are used for editing CD33 via CRISPR. Also provided herein are methods of genetically editing CD33 in hematopoietic cells (e.g., HSCs) via CRISPR, using one or more of the gRNAs described herein, for example, the pair of gRNA18+gRNA24. As described herein, the length of a gRNA sequence may be modified (increased or decreased), for example, to enhance editing specificity and/or efficiency. In some embodiments, the length of gRNA 24 is 20 base pairs. In some embodiments, reducing the length of gRNA 24 may reduce the editing efficiency of gRNA 24 for CD33.

Because of the mechanism of Cas9 cutting and DNA repair, there will be a spectrum of repair events including small insertions on 1-2 nucleotides and occasionally longer deletions. Representative sequences of repaired CD33exon 2 deletion products (intron 1-intron 2 displayed) are shown below (SEQ ID NOs:59-65):

| Example Comment | Repair | Sequence | Length |
|---|---|---|---|
| 1. | Ligation: | CCCTGCTGTGGGCAGgtgagtggctgtggggagcagggctgggatgggaccct | 0 |
| 2. | Insertion: | CCCTGCTGTGGGCAGgtgaAtggctgCggggagcagggctgggatgggaccc | +1 |
| 3. | Insertion: | CCCTGCTGTGGGCAGgtgagtggctgtgggcaggtgagtggctgggatgggaccct | +6/-3 |
| 4. | Insertion: | CCCTGCTGTGGGCAGgtgaAtggctgCggggTactgcagggcagggctgggatgggaccct | +8 |
| 5. | Deletion: | CCCTGCTGTGGGCAGgtgaAt-------------ggctggatgggaccct | +1/-14 |

| Example Comment | Repair | Sequence | Length |
|---|---|---|---|
| 6. | Deletion: | CCCTGCTGTGGGCAGgtgaatggctg-------cagggctgggatgggaccct | -7 |
| 7. | Deletion: -3 nt in exon 1 | CCCTGCTGTGGG--------------------------ctgggatgggaccct | -2 |

Despite the heterogeneity at the genomic DNA level, the RNA transcripts provided from the edited CD33 gene all encode CD33 mutants having the fragment encoded by exon 2 deleted.

(iii) Genetically Engineered Hematopoietic Cells Expressing Both CD19 and CD33 Mutants Also provided herein are a genetically engineered hematopoietic cells such as HSCs that have both the CD19 and CD33 genes edited. In some embodiments, provide herein is a population of genetically engineered hematopoietic HSCs in which at least 50% of the cells carry genetically edited CD19 and CD33 cells in at least on chromosome.

In some embodiments, the edited CD19 gene is capable of expressing a CD19 mutant having the fragment encoded by exon 2 deleted. Alternatively or in addition, the edited CD33 gene is capable of expressing a CD33 mutant having the fragment encoded by exon 3 deleted.

The genetically engineered hematopoietic cells having both CD19 and CD33 genes edited can be prepared by conventional methods. In some embodiments, such cells are prepared by CRISPR using a pair of gRNAs, one targeting CD19 and the other targeting CD33. Examples are provided in Example 3, Table 8 below. In one example, the pair of gRNAs can be introduced into parent HSCs simultaneously and cells having genetic edits in CD19 and/or CD33 can be harvested for further use.

Masked Lineage-Specific Cell Surface Antigens

While many of the embodiments described herein involve mutations to the endogenous genes encoding lineage-specific cell surface antigens, it is understood that other approaches may be used instead of or in addition to mutation. For instance, a lineage-specific cell surface antigen can be masked, e.g., to prevent or reduce its recognition by an immunotherapeutic agent. In some embodiments, masking is used on a lineage-specific cell surface antigen that is difficult to mutate, e.g., because mutation of the gene is inefficient or is deleterious to cells expressing the mutant. In some embodiments, the lineage-specific cell surface protein is CD45. In some embodiments, masking is performed on a cell type described herein, e.g., an HSC or HPC.

In some embodiments, masking is accomplished by expressing a masking protein in the cell of interest (e.g., by stably expressing DNA encoding the masking protein in the cell). In some embodiments, the masking protein comprises a binding domain (e.g., an antibody or antigen-binding fragment, e.g., an scFv) that binds the lineage-specific cell surface protein, e.g., in a way that reduces binding of an immunotherapeutic agent to the lineage-specific cell surface protein, e.g., by competing for binding at the same epitope. In some embodiments, the binding domain binds CD45. In some embodiments, the making protein further comprises one or more sequences that direct its localization to the surface of the cell. In some embodiments, the masking protein comprises a transmembrane domain fused to the binding domain. The masking protein may comprise a linker disposed between the transmembrane domain and the binding domain. The masking protein may be expressed at a level that binds to a sufficient amount of the lineage-specific cells surface antigen that an immunotherapeutic agent displays reduced binding to and/or reduced killing of a cell expressing the masking protein compared to an otherwise similar cell that does not express the masking protein.

In some embodiments, a cell described herein has reduced binding to (and/or reduced killing by) two different immunotherapeutic agents that recognize two different lineage-specific cell surface antigens. For instance, the cell may have a mutation at a gene encoding a first lineage-specific cell surface antigen, and may comprise a masking protein that masks a second lineage-specific cell surface antigen. In some embodiments, the cell may comprise a first masking protein that masks a first lineage-specific cell surface antigen and a second masking protein that masks a second lineage-specific cell surface antigen. In some embodiments, the first and second lineage-specific cell surface antigens are antigens listed in Table 1A.

Cells Altered at One or More Lineage-Specific Cell Surface Antigens

While many of the embodiments described herein involve two or more lineage-specific cell surface antigens, the application also discloses various cells altered with respect to a single lineage-specific cell surface antigen. For instance, the disclosure describes cells mutated at any one of the lineage-specific cell surface antigens described herein (e.g., mutated at one or both alleles of the lineage-specific cell surface antigen). The disclosure also describes cells expressing a single masking protein for a single lineage-specific cell surface antigen.

II. Cytotoxic Agents Specific to Lineage-Specific Cell-Surface Antigens

Cytotoxic agents targeting cells (e.g., cancer cells) expressing a lineage-specific cell-surface antigen can be co-used with the genetically engineered hematopoietic cells as described herein. As used herein, the term "cytotoxic agent" refers to any agent that can directly or indirectly induce cytotoxicity of a target cell, which expresses the lineage-specific cell-surface antigen (e.g., a target cancer cell). Such a cytotoxic agent may comprise a protein-binding fragment that binds and targets an epitope of the lineage-specific cell-surface antigen. In some instances, the cytotoxic agent may comprise an antibody, which may be conjugated to a drug (e.g., an anti-cancer drug) to form an antibody-drug conjugate (ADC).

The cytotoxic agent for use in the methods described herein may directly cause cell death of a target cell. For example, the cytotoxic agent can be an immune cell (e.g., a cytotoxic T cell) expressing a chimeric receptor. Upon engagement of the protein binding domain of the chimeric receptor with the corresponding epitope in a lineage-specific cell-surface antigen, a signal (e.g., activation signal) may be transduced to the immune cell resulting in release of cytotoxic molecules, such as perforins and granzymes, as well as activation of effector functions, leading to death of the target cell. In another example, the cytotoxic agent may be an ADC molecule. Upon binding to a target cell, the drug moiety in the ADC would exert cytotoxic activity, leading to target cell death.

In other embodiments, the cytotoxic agent may indirectly induce cell death of the target cell. For example, the cytotoxic agent may be an antibody, which, upon binding to the target cell, would trigger effector activities (e.g., ADCC) and/or recruit other factors (e.g., complements), resulting in target cell death.

Any of the cytotoxic agents described herein target a lineage-specific cell-surface antigen, e.g., comprising a protein-binding fragment that specifically binds an epitope in the lineage-specific protein.

For leukemias that become resistance to CAR-T therapy, an emerging strategy is to simultaneously target alternative or multiple antigens (see e.g., *Nature Reviews Immunology* (2019), Volume 19, pages 73-74 and *Cancer Discov.* (2018) October; 8(10):1219-1226).

In some embodiments, more than one (e.g., 2, 3, 4, 5 or more) cytotoxic agent is used to target more than one (e.g., 1, 2, 3, 4, 5 or more) epitopes of a lineage-specific cell-surface antigen. In some embodiments, more than one (e.g., 1, 2, 3, 4, 5 or more) cytotoxic agent is used to target an epitope(s) of one or more lineage-specific cell-surface antigen(s) (e.g., additional/alternative antigens). In some embodiments, targeting more than one lineage-specific cell-surface antigen reduces relapse of a hematopoietic malignancy. In one embodiment, two or more cytotoxic agents are used in the methods described herein. In some embodiments, the two or more cytotoxic agents are administered concurrently. In some embodiments, the two or more cytotoxic agents are administered sequentially.

Examples of additional cell-surface proteins that may be targeted are known in the art (see, e.g., Tasian, *Ther. Adv. Hematol.* (2018) 9(6): 135-148; Hoseini and Cheung, *Blood Cancer Journal* (2017) 7, e522; doi:10.1038/bcj.2017.2; Taraseviciute et al. *Hematology and Oncology* (2019) 31(1)). In some embodiments, the methods described herein involve targeting a lineage-specific cell-surface antigen and one or more additional cell-surface proteins. In some embodiments, the methods described herein involved administering a cytotoxic agent targeting CD33 and at least one additional cytotoxic agent that targets an additional cell-surface protein, such as CD7, CD13, CD15, CD25 (IL-2Ra), CD30, CD32 (FcγRIII), CD38, CD44v6, CD45, CD47, CD56, CD90 (Thy1), CD96, CD117 (c-KIT), CD123 (IL3Ra), CD135 (FLT3R), CD174 (Lewis-Y), CLL-1 (CLEC12A), folate receptor-b, IL1RAP, MUC1, NKG2D/NKG2DL, TIM-3 (HAVCR2), CD19, and WT1. In some embodiments, the methods described herein involved administering a cytotoxic agent targeting CD19 and at least one additional cytotoxic agent that targets an additional cell-surface protein, such as CD7, CD13, CD15, CD25 (IL-2Ra), CD30, CD32 (FcγRIII), CD38, CD44v6, CD45, CD47, CD56, CD90 (Thy1), CD96, CD117 (c-KIT), CD123 (IL3Ra), CD135 (FLT3R), CD174 (Lewis-Y), CLL-1 (CLEC12A), folate receptor-b, IL1RAP, MUC1, NKG2D/NKG2DL, TIM-3 (HAVCR2), CD19, and WT1.

In some examples, a cytotoxic agent is used to target CD33 and a second cytotoxic agent is used to target CD19. In some examples, a cytotoxic agent is used to target CD33 and a second cytotoxic agent is used to target an additional cell-surface protein. In some examples, a cytotoxic agent is used to target CD19 and a second cytotoxic agent is used to target an additional cell-surface protein. In some examples, a cytotoxic agent is used to target CD33 and a second cytotoxic agent is used to target CD13. In some examples, a cytotoxic agent is used to target CD33 and a second cytotoxic agent is used to target CD13. In some examples, a cytotoxic agent is used to target CD33 and a second cytotoxic agent is used to target CD123. In some examples, a cytotoxic agent is used to target CD19 and a second cytotoxic agent is used to target CD13. In some examples, a cytotoxic agent is used to target CD19 and a second cytotoxic agent is used to target CD123. In some examples, a cytotoxic agent is used to target CD13 and a second cytotoxic agent is used to target CD123.

In some examples, a cytotoxic agent is used to target CD33, a second cytotoxic agent is used to target CD19, and a third cytotoxic agent is used to target CD13. In some examples, a cytotoxic agent is used to target CD33, a second cytotoxic agent is used to target CD19, and a third cytotoxic agent is used to target CD123. In some examples, a cytotoxic agent is used to target CD33, a second cytotoxic agent is used to target CD13, and a third cytotoxic agent is used to target CD123. In some examples, a cytotoxic agent is used to target CD19, a second cytotoxic agent is used to target CD19, and a third cytotoxic agent is used to target CD13. In some examples, a cytotoxic agent is used to target CD33, a second cytotoxic agent is used to target CD19, a third cytotoxic agent is used to target CD13, and fourth cytotoxic agent used to target CD123.

(i) Therapeutic Antibodies

Any antibody or an antigen-binding fragment thereof can be used as a cytotoxic agent or for constructing a cytotoxic agent that targets an epitope of a lineage-specific cell-surface antigen, as described herein. Such an antibody or antigen-binding fragment can be prepared by a conventional method, for example, the hybridoma technology or recombinant technology.

As used herein, the term "antibody" refers to a glycoprotein comprising at least two heavy (H) chains and two light (L) chains inter-connected by disulfide bonds, i.e., covalent heterotetramers comprised of two identical Ig H chains and two identical L chains that are encoded by different genes. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Formation of a mature functional antibody molecule can be accomplished when two proteins are expressed in stoichiometric quantities and self-assemble with the proper configuration.

In some embodiments, the antigen-binding fragment is a single-chain antibody fragment (scFv) that specifically binds the epitope of the lineage-specific cell-surface antigen. In other embodiments, the antigen-binding fragment is a full-length antibody that specifically binds the epitope of the lineage-specific cell-surface antigen.

As described herein and as will be evident to a skilled artisan, the CDRs of an antibody specifically bind to the epitope of a target protein/antigen (the lineage-specific cell-surface protein/antigen).

In some embodiments, the antibodies are full-length antibodies, meaning the antibodies comprise a fragment crystallizable (Fc) portion and a fragment antigen-binding (Fab) portion. In some embodiments, the antibodies are of the isotype IgG, IgA, IgM, IgA, or IgD. In some embodiments, a population of antibodies comprises one isotype of antibody. In some embodiments, the antibodies are IgG antibodies. In some embodiments, the antibodies are IgM antibodies. In some embodiments, a population of antibodies comprises more than one isotype of antibody. In some embodiments, a population of antibodies is comprised of a majority of one isotype of antibodies but also contains one or more other isotypes of antibodies. In some embodiments, the antibodies are selected from the group consisting of IgG1, IgG2, IgG3, IgG4, IgM, IgA1, IgA2, IgAsec, IgD, IgE.

The antibodies described herein may specifically bind to a target protein. As used herein, "specific binding" refers to antibody binding to a predetermined protein, such as a cancer antigen. "Specific binding" involves more frequent, more rapid, greater duration of interaction, and/or greater affinity to a target protein relative to alternative proteins. In some embodiments, a population of antibodies specifically binds to a particular epitope of a target protein, meaning the antibodies bind to the particular protein with more frequently, more rapidly, for greater duration of interaction, and/or with greater affinity to the epitope relative to alternative epitopes of the same target protein or to epitopes of another protein. In some embodiments, the antibodies that specifically bind to a particular epitope of a target protein may not bind to other epitopes of the same protein.

Antibodies may be selected based on the binding affinity of the antibody to the target protein or epitope. Alternatively or in additional, the antibodies may be mutated to introduce one or more mutations to modify (e.g., enhance or reduce) the binding affinity of the antibody to the target protein or epitope.

The present antibodies or antigen-binding portions can specifically bind with a dissociation constant ($K_D$) of less than about $10^{-7}$ M, less than about $10^{-8}$ M, less than about $10^{-9}$ M, less than about $10^{-10}$ M, less than about $10^{-11}$ M, or less than about $10^{-12}$ M. Affinities of the antibodies according to the present disclosure can be readily determined using conventional techniques (see, e.g., Scatchard et al., Ann. N.Y. Acad. Sci. (1949) 51:660; and U.S. Pat. Nos. 5,283,173, 5,468,614, or the equivalent).

The binding affinity or binding specificity for an epitope or protein can be determined by a variety of methods including equilibrium dialysis, equilibrium binding, gel filtration, ELISA, surface plasmon resonance, or spectroscopy.

For example, antibodies (of antigen-binding fragments thereof) specific to an epitope of a lineage-specific protein of interest can be made by the conventional hybridoma technology. The lineage-specific protein, which may be coupled to a carrier protein such as KLH, can be used to immunize a host animal for generating antibodies binding to that complex. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute®, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the TCR-like monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of binding to a lineage-specific protein. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target protein or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the lineage-specific protein. In some examples, the antibody sequence is manipulated to increase binding affinity of the antibody to the lineage-specific protein such that lower levels of the lineage-specific protein are detected by the antibody. In some embodiments, antibodies that have increased binding to the lineage-specific protein may be used to reduce or prevent relapse of a hematopoietic malignancy. It will be apparent to one of skill in the art that one or more polynucleotide changes can be made to the antibody and still maintain its binding specificity to the target protein.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen®, Inc. (Fremont, Calif.) and HuMAb-Mouse® and TC Mouse™ from Medarex®, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target protein can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target protein.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a lineage-specific protein can be identified from the library following routine procedures. Positive clones can be subjected to further screening to identify those that bind lineage-specific protein.

In some instances, the cytotoxic agent for use in the methods described herein comprises an antigen-binding fragment that targets the lineage-specific protein CD33. In other examples, the cytotoxic agent for use in the methods described herein comprises an antigen-binding fragment that targets the lineage-specific protein CD19. In other example, two or more cytotoxic agents are used in the methods described herein. In some embodiments, the two or more cytotoxic agents are administered concurrently. In some embodiments, the two or more cytotoxic agents are administered sequentially. In one non-limiting example, antibodies and antigen-binding fragments targeting CD33 and CD19 in combination are used in the methods described herein. In one non-limiting example, antibodies and antigen-binding fragments targeting CD33 are used in combination with a cytotoxic agent (e.g., antibodies, immune cells expressing chimeric antigen receptors, antibody-drug conjugates) that targets a second lineage-specific cell-surface antigen or an additional cell-surface protein. In one non-limiting example, antibodies and antigen-binding fragments targeting CD19 are used in combination with a cytotoxic agent (e.g., antibodies, immune cells expressing chimeric antigen receptors, antibody-drug conjugates) that targets a second lineage-specific cell-surface antigen or an additional cell-surface protein.

In some embodiments, bispecific or multi-specific antibodies may be used to target more than one epitope (e.g., more than one epitope of a lineage-specific cell-surface antigen, epitopes of more than one lineage-specific cell-surface antigen, an epitope of lineage-specific cell-surface antigen and an epitope of an additional cell-surface antigen). See, e.g., Hoseini et al. *Blood Cancer Journal* (2017) 7, e552. Non-limiting examples of bispecific antibodies include tandem double scFv (e.g., single-chain bispecific tandem fragment variable (scBsTaFv), bispecific T-cell engager (BiTE), bispecific single-chain Fv (bsscFv), bispecific killer-cell engager (BiKE), dual-affinity re-targeting (DART), diabody, tandem diabodies (TandAb), single-chain Fv triplebody (sctb), bispecific scFv immunofusion (Blf), Fabsc, dual-variable-domain immunoglobulin (DVD-Ig), CrossMab (CH1-CL), modular bispecific antibody (IgG-scFv). See, e.g., Marin-Acevedo et al. *J. Hematol. Oncol.* (2018)11: 8; Slaney et al. *Cancer Discovery* (2018) 8(8): 924-934, and Elgundi et al. *Advanced Drug Discovery Reviews* (2017) 122: 2-19.

In some embodiments, the antibody is a bispecific T-cell engager (BiTE) comprising two linked scFv molecules. In some embodiments, at least of the linked scFv of the BiTE binds an epitope of a lineage-specific cell-surface protein (e.g., CD33 or CD19). In one example, the BiTE is blinatumomab. See, e.g. Slaney et al. *Cancer Discovery* (2018) 8(8): 924-934.

For example, an antibody that targets both CD33 and CD19 may be used in the methods described herein. Antibodies and antigen-binding fragments targeting CD33 or CD19 or a combination thereof can be prepared by routine practice. Non-limited examples of antigen-binding fragments that target CD19 can be found in Porter D L et al. *NEJM* (2011) 365:725-33 and Kalos M et al. *Sci Transl Med.* (2011) 3:95ra73. See also descriptions herein. Such CD19-targeting antigen-binding fragments can be used for making the CAR constructs described herein.

In some embodiments, a bispecific antibody may be used in which one molecule targets an epitope of a lineage-specific cell-surface protein on a target cell and the other molecule targets a surface antigen on an effector cell (e.g., T cell, NK cell) such that the target cell is brought into proximity with the effector cell. See, e.g., Hoseini et al. *Blood Cancer Journal* (2017) 7, e552.

In some embodiments, two or more (e.g., 2, 3, 4, 5 or more) epitopes of a lineage-specific cell-surface protein have been modified, enabling two or more (e.g., 2, 3, 4, 5 or more) different cytotoxic agents (e.g., two antibodies) to be targeted to the two or more epitopes. In some embodiments, the antibodies could work synergistically to enhance efficacy. In some embodiments, epitopes of two or more (e.g., 2, 3, 4, 5 or more) lineage-specific cell surface protein have been modified, enabling two or more (e.g., 2, 3, 4, 5 or more) different cytotoxic agents (e.g., two antibodies) to be targeted to epitopes of the two or more lineage-specific cell-surface proteins. In some embodiments, one or more (e.g., 1, 2, 3, 4, 5 or more) epitopes of a lineage-specific cell-surface protein have been modified and one or more (e.g., 1, 2, 3, 4, 5 or more) epitopes of an additional cell-surface protein have been modified, enabling two or more (e.g., 2, 3, 4, 5 or more) different cytotoxic agents (e.g., two antibodies) to be targeted to epitopes of the lineage-specific cell-surface protein and epitopes of additional cell-surface protein. In some embodiments, targeting of two or more lineage-specific cell-surface protein may reduce relapse of a hematopoietic malignancy.

In some embodiments, the methods described herein involve administering a cytotoxic agent that targets an epitope of a lineage-specific cell-surface antigen that is mutated in the population of genetically engineered hematopoietic cells. In some embodiments, the methods described herein involve administering a cytotoxic agent that targets an epitope of a lineage-specific cell-surface antigen that is mutated in the population of genetically engineered hematopoietic cells and one or more additional cytotoxic agents that target one or more additional cell-surface proteins. In some embodiments, the antibodies work synergistically to enhance efficacy by targeting more than one cell-surface protein.

In some embodiments, the methods described herein involve administering to the subject a population of genetically engineered cells lacking a non-essential epitope in a lineage-specific cell-surface antigen and one or more immunotherapeutic agents (e.g., antibodies) that target cells expressing the lineage-specific cell-surface antigen. In some embodiments, the methods described herein involve administering to the subject a population of genetically engineered cells lacking a non-essential epitope in a type 1 lineage-specific cell-surface antigen and one or more immunotherapeutic agents (e.g., antibodies) that target cells expressing the lineage-specific cell-surface antigen. In some embodiments, the methods described herein involve administering to the subject a population of genetically engineered cells lacking a non-essential epitope in a type 2 lineage-specific cell-surface antigen and one or more immunotherapeutic agents (e.g., antibodies) that target cells expressing the lineage-specific cell-surface antigen. In any of the embodiments described herein, one or more additional immunotherapeutic agents may be further administered to the subject (e.g., targeting one or more additional epitopes and/or antigens), for example if the hematopoietic malignancy relapses.

In some examples, the methods described herein involve administering to the subject a population of genetically engineered cells lacking a non-essential epitope of CD33 and one or more antibodies that target cells expressing CD33. In some examples, the methods described herein involve administering to the subject a population of genetically engineered cells lacking an epitope in exon 2 or exon 3 of CD33 and one or more antibodies that target cells expressing CD33. In some examples, the methods described herein involve administering to the subject a population of genetically engineered cells expressing a mutated CD33 comprising the amino acid sequence of SEQ ID NO: 56 or SEQ ID NO: 58 and one or more antibodies that target cells expressing CD33.

In some examples, the methods described herein involve administering to the subject a population of genetically engineered cells lacking a non-essential epitope of CD19 and one or more antibodies that target cells expressing CD19. In some examples, the methods described herein involve administering to the subject a population of genetically engineered cells lacking an epitope in exon 2 or exon 4 of CD19 and one or more antibodies that target cells expressing CD19. In some examples, the methods described herein involve administering to the subject a population of genetically engineered cells expressing a mutated CD19 comprising the amino acid sequence of SEQ ID NO: 52 or SEQ ID NO: 73 and one or more antibodies that target cells expressing CD19.

(ii) Immune Cells Expressing Chimeric Antigen Receptors

In some embodiments, the cytotoxic agent that targets an epitope of a lineage-specific cell-surface antigen as described herein is an immune cell that expresses a chimeric receptor, which comprises an antigen-binding fragment (e.g., a single-chain antibody) capable of binding to the epitope of the lineage-specific protein (e.g., CD33 or CD19). Recognition of a target cell (e.g., a cancer cell) having the epitope of the lineage-specific protein on its cell surface by the antigen-binding fragment of the chimeric receptor transduces an activation signal to the signaling domain(s) (e.g., co-stimulatory signaling domain and/or the cytoplasmic signaling domain) of the chimeric receptor, which may activate an effector function in the immune cell expressing the chimeric receptor. In some embodiments, the immune cell expresses more than one chimeric receptor (e.g., 2, 3, 4, 5 or more), referred to as a bispecific or multi-specific immune cell. In some embodiments, the immune cell expresses more than one chimeric receptor, at least one of which targets an epitope of a lineage-specific cell-surface antigen. In some embodiments, the immune cell expresses more than one chimeric receptor, each of which targets an epitope of a lineage-specific cell-surface antigen. In some embodiments, the immune cell expresses more than one chimeric receptor, at least one of which targets an epitope of a lineage-specific cell-surface antigen and at least one of which targets an epitope of an additional cell-surface antigen. In some embodiments, targeting of more than one lineage-specific cell-surface protein or a lineage-specific cell-surface protein and one or more additional cell-surface protein may reduce relapse of a hematopoietic malignancy. In some embodiments, the immune cell expresses a chimeric receptor that targets more than one epitopes (e.g., more than one epitopes of one antigen or epitopes of more than one antigen), referred to as a bispecific chimeric receptor.

In some embodiments, epitopes of two or more lineage-specific cell-surface proteins are targeted by cytotoxic agents. In some embodiments, two or more chimeric receptors are expressed in the same immune cell, e.g., bispecific chimeric receptors. Such cells can be used in any of the methods described herein. In some embodiments, cells expressing a chimeric receptor are "pooled", i.e., two or more groups of cells express two or more different chimeric receptors. In some embodiments, two or more cells expressing different chimeric antigen receptors are administered concurrently. In some embodiments, two or more cells expressing different chimeric antigen receptors are administered sequentially. In some embodiments, epitopes of CD33 and CD19 are targeted by cytotoxic agents. In some embodiments, the chimeric receptors targeting CD33 and CD19 are expressed in the same immune cell (i.e., a bispecific immune cell). Such cells can be used in any of the methods described herein. In some embodiments, cells expressing chimeric receptors targeting CD33 and CD19 "pooled", i.e., two or more groups of cells express two or more different chimeric receptors. In some embodiments, two or more groups of cells expressing chimeric receptors targeting CD33 and CD19 are administered concurrently. In some embodiments, two or more groups of cells expressing chimeric receptors targeting CD33 and CD19 are administered sequentially.

As used herein, a chimeric receptor refers to a non-naturally occurring molecule that can be expressed on the surface of a host cell and comprises binding domain that provides specificity of the chimeric receptor (e.g., an antigen-binding fragment that binds to an epitope of a cell-surface lineage-specific protein). In general, chimeric receptors comprise at least two domains that are derived from different molecules. In addition to the epitope-binding fragment described herein, the chimeric receptor may further comprise one or more of the following: a hinge domain, a transmembrane domain, a co-stimulatory domain, a cytoplasmic signaling domain, and combinations thereof. In some embodiments, the chimeric receptor comprises from N terminus to C terminus, an antigen-binding fragment that binds to a cell-surface lineage-specific protein, a hinge domain, a transmembrane domain, and a cytoplasmic signaling domain. In some embodiments, the chimeric receptor further comprises at least one co-stimulatory domain. See, e.g., Marin-Acevedo et al. *J. Hematol. Oncol.* (2018)11: 8.

Alternatively or in addition, the chimeric receptor may be a switchable chimeric receptor. See, e.g., Rodger et al. *PNAS* (2016) 113: 459-468; Cao et al. *Angew. Chem. Int. Ed.* (2016) 55: 7520-7524. In general, a switchable chimeric receptor comprises a binding domain that binds a soluble antigen-binding fragment, which has antigen binding specificity and may be administered concomitantly with the immune cells.

In some embodiments, the chimeric receptor may be a masked chimeric receptor, which is maintained in an "off" state until the immune cell expressing the chimeric receptor is localized to a desired location in the subject. For example, the binding domain of the chimeric receptor (e.g., antigen-binding fragment) may be blocked by an inhibitory peptide that is cleaved by a protease present at a desired location in the subject.

In some embodiments, it may be advantageous to modulate the binding affinity of the binding domain (e.g., antigen-binding fragment). For example, in some instances, relapse of hematopoietic malignancies results due to the reduced expression of the targeted antigen on the surface of target cells (e.g., antigen escape) and the lower levels of antigen any be inefficient or less efficient in stimulating cytotoxicity of the target cells. See, e.g., Majzner et al. *Cancer Discovery* (2018) 8(10). In some embodiments, the binding affinity of the binding domain (e.g., antigen-binding fragment) may be enhanced, for example by mutating one or more amino acid residues of the binding domain. Binding domains having enhanced binding affinity to an antigen may result in immune cells that response to lower levels of antigen (lower antigen density) and reduce or prevent relapse.

In some embodiments, the chimeric receptors described herein comprise one or more hinge domain(s). In some embodiments, the hinge domain may be located between the antigen-binding fragment and a transmembrane domain. A hinge domain is an amino acid segment that is generally found between two domains of a protein and may allow for flexibility of the protein and movement of one or both of the domains relative to one another. Any amino acid sequence that provides such flexibility and movement of the antigen-binding fragment relative to another domain of the chimeric receptor can be used.

The hinge domain may contain about 10-200 amino acids, e.g., 15-150 amino acids, 20-100 amino acids, or 30-60 amino acids. In some embodiments, the hinge domain may be of about 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, or 200 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is of CD8α or CD28. In some embodiments, the hinge domain is a portion of the hinge domain of CD8α, e.g., a fragment containing at least 15 (e.g., 20, 25, 30, 35, or 40) consecutive amino acids of the hinge domain of CD8α or CD28.

Hinge domains of antibodies, such as an IgG, IgA, IgM, IgE, or IgD antibody, are also compatible for use in the chimeric receptors described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Also within the scope of the present disclosure are chimeric receptors comprising a hinge domain that is a non-naturally occurring peptide. In some embodiments, the hinge domain between the C-terminus of the extracellular ligand-binding domain of an Fc receptor and the N-terminus of the transmembrane domain is a peptide linker, such as a $(Gly_xSer)n$ linker (SEQ ID NOs: 124-133), wherein x and n, independently can be an integer between 3 and 12, including 3 (SEQ ID NO: 124), 4 (SEQ ID NO: 125), 5 (SEQ ID NO: 126), 6 (SEQ ID NO: 127), 7 (SEQ ID NO: 128), 8 (SEQ ID NO: 129), 9 (SEQ ID NO: 130), 10 (SEQ ID NO: 131), 11 (SEQ ID NO: 132), 12 (SEQ ID NO: 133), or more.

Additional peptide linkers that may be used in a hinge domain of the chimeric receptors described herein are known in the art. See, e.g., Wriggers et al. *Current Trends in Peptide Science* (2005) 80(6): 736-746 and PCT Publication WO 2012/088461.

In some embodiments, the chimeric receptors described herein may comprise one or more transmembrane domain(s). The transmembrane domain for use in the chimeric receptors can be in any form known in the art. As used herein, a "transmembrane domain" refers to any protein structure that is thermodynamically stable in a cell membrane, preferably a eukaryotic cell membrane. Transmembrane domains compatible for use in the chimeric receptors used herein may be obtained from a naturally occurring protein. Alternatively, the transmembrane domain may be a synthetic, non-naturally occurring protein segment, e.g., a hydrophobic protein segment that is thermodynamically stable in a cell membrane.

Transmembrane domains are classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). In some embodiments, the transmembrane domain is a single-pass transmembrane domain. In some embodiments, the transmembrane domain is a single-pass transmembrane domain that orients the N terminus of the chimeric receptor to the extracellular side of the cell and the C terminus of the chimeric receptor to the intracellular side of the cell. In some embodiments, the transmembrane domain is obtained from a single pass transmembrane protein. In some embodiments, the transmembrane domain is of CD8α. In some embodiments, the transmembrane domain is of CD28. In some embodiments, the transmembrane domain is of ICOS.

In some embodiments, the chimeric receptors described herein comprise one or more costimulatory signaling domains. The term "co-stimulatory signaling domain," as used herein, refers to at least a portion of a protein that mediates signal transduction within a cell to induce an immune response, such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils.

In some embodiments, the chimeric receptor comprises more than one (at least 2, 3, 4, or more) co-stimulatory signaling domains. In some embodiments, the chimeric receptor comprises more than one co-stimulatory signaling domains obtained from different costimulatory proteins. In some embodiments, the chimeric receptor does not comprise a co-stimulatory signaling domain.

In general, many immune cells require co-stimulation, in addition to stimulation of an antigen-specific signal, to promote cell proliferation, differentiation and survival, and to activate effector functions of the cell. Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory protein may be compatible for use in the chimeric receptors described herein. The type(s) of co-stimulatory signaling domain is selected based on factors such as the type of the immune cells in which the chimeric receptors would be expressed (e.g., primary T cells, T cell lines, NK cell lines) and the desired immune effector function (e.g., cytotoxicity). Examples of co-stimulatory signaling domains for use in the chimeric receptors can be the cytoplasmic signaling domain of co-stimulatory proteins, including, without limitation, CD27, CD28, 4-1BB, OX40, CD30, ICOS, CD2, CD7, LIGHT, NKG2C, B7-H3. In some embodiments, the co-stimulatory domain is derived from 4-1BB, CD28, or ICOS. In some embodiments, the costimulatory domain is derived from CD28 and chimeric receptor comprises a second co-stimulatory domain from 4-1BB or ICOS.

In some embodiments, the costimulatory domain is a fusion domain comprising more than one costimulatory domain or portions of more than one costimulatory domains. In some embodiments, the costimulatory domain is a fusion of costimulatory domains from CD28 and ICOS.

In some embodiments, the chimeric receptors described herein comprise one or more cytoplasmic signaling domain(s). Any cytoplasmic signaling domain can be used in the chimeric receptors described herein. In general, a cytoplasmic signaling domain relays a signal, such as interaction of an extracellular ligand-binding domain with its ligand, to stimulate a cellular response, such as inducing an effector function of the cell (e.g., cytotoxicity).

As will be evident to one of ordinary skill in the art, a factor involved in T cell activation is the phosphorylation of immunoreceptor tyrosine-based activation motif (ITAM) of a cytoplasmic signaling domain. Any ITAM-containing domain known in the art may be used to construct the chimeric receptors described herein. In general, an ITAM motif may comprise two repeats of the amino acid sequence YxxL/I separated by 6-8 amino acids, wherein each x is independently any amino acid, producing the conserved motif YxxL/Ix(6-8)YxxL/I. In some embodiments, the cytoplasmic signaling domain is from CD3ζ.

In some embodiments, the chimeric receptor described herein targets a type 2 protein. In some embodiments, the chimeric receptor targets CD33. In some embodiments, the chimeric receptor described herein targets a type 1 protein. In some embodiments, the chimeric receptor targets CD19. In some embodiments, the chimeric receptor targets a type 0 protein. Such a chimeric receptor may comprise an antigen-binding fragment (e.g., an scFv) comprising a heavy chain variable region and a light chain variable region that bind to CD19. Alternatively, the chimeric receptor may comprise an antigen-binding fragment (e.g., scFv) comprising a heavy chain variable region and a light chain variable region that bind to CD33.

In some embodiments, the immune cells described herein express a chimeric receptor (e.g., bispecific chimeric receptor) that targets a type 2 protein and a chimeric receptor that targets a type 1 protein. In some embodiments, the immune cells described herein express a chimeric receptor (e.g., bispecific chimeric receptor) that targets a type 2 protein and at least one additional cell-surface protein, such as any of those described herein. In some embodiments, the immune cells described herein express a chimeric receptor that targets CD33 and at least one additional cell-surface protein, such as any of those described herein. In some embodiments, the immune cells described herein express a chimeric receptor that targets a type 1 protein and at least one additional cell-surface protein, such as any of those described herein. In some embodiments, the immune cells described herein express a chimeric receptor that targets CD19 and at least one additional cell-surface protein, such as any of those described herein. In some embodiments, the chimeric receptor described herein targets CD33 and CD19.

In some embodiments, the immune cells described herein express a chimeric receptor that targets a type 2 protein and at least one additional chimeric receptor that targets an additional cell-surface protein, such as any of those described herein. In some embodiments, the immune cells described herein express a chimeric receptor that targets CD33 and at least one additional chimeric receptor that targets another cell-surface protein, such as any of those described herein. In some embodiments, the immune cells described herein express a chimeric receptor that targets a type 1 protein and at least one additional chimeric receptor that targets another cell-surface protein, such as any of those described herein. In some embodiments, the immune cells described herein express a chimeric receptor that targets CD19 and at least one additional chimeric receptor that targets another cell-surface protein, such as any of those described herein. In some embodiments, the immune cells express a chimeric receptor that targets CD33 and a chimeric receptor that targets CD19.

A chimeric receptor construct targeting CD33 and/or CD19 may further comprise at least a hinge domain (e.g., from CD28, CD8α, or an antibody), a transmembrane domain (e.g., from CD8α, CD28 or ICOS), one or more co-stimulatory domains (from one or more of CD28, ICOS, or 4-1BB) and a cytoplasmic signaling domain (e.g., from CD3ζ), or a combination thereof. In some examples, the methods described herein involve administering to a subject a population of genetically engineered hematopoietic cells and an immune cell expressing a chimeric receptor that targets CD33 and/or CD19, which may further comprise at least a hinge domain (e.g., from CD28, CD8α, or an antibody), a transmembrane domain (e.g., from CD8α, CD28 or ICOS), one or more co-stimulatory domains (from one or more of CD28, ICOS, or 4-1BB) and a cytoplasmic signaling domain (e.g., from CD3ζ, or a combination thereof Any of the chimeric receptors described herein can be prepared by routine methods, such as recombinant technology. Methods for preparing the chimeric receptors herein involve generation of a nucleic acid that encodes a polypeptide comprising each of the domains of the chimeric receptors, including the antigen-binding fragment and optionally, the hinge domain, the transmembrane domain, at least one co-stimulatory signaling domain, and the cytoplasmic signaling domain. In some embodiments, nucleic acids encoding the components of a chimeric receptor are joined together using recombinant technology.

Sequences of each of the components of the chimeric receptors may be obtained via routine technology, e.g., PCR amplification from any one of a variety of sources known in the art. In some embodiments, sequences of one or more of the components of the chimeric receptors are obtained from a human cell. Alternatively, the sequences of one or more components of the chimeric receptors can be synthesized. Sequences of each of the components (e.g., domains) can be joined directly or indirectly (e.g., using a nucleic acid sequence encoding a peptide linker) to form a nucleic acid sequence encoding the chimeric receptor, using methods such as PCR amplification or ligation. Alternatively, the nucleic acid encoding the chimeric receptor may be synthesized. In some embodiments, the nucleic acid is DNA. In other embodiments, the nucleic acid is RNA.

Mutation of one or more residues within one or more of the components of the chimeric receptor (e.g., the antigen-binding fragment, etc) may be performed prior to or after joining the sequences of each of the components. In some embodiments, one or more mutations in a component of the chimeric receptor may be made to modulate (increase or decrease) the affinity of the component for an epitope (e.g., the antigen-binding fragment for the target protein) and/or modulate the activity of the component.

Any of the chimeric receptors described herein can be introduced into a suitable immune cell for expression via conventional technology. In some embodiments, the immune cells are T cells, such as primary T cells or T cell lines. Alternatively, the immune cells can be NK cells, such as established NK cell lines (e.g., NK-92 cells). In some embodiments, the immune cells are T cells that express CD8 (CD8$^+$) or CD8 and CD4 (CD8$^+$/CD4$^+$). In some embodiments, the T cells are T cells of an established T cell line, for example, 293T cells or Jurkat cells.

Primary T cells may be obtained from any source, such as peripheral blood mononuclear cells (PBMCs), bone marrow, tissues such as spleen, lymph node, thymus, or tumor tissue. A source suitable for obtaining the type of immune cells desired would be evident to one of skill in the art. In some embodiments, the population of immune cells is derived from a human patient having a hematopoietic malignancy, such as from the bone marrow or from PBMCs obtained from the patient. In some embodiments, the population of immune cells is derived from a healthy donor. In some embodiments, the immune cells are obtained from the subject to whom the immune cells expressing the chimeric receptors will be subsequently administered. Immune cells that are administered to the same subject from which the cells were obtained are referred to as autologous cells, whereas immune cells that are obtained from a subject who is not the subject to whom the cells will be administered are referred to as allogeneic cells.

The type of host cells desired may be expanded within the population of cells obtained by co-incubating the cells with stimulatory molecules, for example, anti-CD3 and anti-CD28 antibodies may be used for expansion of T cells.

To construct the immune cells that express any of the chimeric receptor constructs described herein, expression vectors for stable or transient expression of the chimeric receptor construct may be constructed via conventional methods as described herein and introduced into immune host cells. For example, nucleic acids encoding the chimeric receptors may be cloned into a suitable expression vector, such as a viral vector in operable linkage to a suitable promoter. The nucleic acids and the vector may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the chimeric receptors. The synthetic linkers may contain nucleic acid sequences that correspond to a particular restriction site in the vector. The selection of expression vectors/plasmids/viral vectors would depend on the type of host cells for expression of the chimeric receptors, but should be suitable for integration and replication in eukaryotic cells.

In some embodiments, the chimeric receptors are expressed using a non-integrating transient expression system. In some embodiments, the chimeric receptors are integrated into the genome of the immune cell. In some embodiments, the chimeric receptors are integrated into a specific loci of the genome of immune cell using gene editing (e.g., zinc-finger nucleases, meganucleases, TALENs, CRISPR systems).

A variety of promoters can be used for expression of the chimeric receptors described herein, including, without limitation, cytomegalovirus (CMV) intermediate early promoter, a viral LTR such as the Rous sarcoma virus LTR, HIV-LTR, HTLV-1 LTR, Maloney murine leukemia virus (MMLV) LTR, myeoloproliferative sarcoma virus (MPSV) LTR, spleen focus-forming virus (SFFV) LTR, the simian virus 40 (SV40) early promoter, herpes simplex tk virus promoter, elongation factor 1-alpha (EF1-α) promoter with or without the EF1-α intron. Additional promoters for expression of the chimeric receptors include any constitutively active promoter in an immune cell. Alternatively, any regulatable promoter may be used, such that its expression can be modulated within an immune cell. In some embodiments, the promoter regulating expression of a chimeric receptor is an inducible promoter. In general, the activity of "inducible promoters" may be regulated based on the presence (or absence) of a signal, such as an endogenous signal or an exogenous signal, for example a small molecule or drug that is administered to the subject.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; 5'- and 3'-untranslated regions for mRNA stability and translation efficiency from highly-expressed genes like α-globin or β-globin; SV40 polyoma origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9, drug-induced suicide switch, monoclonal antibody mediated suicide switch), and reporter gene for assessing expression of the chimeric receptor. Suitable vectors and methods for producing vectors containing transgenes are well known and available in the art. Examples of the preparation of vectors for expression of chimeric receptors can be found, for example, in US2014/0106449, herein incorporated by reference in its entirety.

As will be appreciated by one of ordinary skill in the art, in some embodiments, it may be advantageous to quickly and efficiently reduce or eliminate the immune cells expressing chimeric receptors, for example at a time point following administration to a subject. Mechanisms of killing immune cells expressing chimeric receptors, or inducing cytotoxicity of such cells, are known in the art, see, e.g., Labanieh et al. *Nature Biomedical Engineering* (2018)2: 337-391; Slaney et al. *Cancer Discovery* (2018) 8(8): 924-934. In some embodiments, the immune cell expressing the chimeric receptor may also express a suicide switch" or "suicide gene," which may or may not be encoded by the same vector as the chimeric receptor, as described above. In some embodiments, the immune cell expressing chimeric receptors further express an epitope tag such that upon engagement of the epitope tag, the immune cell is killed through antibody-dependent cell-mediated cytotoxicity and/or complement-mediated cytotoxicity. See, e.g., Paszkiewicz et al. *J. Clin. Invest*. (2016) 126: 4262-4272; Wang et al. *Blood* (2011) 118: 1255-1263; Tasian et al. *Blood* (2017) 129: 2395-2407; Philip et al. *Blood* (2014) 124: 1277-1287.

In some embodiments, the chimeric receptor construct or the nucleic acid encoding said chimeric receptor is a DNA molecule. In some embodiments, chimeric receptor construct or the nucleic acid encoding said chimeric receptor is a DNA vector and may be electroporated to immune cells (see, e.g., Till, et al. Blood (2012) 119(17): 3940-3950). In some embodiments, the nucleic acid encoding the chimeric receptor is an RNA molecule, which may be electroporated to immune cells.

Any of the vectors comprising a nucleic acid sequence that encodes a chimeric receptor construct described herein is also within the scope of the present disclosure. Such a vector may be delivered into host cells such as host immune cells by a suitable method. Methods of delivering vectors to immune cells are well known in the art and may include DNA, RNA, or transposon electroporation, transfection reagents such as liposomes or nanoparticles to delivery DNA, RNA, or transposons; delivery of DNA, RNA, or transposons or protein by mechanical deformation (see, e.g., Sharei et al. *Proc. Natl. Acad. Sci. USA* (2013) 110(6): 2082-2087); or viral transduction. In some embodiments, the vectors for expression of the chimeric receptors are delivered to host cells by viral transduction. Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191; WO 94/28938; WO 95/11984 and WO 95/00655). In some embodiments, the vectors for expression of the chimeric receptors are retroviruses. In some embodiments, the vectors for expression of the chimeric receptors are lentiviruses. In some embodiments, the vectors for expression of the chimeric receptors are adeno-associated viruses.

In examples in which the vectors encoding chimeric receptors are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

In some embodiments, the methods described herein involve use of immune cells that express more than one chimeric receptor (e.g., a chimeric receptors that target first epitope and chimeric receptors that target a second epitope). In some embodiments, more than one chimeric receptor (e.g., a chimeric receptors that target first epitope and chimeric receptors that target a second epitope) are expressed from a single vector. In some embodiments, more than one chimeric receptor (e.g., a chimeric receptors that target first epitope and chimeric receptors that target a second epitope) are expressed from a more than one vector. Such immune cells may be prepared using methods known in the art, for example by delivering a vector that encodes a first chimeric receptor simultaneously or sequentially with a second vector that encodes a second chimeric receptor. In some embodiments, the resulting immune cell population is a mixed population comprising a subset of immune cells that express one chimeric receptor and a subset of immune cells that express both chimeric receptors.

In some embodiments, the domains of the chimeric receptor are encoded by and expressed from a single vector. Alternatively, the domains of the chimeric receptor may be encoded by and expressed from more than one vector. In some embodiments, activity of immune cells expressing the chimeric receptors may be regulated by controlling assembly of the chimeric receptor. The domains of a chimeric receptor may be expressed as two or more non-functional segments of the chimeric receptor and induced to assemble at a desired time and/or location, for example through use of a dimerization agent (e.g., dimerizing drug).

The methods of preparing host cells expressing any of the chimeric receptors described herein may comprise activating and/or expanding the immune cells ex vivo. Activating a host cell means stimulating a host cell into an activate state in which the cell may be able to perform effector functions (e.g., cytotoxicity). Methods of activating a host cell will depend on the type of host cell used for expression of the chimeric receptors. Expanding host cells may involve any method that results in an increase in the number of cells expressing chimeric receptors, for example, allowing the host cells to proliferate or stimulating the host cells to proliferate. Methods for stimulating expansion of host cells will depend on the type of host cell used for expression of the chimeric receptors and will be evident to one of skill in the art. In some embodiments, the host cells expressing any of the chimeric receptors described herein are activated and/or expanded ex vivo prior to administration to a subject.

It has been appreciated that administration of immunostimulatory cytokines may enhance proliferation of immune cells expressing chimeric receptors following administration to a subject and/or promote engraftment of the immune cells. See, e.g., Pegram et al. *Leukemia* (2015) 29:415-422; Chinnasamy et al. *Clin. Cancer Res.* (2012) 18: 1672-1683; Krenciute et al. *Cancer Immunol. Res.* (2017) 5: 571-581; Hu et al. *Cell Rep.* (2017) 20: 3025-3033; Markley et al. *Blood* (2010) 115: 3508-3519). Any of the methods described herein may further involve administering one or more immunostimulatory cytokines concurrently with any of the immune cells expressing chimeric receptors. Non-limiting example of immunostimulatory cytokines include IL-12, IL-15, IL-1, IL-21, and combinations thereof.

Any anti-CD19 CAR and anti-CD33 CAR molecules known in the art can be used together with the genetically engineered HSCs described herein. Exemplary anti-CD19 CARs include axicabtagene and tisagenlecleucel. Exemplary anti-CD33 CARs include those disclosed in WO2017/066760 and WO2017/079400.

In one specific example, primary human $CD8^+$ T cells are isolated from patients' peripheral blood by immunomagnetic separation (Miltenyi Biotec). T cells are cultured and stimulated with anti-CD3 and anti-CD28 mAbs-coated beads (Invitrogen) as previously described (Levine et al., *J. Immunol.* (1997) 159(12):5921).

Chimeric receptors that target a lineage-specific cell-surface proteins (e.g., CD19 or CD33) are generated using conventional recombinant DNA technologies and inserted into a lentiviral vector. The vectors containing the chimeric receptors are used to generate lentiviral particles, which are used to transduce primary $CD8^+$ T cells. Human recombinant IL-2 may be added every other day (50 IU/mL). T cells are cultured for ~14 days after stimulation. Expression of the chimeric receptors can be confirmed using methods, such as Western blotting and flow cytometry.

Figure 3A:
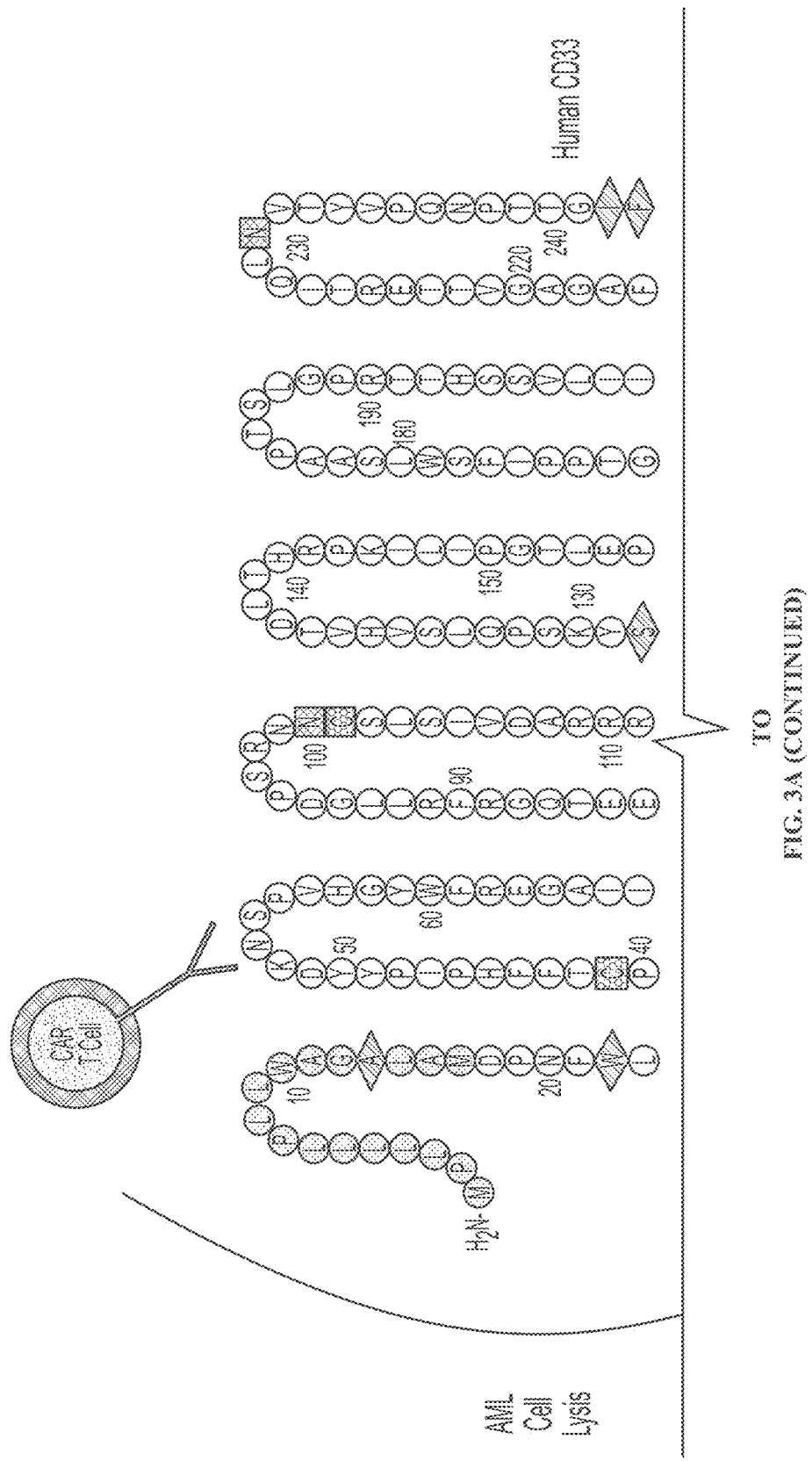
FIGS. 3A-3B are schematic illustrations showing CAR T cells bind to cells expressing human CD33 but not to cells expressing human CD33 in which an epitope of CD33 has been modified or deleted.
Figure 3A:
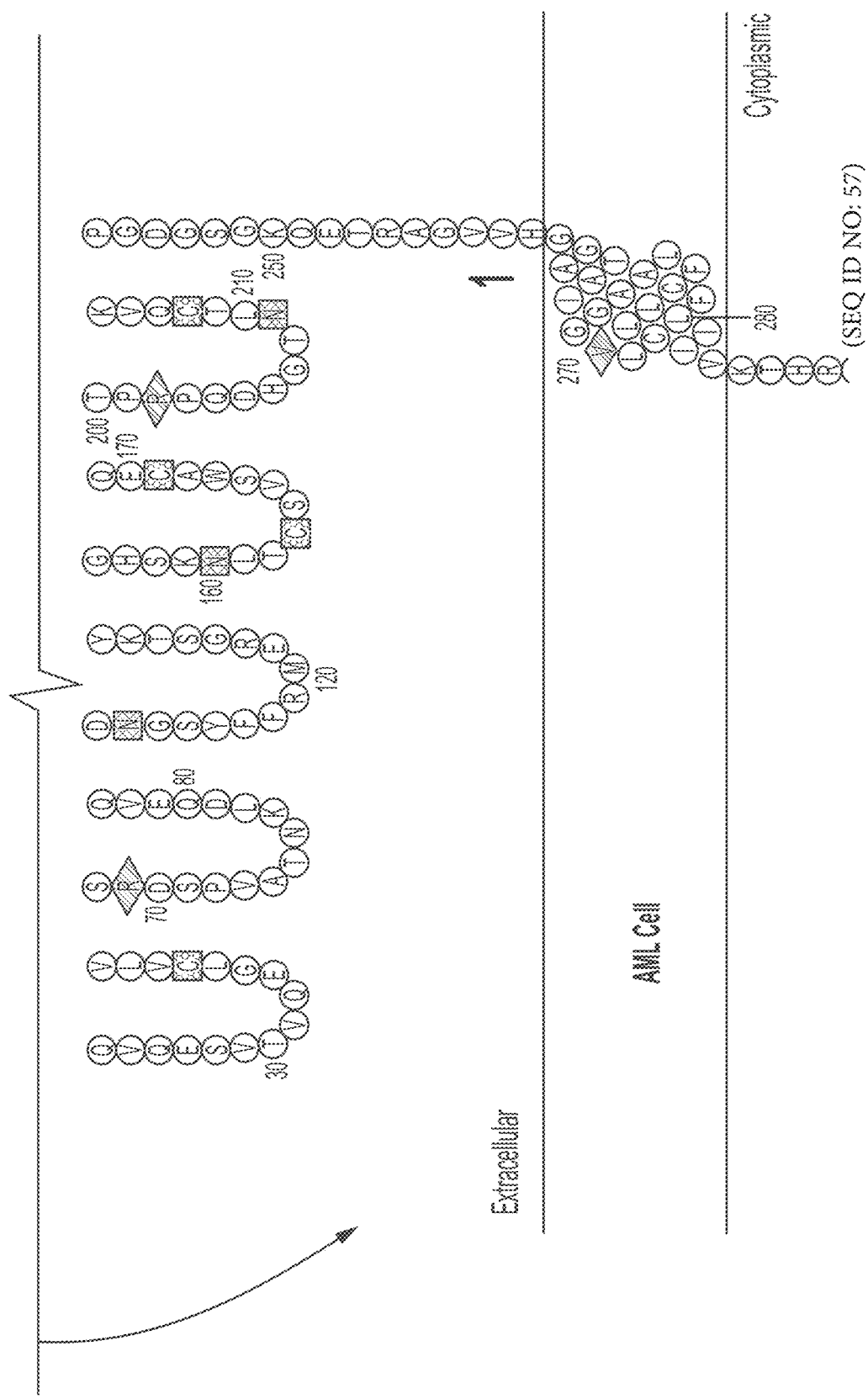
Figure 3B:
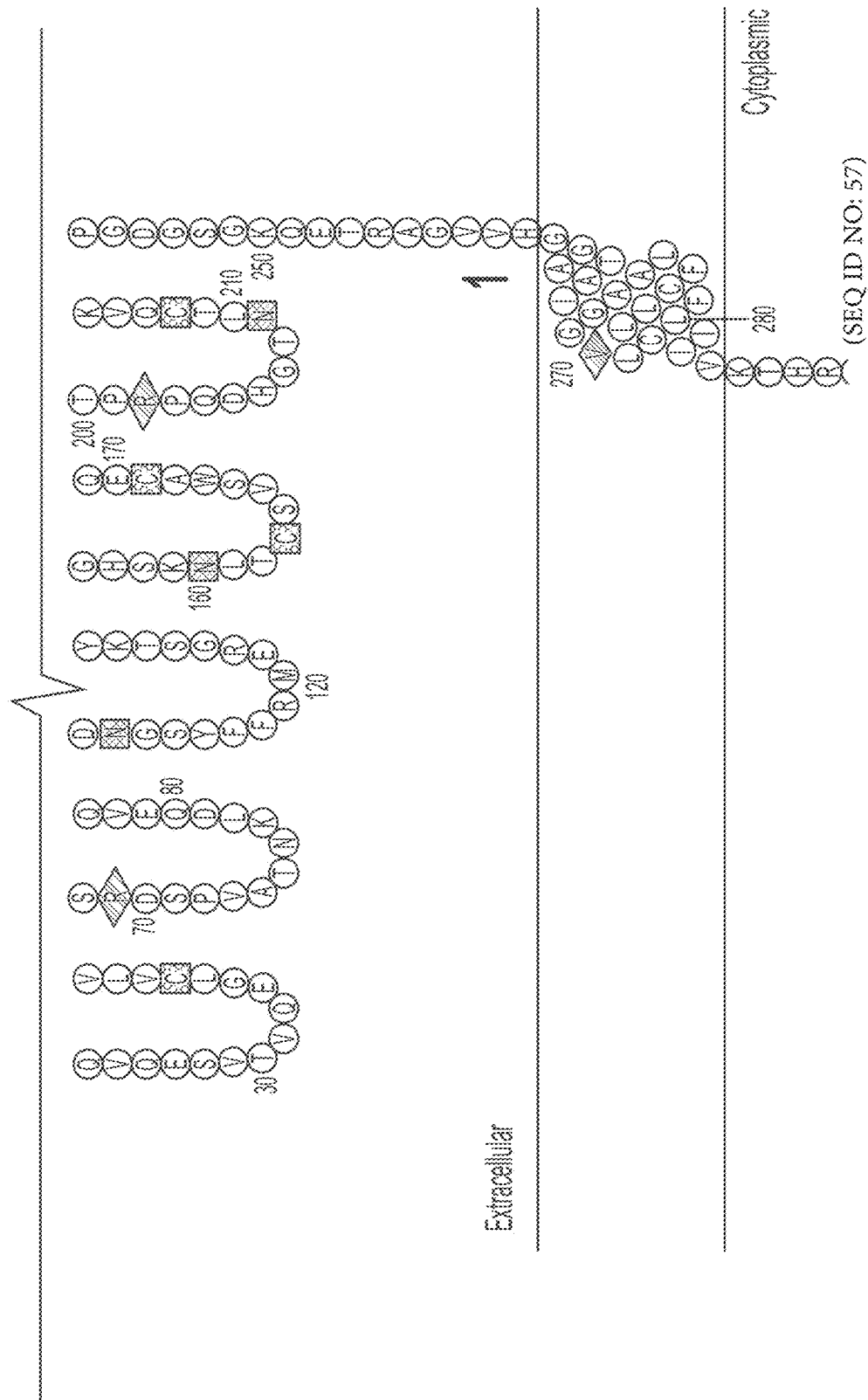

T cells expressing the chimeric receptors are selected and assessed for their ability to bind to the lineage-specific cell-surface protein such as CD19 or CD33 and to induce cytotoxicity of cells expressing the lineage-specific protein. Immune cells expressing the chimeric receptor are also evaluated for their ability to induce cytotoxicity of cells expressing the lineage-specific antigen in mutated form. Preferably, immune cells expressing chimeric receptors that binds to the wild-type lineage-specific protein but not the mutated form. (FIG. 3, using CD33 as an example).

The cells (e.g., hematopoietic stem cells) that express the mutated lineage-specific protein are also assessed for various characteristics, including proliferation, erythropoietic differentiation, and colony formation to confirm that the mutated lineage-specific protein retained the bioactivity as the wild-type counterpart.

The immune cells expressing one or more CAR-T receptors may be further modified genetically, for example, by knock-out of the native T-cell receptor (TCR) or an MHC chain and/or by introducing a new TCR. Alternatively, the immune cells may retain the native TCR loci.

In some embodiments, the methods described herein involve administering to the subject a population of genetically engineered cells lacking a non-essential epitope in a lineage-specific cell-surface antigen and one or more immunotherapeutic agents (e.g., immune cells expressing chimeric receptor(s)) that target cells expressing the lineage-specific cell-surface antigen. In some embodiments, the methods described herein involve administering to the subject a population of genetically engineered cells lacking a non-essential epitope in a type 1 lineage-specific cell-surface antigen and one or more immunotherapeutic agents (e.g., immune cells expressing chimeric receptor(s)) that target cells expressing the lineage-specific cell-surface antigen. In some embodiments, the methods described herein involve administering to the subject a population of genetically engineered cells lacking a non-essential epitope in a type 2 lineage-specific cell-surface antigen and one or more immunotherapeutic agents (e.g., immune cells expressing chimeric receptor(s)) that target cells expressing the lineage-specific cell-surface antigen. In any of the embodiments described herein, one or more additional immunotherapeutic agents may be further administered to the subject (e.g., targeting one or more additional epitopes and/or antigens), for example if the hematopoietic malignancy relapses.

In some embodiments, the methods described herein involve administering immune cells expressing chimeric receptors that target an epitope of a lineage-specific cell-surface protein that is mutated in the population of genetically engineered hematopoietic cells. In some embodiments, the methods described herein involve administering immune cells expressing chimeric receptors that target an epitope of a lineage-specific cell-surface protein that is mutated in the population of genetically engineered hematopoietic cells and one or more additional cytotoxic agents that may target one or more additional cell-surface proteins. In some embodiments, the agents could work synergistically to enhance efficacy by targeting more than one cell-surface protein.

In some examples, the methods described herein involve administering to the subject a population of genetically engineered cells lacking a non-essential epitope of CD33 and one or more immune cells expressing chimeric receptor(s) that target cells expressing CD33. In some examples, the methods described herein involve administering to the subject a population of genetically engineered cells lacking an epitope in exon 2 or exon 3 of CD33 and one or more immune cells expressing chimeric receptor(s) that target cells expressing CD33. In some examples, the methods described herein involve administering to the subject a population of genetically engineered cells expressing a mutated CD33 comprising the amino acid sequence of SEQ ID NO: 56 or SEQ ID NO: 58 and one or more immune cells expressing chimeric receptor(s) that target cells expressing CD33.

In some examples, the methods described herein involve administering to the subject a population of genetically engineered cells lacking a non-essential epitope of CD19 and one or more immune cells expressing chimeric receptor(s) that target cells expressing CD19. In some examples, the methods described herein involve administering to the subject a population of genetically engineered cells lacking an epitope in exon 2 or exon 4 of CD19 and one or more immune cells expressing chimeric receptor(s) that target cells expressing CD19. In some examples, the methods described herein involve administering to the subject a population of genetically engineered cells expressing a mutated CD19 comprising the amino acid sequence of SEQ ID NO: 52 or SEQ ID NO: 73 and one or more immune cells expressing chimeric receptor(s) that target cells expressing CD19.

(iii) Antibody-Drug Conjugate

In some embodiments, the cytotoxic agent targeting an epitope of a cell-surface lineage-specific protein is an antibody-drug conjugate (ADC). As will be evident to one of ordinary skill in the art, the term "antibody-drug conjugate" can be used interchangeably with "immunotoxin" and refers to a fusion molecule comprising an antibody (or antigen-binding fragment thereof) conjugated to a toxin or drug molecule. Binding of the antibody to the corresponding epitope of the target protein allows for delivery of the toxin or drug molecule to a cell that presents the protein (and epitope thereof) on the cell surface (e.g., target cell), thereby resulting in death of the target cell. In some embodiments, the antibody-drug conjugate (or antigen-binding fragment thereof) binds to its corresponding epitope of a lineage-specific cell-surface antigen but does not bind to a lineage-specific cell-surface antigen that lacks the epitope or in which the epitope has been mutated.

In some embodiments, the agent is an antibody-drug conjugate. In some embodiments, the antibody-drug conjugate comprises an antigen-binding fragment and a toxin or drug that induces cytotoxicity in a target cell. In some embodiments, the antibody-drug conjugate targets a type 2 protein. In some embodiments, the antibody-drug conjugate targets CD33. In some embodiments, the antibody-drug conjugate binds to an epitope in exon 2 or exon 3 of CD33. In some embodiments, the antibody-drug conjugate targets a type 1 protein. In some embodiments, the antibody-drug conjugate binds to an epitope in exon 2 or exon 4 of CD19. In some embodiments, the antibody-drug conjugate targets CD19. In some embodiments, the antibody-drug conjugate targets a type 0 protein.

Toxins or drugs compatible for use in antibody-drug conjugates are well known in the art and will be evident to one of ordinary skill in the art. See, e.g., Peters et al. *Biosci. Rep.* (2015) 35(4): e00225, Beck et al. *Nature Reviews Drug Discovery* (2017) 16:315-337; Marin-Acevedo et al. *J. Hematol. Oncol.* (2018)11: 8; Elgundi et al. *Advanced Drug Delivery Reviews* (2017) 122: 2-19. In some embodiments, the antibody-drug conjugate may further comprise a linker (e.g., a peptide linker, such as a cleavable linker or a non-cleavable linker) attaching the antibody and drug molecule. Examples of antibody-drug conjugates include, without limitation, brentuximab vedotin, glembatumumab vedotin/CDX-011, depatuxizumab mafodotin/ABT-414, PSMA ADC, polatuzumab vedotin/RG7596/DCDS4501A, denintuzumab mafodotin/SGN-CD19A, AGS-16C3F, CDX-014, RG7841/DLYE5953A, RG7882/DMUC406A, RG7986/DCDS0780A, SGN-LIV1A, enfortumab vedotin/ASG-22ME, AG-15ME, AGS67E, telisotuzumab vedotin/ABBV-399, ABBV-221, ABBV-085, GSK-2857916, tisotumab vedotin/HuMax®-TF-ADC, HuMax®-Axl-ADC, pinatuzumab veodtin/RG7593/DCDT2980S, lifastuzumab vedotin/RG7599/DNIB0600A, indusatumab vedotin/MLN-0264/TAK-264, vandortuzumab vedotin/RG7450/DSTP3086S, sofituzumab vedotin/RG7458/DMUC5754A, RG7600/DMOT4039A, RG7336/DEDN6526A, ME1547, PF-06263507/ADC 5T4, trastuzumab emtansine/T-DM1, mirvetuximab soravtansine/IMGN853, coltuximab ravtansine/SAR3419, naratuximab emtansine/IMGN529, indatuximab ravtansine/BT-062, anetumab ravtansine/BAY 94-9343, SAR408701, SAR428926, AMG 224, PCA062, HKT288, LY3076226, SAR566658, lorvotuzumab mertansine/IMGN901, cantuzumab mertansine/SB-408075, cantuzumab ravtansine/IMGN242, laprituximab emtansine/IMGN289, IMGN388, bivatuzumab mertansine, AVE9633, BIIB015, MLN2704, AMG 172, AMG 595, LOP 628, vadastuximab talirine/SGN-CD33A, SGN-CD70A, SGN-CD19B, SGN-CD123A, SGN-CD352A, rovalpituzumab tesirine/SC16LD6.5, SC-002, SC-003, ADCT-301/HuMax®-TAC-PBD, ADCT-402, MEDI3726/ADC-401, IMGN779, IMGN632, gemtuzumab ozogamicin, inotuzumab ozogamicin/CMC-544, PF-06647263, CMD-193, CMB-401, trastuzumab duocarmazine/SYD985, BMS-936561/MDX-1203, sacituzumab govitecan/IMMU-132, labetuzumab govitecan/IMMU-130, DS-8201a, U3-1402, milatuzumab doxorubicin/IMMU-110/hLL1-DOX, BMS-986148, RC48-ADC/hertuzumab-vc-MMAE, PF-06647020, PF-06650808, PF-06664178/RN927C, lupartumab amadotin/BAY1129980, aprutumab ixadotin/BAY1187982, ARX788, AGS62P1, XMT-1522, AbGn-107, MEDI4276, DSTA4637S/RG7861. In one example, the antibody-drug conjugate is gemtuzumab ozogamicin.

In some embodiments, binding of the antibody-drug conjugate to the epitope of the cell-surface lineage-specific protein induces internalization of the antibody-drug conjugate, and the drug (or toxin) may be released intracellularly. In some embodiments, binding of the antibody-drug conjugate to the epitope of a cell-surface lineage-specific protein induces internalization of the toxin or drug, which allows the toxin or drug to kill the cells expressing the lineage-specific protein (target cells). In some embodiments, binding of the antibody-drug conjugate to the epitope of a cell-surface lineage-specific protein induces internalization of the toxin or drug, which may regulate the activity of the cell expressing the lineage-specific protein (target cells). The type of toxin or drug used in the antibody-drug conjugates described herein is not limited to any specific type.

In some embodiments, two or more (e.g., 2, 3, 4, 5 or more) epitopes of a lineage-specific cell-surface antigen have been modified, enabling two or more (e.g., 2, 3, 4, 5 or more) different cytotoxic agents (e.g., two ADCs) to be targeted to the two or more epitopes. In some embodiments, the toxins carried by the ADCs could work synergistically to enhance efficacy (e.g., death of the target cells). In some embodiments, epitopes of two or more (e.g., 2, 3, 4, 5 or more) lineage-specific cell surface protein have been modified, enabling two or more (e.g., 2, 3, 4, 5 or more) different cytotoxic agents (e.g., two ADCs) to be targeted to epitopes of the two or more lineage-specific cell-surface antigens. In some embodiments, one or more (e.g., 1, 2, 3, 4, 5 or more) epitopes of a lineage-specific cell-surface antigen have been modified and one or more (e.g., 1, 2, 3, 4, 5 or more) epitopes of an additional cell-surface protein have been modified, enabling two or more (e.g., 2, 3, 4, 5 or more) different cytotoxic agents (e.g., two ADCs) to be targeted to epitopes of the lineage-specific cell-surface antigen and epitopes of additional cell-surface antigen. In some embodiments, targeting of more than one lineage-specific cell-surface antigen or a lineage-specific cell-surface antigen and one or more additional cell-surface protein/antigen may reduce relapse of a hematopoietic malignancy.

In some embodiments, the methods described herein involve administering ADCs that target an epitope of a lineage-specific cell-surface antigen that is mutated in the population of genetically engineered hematopoietic cells. In some embodiments, the methods described herein involve administering ADCs that target an epitope of a lineage-specific cell-surface antigen that is mutated in the population of genetically engineered hematopoietic cells and one or more additional cytotoxic agents that may target one or more additional cell-surface proteins. In some embodiments, the agents could work synergistically to enhance efficacy by targeting more than one cell-surface protein.

An ADC described herein may be used as a follow-on treatment to subjects who have been undergone the combined therapy as described herein.

In some embodiments, the methods described herein involve administering to the subject a population of genetically engineered cells lacking a non-essential epitope in a lineage-specific cell-surface antigen and one or more immunotherapeutic agents (e.g., ADCs) that target cells expressing the lineage-specific cell-surface antigen. In some embodiments, the methods described herein involve administering to the subject a population of genetically engineered cells lacking a non-essential epitope in a type 1 lineage-specific cell-surface antigen and one or more immunotherapeutic agents (e.g., ADCs) that target cells expressing the lineage-specific cell-surface antigen. In some embodiments, the methods described herein involve administering to the subject a population of genetically engineered cells lacking a non-essential epitope in a type 2 lineage-specific cell-surface antigen and one or more immunotherapeutic agents (e.g., ADCs) that target cells expressing the lineage-specific cell-surface antigen. In any of the embodiments described herein, one or more additional immunotherapeutic agents may be further administered to the subject (e.g., targeting one or more additional epitopes and/or antigens), for example if the hematopoietic malignancy relapses.

In some examples, the methods described herein involve administering to the subject a population of genetically engineered cells lacking a non-essential epitope of CD33 and one or more antibody-drug conjugates that target cells expressing CD33. In some examples, the methods described herein involve administering to the subject a population of genetically engineered cells lacking an epitope in exon 2 or exon 3 of CD33 and one or more antibodies antibody-drug conjugates that target cells expressing CD33. In some examples, the methods described herein involve administering to the subject a population of genetically engineered cells expressing a mutated CD33 comprising the amino acid sequence of SEQ ID NO: 56 or SEQ ID NO: 58 and one or more antibody-drug conjugates that target cells expressing CD33.

In some examples, the methods described herein involve administering to the subject a population of genetically engineered cells lacking a non-essential epitope of CD19 and one or more antibody-drug conjugates that target cells expressing CD19. In some examples, the methods described herein involve administering to the subject a population of genetically engineered cells lacking an epitope in exon 2 or exon 4 of CD19 and one or more antibody-drug conjugates that target cells expressing CD19. In some examples, the methods described herein involve administering to the subject a population of genetically engineered cells expressing a mutated CD19 comprising the amino acid sequence of SEQ ID NO: 52 or SEQ ID NO: 73 and one or more antibody-drug conjugates that target cells expressing CD19.

III. Methods of Treatment and Combination Therapies

The genetically engineered hematopoietic cells such as HSCs may be administered to a subject in need of the treatment, either taken alone or in combination of one or more cytotoxic agents that target one or more lineage-specific cell-surface antigens as described herein. Since the hematopoietic cells are genetically edited in the genes of the one or more lineage-specific cell-surface antigens, the hematopoietic cells and/or descendant cells thereof would express the one or more lineage-specific cell-surface antigens in mutated form (e.g., but functional) such that they can escape being targeted by the cytotoxic agents, for example, CAR-T cells.

Thus, the present disclosure provides methods for treating a hematopoietic malignancy, the method comprising administering to a subject in need thereof (i) a population of the genetically engineered hematopoietic cells described herein, and optionally (ii) a cytotoxic agent such as CAR-T cells that target a lineage-specific cell-surface antigen, the gene of which is genetically edited in the hematopoietic cells such that the cytotoxic agent does not target hematopoietic cells or descendant cells thereof. The administration of (i) and (ii) may be concurrently or in any order. In some embodiments, the cytotoxic agents and/or the hematopoietic cells may be mixed with a pharmaceutically acceptable carrier to form a pharmaceutical composition, which is also within the scope of the present disclosure.

In some embodiments, the genetically engineered hematopoietic stem cells have genetic editing in genes of at least two lineage-specific cell-surface proteins/antigens A and B. Such hematopoietic stem cells can be administered to a subject, who has been or will be treated with a first cytotoxic agent specific to A (e.g., anti-protein A CAR-T cells), or who is at risk of a hematopoietic malignancy that would need treatment of the cytotoxic agent. When the subject developed resistance to the cytotoxic agent after the treatment or has relapse of the hematopoietic malignancy, a second cytotoxic agent specific to B (e.g., anti-protein B CAR-T cells) may be administered to the subject. Because the genetically engineered hematopoietic cells have genetic editing in both A and B genes, those cells and descendant cells thereof would also be resistant to cytotoxicity induced by the second cytotoxic agent. As such, administering once the genetically engineered hematopoietic cells would be sufficient to compensate loss of normal cells expressing at least lineage-specific cell-surface proteins/antigens A and B due to multiple treatment by cytotoxic agents specific to at least proteins/antigens A and B.

As used herein, "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human patient having a hematopoietic malignancy.

To perform the methods described herein, an effective amount of the genetically engineered hematopoietic cells can be administered to a subject in need of the treatment. Optionally, the hematopoietic cells can be co-used with a cytotoxic agent as described herein. As used herein the term "effective amount" may be used interchangeably with the term "therapeutically effective amount" and refers to that quantity of a cytotoxic agent, hematopoietic cell population, or pharmaceutical composition (e.g., a composition comprising cytotoxic agents and/or hematopoietic cells) that is sufficient to result in a desired activity upon administration to a subject in need thereof. Within the context of the present disclosure, the term "effective amount" refers to that quantity of a compound, cell population, or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject is a human patient having a hematopoietic malignancy.

As described herein, the hematopoietic cells and/or immune cells expressing chimeric receptors may be autologous to the subject, i.e., the cells are obtained from the subject in need of the treatment, manipulated such that the cells do not bind the cytotoxic agents, and then administered to the same subject. Administration of autologous cells to a subject may result in reduced rejection of the host cells as compared to administration of non-autologous cells. Alternatively, the host cells are allogeneic cells, i.e., the cells are obtained from a first subject, manipulated such that the cells do not bind the cytotoxic agents, and then administered to a second subject that is different from the first subject but of the same species. For example, allogeneic immune cells may be derived from a human donor and administered to a human recipient who is different from the donor.

In some embodiments, engineered hematopoietic cells comprising one or more genetically engineered gene(s) encoding lineage-specific cell-surface protein(s) (e.g., CD33 or CD19 or another lineage-specific cell-surface protein described herein) and the immune cells engineered to target an epitope of the lineage-specific cell-surface protein(s) are both allogeneic to the subject. In some embodiments, engineered hematopoietic cells comprising one or more genetically engineered gene(s) encoding lineage-specific cell-surface protein(s) (e.g., CD33 or CD19 or another lineage-specific cell-surface protein described herein) and the immune cells engineered to target an epitope of the lineage-specific cell-surface protein(s) are from the same allogeneic donor. In some embodiments, engineered hematopoietic cells comprising one or more genetically engineered gene(s) encoding lineage-specific cell-surface protein(s) (e.g., CD33 or CD19 or another lineage-specific cell-surface protein described herein) and the immune cells engineered to target an epitope of the lineage-specific cell-surface protein(s) are from two different allogeneic donors.

In some embodiments, engineered hematopoietic cells comprising one or more genetically engineered gene(s) encoding lineage-specific cell-surface protein(s) (e.g., CD33 or CD19 or another lineage-specific cell-surface protein described herein) and the immune cells engineered to target an epitope of the lineage-specific cell-surface protein(s) are both autologous to the subject.

In some embodiments, engineered hematopoietic cells comprising one or more genetically engineered gene(s) encoding lineage-specific cell-surface protein(s) (e.g., CD33 or CD19 or another lineage-specific cell-surface protein described herein) are autologous to the subject and the immune cells engineered to target an epitope of the lineage-specific cell-surface protein(s) are from an allogeneic donor. In some embodiments, engineered hematopoietic cells comprising one or more genetically engineered gene(s) encoding lineage-specific cell-surface protein(s) (e.g., CD33 or CD19 or another lineage-specific cell-surface protein described herein) are from an allogeneic donor and the immune cells engineered to target an epitope of the lineage-specific cell-surface protein(s) are autologous to the subject.

In some embodiments, the immune cells and/or hematopoietic cells are allogeneic cells and have been further genetically engineered to reduce graft-versus-host disease. For example, as described herein, the hematopoietic stem cells may be genetically engineered (e.g., using genome editing) to have reduced expression of CD45RA. Methods for reducing graft-versus-host disease are known in the art, see, e.g., Yang et al. *Curr. Opin. Hematol.* (2015) 22(6): 509-515. In some embodiments, the immune cells (e.g., T cells) may be genetically engineered to reduce or eliminate expression of the T cell receptor (TCR) or reduce or eliminate cell surface localization of the TCR. In some examples, the gene encoding the TCR is knocked out or silenced (e.g., using gene editing methods, or shRNAs). In some embodiments, the TCR is silenced using peptide inhibitors of the TCR. In some embodiments, the immune cells (e.g., T cells) are subjected to a selection process to select for immune cells or a population of immune cells that do not contain an alloreactive TCR. Alternatively, in some embodiments, immune cells that naturally do not express TCRs (e.g., NK cells) may be used in any of the methods described herein.

In some embodiments, the immune cells and/or hematopoietic cells have been further genetically engineered to reduce host-versus-graft effects. For example, in some embodiments, immune cells and/or hematopoietic cells may be subjected to gene editing or silencing methods to reduce or eliminate expression of one or more proteins involved in inducing host immune responses, e.g., CD52, MHC molecules, and/or MHC beta-2 microglobulin.

In some embodiments, the immune cells expressing any of the chimeric receptors described herein are administered to a subject in an amount effective in to reduce the number of target cells (e.g., cancer cells) by least 20%, e.g., 50%, 80%, 100%, 2-fold, 5-fold, 10-fold, 20-fold, 50-fold, 100-fold or more.

A typical amount of cells, i.e., immune cells or hematopoietic cells, administered to a mammal (e.g., a human) can be, for example, in the range of about $10^6$ to $10^{11}$ cells. In some embodiments it may be desirable to administer fewer than $10^6$ cells to the subject. In some embodiments, it may be desirable to administer more than $10^{11}$ cells to the subject. In some embodiments, one or more doses of cells includes about $10^6$ cells to about $10^{11}$ cells, about $10^7$ cells to about $10^{10}$ cells, about $10^8$ cells to about $10^9$ cells, about $10^6$ cells to about $10^8$ cells, about $10^7$ cells to about $10^9$ cells, about $10^7$ cells to about $10^{10}$ cells, about $10^7$ cells to about $10^{11}$ cells, about $10^8$ cells to about $10^{10}$ cells, about $10^8$ cells to about $10^{11}$ cells, about $10^9$ cells to about $10^{10}$ cells, about $10^9$ cells to about $10^{11}$ cells, or about $10^{10}$ cells to about $10^{11}$ cells.

In some embodiments, the subject is preconditioned prior to administration of the cytotoxic agent and/or hematopoietic cells. In some embodiments, the method further comprises pre-conditioning the subject. In general, preconditioning a subject involves subjecting the patient to one or more therapy, such as a chemotherapy or other type of therapy, such as irradiation. In some embodiments, the preconditioning may induce or enhance the patient's tolerance of one or more subsequent therapy (e.g., a targeted therapy), as described herein. In some embodiments, the pre-conditioning involves administering one or more chemotherapeutic agents to the subject. Non-limiting examples of chemotherapeutic agents include actinomycin, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fludarabine, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vinblastine, vincristine, vindesine, and vinorelbine.

In some embodiments, the subject is preconditioned at least one day, two days, three days, four days, 5 days, 6 days, 7 days, 8 days, 9 days, 10 days, 11 days, 12 days, 13 days, two weeks, three weeks, four weeks, five weeks, six weeks, seven weeks, eight weeks, nine weeks, ten weeks, two months, three months, four months, five months, or at least six months prior to administering the cytotoxic agent and/or hematopoietic cells.

In other embodiments, the chemotherapy(ies) or other therapy(ies) are administered concurrently with the cytotoxic agent and manipulated hematopoietic cells. In other embodiments, the chemotherapy(ies) or other therapy(ies) are administered after the cytotoxic agent and manipulated hematopoietic cells.

In one embodiment, the chimeric receptor (e.g., a nucleic acid encoding the chimeric receptor) is introduced into an immune cell, and the subject (e.g., human patient) receives an initial administration or dose of the immune cells expressing the chimeric receptor. One or more subsequent administrations of the cytotoxic agent (e.g., immune cells expressing the chimeric receptor) may be provided to the patient at intervals of 15 days, 14, 13, 12, 11, 10, 9, 8, 7, 6, 5, 4, 3, or 2 days after the previous administration. More than one dose of the cytotoxic agent can be administered to the subject per week, e.g., 2, 3, 4, or more administrations of the agent. The subject may receive more than one doses of the cytotoxic agent (e.g., an immune cell expressing a chimeric receptor) per week, followed by a week of no administration of the agent, and finally followed by one or more additional doses of the cytotoxic agent (e.g., more than one administration of immune cells expressing a chimeric receptor per week). The immune cells expressing a chimeric receptor may be administered every other day for 3 administrations per week for two, three, four, five, six, seven, eight or more weeks.

Any of the methods described herein may be for the treatment of a hematological malignancy in a subject. As used herein, the terms "treat," "treating," and "treatment" mean to relieve or alleviate at least one symptom associated with the disease or disorder, or to slow or reverse the progression of the disease or disorder. Within the meaning of the present disclosure, the term "treat" also denotes to arrest, delay the onset (i.e., the period prior to clinical manifestation of a disease) and/or reduce the risk of developing or worsening a disease. For example, in connection with cancer, the term "treat" may mean eliminate or reduce the number or replication of cancer cells, and/or prevent, delay or inhibit metastasis, etc.

In some embodiments, a population of genetically engineered hematopoietic cells (e.g., carrying genetic edits in genes of one or more lineage-specific cell-surface proteins for expressing those proteins in mutated form) and a cytotoxic agent(s) specific to the lineage-specific cell-surface protein are co-administered to a subject via a suitable route (e.g., infusion). In such a combined therapeutic methods, the cytotoxic agent recognizes (binds) a target cell expressing the cell-surface lineage-specific protein for targeted killing. The hematopoietic cells that express the protein in mutated form, which has reduced binding activity or do not bind the cytotoxic acid (e.g., because of lacking binding epitope) allow for repopulation of a cell type that is targeted by the cytotoxic agent.

In some embodiments, the methods described herein involve administering a population of genetically engineered hematopoietic cells to a subject and administering one or more immunotherapeutic agents (e.g., cytotoxic agents). As will be appreciated by one of ordinary skill in the art, the immunotherapeutic agents may be of the same or different type (e.g., therapeutic antibodies, populations of immune cells expressing chimeric antigen receptor(s), and/or antibody-drug conjugates).

In some embodiments, the methods described herein involve administering a population of genetically engineered hematopoietic cells in which CD33 is mutated to a subject and administering one or immunotherapeutic agents (e.g., cytotoxic agents). In some embodiments, the methods described herein involve administering a population of genetically engineered hematopoietic cells in which CD33 is mutated to a subject and administering one or more therapeutic antibodies. In some embodiments, the methods described herein involve administering a population of genetically engineered hematopoietic cells in which CD33 is mutated to a subject and administering one or more populations of immune cells expressing chimeric antigen receptor(s). In some embodiments, the methods described herein involve administering a population of genetically engineered hematopoietic cells in which CD33 is mutated to a subject and administering one or more antibody-drug conjugates. In some embodiments, the methods described herein involve administering a population of genetically engineered hematopoietic cells comprising a mutated CD33 set forth by SEQ ID NO: 56 or 58 to a subject and administering one or more antibody-drug conjugates.

In some embodiments, the methods described herein involve administering a population of genetically engineered hematopoietic cells in which CD19 is mutated to a subject and administering one or immunotherapeutic agents (e.g., cytotoxic agents). In some embodiments, the methods described herein involve administering a population of genetically engineered hematopoietic cells in which CD19 is mutated to a subject and administering one or more therapeutic antibodies. In some embodiments, the methods described herein involve administering a population of genetically engineered hematopoietic cells in which CD19 is mutated to a subject and administering one or more populations of immune cells expressing chimeric antigen receptor(s). In some embodiments, the methods described herein involve administering a population of genetically engineered hematopoietic cells in which CD19 is mutated to a subject and administering one or more antibody-drug conjugates. In some embodiments, the methods described herein involve administering a population of genetically engineered hematopoietic cells comprising a mutated CD19 set forth by SEQ ID NO: 52 or 73 to a subject and administering one or more antibody-drug conjugates.

In some embodiments, the treatment of the patient can involve the following steps: (1) administering a therapeutically effective amount of the cytotoxic agent to the patient and (2) infusing or reinfusing the patient with hematopoietic stem cells, either autologous or allogenic. In some embodiments, the treatment of the patient can involve the following steps: (1) administering a therapeutically effective amount of an immune cell expressing a chimeric receptor to the patient, wherein the immune cell comprises a nucleic acid sequence encoding a chimeric receptor that binds an epitope of a cell-surface lineage-specific, disease-associated protein; and (2) infusing or reinfusing the patient with hematopoietic cells (e.g., hematopoietic stem cells), either autologous or allogenic. In each of the methods described herein, the cytotoxic agent (e.g., CAR-T cells) and the genetically engineered hematopoietic cells can be administered to the subject in any order. In some instances, the hematopoietic cells are given to the subject prior to the cytotoxic agent. In some instances, a second cytotoxic agent can be administered to the subject after treatment with the first cytotoxic agent, e.g., when the patient develops resistance or disease relapse. The hematopoietic cells given the same subject may have multiple edited genes expressing lineage-specific cell-surface proteins in mutated form such that the cytotoxic agents can target wild-type proteins but not the mutated form.

The efficacy of the therapeutic methods using a population of genetically engineered hematopoietic cells described herein, optionally in combination with a cytotoxic agent (e.g., CART) may be assessed by any method known in the art and would be evident to a skilled medical professional. For example, the efficacy of the therapy may be assessed by survival of the subject or cancer burden in the subject or tissue or sample thereof. In some embodiments, the efficacy of the therapy is assessed by quantifying the number of cells belonging to a particular population or lineage of cells. In some embodiments, the efficacy of the therapy is assessed by quantifying the number of cells presenting the cell-surface lineage-specific protein.

In some embodiments, the cytotoxic agent comprising an antigen-binding fragment that binds to the epitope of the cell-surface lineage-specific protein and the population of hematopoietic cells is administered concomitantly.

In some embodiments, the cytotoxic agent comprising an antigen-binding fragment that binds an epitope of a cell-surface lineage-specific protein (e.g., immune cells expressing a chimeric receptor as described herein) is administered prior to administration of the hematopoietic cells. In some embodiments, the agent comprising an antigen-binding fragment that binds an epitope of a cell-surface lineage-specific protein (e.g., immune cells expressing a chimeric receptor as described herein) is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the hematopoietic cells.

In some embodiments, the hematopoietic cells are administered prior to the cytotoxic agent comprising an antigen-binding fragment that binds an epitope of the cell-surface lineage-specific protein (e.g., immune cells expressing a chimeric receptor as described herein). In some embodiments, the population of hematopoietic cells is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the cytotoxic agent comprising an antigen-binding fragment that binds to an epitope of the cell-surface lineage-specific protein.

In some embodiments, the cytotoxic agent targeting the cell-surface lineage-specific protein and the population of hematopoietic cells are administered at substantially the same time. In some embodiments, the cytotoxic agent targeting the cell-surface lineage-specific protein is administered and the patient is assessed for a period of time, after which the population of hematopoietic cells is administered. In some embodiments, the population of hematopoietic cells is administered and the patient is assessed for a period of time, after which the cytotoxic agent targeting the cell-surface lineage-specific protein is administered.

Also within the scope of the present disclosure are multiple administrations (e.g., doses) of the cytotoxic agents and/or populations of hematopoietic cells. In some embodiments, the cytotoxic agents and/or populations of hematopoietic cells are administered to the subject once. In some embodiments, cytotoxic agents and/or populations of hematopoietic cells are administered to the subject more than once (e.g., at least 2, 3, 4, 5, or more times). In some embodiments, the cytotoxic agents and/or populations of hematopoietic cells are administered to the subject at a regular interval, e.g., every six months.

In some embodiments, the subject is a human subject having a hematopoietic malignancy. As used herein a hematopoietic malignancy refers to a malignant abnormality involving hematopoietic cells (e.g., blood cells, including progenitor and stem cells). Examples of hematopoietic malignancies include, without limitation, Hodgkin's lymphoma, non-Hodgkin's lymphoma, leukemia, or multiple myeloma. Exemplary leukemias include, without limitation, acute myeloid leukemia, acute lymphoid leukemia, chronic myelogenous leukemia, acute lymphoblastic leukemia or chronic lymphoblastic leukemia, and chronic lymphoid leukemia.

In some embodiments, cells involved in the hematopoietic malignancy are resistant to convention or standard therapeutics used to treat the malignancy. For example, the cells (e.g., cancer cells) may be resistant to a chemotherapeutic agent and/or CAR T cells used to treat the malignancy.

In some embodiments, the hematopoietic malignancy is associated with CD19+ cells. Examples include, but are not limited to, B cell malignancies such as non-Hodgkin's lymphoma, Hodgkin's lymphoma, leukemia, multiple myeloma, acute lymphoblastic leukemia, acute lymphoid leukemia, acute lymphocytic leukemia, chronic lymphoblastic leukemia, chronic lymphoid leukemia, and chronic lymphocytic leukemia. In some embodiments, the hematopoietic malignancy is a relapsing hematopoietic malignancy.

In some embodiments, the leukemia is acute myeloid leukemia (AML). AML is characterized as a heterogeneous, clonal, neoplastic disease that originates from transformed cells that have progressively acquired critical genetic changes that disrupt key differentiation and growth-regulatory pathways. (Dohner et al., NEJM, (2015) 373:1136). CD33 glycoprotein is expressed on the majority of myeloid leukemia cells as well as on normal myeloid and monocytic precursors and has been considered to be an attractive target for AML therapy (Laszlo et al., Blood Rev. (2014) 28(4): 143-53). While clinical trials using anti-CD33 monoclonal antibody based therapy have shown improved survival in a subset of AML patients when combined with standard chemotherapy, these effects were also accompanied by safety and efficacy concerns.

In some cases, a subject may initially respond to a therapy (e.g., for a hematopoietic malignancy) and subsequently experience relapse. Any of the methods or populations of genetically engineered hematopoietic cells described herein may be used to reduce or prevent relapse of a hematopoietic malignancy. Alternatively or in addition, any of the methods described herein may involve administering any of the populations of genetically engineered hematopoietic cells described herein and an immunotherapeutic agent (e.g., cytotoxic agent) that targets cells associated with the hematopoietic malignancy and further administering one or more additional immunotherapeutic agents when the hematopoietic malignancy relapses.

As used herein, the term "relapse" refers to the reemergence or reappearance of cells associated with a hematopoietic malignancy following a period of responsiveness to a therapy. Methods of determining whether a hematopoietic malignancy has relapsed in a subject will appreciated by one of ordinary skill in the art. In some embodiments, the period of responsiveness to a therapy involves the level or quantity of cells associated with the hematopoietic malignancy the falling below a threshold, e.g., below 20%, 15%, 10%, 5%, 4%, 3%, 2%, or 1% of the level or quantity of cells prior to administration of the therapy. In some embodiments, a relapse is characterized by the level or quantity of cells associated with the hematopoietic malignancy above a threshold, e.g., above 20%, 15%, 10%, 5%, 4%, 3%, 2%, or 1% higher than the level or quantity of cells during the period of responsiveness. Methods of determining the minimal residual disease in a subject are known in the art and may be used, for example to assess whether a hematopoietic malignancy has relapsed or is likely to relapse. See, e.g., Taraseviciute et al. Hematology and Oncology (2019) 31(1)).

In some embodiments, the subject has or is susceptible to relapse of a hematopoietic malignancy (e.g., AML) following administration of one or more previous therapies. In some embodiments, the methods described herein reduce the subject's risk of relapse or the severity of relapse.

Without wishing to be bound by any particular theory, some cancers, including hematopoietic malignancies, are thought to relapse after an initial period of responsiveness to a therapy due to mechanisms such as antigen loss/antigen escape or lineage switch. In general, antigen loss/antigen escape results in relapse with a phenotypically similar hematopoietic malignancy characterized by cells that lack surface expression of the antigen targeted by the previous therapy (e.g., immunotherapeutic agent) such that the cells are no longer targeted by the previous therapy. In contrast, lineage switch presents as a genetically related but phenotypically different malignancy in which the cells lack surface expression of the antigen targeted by the previous therapy (e.g., immunotherapeutic agent) such that the cells are no longer targeted by the previous therapy. See, e.g., Brown et al. Nature Reviews Immunology (2019) 19:73-74; Majzner et al. Cancer Discovery (2018) 8(10).

Antigen loss/antigen escape in which the target antigen is no longer present on the target cells (e.g., cells of the hematopoietic malignancy) frequently occurs as a result of genetic mutation and/or enrichment of cells that express a variant of the antigen (e.g., lineage-specific cell-surface antigen) that is not targeted by the immunotherapeutic agent (e.g., cytotoxic agent). In some embodiments, the hematopoietic malignancy has relapsed due to antigen loss/antigen escape. In some embodiments, the target cells have lost the targeted epitope (e.g., of a lineage-specific cell-surface antigen) or have reduced expression of the antigen (e.g., lineage-specific cell-surface antigen) such that the targeted epitope is not recognized by the immunotherapeutic agent or is not sufficient to induce cytotoxicity. In some embodiments, the hematopoietic malignancy has relapsed due to lineage switch.

In some embodiments, the methods described herein reduce or avoid relapse of a hematopoietic malignancy by targeting more than one antigen (e.g., more than one lineage-specific cell-surface antigen). In some embodiments, the populations of genetically engineered hematopoietic cells express mutants of more than one lineage-specific surface antigens such that the mutated lineage-specific surface antigens are not targeted by an immunotherapeutic agent(s).

In some embodiments, a cancer treated with the methods herein comprises a first sub-population of cancer cells and a second sub-population of cancer cells. One of the sub-populations may be cancer stem cells. One of the sub-populations may be cancer bulk cells. One of the sub-populations may have one or more (e.g., at least 2, 3, 4, 5, or all) markers of differentiated hematopoietic cells. One of the sub-populations may have one or more (e.g., at least 2, 3, 4, 5, or all) markers of earlier lineage cells, e.g., HSCs or HPCs.

Markers characteristic of different sub-populations of cancer cells (e.g., cancer stem cells and cancer bulk cells) are described, e.g., in van Galen et al. Cell 176, 1-17, Mar. 7, 2019, which is herein incorporated by reference in its entirety. For instance, in some embodiments, the first sub-population of cancer cells comprises primitive AML cells and/or the second sub-population of cancer cells comprises differentiated AML cells (e.g., differentiated monocyte-like AML cells). In some embodiments, a primitive AML cells expresses stemness genes (e.g., as described in van Galen et al., supra) and/or myeloid priming genes (e.g., as described in van Galen et al., supra). In some embodiments, a differentiated monocyte-like AML cell expresses immunomodulatory genes (e.g., as described in van Galen et al., supra). In some embodiments, one or more of the sub-populations of cancer cells are chosen from: HSC-like, progenitor-like, GMP-like, promonocyte-like, monocyte-like, or conventional dendritic cell (cDC)-like, e.g., as described in van Galen et al., supra.

Any of the immune cells expressing chimeric receptors described herein may be administered in a pharmaceutically acceptable carrier or excipient as a pharmaceutical composition.

The phrase "pharmaceutically acceptable," as used in connection with compositions and/or cells of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions and/or cells to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers;

monosaccharides; disaccharides; and other carbohydrates; metal complexes; and/or non-ionic surfactants. See, e.g. *Remington: The Science and Practice of Pharmacy* 20th Ed. (2000) Lippincott Williams and Wilkins, Ed. K. E. Hoover.

Kits for Therapeutic Uses

Also within the scope of the present disclosure are kits for use in treating hematopoietic malignancy. Such a kit may comprise the genetically engineered hematopoietic cells such as HSCs, and optionally one or more cytotoxic agents targeting lineage-specific cell-surface antigens, the genes of which are edited in the hematopoietic cells. Such kits may include a container comprising a first pharmaceutical composition that comprises any of the genetically engineered hematopoietic cells as described herein, and optionally one or more additional containers comprising one or more cytotoxic agents (e.g., immune cells expressing chimeric receptors described herein) targeting the lineage-specific cell-surface antigens as also described herein.

In some embodiments, the kit can comprise instructions for use in any of the methods described herein. The included instructions can comprise a description of administration of the genetically engineered hematopoietic cells and optionally descriptions of administration of the one or more cytotoxic agents to a subject to achieve the intended activity in a subject. The kit may further comprise a description of selecting a subject suitable for treatment based on identifying whether the subject is in need of the treatment. In some embodiments, the instructions comprise a description of administering the genetically engineered hematopoietic cells and optionally the one or more cytotoxic agents to a subject who is in need of the treatment.

The instructions relating to the use of the genetically engineered hematopoietic cells and optionally the cytotoxic agents described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a chimeric receptor variants as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»;

*Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Deletion Exon 2 of CD19 Via CRISPR/Cas9-Mediated Gene Editing and Characterization of Cells Expressing Exon 2-Deleted CD19

This Example reports genetic engineering of CD19 genes via CRISPR/Cas9 in cells to produce edited cells expressing mutated CD19, in which the fragment encoded by exon 2 is deleted (CD19ex2), and in vitro and in vivo characterization of such edited cells. See also above disclosures for exemplary exon-2 deleted CD19 gene products.

Materials and Methods

Design of sgRNA Constructs

All sgRNAs were designed by manual inspection for the SpCas9 PAM (5'-NGG-3') with close proximity to the target region and prioritized according to predicted specificity by minimizing potential off-target sites in the human genome with an online search algorithm (Benchling, Doench et al 2016, Hsu et al 2013). All designed synthetic sgRNAs were purchased from Synthego® with chemically modified nucleotides at the three terminal positions at both the 5' and 3' ends. Modified nucleotides contained 2'-O-methyl-3'-phosphorothioate (abbreviated as "ms") and the ms-sgRNAs were HPLC-purified. Cas9 protein was purchased from Synthego® (FIGS. 5-8B) and Aldervon® (FIGS. 9A, 9B, 10A-10D, 14A-14D, 17, 18A and 18B).

Cell Maintenance and Electroporation of Immortalized Human Cell Lines

K562 human leukemia cell lines were obtained from American Type Culture Collection® (ATCC®) and maintained in DMEM+10% FBS and maintained at 37° C. at 5% CO2. K562 cells were edited by electroporation of the Cas9 ribonucleoprotein (RNP) using the Lonza® Nucleofector™ (program SF-220) and the Human P3 Cell Nucleofection Kit (VPA-1002, Lonza®). Raji-Fluc-GFP cells were purchased from Capital Biosciences™ and maintained in RPMI+10% FBS+1% Glutamine at 37° C. at 5% CO2. Raji-Fluc-GFP cells were edited by electroporation of RNP using the Lonza® Nucleofector™ (program DS-104) and SG Cell line 4D-Nucleofector™ X Kit S (V4XC-3032, Lonza®). Cas9 RNP was made by incubating protein with ms-sgRNA at a molar ratio of 1:9 (20:180 pmol) at 25° C. for 10 minutes immediately before electroporation. After electroporation, cells were incubated for 10 minutes in the cuvette, transferred to 1 mL of the above medium, and cultured for 24-72 hrs for downstream analysis.

Editing in Primary Human CD34+ HSCs

Frozen CD34+ HSCs derived from mobilized peripheral blood were purchased from AllCells® and thawed according to manufacturer's instructions. Frozen CD34+ HSCs derived from cord blood were either purchased frozen from AllCells® or Stemcell™ and thawed and maintained according to manufacturer's instructions. To edit HSCs, ~1e6 HSCs were thawed and cultured in StemSpan™ SFEM medium supplemented with StemSpan™ CC110 cocktail (StemCell Technologies™) for 24 h before electroporation with RNP. To electroporate HSCs, 1.5e5 were pelleted and resuspended in 20 µL Lonza® P3 solution, and mixed with 10 uL Cas9 RNP as described above. CD34+ HSCs were electroporated using the Lonza® Nucleofector™ 2 (program DU-100) and the Human P3 Cell Nucleofection Kit (VPA-1002, Lonza®).

Genomic DNA Analysis

For all genomic analysis, DNA was harvested from cells using the Qiagen® DNeasy® kit. For T7E1 assays, PCR was performed with primers flanking the CRISPR cut sites. Products were purified by PCR purification (Qiagen®) and 200 ng was denatured and re-annealed in a thermocycler and digested with T7 Endonuclease I (New England Biolabs®) according to manufacturer's protocol. Digested DNA were electrophoresed in a 1% agarose gel and viewed on a BioRad® ChemiDoc® imager. Band intensities were analyzed using the Image Lab Software (Bio-Rad®) and allele modification frequencies (INDEL) were calculated with the formula: 100×(1−(1−fraction cleaved)^0.5). For analyzing allele modification frequencies using TIDE (Tracking of In/dels by Decomposition), the purified PCR products were Sanger-sequenced (Eton™) using both PCR primers and each sequence chromatogram was analyzed with the online TIDE software (Deskgen). Analyses were performed using a reference sequence from a mock-transfected (Cas9 protein only) sample. Parameters were set to the default maximum indel size of 10 nucleotides and the decomposition window to cover the largest possible window with high quality traces. All TIDE analyses below the detection sensitivity of 3.5% were set to 0%.

To determine the extent genomic deletion with dual ms-sgRNAs, endpoint PCR was performed with primers flanking CRISPR cut sites that amplify an 804 bp region. PCR products were electrophoresed in a 1% agarose gel and viewed on a BioRad® ChemiDoc® imager to observe the intact parental band and the expected smaller (400-600 bp depending on ms-sgRNA combination) deletion product. Band intensities were analyzed using the Image Lab Software (Bio-Rad®) and percent deletions were calculated with the formula: 100×fraction cleaved). Gel bands were extracted with a gel extraction kit (Qiagen®) and further purified by PCR purification (Qiagen®) for Sanger sequencing (Eton Bioscience™)

Flow Cytometry and FACS Analysis

Raji-fluc-GFP cells nucleofected with RNP as described above were maintained in cell culture for 48 hrs. Live cells were stained with PE-conjugated CD19 antibody (IM1285U; Beckman Coulter®) and analyzed sorted on a BD FACS Aria™ by expression of CD19. CD34+ HSCs were stained for CD33 using an anti-CD33 antibody (P67.7) and analyzed by flow cytometry on the Attune® NxT flow cytometer (Life Technologies®).

CAR-T Cell Cytotoxicity Assays

CD19-directed CAR-T cells (CART19) were generated by transduction of CART19-expressing lentivirus into CD4+ and CD8+ T cells from healthy human donors. CART19 construct contains a CD19-recognizing domain (single chain variable fragment derived from FMC63 monoclonal antibody), a costimulatory domain derived from CD28, and the CD3 zeta domain. The cytotoxicity of CART19 was assessed by flow cytometry-based assay. Raji-fluc-GFP cells stained with CellTrace™ Violet dye served as target cells. T cells not transduced with CART19 construct were used as a negative control for the cytotoxicity assay. The effector (E) and tumor target (T) cells were co-cultured at the indicated E/T ratios (10:1, 3:1, 0:1), with $1 \times 10^4$ target cells in a total volume of 200 μl per well in CTS™ OpTmizer™-based serum free medium. After 20 hours of incubation, cells were stained for Propidium Iodide and analyzed by Attune® NxT flow cytometer (Life Technologies®). Live target cells were gated as Propidium Iodide-negative and CellTrace™ Violet-positive. Cytotoxicity was calculated as (1−(Live target cell fraction in CART19 group)/(Live target cell fraction in negative control group))×100%.

In Vivo Engraftment Experiments

For CD19 in vivo engraftment experiments, cells are engrafted into NOD scid gamma mice (NSG™ mice; The Jackson Laboratory). For CD33 in vivo engraftment experiments, cells are engrafted into NSG™-SGM3 mice (The Jackson Laboratory).

In Vitro CFU Assay 1500 sorted CD34+ HSPCs were plated in 1.5 ml of methylcellulose (MethoCult™ H4034 Optimum, Stem Cell Technologies™) on a 35 mm cell culture dish and cultured for two weeks at 37° C. in a 5% CO2 incubator. Colonies were then counted and scored based on morphological appearance.

Results (i) Selection of gRNAs

Figure 4:
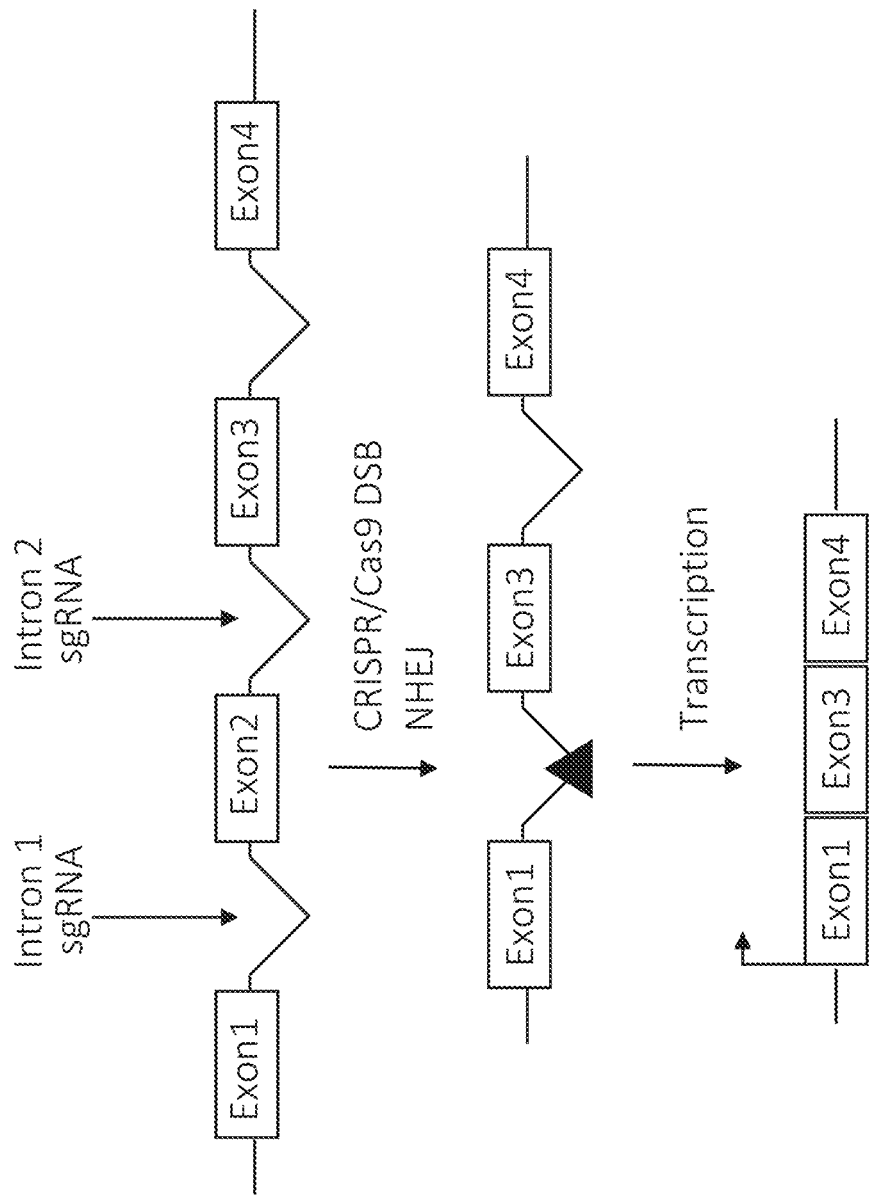
FIG. 4 is a schematic of CRISPR/Cas9-mediated genomic deletion of CD19 exon 2, resulting in expression of a CD19 variant having exon 2 deleted.

Exon 2 of CD19 was targeted for CRISPR/Cas9-mediated genomic deletion as exemplified in FIG. 4. A pair of sgRNAs, one sgRNA targeting intron 1 and one sgRNA targeting intron 2, leads to simultaneous generation of DNA double stranded breaks (DSBs) by Cas9 and excision of the region including complete loss of exon 2 of CD19. The ends distal to the cut site are repaired through ligation of introns 1 and 2 via non-homologous end joining (NHEJ). Transcription of the modified CD19 gene results in expression of a CD19 variant lacking exon 2 ("CD19exon2 deletion") via exon 2 skipping during RNA splicing.

A panel of sgRNAs targeting introns 1 and 2 was designed by manual inspection for the SpCas9 PAM (5'-NGG-3') with close proximity to CD19 exon 2 and prioritized according to predicted specificity by maximizing on-target and minimizing potential off-target sites in the human genome with an online search algorithm (Benchling, Doench et al (2016); Hsu et al (2013)) (Table 3). Exon 4 of CD19 may also be targeted for CRISPR/Cas9-mediated genomic deletion, for example using sgRNA-23 and sgRNA-24 (Table 3). For each of the example CD19 sgRNAs, the sequence targets CD19 and the Cas type is SpCas9.

TABLE 3

CD19 sgRNA panel

| Name | sgRNA Sequence | Location | Strand | PAM | On Target (Doench et al 2016)[1] | Off Target (Hsu et al 2013)[1] |
|---|---|---|---|---|---|---|
| CD19_sgRNA-1 | GAGGCTGGAAACTTGAGTTG (SEQ ID NO: 14) | Intron 1 | 1 | TGG | 57 | 67 |
| CD19_sgRNA-3 | GAGGGTAAGTTACTCAGCCA (SEQ ID NO: 15) | Intron 1 | -1 | AGG | 68 | 60 |
| CD19_sgRNA-4 | AAATTCAGGAAAGGGTTGGA (SEQ ID NO: 16) | Intron 1 | 1 | AGG | 53 | 62 |
| CD19_sgRNA-5 | AAGGGTTGGAAGGACTCTGC (SEQ ID NO: 17) | Intron 1 | 1 | CGG | 60 | 64 |
| CD19_sgRNA-6 | AGCAGAGGACTCCAAAAGCT (SEQ ID NO: 18) | Intron 1 | -1 | GGG | 62 | 59 |
| CD19_sgRNA-7 | CACACCAGGTTATAGAGCAG (SEQ ID NO: 19) | Intron 1 | -1 | AGG | 63 | 67 |
| CD19_sgRNA-8 | CTGCTCTATAACCTGGTGTG (SEQ ID NO: 20) | Intron 1 | 1 | AGG | 71 | 63 |
| CD19_sgRNA-9 | ACCTGGTGTGAGGAGTCGGG (SEQ ID NO: 21) | Intron 1 | 1 | GGG | 58 | 69 |
| CD19_sgRNA-10 | CACAGCGTTATCTCCCTCTG (SEQ ID NO: 22) | Exon 2 | -1 | TGG | 68 | 69 |
| CD19_sgRNA-13 | CGGACCTCTTCTGTCCATGG (SEQ ID NO: 23) | Intron 2 | -1 | TGG | 65 | 65 |
| CD19_sgRNA-14 | CCATGGACAGAAGAGGTCCG (SEQ ID NO: 24) | Intron 2 | 1 | CGG | 72 | 65 |
| CD19_sgRNA-15 | GGGCGAAACTCGGAGCTAGG (SEQ ID NO: 25) | Intron 2 | 1 | TGG | 80 | 65 |
| CD19_sgRNA-16 | GCTAGGTGGGCAGACTCCTG (SEQ ID NO: 26) | Intron 2 | 1 | GGG | 59 | 60 |
| CD19_sgRNA-18 | GGAACCTCTAGTGGTGAAGG (SEQ ID NO: 69) | Exon 1 | | TGG | | |
| CD19_sgRNA-19 | CACAGCGTTATCTCCCTCTG (SEQ ID NO: 70) | Exon 2 | | GGT | | |

TABLE 3-continued

CD19 sgRNA panel

| Name | sgRNA Sequence | Location | Strand | PAM | On Target (Doench et al 2016)[1] | Off Target (Hsu et al 2013)[1] |
|---|---|---|---|---|---|---|
| CD19_sgRNA-23 | GGACAGGGAGAGATAAGACA (SEQ ID NO: 71) | Intron 4 | | AGG | | |
| CD19_sgRNA-24 | AGGTAGAGTTTCTCTCAACT (SEQ ID NO: 72) | Intron 4 | | GGG | | |

[1]On and Off-target predictions based on the indicated published algorithms. Score is out of 100 and is a prediction of success.

Figure 5A:
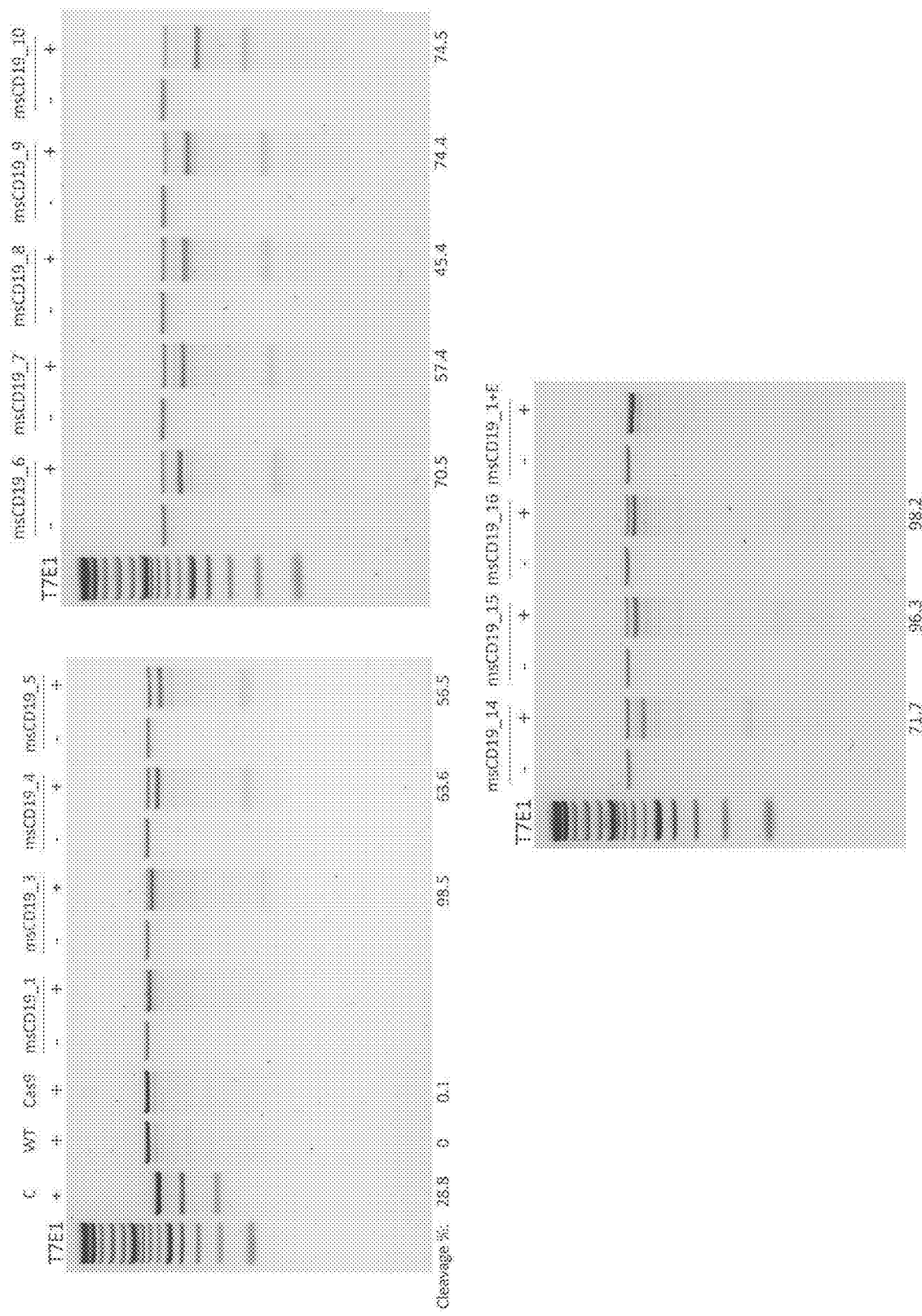
FIGS. 5A-5B include diagrams showing investigation of various modified single guide RNAs (ms-sgRNAs) targeting CD19 in a human leukemic cell line (K562 cells).
Figure 5B:
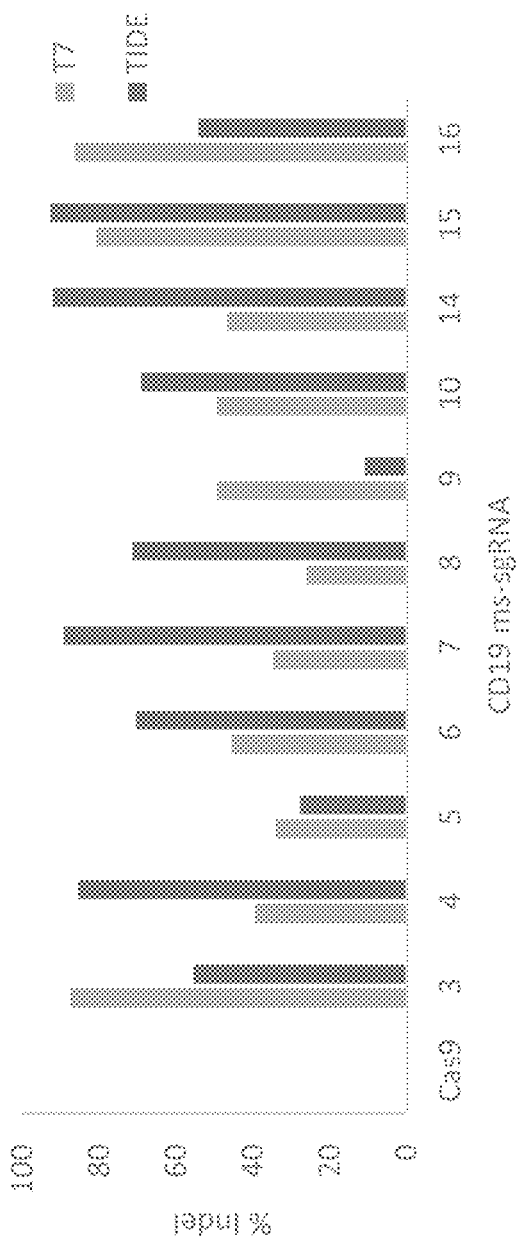

For gene editing, the sgRNAs were modified as described in the Materials and Methods. The modified sgRNAs are denoted with "ms" prefix. The CD19 sgRNAs targeting either intron 1 or 2 were screened in K562 cells, a human leukemic cell line and analyzed by T7E1 assay and TIDE analysis (FIG. 5). Of the 12 ms-sgRNAs assessed, ms-sgRNAs 1, 3-9 target intron 1, ms-sgRNA 10 targets exon 2, and ms-sgRNA 14-16 target intron 2. The percent INDEL for ms-sgRNA-1 was not calculated for this sample because the size-change between edited and unedited bands could not be accurately distinguished using the current set of PCR primers.

Figure 6A:
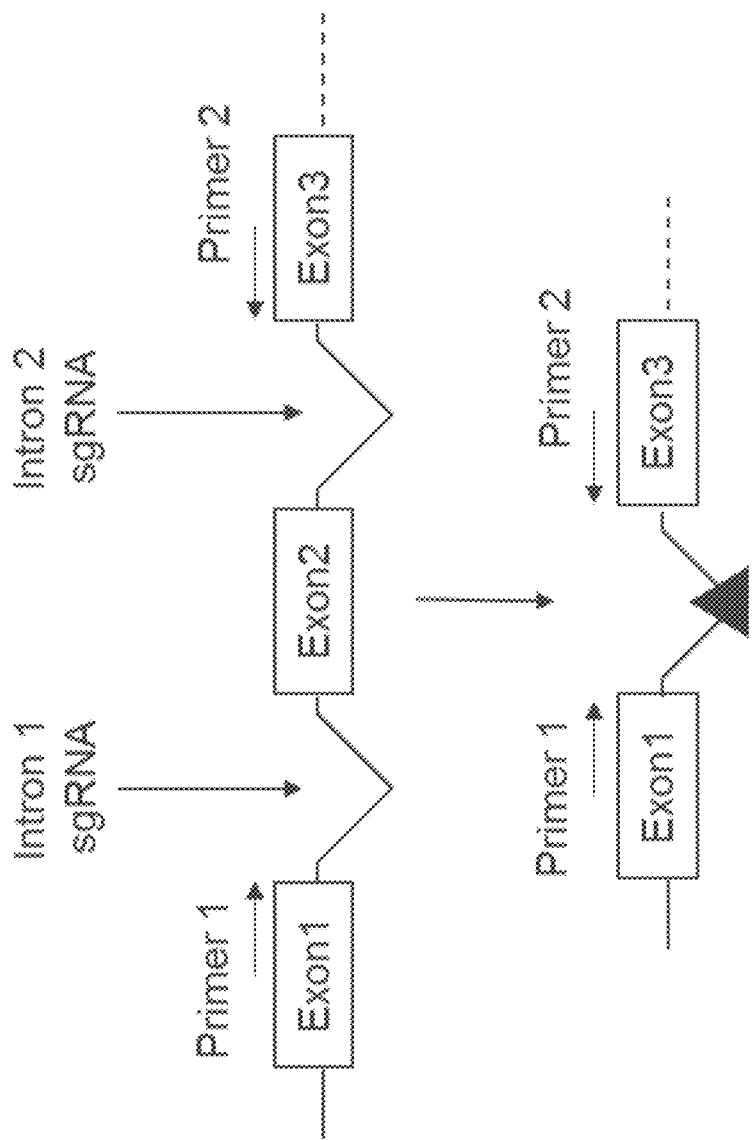
FIGS. 6A-6C include diagrams showing dual ms-sgRNA-mediated deletion of exon 2 of CD19 in K562 cells.
Figure 6B:
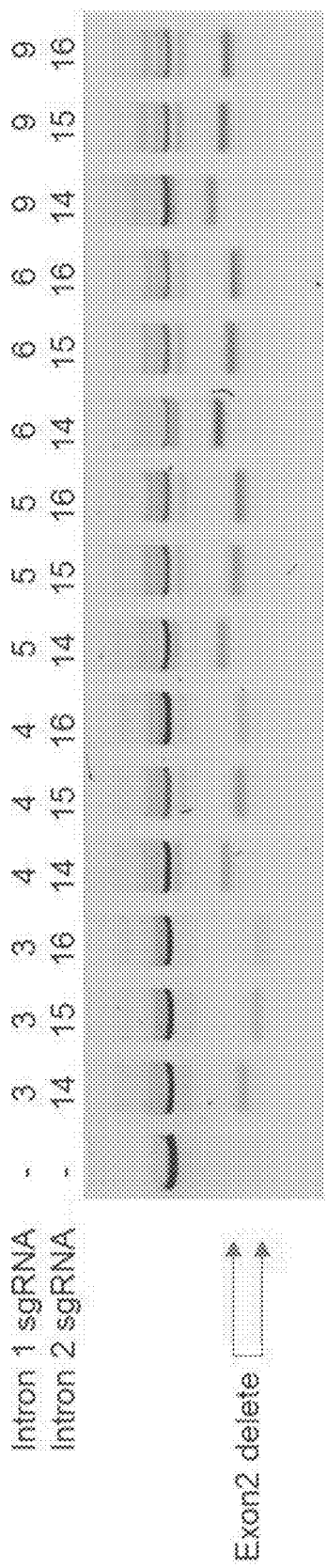
Figure 6C:
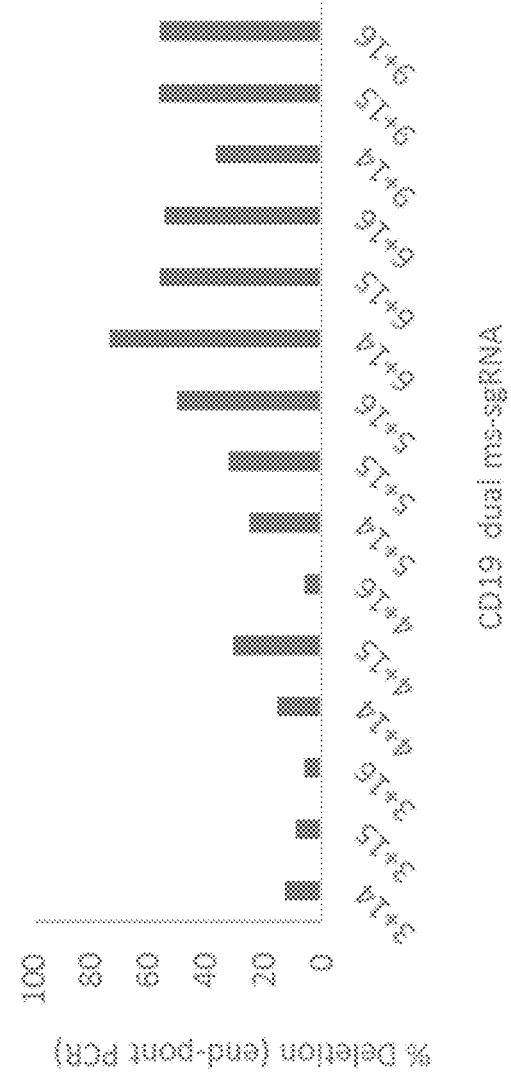

Pairs of ms-sgRNAs were used to delete exon 2 of CD19 in K562 cells, and a PCR-based assay was used to detect CRISPR/Cas9-mediated genomic deletion of CD19 exon 2 (FIG. 6). The combined activity of ms-sgRNAs targeting intron 1 (ms-sgRNAs 3, 4, 5, 6, 9) were screened in combination with ms-sgRNAs targeting intron 2 (ms-sgRNAs 14, 15, 16) to generate genomic deletions. PCR across the genomic deletion region shows the smaller deletion PCR product (400-560 bp) compared to the larger parental band (801 bp). The editing efficiency was quantified as percent deletion by end-point PCR (FIG. 6, panel C).

(ii) In Vitro Characterization of CD34$^+$ Cells Expressing Exon 2-Deleted CD19

Figure 7A:
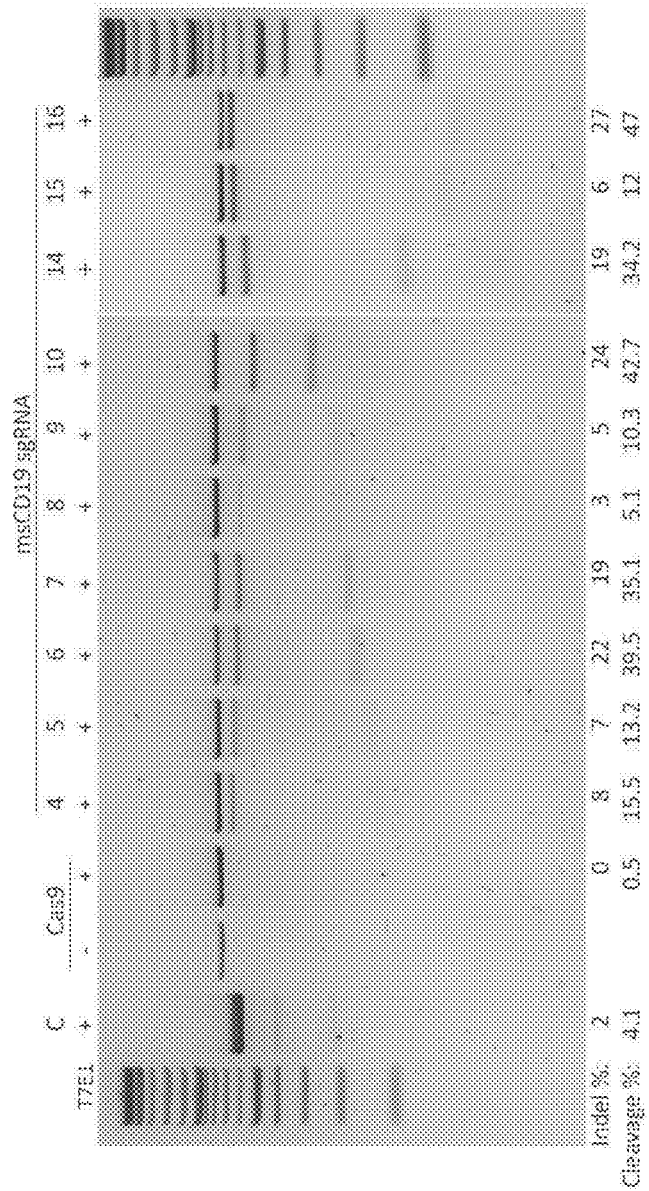
FIGS. 7A-7B include diagrams showing screening of CD19 ms-sgRNAs targeting introns 1 or 2 in CD34+ HSCs by T7E1 assay and TIDE analysis.
Figure 7B:
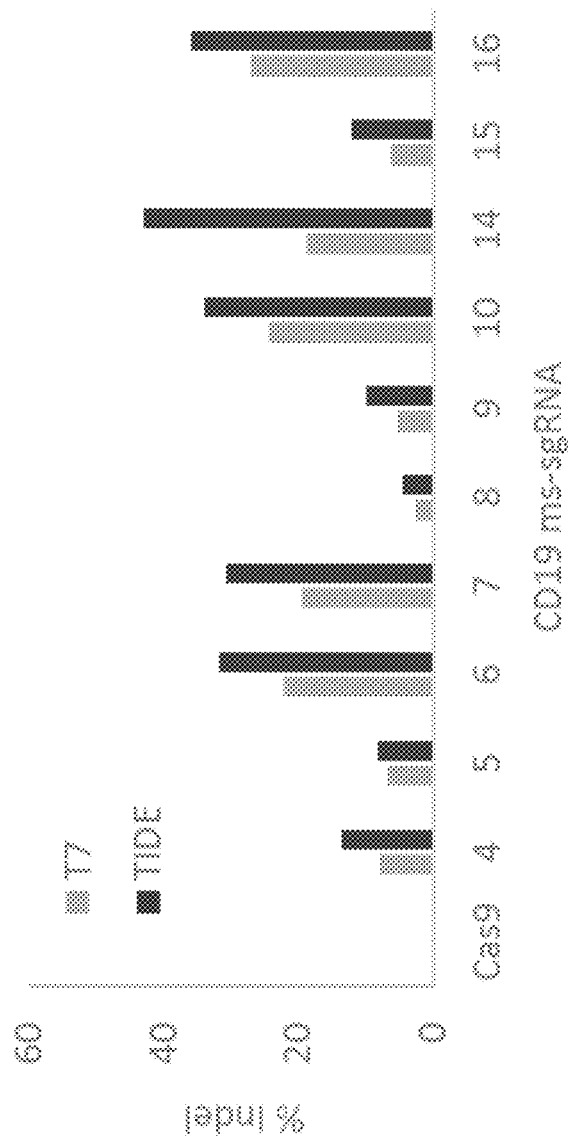
Figure 8A:
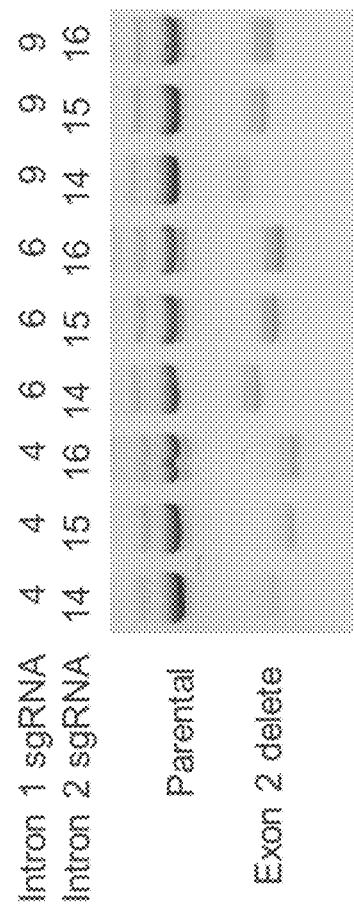
FIGS. 8A-8B include diagrams showing dual ms-sgRNA-mediated deletion of CD19 exon 2 in CD34+ HSCs.
Figure 8B:
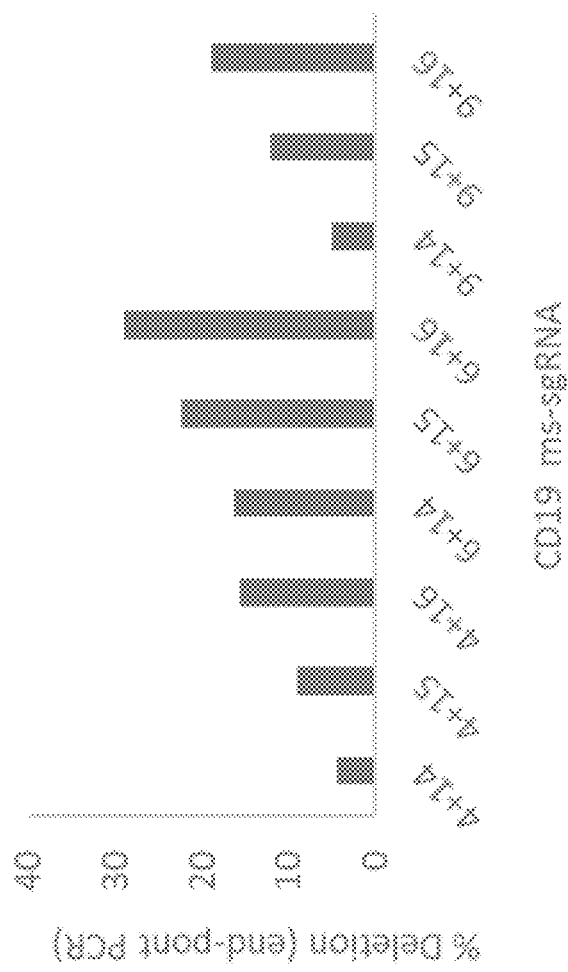
Figure 9B:
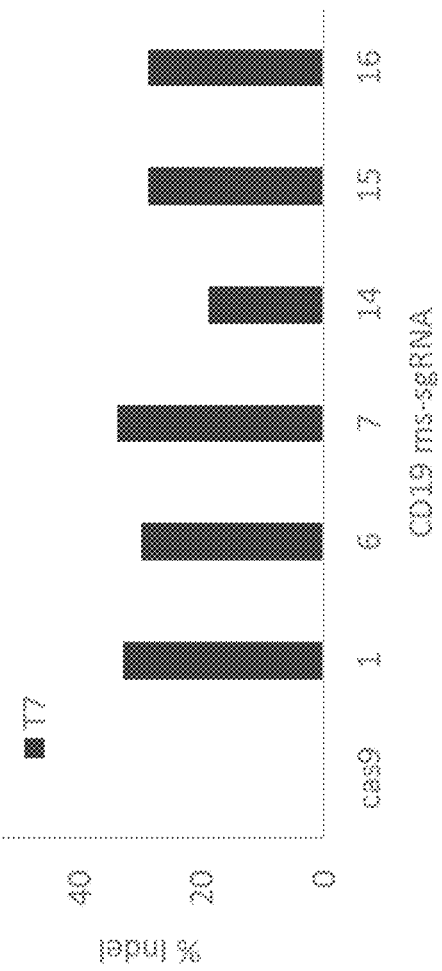
FIGS. 9A-9B include diagrams showing investigation of ms-sgRNAs targeting introns 1 or 2 of CD19 in CD34+ HSCs.
Figure 9A:
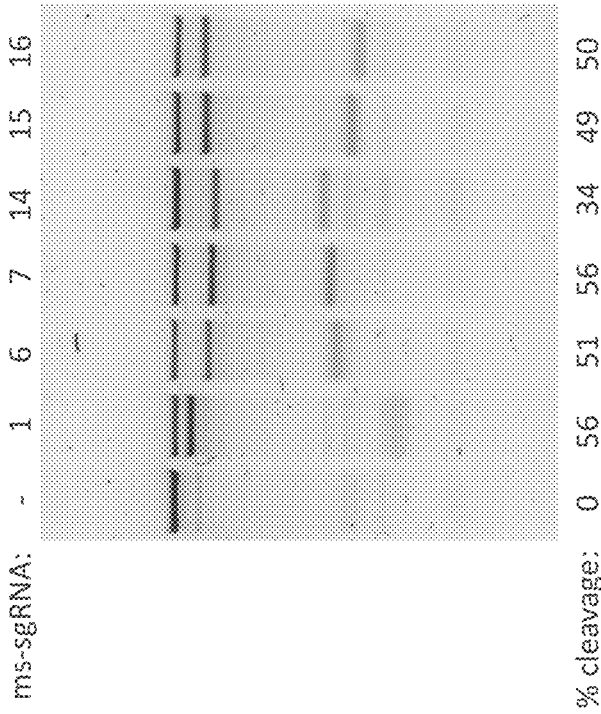

The CD19 sgRNAs targeting either intron 1 or 2 were screened in CD34$^+$ HSCs (FIGS. 7 and 9). Pairs of ms-gRNAs were used to delete exon 2 of CD19 in CD34$^+$ HSCs. The combined activity of ms-sgRNAs targeting intron 1 (ms-sgRNAs 4, 6, 9) were screened in combination with ms-sgRNAs targeting intron 2 (ms-gRNAs 14, 15, 16) to generate genomic deletions (FIGS. 8A and 8B). PCR across the genomic deletion region shows the smaller deletion PCR product compared to the larger parental band. The editing efficiency was quantified a percent deletion by end-point PCR.

Figure 10A:
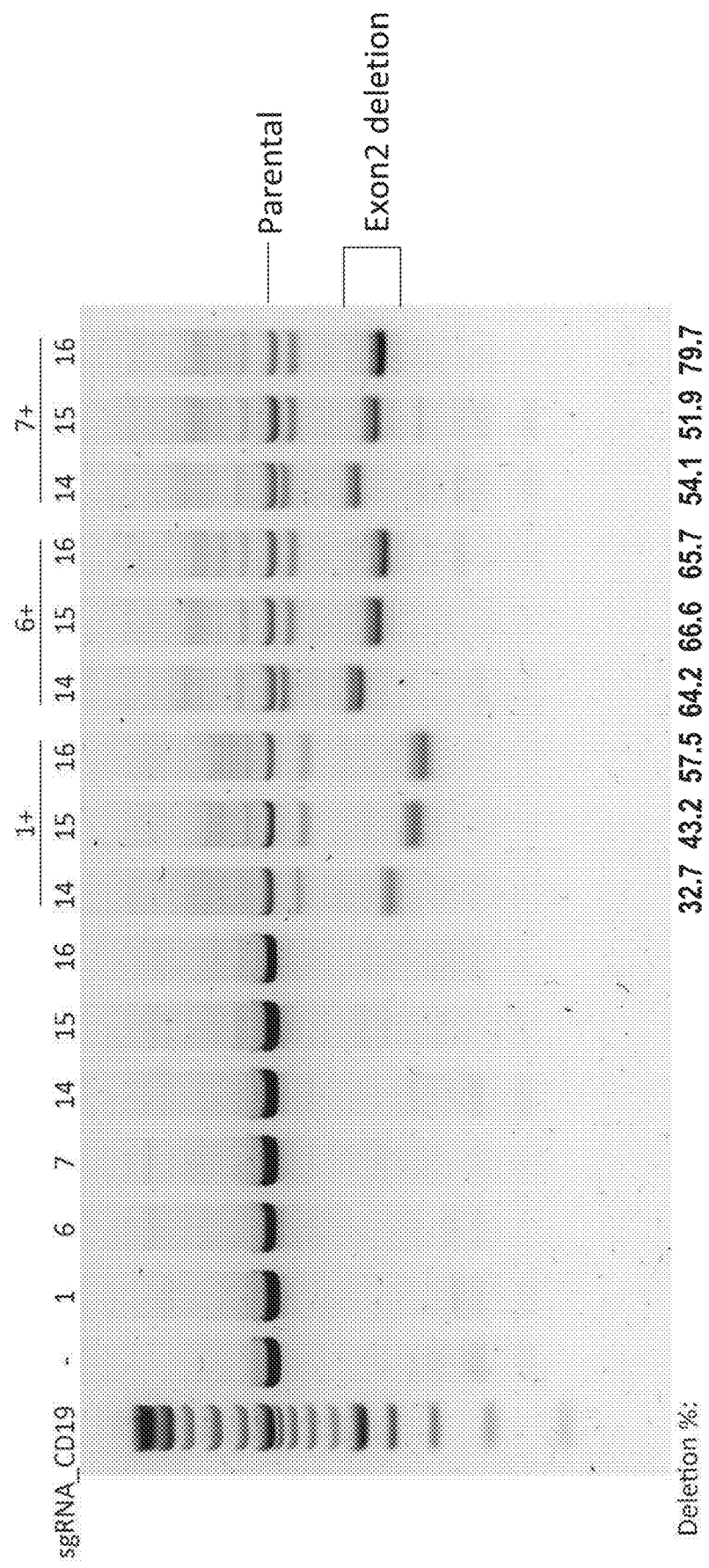
Figure 10B:
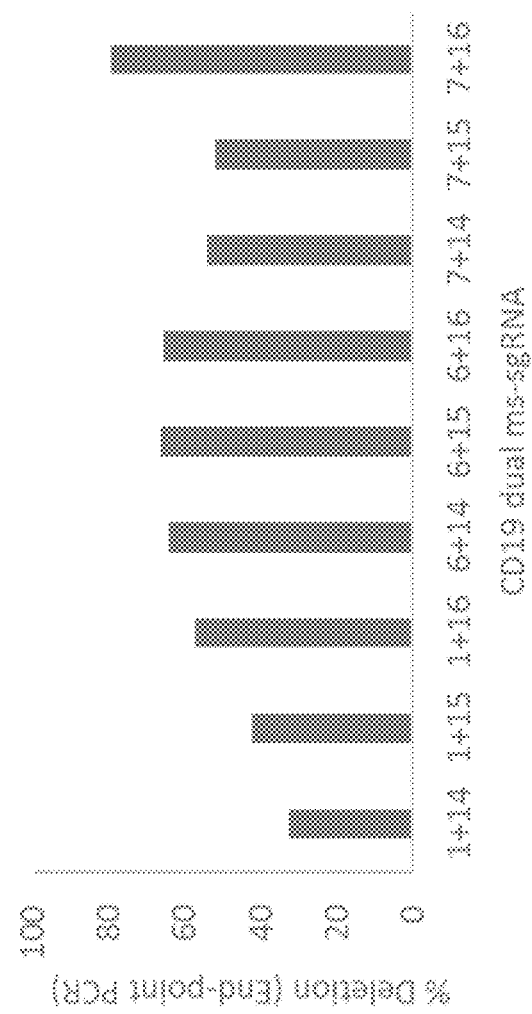

Additional pairs of ms-gRNAs were used to delete exon 2 of CD19 in CD34$^+$ HSCs. The combined us of ms-sgRNAs targeting intron 1 (ms-sgRNAs 1, 6, 7) in combination with ms-sgRNAs targeting intron 2 (ms-gRNAs 14, 15, 16) were found to efficiently generate genomic deletions of exon 2 (FIG. 10A and FIG. 10B).

PCR across the genomic deletion region shows the smaller deletion PCR product compared to the larger parental band. The results show high efficiency generation of HSCs expression CD19ex2 upon CRISPR editing using the gRNA6/gRNA14 pair. FIG. 10C. In vitro CFU assay shows that CD19ex2 HSCs did not affect in vitro differentiation. FIG. 10D. For the CFU assay, 1500 sorted CD34+ HSPCs were plated in 1.5 ml of methylcellulose (MethoCult™ H4034 Optimum, Stem Cell Technologies®) on a 35 mm cell culture dish and cultured for two weeks at 37° C. in a 5% CO2 incubator. Colonies were then counted and scored based on morphological appearance (iii) Characterization of Raji B-Cell Lymphoma Cells Expressing Exon 2-Deleted CD19

Figure 11A:
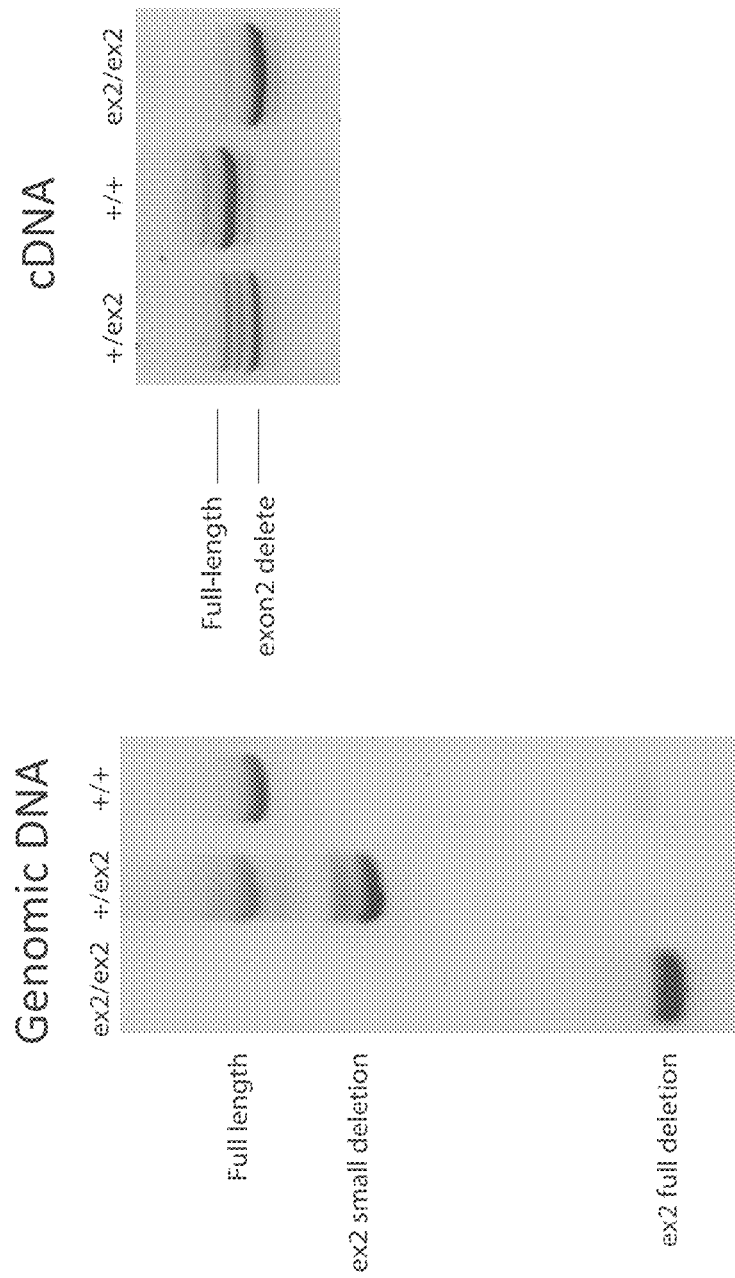
FIGS. 11A-11E are diagrams showing production and characterization of B-cell lymphoma cells having exon 2 deletion in CD19 using a pair of gRNAs, gRNA6 and gRNA14.
Figure 11B:
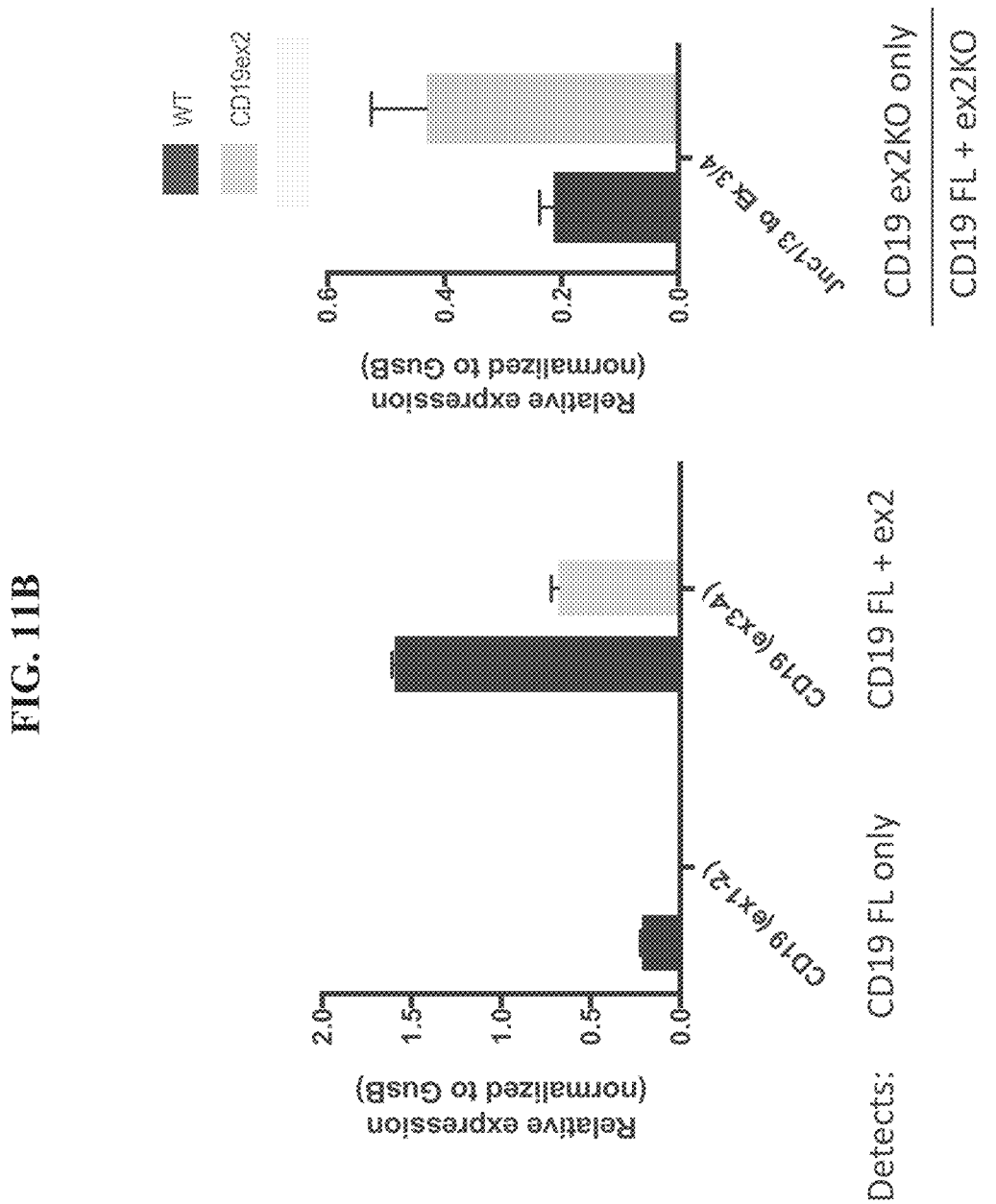

The CD19 sgRNAs targeting either intron 1 or 2 were also screened in Raji B-cell lymphoma cells HSCs. Pairs of ms-gRNAs were used to delete exon 2 of CD19 (CD19ex2) in Raji B-cell lymphoma cells. The combined activity of ms-sgRNAs targeting intron 1 (ms-sgRNA 6) were used in combination with ms-sgRNAs targeting intron 2 (ms-gRNA 14) to generate genomic deletions. FIG. 11A. PCR across the genomic deletion region shows the smaller deletion PCR product compared to the larger parental band. The ex2 small deletion band represents a product resulting from an alternative DNA repair event after Cas9 cleavage. The ex2 small deletion sequence encodes the same CD19 mutant with deletion of the fragment encoded by exon 2. The editing efficiency was quantified a percent deletion by end-point PCR. FIG. 11B.

Protein analysis of clonal lymphoma cells expression exon 2-deleted CD19 (CD19ex2) was analyzed by both Western Blot using an antibody that recognizes the C-terminus of CD19 and Flow Cytometry using the FMC63 anti-CD19 antibody (recognizing the CD19 region encoded by exon 2) or a polyclonal anti-CD19 antibody. Expression levels of exon 2-deleted CD19 (CD19ex2) in clonal lymphoma cells was analyzed by both Western Blot using an antibody that recognizes the C-terminus of CD19 (#3574 Rabbit anti-human CD19 Pab, Cell Signaling Technology®) of whole cell lysates or flow cytometry using the FMC63 anti-CD19 antibody (FMC63 R-PE Mouse anti-human CD19 Mab, EMD Millipore®) that recognizes the CD19 region encoded by exon 2. A polyclonal anti-CD19 antibody (#3574 Rabbit anti-human CD19 Pab, Cell Signaling Technology®) was used to identify intracellular CD19 by intracellular staining and flow cytometry.

Figure 11C:
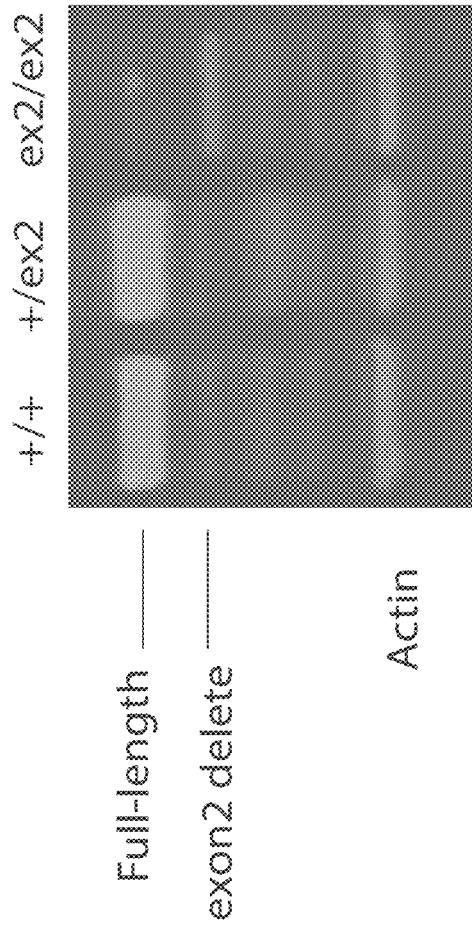
Figure 11D:
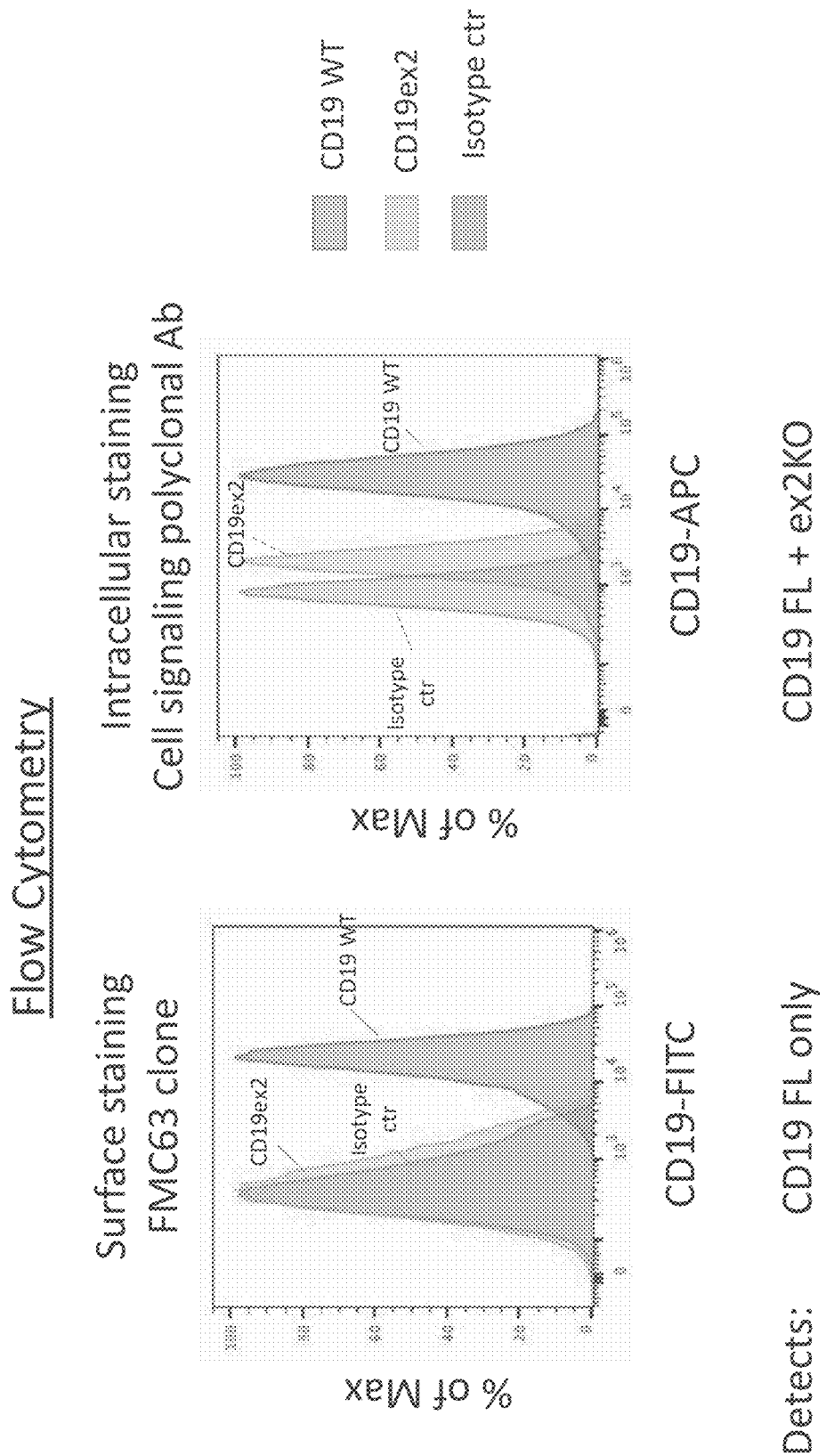

Expression of exon 2-deleted CD19 was observed in Raji B-cells with one or both chromosomes edited as detected by Western Blot. FIG. 11C. Similarly, surface expression and intracellular presence of exon 2-deleted CD19 were also detected in Raji B-cells by Flow Cytometry. FIG. 11D.

Figure 11E:
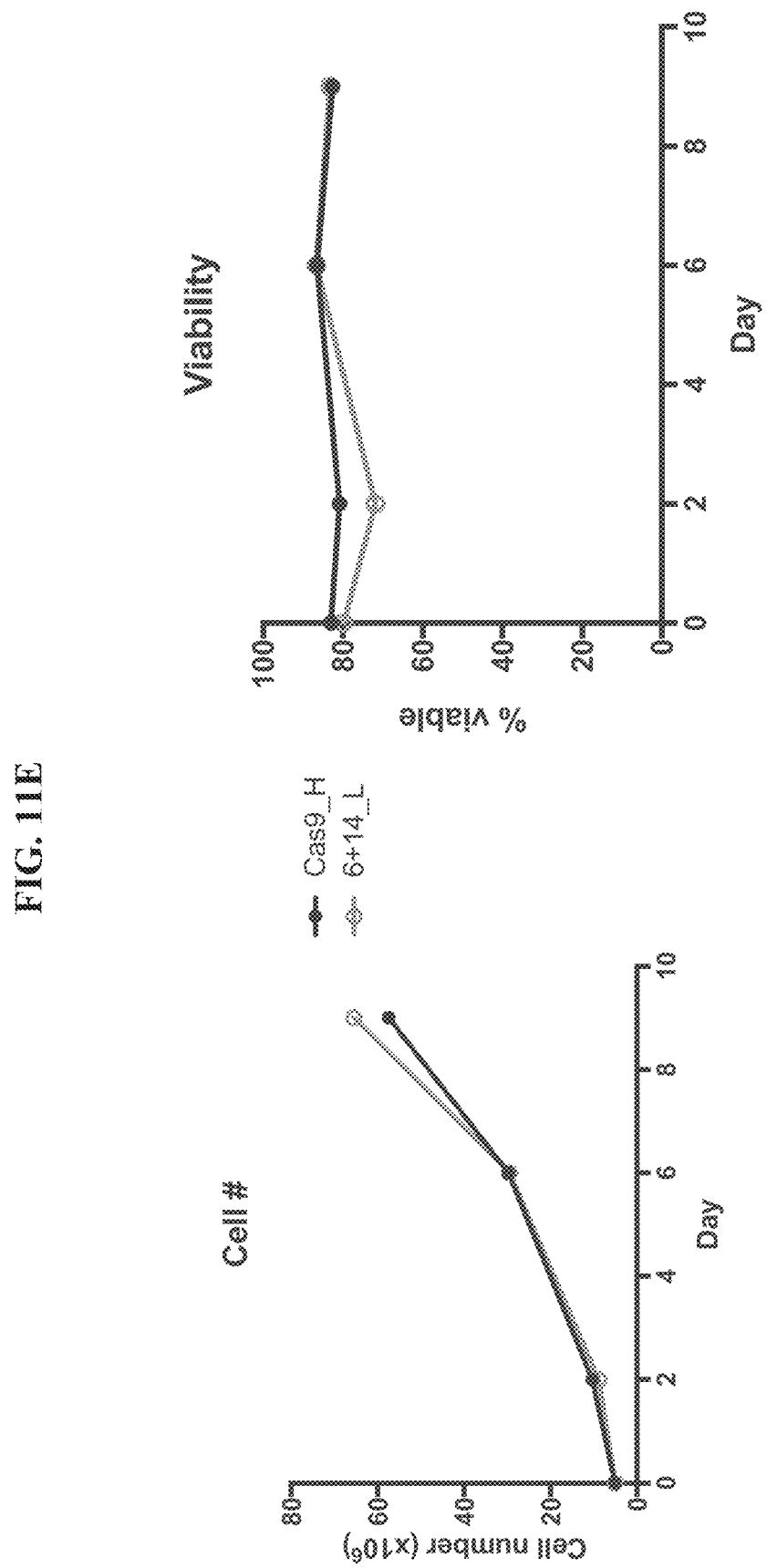

Further, growth and viability of Raji B-cells expressing CD19exon2 were analyzed. Human lymphoma cell line, Raji, was obtained from the American Type Culture Collection® (ATCC®). Raji cells were cultured in RPMI-1640 media (ATCC®) supplemented with 10% heat-inactivated HyClone™ Fetal Bovine Serum (GE Healthcare®). Cell viability and live cell number were measured by an automated cell counter, Cellmoter (Nexcelom™). As shown in FIG. 11E, cells expressing CD19exon2 did not show defects in proliferation (left panel) and viability (right panel).

Figure 12A:
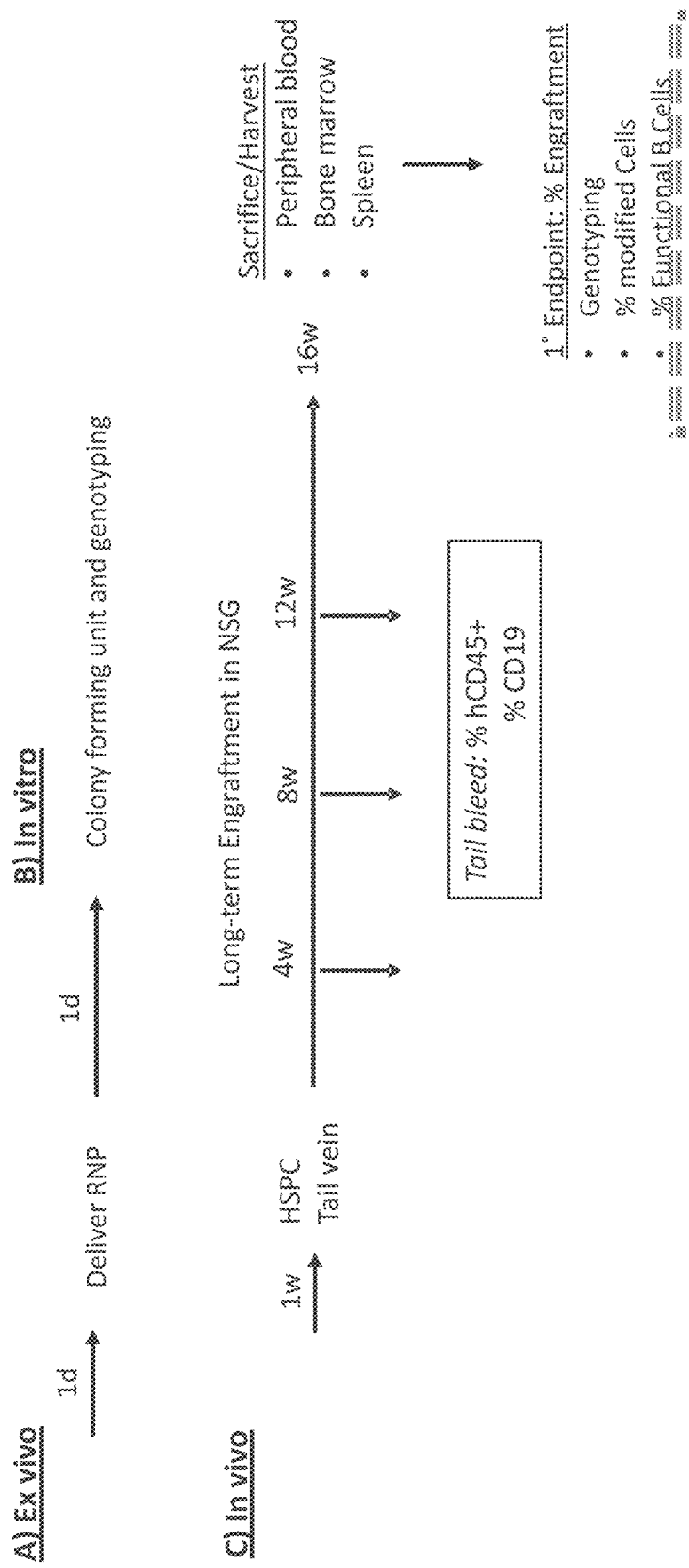
FIGS. 12A-12C include diagrams illustrating engraftment of CD19ex2 hematopoietic stem cells (HSCs) in a mouse model.

(iv) Engraftment of CD19ex2 Hematopoietic Stem Cells (HSCs) in a Humanized Mouse Model An exemplary flowchart for generating HSCs expression CD19ex2 and characterization of the in vivo differentiation of the HSCs in a humanized mouse model (e.g., NSG mice) is provided in FIG. 12A. In some examples, CAR-T treatment can be performed at 14 w after HSPC engraftment. The NSG mice can be assigned the four groups shown in Table 4 below:

TABLE 4

In vivo characterization groups

| Group | Condition | Value | Endpoint Expectation |
|---|---|---|---|
| 1 | RNP Control + Mock CAR-T | EP control | Functional B Cell |
| 2 | CD19ex2 + Mock CAR-T | Target | Functional FL/CD19ex2 B Cell |
| 3 | RNP control + CART19 | CAR-T selectivity | B-Cell Loss |
| 4 | CD19ex2 + CART19 | CAR-T selectivity | Retained B-Cell |

CD34+ HSC cells expressing CD19ex2 were produced using the combination of ms-sgRNAs targeting intron 1 (ms-sgRNA 6) and ms-sgRNAs targeting intron 2 (ms-gRNA 14) to generate genomic deletions as described above. See also the Materials and Methods. Samples were split into two fractions: 2% of cells were characterized in vitro and the remaining fraction is engraftment into 6-8 week old NOD scid gamma mice (NOD.Cg-Prkdc$^{scid}$ Il2rg$^{tm1WJl}$/SzJ (NSG mice), a humanized mouse model. The Jackson Laboratory. The in vitro fraction was characterized by colony forming unit (CFU) assay and genotyping as described above.

The in vivo fraction was administered to irradiated NSG™ mice. Blood samples can be obtained from the mice at various time points (e.g., 4 weeks, 8 weeks, 12 weeks) and analyzed by genotyping and to assess the percentage human CD45+ cells. At 16 weeks, the mice can be sacrificed and peripheral blood, bone marrow, and spleens were harvested for analysis. The primary endpoint is percent engraftment, which can be assessed by genotyping and flow cytometric analysis (e.g., mouse vs human CD45, CD20/CD19, CD19 deficient in exon 2, Cd34, CD33, CD3). A secondary endpoint can be expression of CD19 that is deficient in exon 2 by Western blotting and/or qRT-PCR.

Figure 12B:
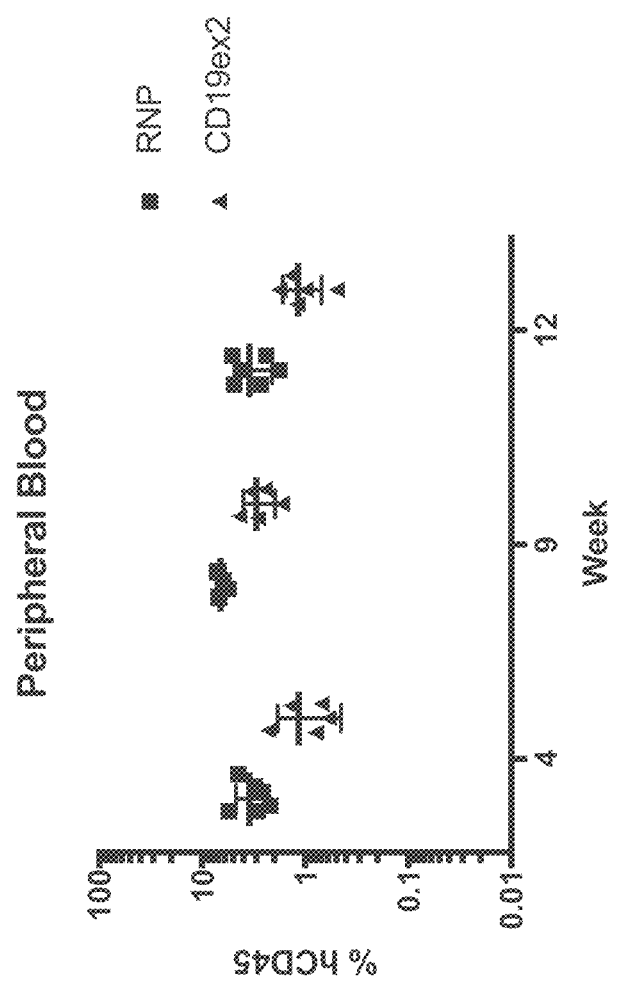

Percentage of hCD45+ cells in peripheral blood collected from the HSC-treated mice was determined by flow cytometry and the results are provided in FIG. 12B. The edited HSCs expressing CD19ex2 showed efficient engraftment in the NSG mice at week 4, 9 and 12 at levels substantially the same as the control HSC cells.

Figure 12C:
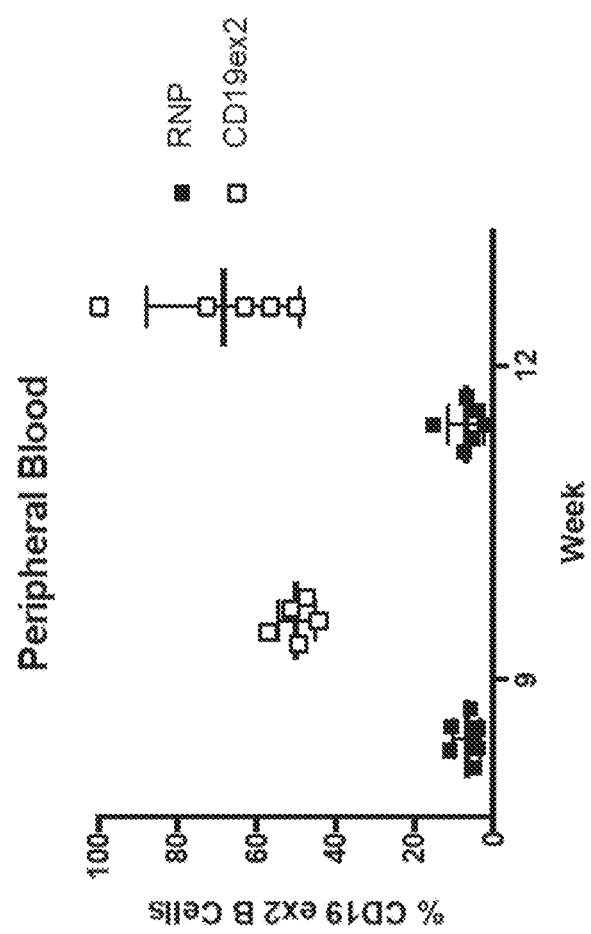

The levels of CD45+/CD20+ cells, representing differentiated B cells, in peripheral blood collected from the NSG™ mice were measured at week 9 after infusion of RNP HSCs or CD19ex2 HSCs. As shown in FIG. 12C, the edited cells (CD19ex2 HSCs) showed a significantly higher level of B cell differentiation than the unedited cells (RNP HSCs) at 9 and 12 weeks.

(v) In Vivo Raji Tumor Model

Figure 13:
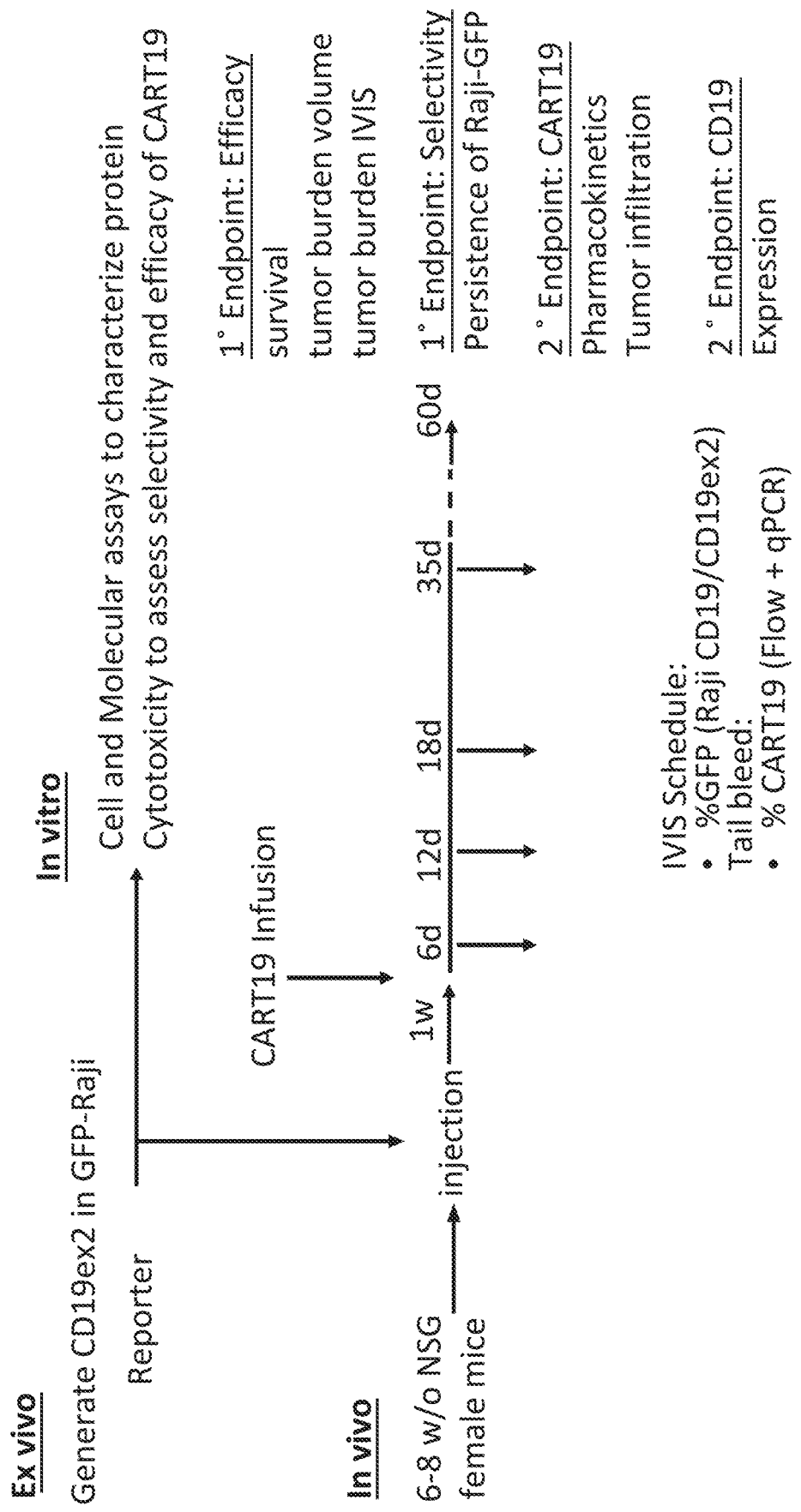
FIG. 13 is a schematic work flow to assess in vivo selectivity and efficacy of CART19 therapy in a Raji Burkitt's lymphoma tumor model. d=days, w=weeks, w/o=week old.

An in vivo Raji tumor model can be used to assay the efficacy of any of the treatment methods described herein. Raji-fluc-GFP cells expressing endogenous CD19 deficient in exon 2 (CD19exon2 delete) were generated ex vivo as described in the Materials and Methods. Following enrichment of edited cells, samples are split into two fractions: one fraction is characterized in vitro and the remaining fraction is xenografted into 6-8 week old NSG™ mice (FIG. 13).

The in vitro fraction is characterized by cytotoxicity and molecular assays as described in the Materials and Methods. The in vivo fraction is assessed for efficacy and selectivity of CART19 in Burkett Lymphoma mouse model and assayed by the indicated assays and as described in Materials and Methods. The groups of mice are shown in Table 5. Briefly, one week following injection of the Raji-fluc-GFP cells expressing endogenous CD19 deficient in exon 2, the mice are infused CART19 cells. The mice are assessed at various time points (e.g., 6 days, 12 days, 18 days, 35 days) by in vivo imaging system (IVIS) to determine the abundance of Raji cells (CD19/CD19ex2). Blood samples are also obtained from the mice to quantify the number of CART19 cells.

TABLE 5

In vivo characterization groups

| Group | Condition | CART19 | # Mice |
|---|---|---|---|
| 1 | Untreated control | − | 4 |
| 2 | Untreated control | + | 10 |
| 3 | Raji Fluc GFP; CD19+/+ | − | 10 |
| 4 | Raji Fluc GFP; CD19+/+ | + | 10 |
| 5 | Raji Fluc GFP; CD19exon2DEL | − | 10 |
| 6 | Raji Fluc GFP; CD19exon2DEL | + | 10 |

The primary endpoint of treatment efficacy is assessed, for example, by survival, tumor burden volume, and tumor burden by IVIS imaging. The primary endpoint of treatment selectivity is assessed, for example, by determining persistence of Raji-GFP cells. Secondary endpoints for CART19 therapy include pharmacokinetics and tumor infiltration, and secondary endpoints for CD19 include expression of CD19 that is deficient in exon 2.

It is expected that Raji cells expressing exon 2 of CD19 will be killed by the CART19 cells, whereas the Raji cells that have been manipulated to delete exon 2 of CD19 will survive and evade CART killing.

(vi) Generation of Raji-Fluc-GFP Cells Lines Deficient in CD19 Exon 2

Raji-fluc-GFP cell lines were transfected with pairs of ms-sgRNAs and assayed for CD19 expression by fluorescence-activated cell sorting (FACS). Cells were gated into three populations based on relative CD19 expression: "hi" (high), "int" (intermediate), and "lo" (low) (FIG. 14A). Parental Raji cells and Raj-fluc-GFP nucleofected with Cas9 only were included as controls. The percentage of live cells in each condition was quantified (FIG. 14B). PCR was also performed across the genomic deletion region of cells in each condition showing the smaller deletion PCR product compared to the larger parental band (FIG. 14C). The percentage CD19 exon 2 in the bulk population was also assayed by end-point PCR in each condition (FIG. 14D), indicating there was a higher percentage of cells with the CD19 exon 2 deletion in the CD19 "int" and CD19 "lo" cell populations.

(vii) CART Cytotoxicity

Figure 15A:
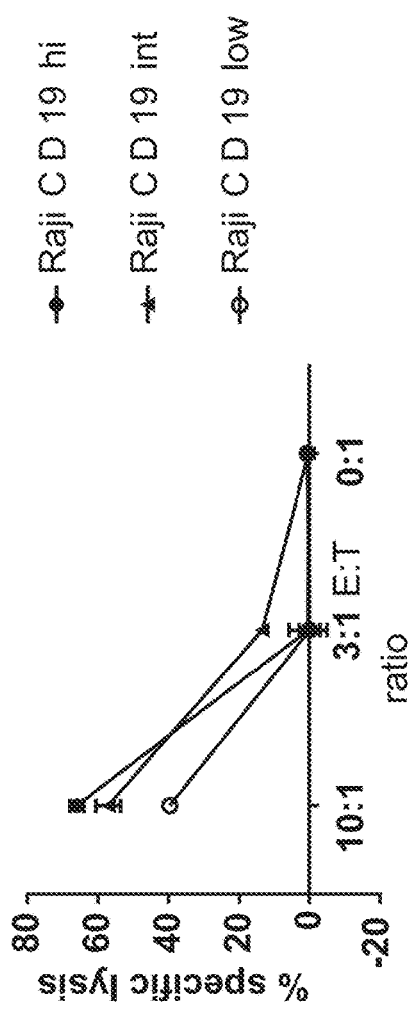
FIGS. 15A-15B include diagrams showing the level of CART19 cytotoxicity against Raji cells in which CD19 exon 2 has been deleted.
Figure 15B:
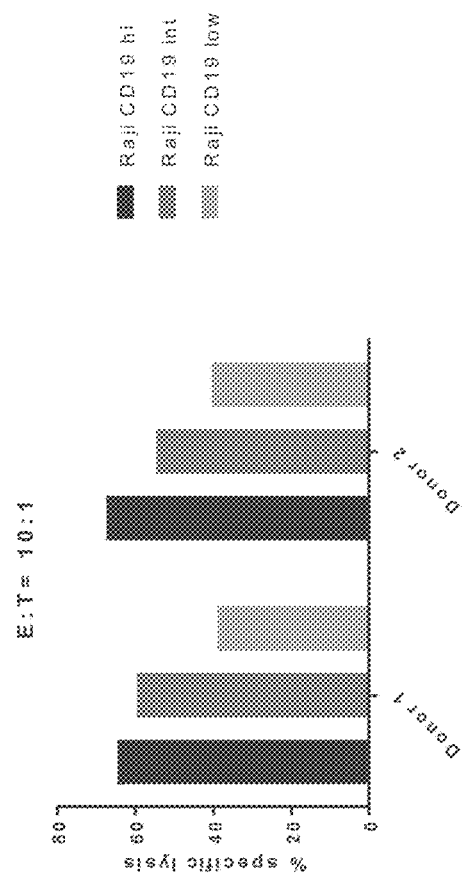

CD19-directed CAR-T cells (CART19) were generated as described in the Materials and Methods and incubated with Raji-fluc-GFP cells. Following 20 hours of incubation, cytotoxicity was assessed by flow cytometry. FIG. 15A and FIG. 15B shows there was reduced specific lysis of CD19 "low" Raji cells as compared to CD19 "hi" populations.

As shown in FIGS. 14A-14D, the Raji "hi" population is genotypically mixed population of cells. Single cells may be enriched to analyze clonal populations as well as unedited parental populations. The control CD19-hi population is a mixed genotype (20-40% CD19exon2 delete), and enhanced killing is expected with wild-type control populations.

(viii) In Vivo Efficacy and Selectivity

Figure 16:
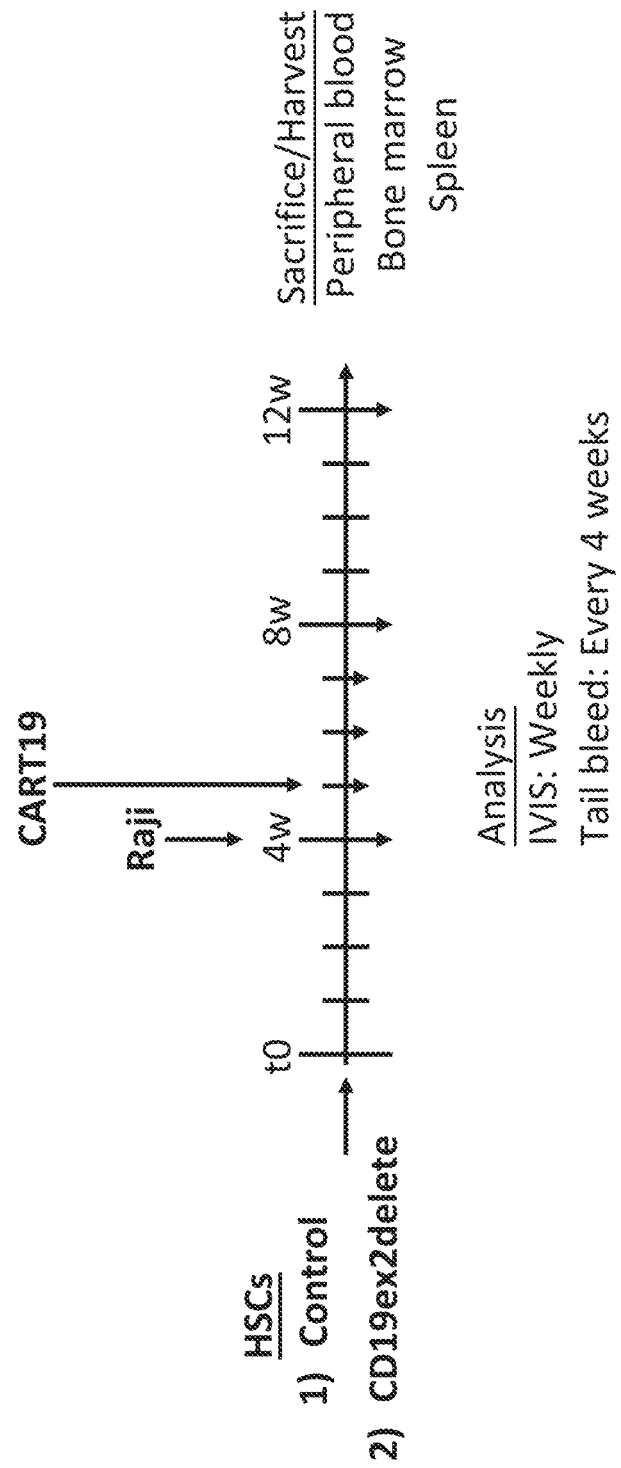
FIG. 16 is a schematic showing an exemplary in vivo model assessing the efficacy and selectivity of a CART therapeutic paired with edited HSCs involving the methods described herein.

FIG. 16 outlines a comprehensive in vivo model assessing efficacy and selectivity of CART therapy paired with edited HSCs. Briefly, HSCs deficient in exon 2 of CD19 (CD19ex2delete) are prepared. Groups of mice are administered either control (unedited) HSCs or HSCs deficient in exon 2 of CD19. After four weeks, the mice are administered Raji Burkitt's lymphoma cells, followed by CART19 cells one week later. The mice are assessed weekly by IVIS® imaging, and blood samples are obtained every four weeks. After 12 weeks, the mice are sacrificed and peripheral blood, bone marrow, and spleens are harvested for analysis.

Example 2: Deletion Exon 2 of CD33 Via CRISPR/Cas9-Mediated Gene Editing and Characterization of Cells Expressing Exon 2-Deleted CD33

This Example reports genetic engineering of CD33 genes via CRISPR/Cas9 in cells to produce edited cells expressing mutated CD33, in which the fragment encoded by exon 2 is deleted (CD33ex2), and in vitro and in vivo characterization of such edited cells using assays described in Example 1 above or known in the art. See also above disclosures for exemplary exon-2 deleted CD33 gene products.

(i) Selection of gRNAs

As shown in FIG. 17, the Cas9 nuclease is targeted to introns 1 and 2 of CD33 by two sgRNAs. Simultaneous generation of DNA double stranded breaks (DSBs) by Cas9 leads to excision of the region including complete loss of exon 2. The ends distal to the cut site are repaired through ligation of introns 1 and 2 via non-homologous end joining (NHEJ) with the repaired junction indicated by the triangle. Transcription of the modified genome results in expression of CD33m isoform.

A panel of ms-sgRNAs was designed by manual inspection for the SpCas9 PAM (5'-NGG-3') with close proximity to CD33 exon 2 and prioritized according to predicted specificity by minimizing potential off-target sites in the human genome with an online search algorithm (Benchling, Doench et al (2016); Hsu et al (2013)) (Table 6). A subset of ms-sgRNAs targeting either intron 1 or 2 was then selected based on in vitro gene editing efficiency. Each of the sgRNAs target human CD33 and use Cas9 type SpCas9.

TABLE 6

CD33 sgRNA panel

| Name | sgRNA Sequence | PAM | Location | On Target (Doench et al 2016)[1] | Off Target (Hsu et al 2013)[1] |
|---|---|---|---|---|---|
| CD33_sgRNA-1 | GCTGTGGGGAGAGGGGTTGT (SEQ ID NO: 27) | CGG | Intron 1 | 39 | 29 |
| CD33_sgRNA-2 | CTGTGGGGAGAGGGGTTGTC (SEQ ID NO: 28) | GGG | Intron 1 | 46 | 35 |
| CD33_sgRNA-3 | TGGGGAAACGAGGGTCAGCT (SEQ ID NO: 29) | CGG | Intron 1 | 60 | 29 |
| CD33_sgRNA-4 | GGGCCCCTGTGGGGAAACGA (SEQ ID NO: 30) | GGG | Intron 1 | 65 | 40 |
| CD33_sgRNA-5 | AGGGCCCCTGTGGGGAAACG (SEQ ID NO: 31) | AGG | Intron 1 | 50 | 36 |
| CD33_sgRNA-6 | GCTGACCCTCGTTTCCCCAC (SEQ ID NO: 32) | AGG | Intron 1 | 47 | 31 |
| CD33_sgRNA-7 | CTGACCCTCGTTTCCCCACA (SEQ ID NO: 33) | GGG | Intron 1 | 52 | 27 |
| CD33_sgRNA-8 | TGACCCTCGTTTCCCCACAG (SEQ ID NO: 34) | GGG | Intron 1 | 71 | 29 |
| CD33_sgRNA-9 | CCATAGCCAGGGCCCCTGTG (SEQ ID NO: 35) | GGG | Intron 1 | 61 | 24 |
| CD33_sgRNA-10 | GCATGTGACAGGTGAGGCAC (SEQ ID NO: 36) | AGG | Intron 2 | 56 | 36 |
| CD33_sgRNA-11 | TGAGGCACAGGCTTCAGAAG (SEQ ID NO: 37) | TGG | Intron 2 | 55 | 32 |
| CD33_sgRNA-12 | AGGCTTCAGAAGTGGCCGCA (SEQ ID NO: 38) | AGG | Intron 2 | 54 | 39 |

TABLE 6-continued

CD33 sgRNA panel

| Name | sgRNA Sequence | PAM | Location | On Target (Doench et al 2016)[1] | Off Target (Hsu et al 2013)[1] |
|---|---|---|---|---|---|
| CD33_sgRNA-13 | GGCTTCAGAAGTGGCCGCAA (SEQ ID NO: 39) | GGG | Intron 2 | 58 | 44 |
| CD33_sgRNA-14 | GTACCCATGAACTTCCCTTG (SEQ ID NO: 40) | CGG | Intron 2 | 75 | 40 |
| CD33_sgRNA-15 | GTGGCCGCAAGGGAAGTTCA (SEQ ID NO: 41) | TGG | Intron 2 | 63 | 42 |
| CD33_sgRNA-16 | TGGCCGCAAGGGAAGTTCAT (SEQ ID NO: 42) | GGG | Intron 2 | 53 | 43 |
| CD33_sgRNA-17 | GGAAGTTCATGGGTACTGCA (SEQ ID NO: 43) | GGG | Intron 2 | 66 | 42 |
| CD33_sgRNA-18 | TTCATGGGTACTGCAGGGCA (SEQ ID NO: 44) | GGG | Intron 2 | 59 | 32 |
| CD33_sgRNA-19 | CTAAACCCTCCCAGTACCA (SEQ ID NO: 45) | GGG | Intron 2 | 61 | 40 |
| CD33_sgRNA-20 | CACTCACCTGCCCACAGCAG (SEQ ID NO: 46) | GGG | Intron 1 | 56 | 23 |
| CD33_sgRNA-21 | CCCTGCTGTGGGCAGGTGAG (SEQ ID NO: 47) | TGG | Intron 1 | 44 | 20 |
| CD33_sgRNA-22 | TGGGCAGGTGAGTGGCTGTG (SEQ ID NO: 48) | GGG | Intron 1 | 61 | 26 |
| CD33_sgRNA-23 | GGTGAGTGGCTGTGGGGAGA (SEQ ID NO: 49) | GGG | Intron 1 | 42 | 24 |
| CD33_sgRNA-24 | GTGAGTGGCTGTGGGGAGAG (SEQ ID NO: 50) | GGG | Intron 1 | 49 | 20 |

[1]On and Off-target predictions based on the indicated published algorithms. Score is out of 100 and is a prediction of success.

The CD33 ms-sgRNAs targeting introns 1 or 2 were screened in primary CD34+ HSCs by TIDE assay (FIGS. 17A and 17B).

Figure 18A:
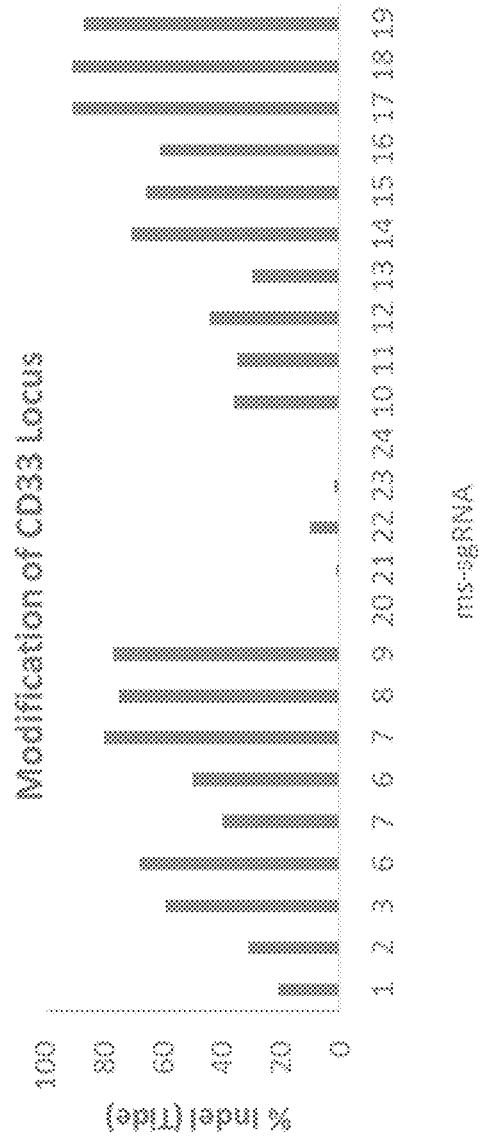
FIGS. 18A-18B include charts showing investigation of various ms-sgRNAs targeting introns 1 or 2 of CD33 in CD34+ HSCs by TIDE analysis. PCR amplicons derived from the region spanning introns 1 and 2 of the CD33 gene were analyzed by TIDE analysis and the percent INDEL was determined.
Figure 18B:
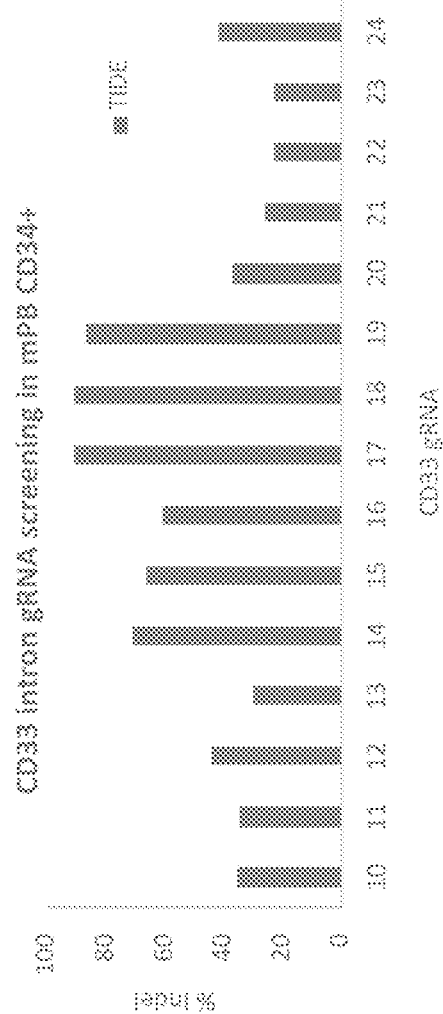
Figure 27:
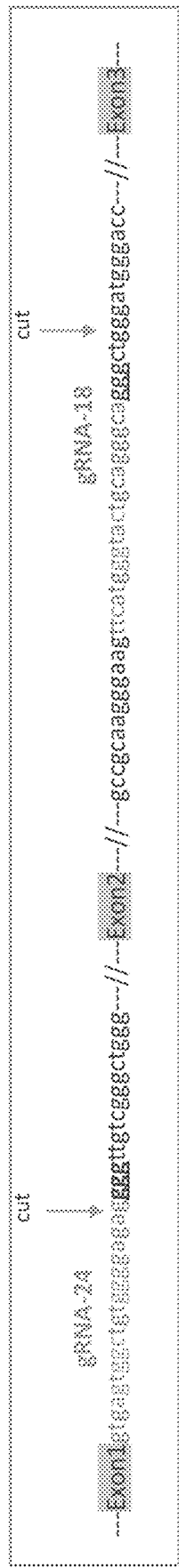
FIG. 27 is a schematic showing the sequence of the CD33 locus including cut sites for CD33 gRNA-24 and gRNA-18. In this figure, the sequence gtgagtggctgtggggagag (SEQ ID NO: 102) is labeled gRNA-24 and the sequence ttcatgggtactgcagggca (SEQ ID NO: 103) is labeled gRNA-18. The entire sequence at left can be found in SEQ ID NO: 138, and the entire sequence at right can be found in SEQ ID NO: 139.

Pairs of ms-gRNAs were used tested in CD34+ HSCs (FIGS. 18B and 18C; FIG. 27). Efficient deletion of exons 2 and 3, leading to knock-out of CD33, was observed using control sgRNAs targeting exons 2 and 3 (Sg and 811, respectively). A reduction in CD33 containing exon 2 was observed with pairs of sgRNAs targeting introns 1 and 2 (e.g., sgRNAs 17 and 23; sgRNAs 18 and 24).

Figure 19B:
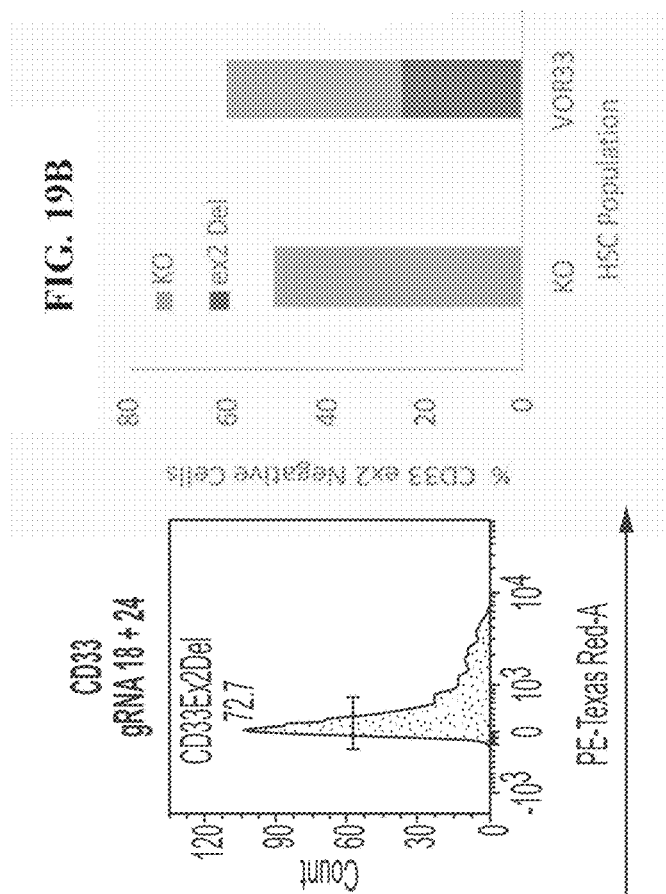
FIGS. 19A-19B include diagrams showing characterization of CD33-edited primary CD34+ HSCs.
Figure 19A:
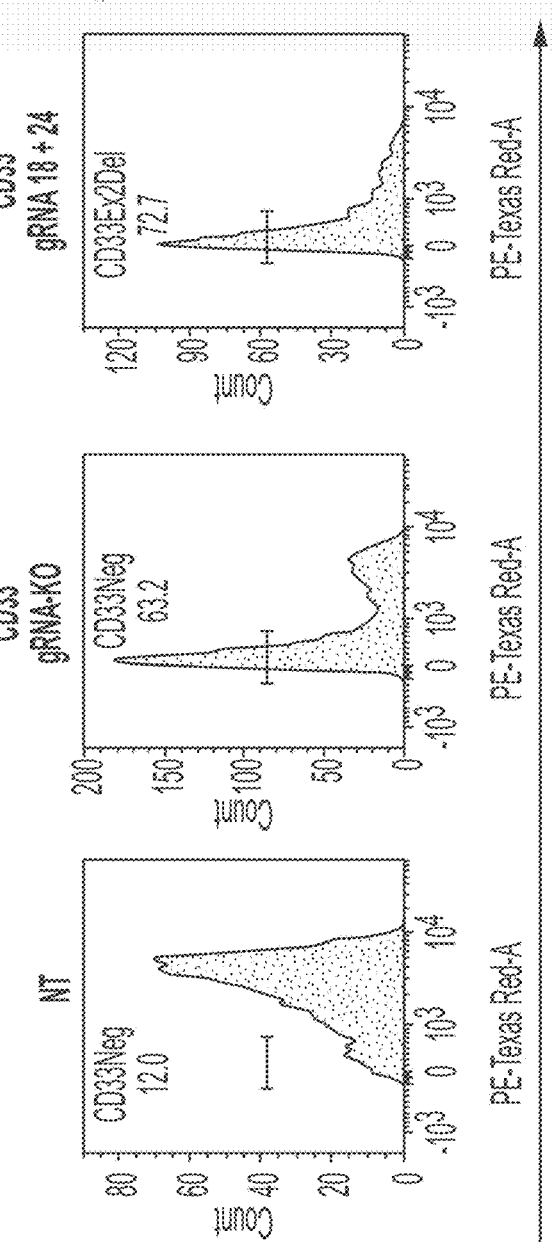

FIG. 19A shows results from flow cytometry showing CD34+ HSCs, either unedited (left panel, mock) or edited with guide RNAs for KO (producing a full CD33 knockout (middle panel) or edited with guide RNAs 18 and 24 resulting in the expression of mutated CD33 with exon 2-encoded fragment deleted (CD33ex2, right panel). FIG. 19B shows the editing efficiency as determined from the flow cytometric analysis shown in FIG. 19A. The percentage of CD34+CD33ex2 events was determined using deletion PCR containing primers flanking exon 2 (shown in black).

Figure 20A:
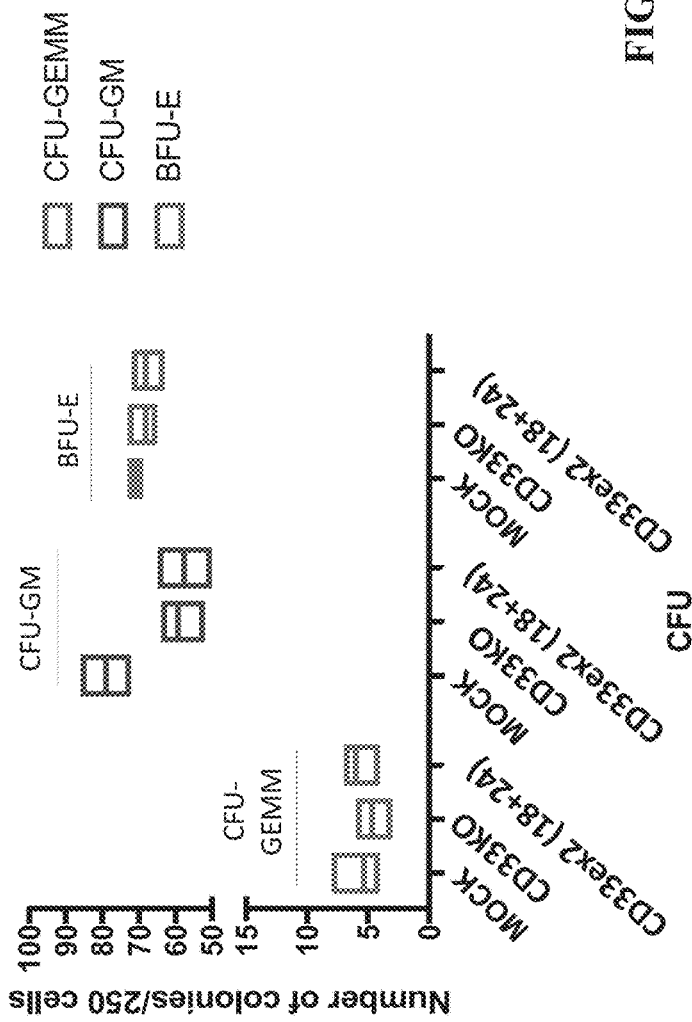
FIGS. 20A-20B include diagrams showing genotyping and in vitro differentiation of cells edited by dual gRNAs targeting CD33.
Figure 20B:
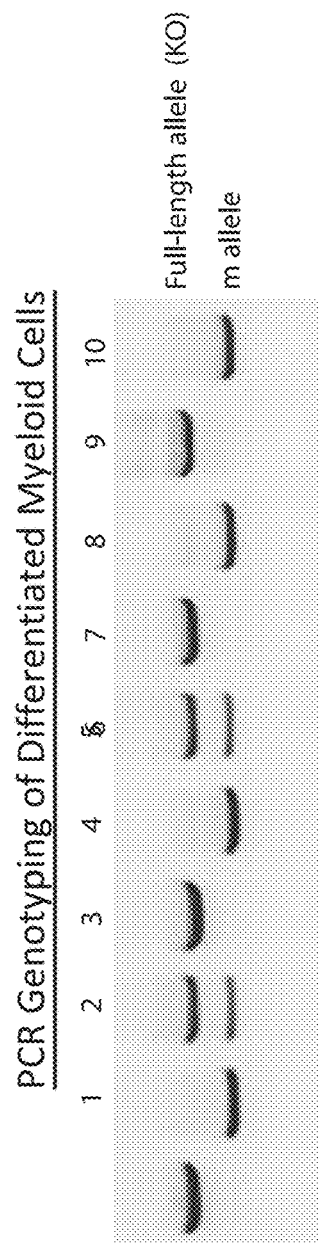

(ii) Genotyping and In Vitro Differentiation of Dual gRNA-Targeted CD33ex2 Cells CFU assays of cells edited by the pair of gRNA18 and gRNA24, as well as CD33-KO CD34+ HSC cells show that both type of cells retain differentiation potential in vitro. FIG. 20A. PCR genotyping of a number of differentiated myeloid cell clones expressing the CD33ex2 mutant show that the pair of gRNA18 and gRNA24 resulted in a mixture of exon 2 deleted CD33 alleles and CD33 knocked-out alleles. FIG. 19B and FIG. 20B. The genotypes and frequencies are provided in Table 7 below.

TABLE 7

Genotype and Frequency of Differentiated CD33ex2 Myeloid Cells

| Genotype | Frequency |
|---|---|
| KO/KO | 44 of 87 |
| ex2/ex2 | 16 of 87 |
| ex2/KO | 27 of 87 |

(iii) Generation and Characterization of CD33ex2 in AML Cell Lines

Figure 21B:
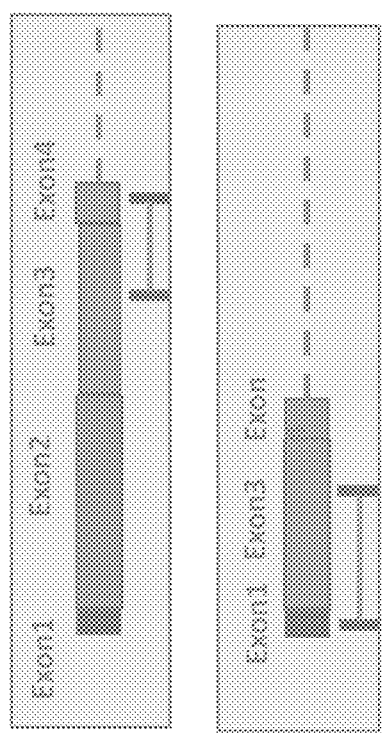
FIGS. 21A-21C include diagrams showing generation and characterization of CD33ex2 in AML cell lines.
Figure 21A:
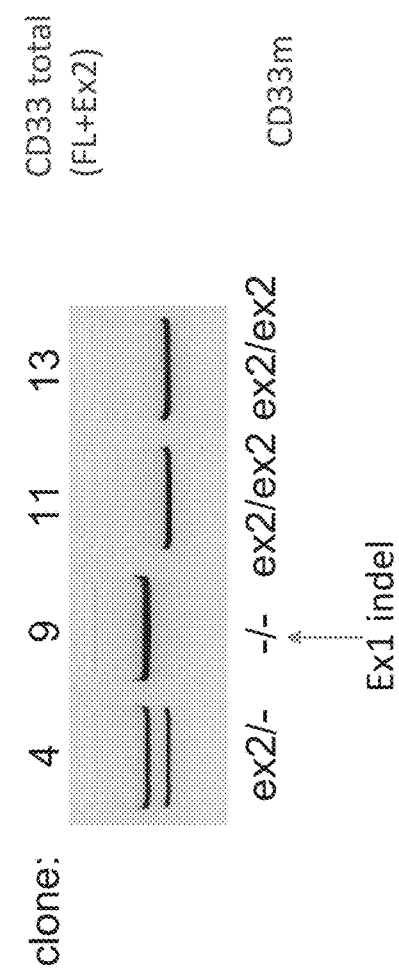
Figure 21C:
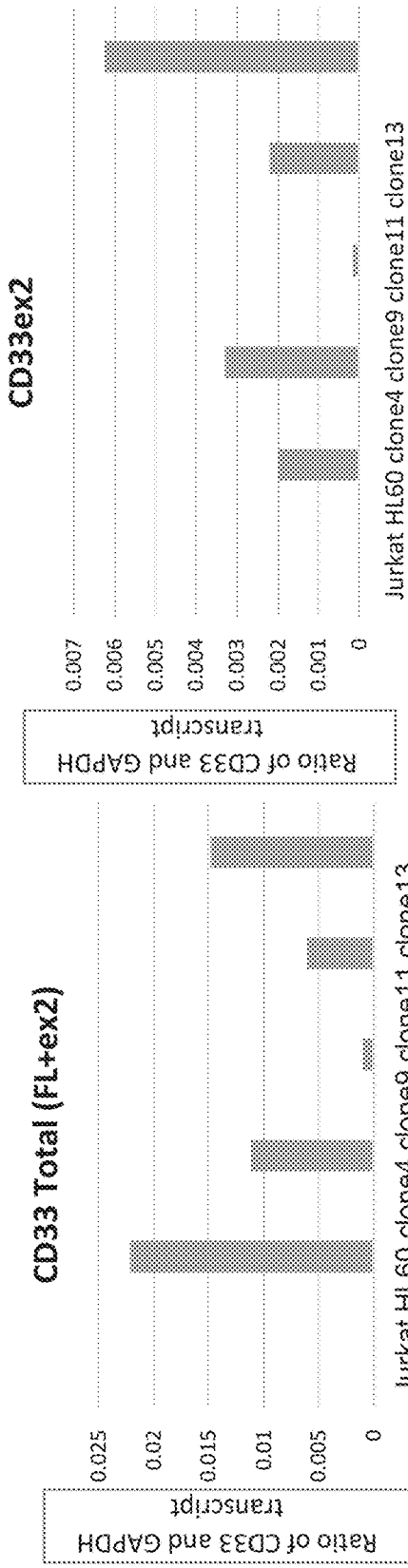

AML cell lines THP1 (monocytic leukemia) and HL-60 (promyeloblast leukemia) were genetically edited via CRISPR/Cas9 using the pair of gRNA18 and gRNA24 to produce cells expressing CD33ex2, which were sorted by flow cytometry. Single cells were expanded to establish clones that express CD33ex2, which were subject to gemtuzumab ozogamicin treatment as disclosed below. Genomic PCR showed that the CD33 exon 2 was deleted either in one CD33 allele or in both alleles. FIG. 21A. FIG. 21B illustrates the PCR primer pairs for detecting total CD33, including both full length (M) and exon 2 deletion (m) and the PCR primer pairs for detecting only CD33m. One clone shows partial deletion in the exon 1 region. The levels of full-length CD33 transcripts and CD33ex2 transcripts were analysed by an RNA analysis and the results are shown in FIG. 21C. Deeper genomic characterization via PCR and sequencing analysis show reproducible repair ligation of intron 1 and intron 2. Depending on the type of IDEL the repair ligation results in either transcripts resulting in CD33ex2 or full CD33 KO. For example, in some cases the INDELS extend into exon 1, resulting in a CD33 KO.

(iv) CD33ex2 Cells are Less Susceptible to Gemtuzumab Ozogamicin (GO) Cytotoxicity The AML cell clones expressing CD33ex2 were treated with gemtuzumab ozogamicin and the viability of the treated cells was determined. Human AML cell lines, THP-1 and HL-60, were obtained from the American Type Culture Collection® (ATCC®). THP-1 cells were cultured in RPMI-1640 media (ATCC) supplemented with 10% heat-inactivated HyClone™ Fetal Bovine Serum (GE Healthcare®) and 0.05 mM 2-mercaptoethanol (Sigma-Aldrich®). HL-60 cells were cultured in Iscove's Modified Dulbecco's Medium (IMDM, Gibco™) supplemented with 20% heat-inactivated HyClone™ Fetal Bovine Serum (GE Healthcare®). For in vitro cytotoxicity assays with AML cell lines, THP-1 and HL-60 cells were incubated with GO in their complete culture media for 72 hours. Increasing concentrations of GO, from 0.1 ng/mL to 10 µg/mL, were used. Cells were plated at 2×104 per well in 96 well plates. Viable cell number was measured with Celltiter Glo (Promega) according to manufacturer's instructions, and luminescence was determined using a GloMax multiplate reader (Promega). IC50 was defined as the concentration of compound needed to yield a 50% reduction in viable cell number compared with no GO treated cells (control=100%). To measure cell death, cells were stained with Annexin V (Invitrogen®) and DAPI (Biolegend) for 15 minutes in 1× Annexin Binding Buffer (Invitrogen®) at room temperature. Data was acquired on Attune NxT flow cytometer (ThermoFisher Scientific®), and analyzed with FlowJo® software (TreeStar).

Figure 22A:
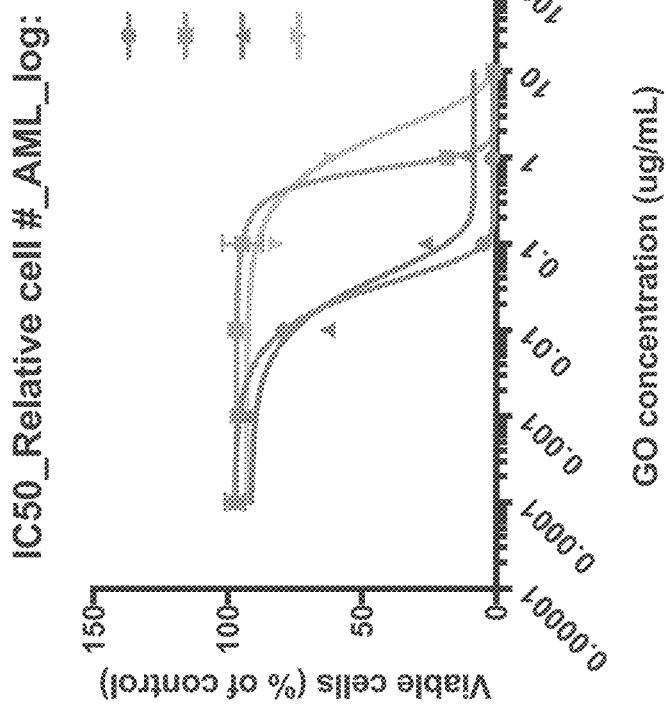
FIGS. 22A-22C include diagrams showing susceptibility of CD33ex2 cells to gemtuzumab ozogamicin (GO).
Figure 22B:
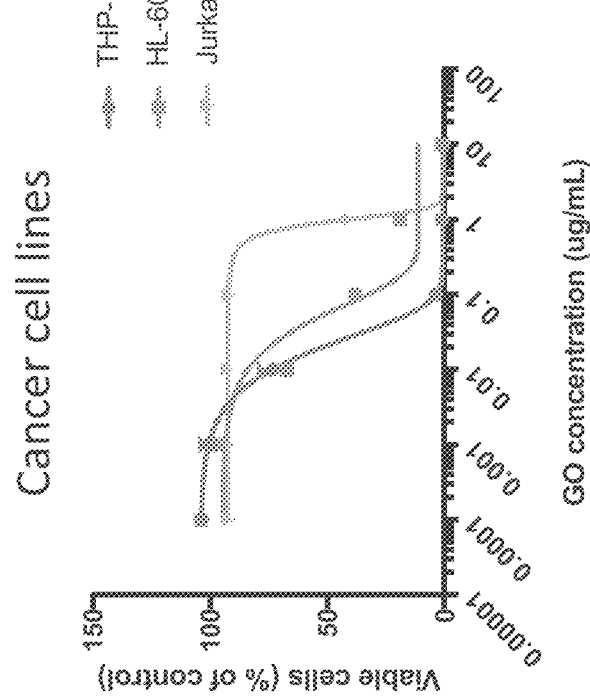

As shown in FIG. 22A, AML cell lines THP-1 and HL-60 are more susceptible to GO cytotoxicity ($IC_{50}$ 16.3 ng/ml and 35.5 ng/ml, respectively) as compared with Jurkat cells ($IC_{50}$ 902.7 ng/ml). Edited AML cells expressing CD33ex2 showed lower susceptibility to GO cytotoxicity as compared with the unedited parent cells. FIG. 22B.

Similar results were observed in edited HSPC cells expressing CD33ex2. In one study, the $IC_{50}$ value of wild-type HSPC was found to be around 93.4 ng/ml, and the $IC_{50}$ values of HSPC CD33KO and HSPC CD33ex2 were found to be around 248.1 ng/ml and 246.4 ng/ml, respectively.

Figure 22C:
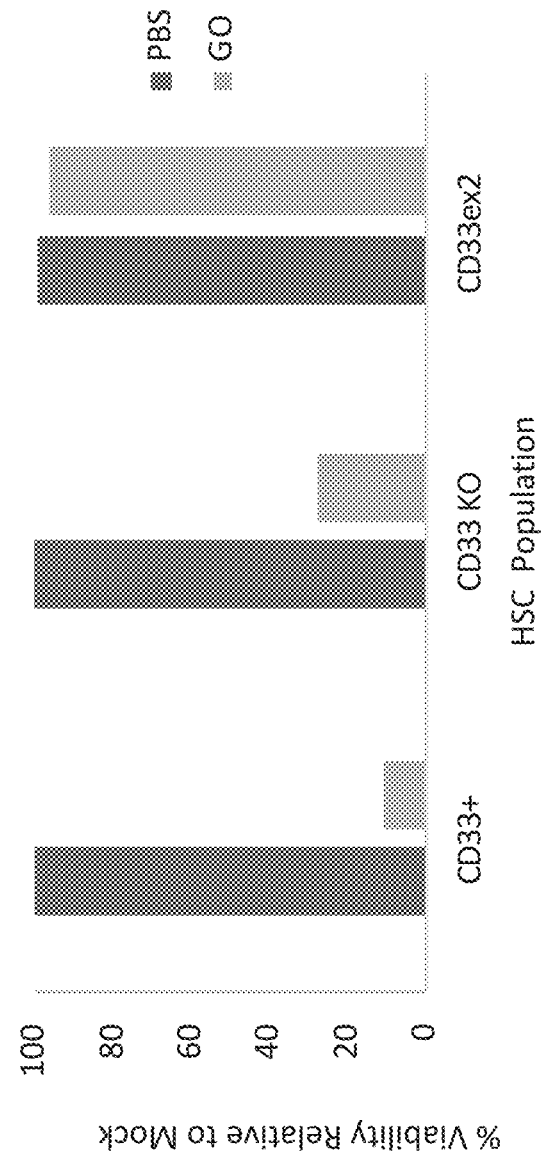

Wild-type HSC cells (CD33+), CD33 KO HSCs and CD33ex2 HSCs were treated with GO and the surviving cells were cultured in a myeloid culture medium for 30 days after withdrawal of GO treatment. The viability of the surviving cells was determined as described above. Surprisingly, CD33ex2 HSCs showed much higher viability post GO treatment, as compared with wild-type and CD33 KO HSC cells. FIG. 22C.

(v) CD33ex2 Cells are Protected from CART33-Mediated Killing

CD33-directed CAR-T cells (CART33 or CAR1) were generated by transduction of CART33-expressing lentivirus into CD4+ and CD8+ T cells from healthy human donors. The CART33 construct contains a single chain variable fragment (scFv) that recognizes the fragment of CD33 encoded by exon 2, a hinge domain of CD8α, a transmembrane domain of CD8, a co-stimulatory domain of 4-1BB, and a cytoplasmic signaling domain of CD3.

The cytotoxicity of CART33 was assessed by flow cytometry-based assay. Raji (CD33−) cells were used as a negative control for the cytotoxicity assay. The effector (E) and tumor target (T) cells were co-cultured at the indicated E/T ratios (5:1 and 1:1), with 1×10$^4$ target cells in a total volume of 200 µl per well in CTS™ OpTmizer™-based serum free medium. After 20 hours of incubation, cells were stained for Propidium Iodide and analyzed by Attune® NxT flow cytometer (Life Technologies®). Live target cells were gated as Propidium Iodide-negative and CellTrace™ Violet-positive. Cytotoxicity was calculated as (1−(Live target cell fraction in CART19 group)/(Live target cell fraction in negative control group))×100%.

The cytotoxicity of CART33 was assessed by flow cytometry-based assay. Raji (CD33−) cells were used as a negative control for the cytotoxicity assay. The effector (E) and tumor target (T) cells were co-cultured at the indicated E/T ratios (5:1 and 1:1), with 1×10$^4$ target cells in a total volume of 200 µl per well in CTS™ OpTmizer™-based serum free medium. After 20 hours of incubation, cells were stained for Propidium Iodide and analyzed by Attune® NxT flow cytometer (Life Technologies®). Live target cells were gated as Propidium Iodide-negative and CellTrace™ Violet-positive. Cytotoxicity was calculated as (1−(Live target cell fraction in CART19 group)/(Live target cell fraction in negative control group))×100%.

Figure 23A:
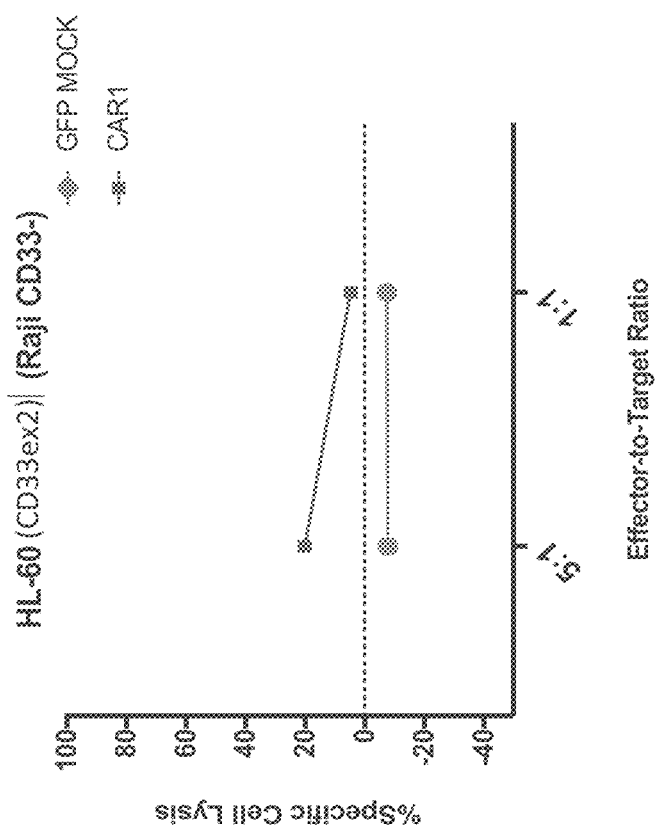
Figure 23B:
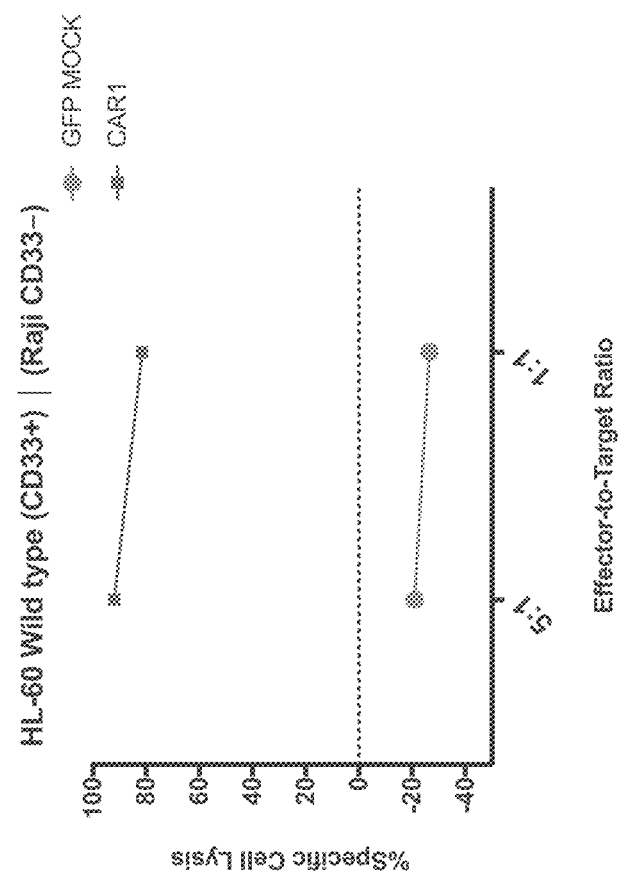
Figure 24A:
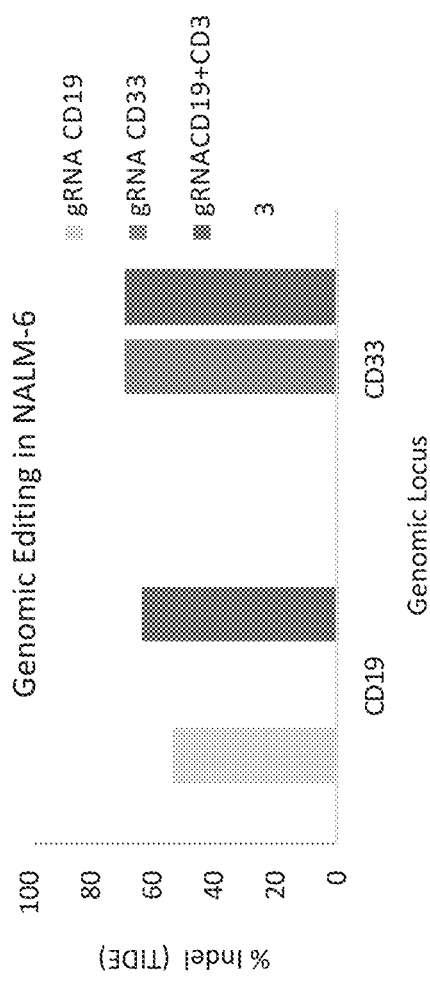
FIGS. 24A-24D include diagrams showing the results of a TIDE assay showing efficient multiplex genomic editing of both CD19 and CD33.
Figure 24B:
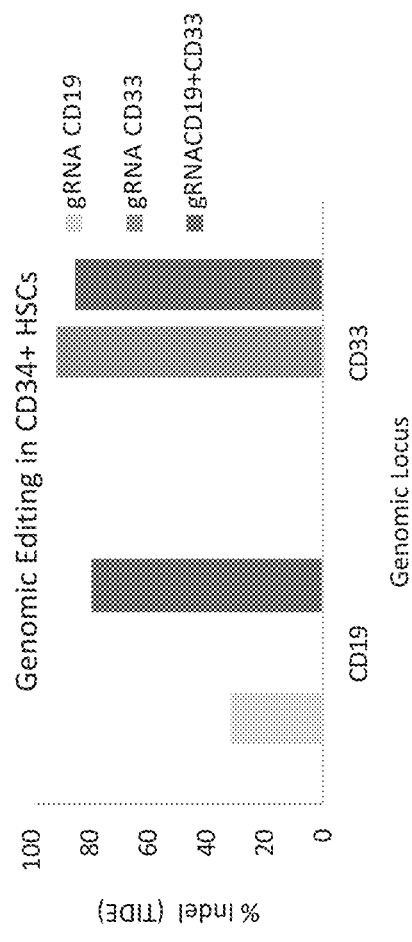
Figure 24D:
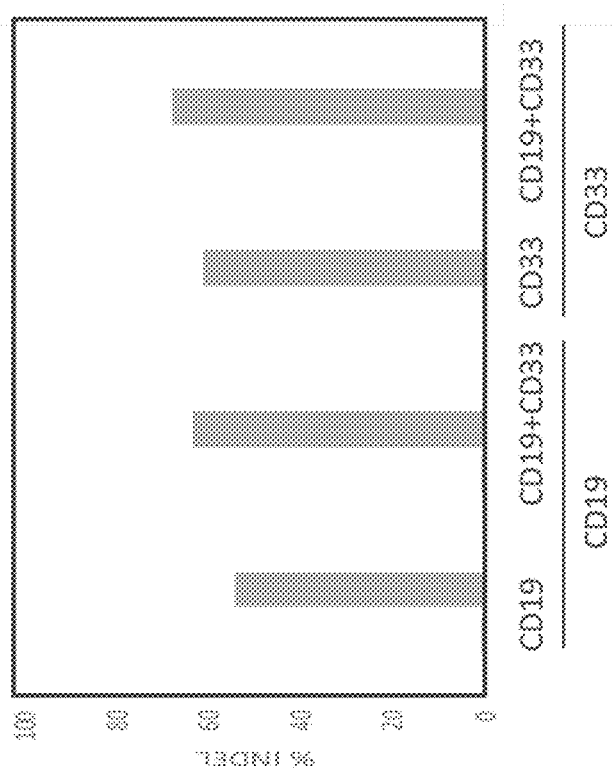
Figure 24C:
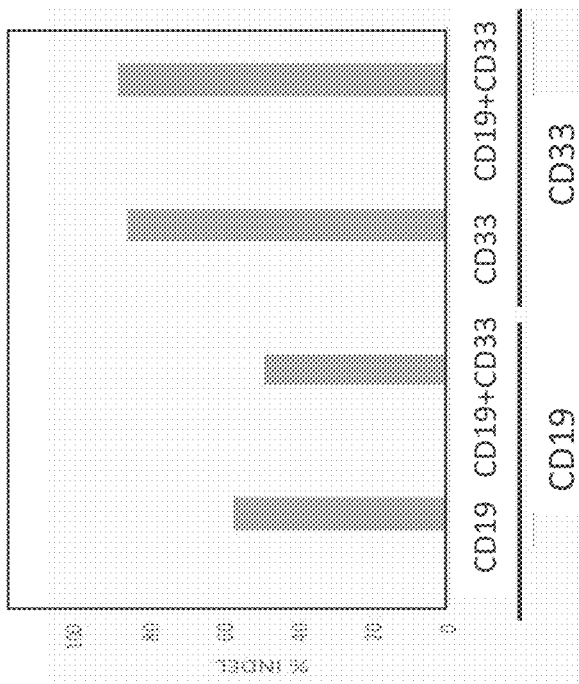

A high level of cell lysis was observed in CD33+HL-60 cells (FIG. 23A) and expression of CD33ex2 mutant in HL-60 cells significantly reduced the level of cell lysis (FIG. 23B), similar to HL-60 cells having CD33 knocked-out (FIG. 23C). The comparison results are provided in FIG. 23D.

Example 3: Efficient Multiplex Genomic Editing

Efficient double genomic editing of CD19 and CD33 genes in HSC cells were performed in either NALM-6 cells or in HSCs following conventional methods or those described herein. Table 8 below provides the gRNAs targeting exon 2 of CD19 and exon 3 of CD33.

TABLE 8

| Guide RNAs for Double Editing of CD19 and CD33 | | | | |
|---|---|---|---|---|
| Gene | gRNA Name | gRNA Sequence | PAM | Location |
| CD19 | CD19_gRNA-19 | CACAGCGTTATCTCCCTCTG (SEQ ID NO: 66) | GGT | Exon 2 |
| CD33 | CD33_gRNA-37 | CCCCAGGACTACTCACTCCT (SEQ ID NO: 67) | CGG | Exon 3 |

Genomic DNA was isolated from bulk-edited cells and TIDE assays were performed to examine genomic editing in NALM-6, HL-60 cells and HSCs. Results are depicted in FIGS. 24A-24D. The results obtained from this study show that ~70% of the HSCs include mutations in both loci of the CD19 gene and ~80% of the HSCs include mutations in both loci of the CD33 gene, indicating that at least 50% of the double-edited cells have both edited CD19 gene and edited CD33 gene on at least one chromosome. Similar levels of edited cells were observed in HL-60 cells and Nalm-6 cells.

Example 4: Effect of Editing Multiple Loci on Viability

Figure 25A:
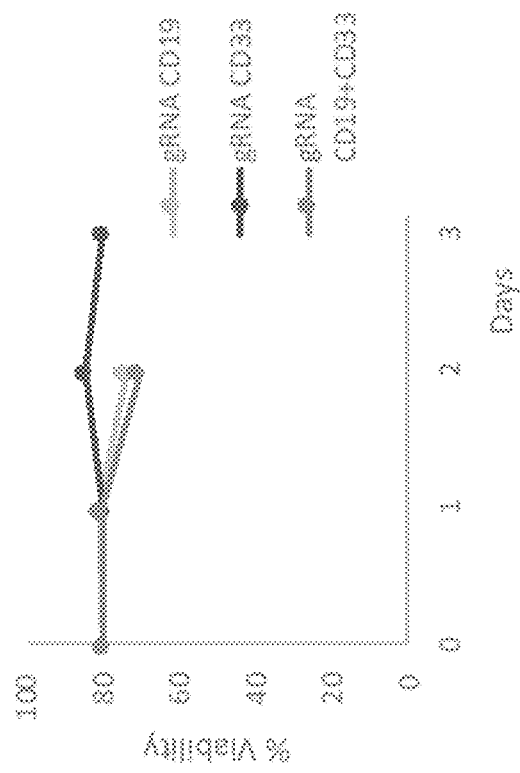
FIGS. 25A-25C include diagrams showing the results of a nucleofection assay showing the effect of multiplex genomic editing of both CD19 and CD33 on viability in HSCs and cell lines as compared to single RNA nucleofection. The gRNAs used in the nucleofections are indicated on the x-axis.
Figure 25B:
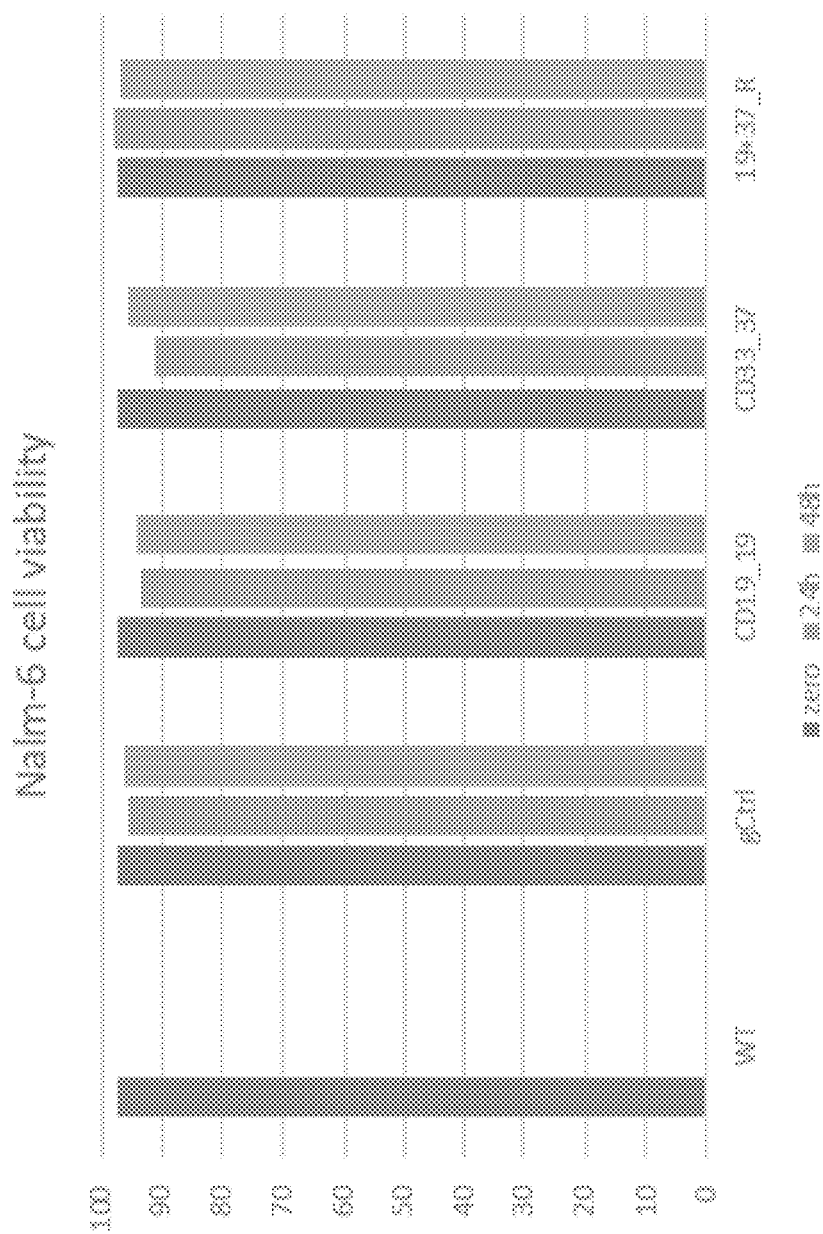
Figure 25C:
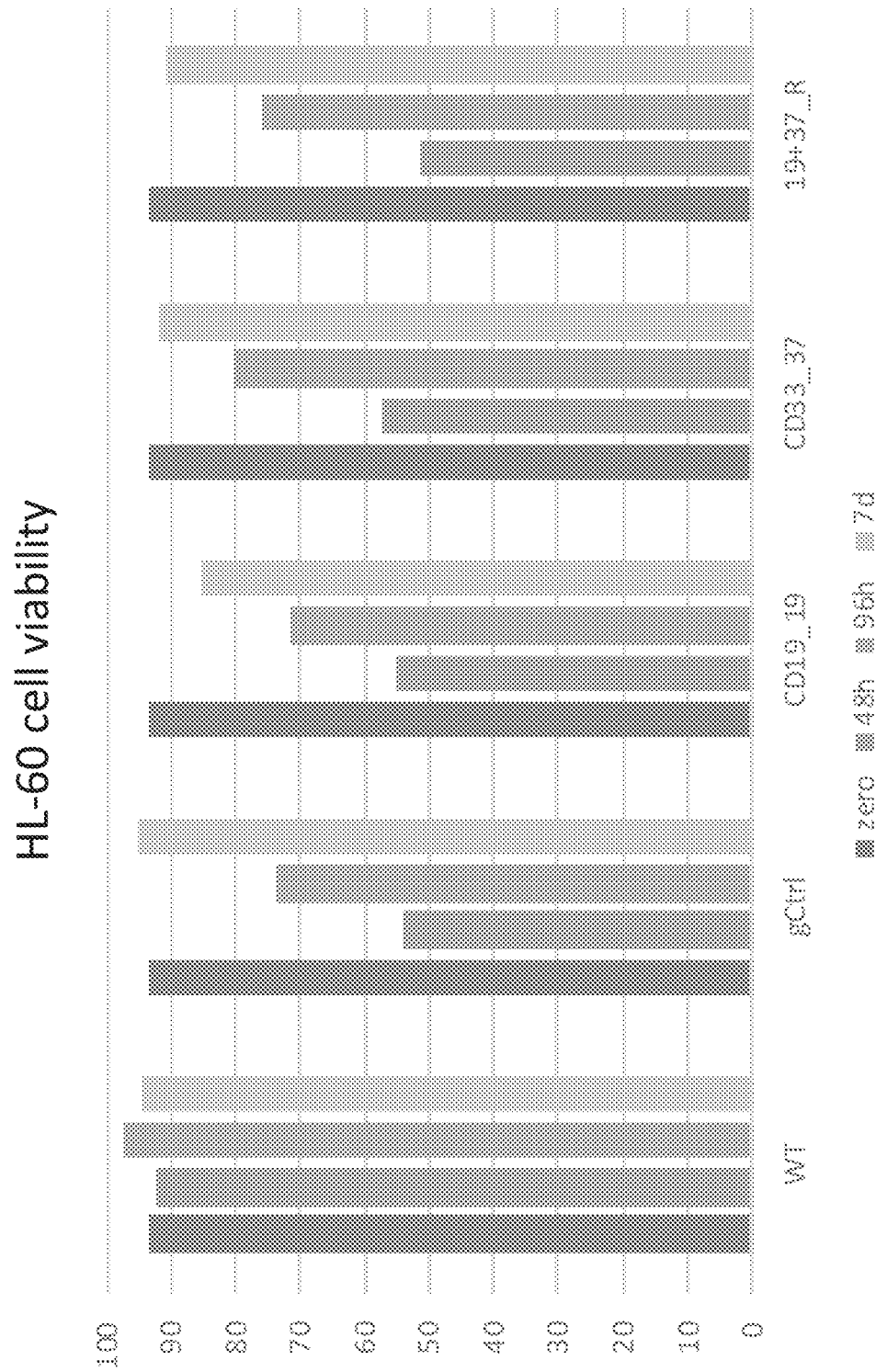
Figure 26B:
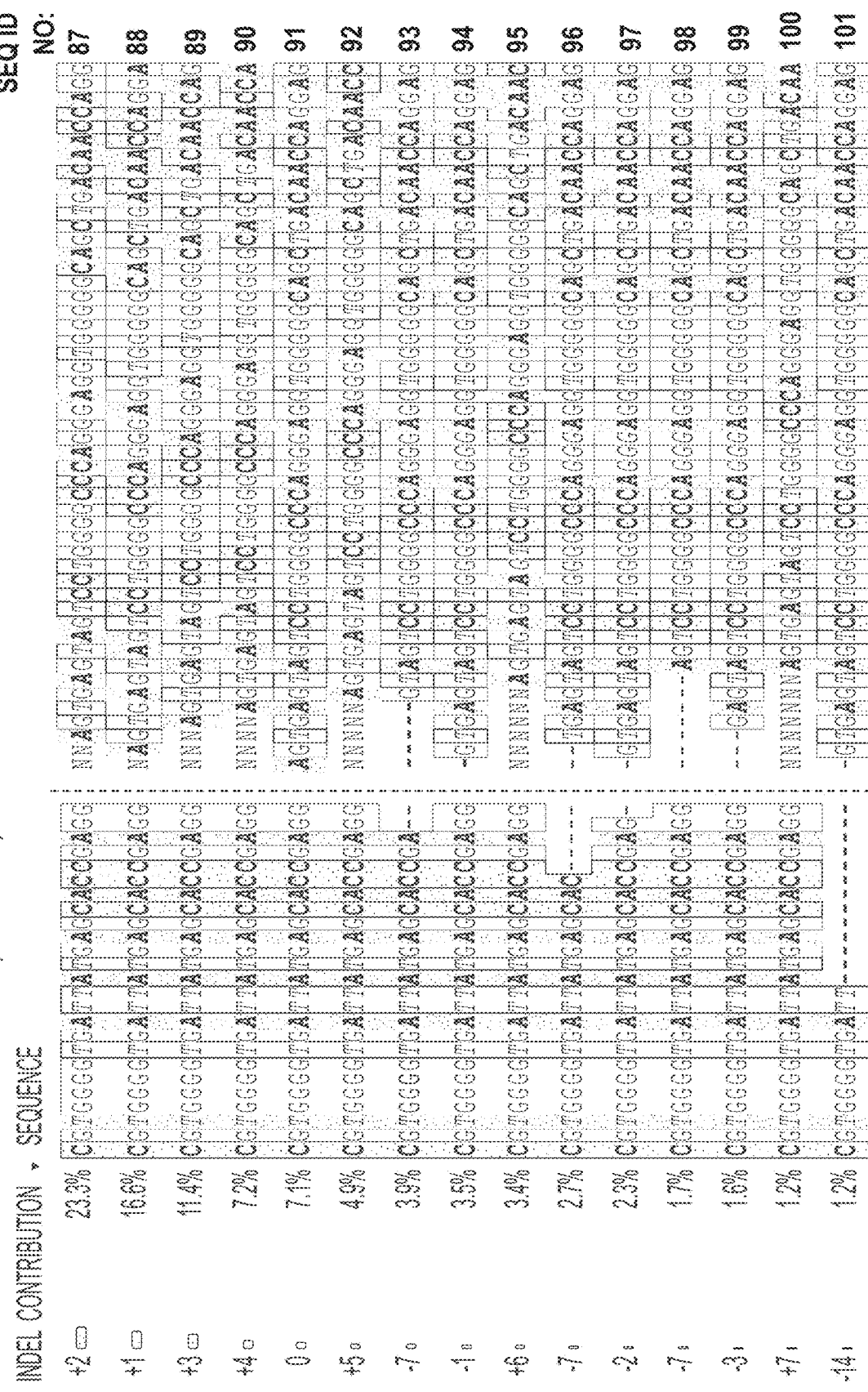
Figure 26C:
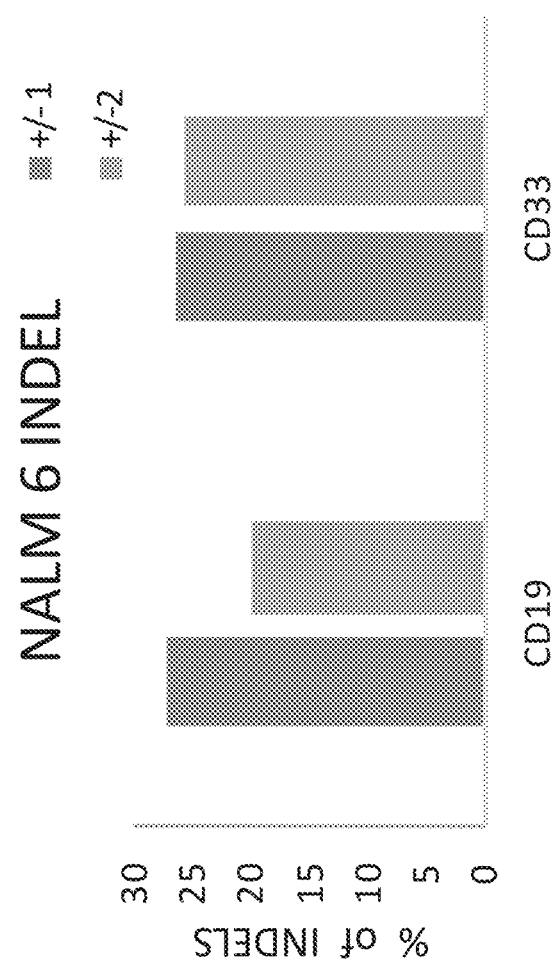

The effect of genomic editing at multiple loci on cell viability was assessed NALM-6, HL-60 cells and HSCs. Two days before nucleofection, HSPCs were thawed or Nalm-6 or HL-60 cells were passaged. At 24 and 48 hours (day of nucleofection), cells were counted and cell viability was assessed. Nucleofection with CD33_gRNA-37 RNP and CD19_gRNA-19 complexes and was performed according to Materials and Methods described herein. Cells were counted and cell viability was assessed at the indicated timepoints. Results are depicted in FIGS. 25A-25C and indicate that dual Cas9/gRNAs delivery does not impair viability in cell lines. No additional toxicity over single guide RNA was observed in HSCs.

Example 5: Performance of Individual Guides

The efficiency of genomic editing for the individual guide RNAs CD33 sgRNA-18 and CD33 sgRNA-24 was assessed in HL-60 cells. Genomic DNA was isolated from bulk-edited cells and TIDE assays were performed to examine genomic editing. Results are depicted in Table 9.

TABLE 9

Percentage of INDELs resulting from gRNA 18 and gRNA 24 individually

| CD33 Guide | Indel in HL60 cells |
| --- | --- |
| 3'-sg 18 | 94% |
| 5'-sg-24 | 46% |

Example 6: Treatment of Hematologic Disease

An example treatment regimen using the methods, cells, and agents described herein for acute myeloid leukemia is provided below.
1) Identify a patient with AML that is a candidate for receiving a hematopoietic cell transplant (HCT);
2) Identify a HCT donor with matched HLA haplotypes, using standard methods and techniques;
3) Extract the bone marrow from the donor;
4) Genetically manipulate the donor bone marrow cells ex vivo. Briefly, introduce a targeted modification (deletion, substitution) of an epitope of the lineage-specific cell-surface antigen n. In general, the epitope should generally be at least 3 amino acids (e.g., about 6-10 amino acids). Genetic modification of this epitope of the targeted lineage-specific cell-surface antigen on the donor bone marrow cells should not substantially impact the function of the protein, and as a consequence, should not substantially impact the function of the bone marrow cells, including their ability to successfully engraft in the patient and mediate graft-vs-tumor (GVT) effects;

Optional Steps 5-7:
In some embodiments, Steps 5-7 provided below may be performed (once or multiple times) in an exemplary treatment method as described herein:
5) Pre-condition the AML patient using standard techniques, such as infusion of chemotherapy agents (e.g., etoposide, cyclophosphamide) and/or irradiation;
6) Administer the engineered donor bone marrow to the AML patient, allowing for successful engraftment;
7) Follow up with a cytotoxic agent, such as immune cells expressing a chimeric receptor (e.g., CAR T cell) or antibody-drug conjugate, wherein the epitope to which the cytotoxic agent binds is the same epitope that was modified and is no longer present on the donor engineered bone marrow graft. The targeted therapy should thus specifically target the epitope of the lineage-specific cell-surface antigen, without simultaneously eliminating the bone marrow graft, in which the epitope is not present;

Optional Steps 8-10:
In some embodiments, Steps 8-10 may be performed (once or multiple times) in an exemplary treatment method as described herein:
8) Administer a cytotoxic agent, such as immune cells expressing a chimeric receptor (e.g., CAR T cell) or antibody-drug conjugate that targets an epitope of a lineage-specific cell-surface antigen. This targeted therapy would be expected to eliminate both cancerous cells as well as the patient's non-cancerous cells;
9) Pre-condition the AML patient using standard techniques, such as infusion of chemotherapy agents;
10) Administer the engineered donor bone marrow to the AML patient, allowing for successful engraftment.

The steps 8-10 result in the elimination of the patient's cancerous and normal cells expressing the targeted protein, while replenishing the normal cell population with donor cells that are resistant to the targeted therapy.

Example 7: Effect of Gemtuzumab Ozogamycin on Engineered HSCs

Figure 28:
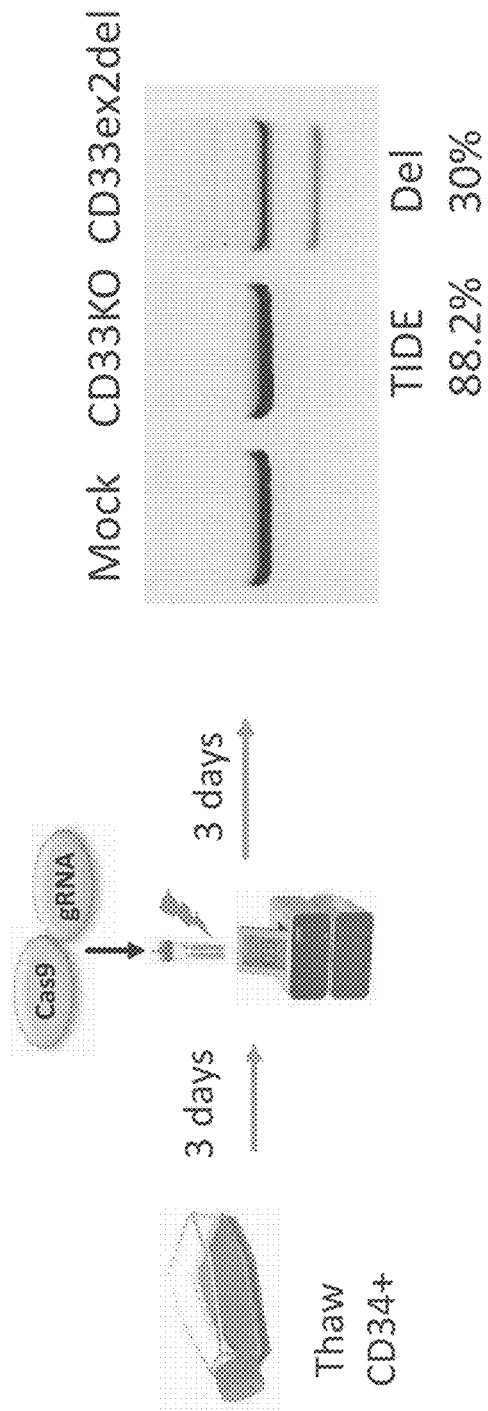
FIG. 28 shows an experimental schematic and results showing the editing efficiency achieved in CD34+ HSCs using control ("Mock," Cas9 only), CD33 knockout ("CD33KO," CD33 gRNA-37), CD33 exon2 deletion ("CD33ex2del," CD33 gRNA18 and gRNA-24). The editing efficiency (percentage modification) of the CD33 knockout was assessed by TIDE analysis, and % INDEL was determined. The fraction population with a deletion of exon 2 was determined by end-point PCR. For the CD33 exon2 deletion edited cells, the deletion efficiency of 30% refers to the editing events that resulted in deletion of exon 2, but does not include the events that resulted in a complete knockout of CD33.

As shown in FIG. 28, frozen CD34+ HSPCs derived from mobilized peripheral blood were thawed and cultured for 72 h before electroporation with ribonucleoprotein comprising Cas9 and an sgRNA. Samples were electroporated with the following conditions:
i.) Mock (Cas9 only),
ii. KO sgRNA (CD33 sgRNA-37), or
iii. Exon2deletion (dual gRNA 18+24).
Cells were allowed to recover for 72 hours and genomic DNA was collected and analyzed by PCR of the gRNA target region. To determine the percentage of cells having an exon 2 knockout were assessed by TIDE, and the percentage INDEL was determined. The fraction of the population with deletion of exon 2 was assayed by end-point PCR.

The percentage of CD33-positive cells were assessed by flow cytometry, confirming that editing with gRNA-37 was effective in knocking out CD33. FIG. 30.

Figure 29:
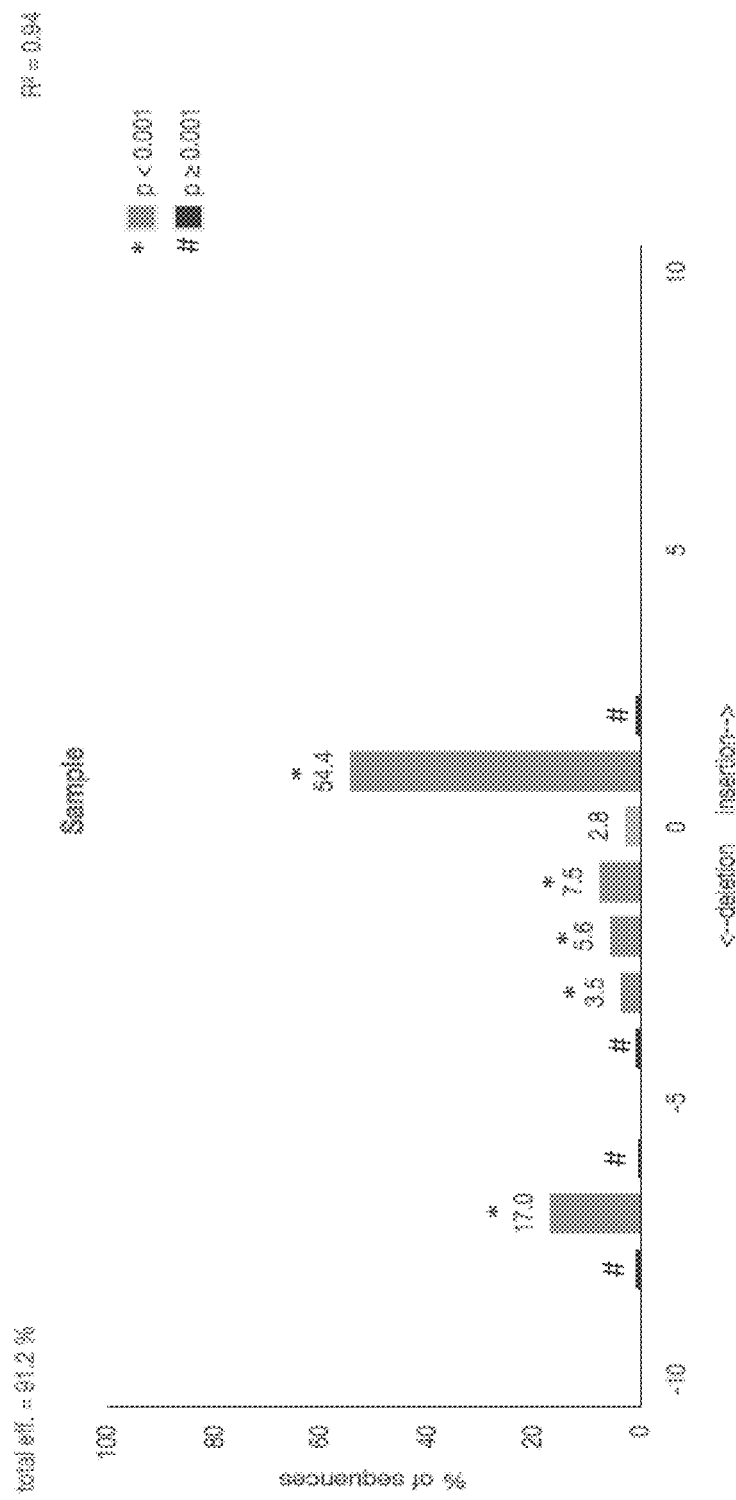
FIG. 29 includes a diagram showing analysis of editing events in HSCs resulting from use of CD33 gRNA-37. TIDE analysis shows the percentage of sequences observed for each INDEL obtained by editing CD34+ HSCs using gRNA37.

The editing events in the HSCs were found to result in a variety of indel sequences, as exemplified in FIG. 29.

(i) Sensitivity of Cells Having CD33exon2 Deletion to Gemtuzumab Ozogramicin (GO)

Figures 31B, 31C:
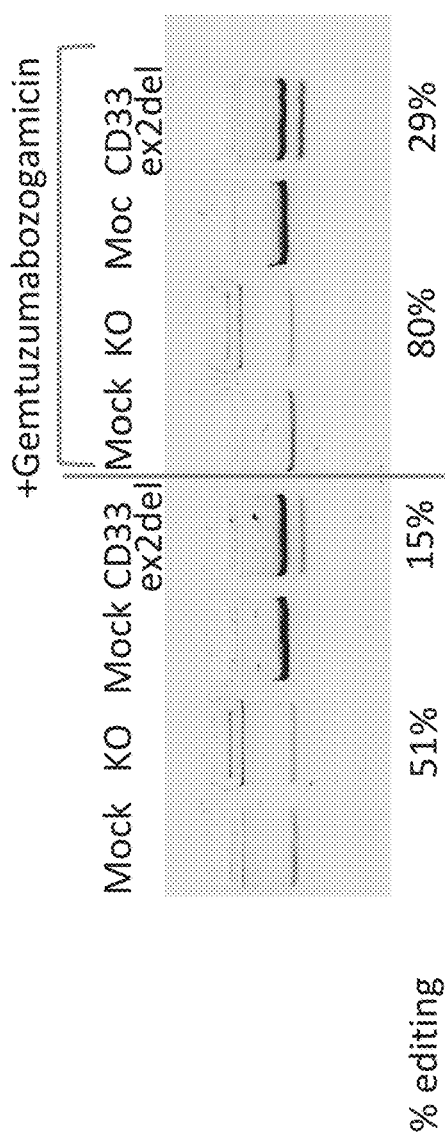

To determine in vitro toxicity, cells were incubated with GO in their culture media and the number of viable cells was quantified over time. As shown in FIGS. 31A and 31B, CD33 knockout cells generated with CD33 sgRNA-37 and CD33ex2 del cells generated with the CD33 gRNA-18 and gRNA-24 pair were more resistant to GO treatment than cells expressing full length CD33 (mock). 50% editing observed in CD33KO cells is considered sufficient protection in dividing cells. The initial decline in the viability of CD33ex2 del cells is thought to correspond to unedited cell death.

(ii) Enrichment of CD33-Modified Cells

To assay if CD33 modified cells were enriched following GO-treatment, CD34+ HSPCs were edited with 50% of standard Cas9/gRNA ratios. The bulk population of cells were analyzed prior to and after GO treatment. As shown in FIG. 31C, prior to GO treatment, 51% of gRNA-37 modified cells (KO) as assayed by TIDE and 15% of gRNA 19+24 (ex2deletion) as assayed by deletion PCR. Following GO-treatment, CD33 modified cells were enriched at least 1.5× so that the percentage of KO cells increased to 80% and exon2delete to 50%. This data indicated that there was an enrichment of CD33 modified cells following GO-treatment.

(iii) In Vitro Differentiation of CD34+ HSPCs

Figure 31D:
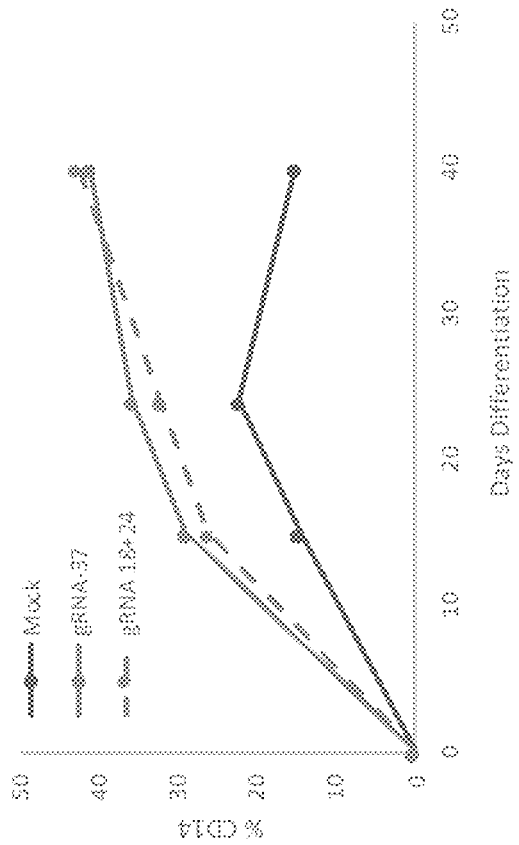
Figure 31E:
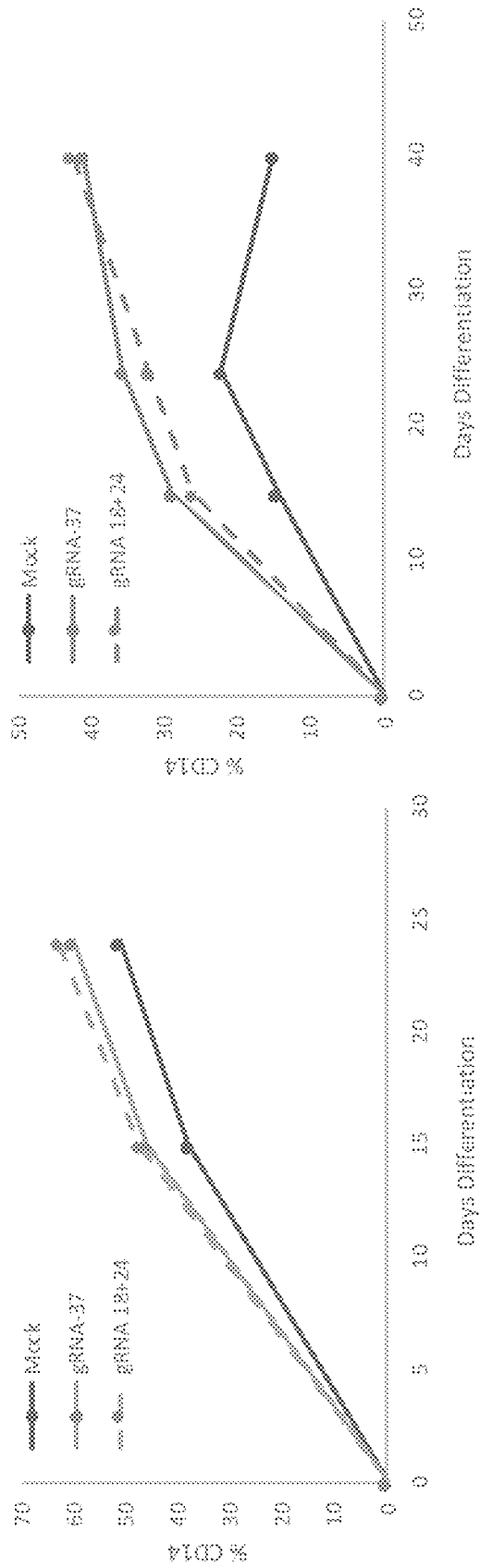

Cell populations were assessed for myeloid differentiation prior to and after GO treatment at various days post differentiation. As shown in FIGS. 31D and 31E, CD33 knockout cells generated with CD33 sgRNA-37 and CD33ex2 del cells generated with the CD33 gRNA-18 and gRNA-24 pair showed increased expression of the differentiation marker, CD14, whereas cells expressing full length CD33 (mock) did not differentiate.

Example 8: Generation of Exon 2 or Exon 4 Deletion in CD19

NALM6 cell lines were transfected with indicated ms-sgRNAs to modify the CD19 locus as follows:
1) WT (wild-type, unmodified),
2) sgRNA 6+14 targeting introns 1 and 2 to generate the CD19exon2deletion protein,
3) sgRNA 7+16 targeting introns 1 and 2 to generate the CD19exon2deletion protein of CD19,
4) sgRNA 23+24 targeting introns 3 and 4 to generate the CD19exon4deletion protein and
5) sgRNA 18 targeting exon 1 to create CD19 knock out.

Transfected cell lines were clonally selected and assayed for CD19 expression by fluorescence-activated cell sorting (FACS). NALM6 cells nucleofected with ribonucleoprotein of Cas9 and the sgRNA(s), as described herein, were maintained in cell culture for 48 hours.

Samples from the cell populations were assessed by Western blot using two different antibodies—one recognizing the Ig-like C2-type domain encoded by exon 4 and the second the C-terminus of CD19. Protein analysis of clonal NALM6 cells expression full-length or those modified with gRNA as indicated (NT=non-targeting control gRNA, WT=wild type). To confirm deletion of CD19 in gRNA nucleofected cells and modified CD19 in the CD19ex2deletion and CD19ex4deletion clones, lysates were blotted using a polyclonal anti-CD19 antibody (#3574 Rabbit anti-human CD19 Pab, Cell Signaling Technology®) that recognizes the CD19 C-terminus. Western blot was performed on cells lysates with anti-CD19 antibody (OTI3B10, Origene®) that recognizes the epitope encoded by exon 4 to confirm deletion of exon 4 in gRNA 23+24 nucleofected cells. Western blot with the C-terminus antibody confirms that CD19ex2delete and CD19ex4delete proteins are smaller than full length CD19. FIGS. 32A and 32B.

Figure 33:
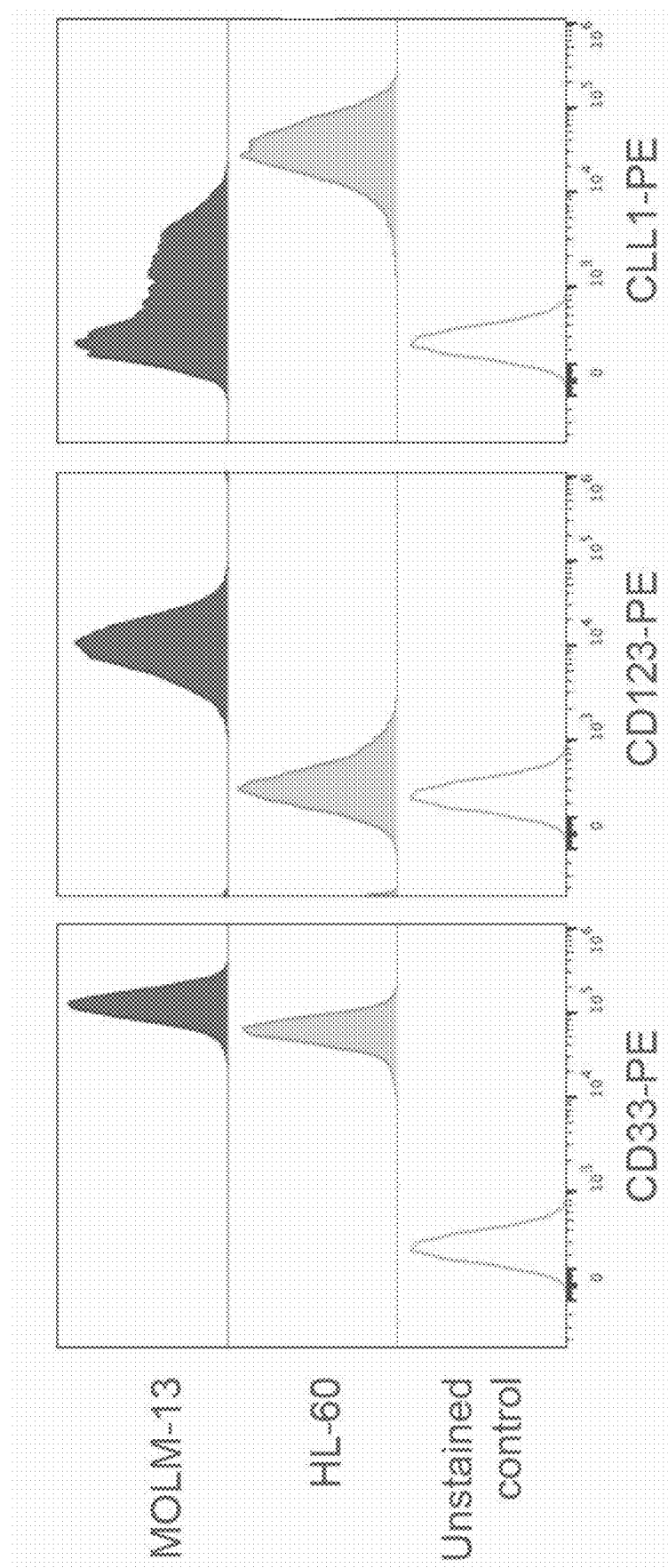
FIG. 33 shows target expression on AML cell lines. The expression of CD33, CD123 and CLL1 in MOLM-13 and THP-1 cells and an unstained control was determined by flow cytometric analysis. The X-axis indicates the intensity of antibody staining and the Y-axis corresponds to number of cells.

Example 9: Generation and Evaluation of Cells Edited for Two Cell Surface Antigens Results Cell surface levels of CD33, CD123 and CLL1 (CLEC12A) were measured in unedited MOLM-13 cells and THP-1 cells (both human AML cell lines) by flow cytometry. MOLM-13 cells had high levels of CD33 and CD123, and moderate-to-low levels of CLL1. HL-60 cells had high levels of CD33 and CLL1, and low levels of CD123 (FIG. 33).

Figure 34:
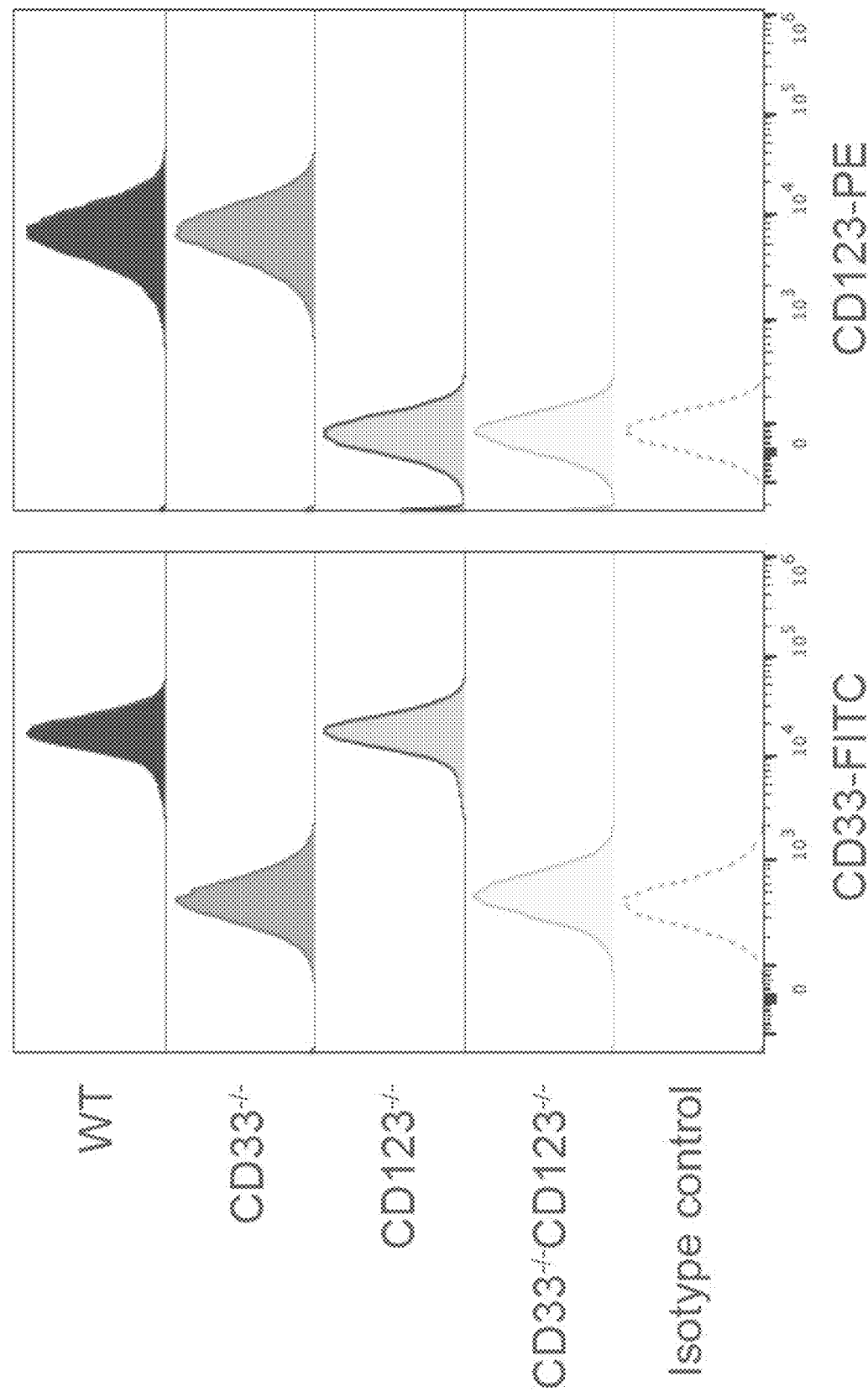
FIG. 34 shows CD33− and CD123− modified MOLM-13 cells. The expression of CD33 and CD123 in wild-type (WT), CD33$^{-/-}$, CD123$^{-/-}$ and CD33$^{-/-}$ CD123$^{-/-}$ MOLM-13 cells was assessed by flow cytometry. For the generation of CD33$^{-/-}$ or CD123$^{-/-}$ MOLM-13 cells, WT MOLM-13 cells were electroporated with CD33− or CD123− targeting RNP, followed by flow cytometric sorting of CD33− or CD123− negative cells. CD33$^{-/-}$ CD123$^{-/-}$ MOLM-13 cells were generated by electroporating CD33$^{-/-}$ cells with CD123− targeting RNP and sorted for CD123− negative population. The X-axis indicates the intensity of antibody staining and the Y-axis corresponds to number of cells.
Figure 35:
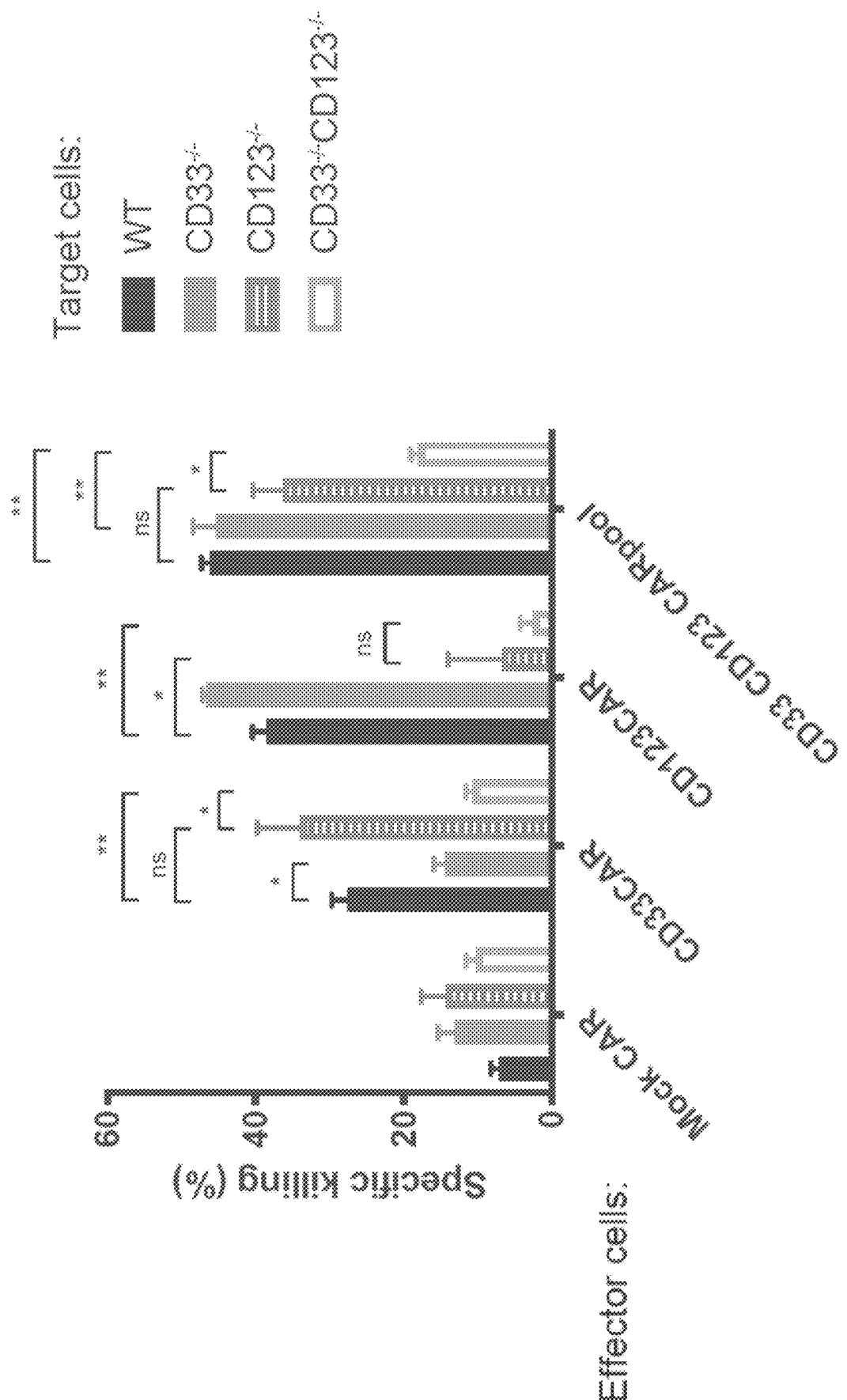
FIG. 35 shows an in vitro cytotoxicity assay of CD33 and CD123 CAR-Ts. Anti-CD33 CAR-T and anti-CD123 CAR-T were incubated with wild-type (WT), CD33$^{-/-}$, CD123$^{-/-}$ and CD33$^{-/-}$ CD123$^{-/-}$ MOLM-13 cells, and cytotoxicity was assessed by flow cytometry. Non-transduced T cells were used as mock CAR-T control. The CARpool group was composed of 1:1 pooled combination of anti-CD33 and anti-CD123 CAR-T cells. Student's t test was used. ns=not significant; *P<0.05; **P<0.01. The Y-axis indicates the percentage of specific killing.

CD33 and CD123 were mutated in MOLM-13 cells using gRNAs and Cas9 as described herein, CD33 and CD123- modified cells were purified by flow cytometric sorting, and the cell surface levels of CD33 and CD123 were measured. CD33 and CD123 levels were high in wild-type MOLM-13 cells; editing of CD33 only resulted in low CD33 levels; editing of CD123 only resulted in low CD123 levels, and editing of both CD33 and CD123 resulted in low levels of both CD33 and CD123 (FIG. 34). The edited cells were then tested for resistance to CART effector cells using an in vitro cytotoxicity assay as described herein. All four cell types (wild-type, $CD33^{-/-}$, $CD123^{-/-}$, and $CD33^{-/-}$ $CD123^{-/-}$) experienced low levels of specific killing in mock CAR control conditions (FIG. 35, leftmost set of bars). CD33 CAR cells effectively killed wild-type and $CD123^{-/-}$ cells, while $CD33^{-/-}$ and $CD33^{-/-}$ $CD123^{-/-}$ cells showed a statistically significant resistance to CD33 CAR (FIG. 35, second set of bars). CD123 CAR cells effectively killed wild-type and $CD33^{-/-}$ cells, while $CD123^{-/-}$ and $CD33^{-/-}$ $CD123^{-/-}$ cells showed a statistically significant resistance to CD123 CAR (FIG. 35, third set of bars). A pool of CD33 CAR and CD123 CAR cells effectively killed wild-type cells, $CD33^{-/-}$ cells, and $CD123^{-/-}$ cells, while $CD33^{-/-}$ $CD123^{-/-}$ cells showed a statistically significant resistance to the pool of CAR cells (FIG. 35, rightmost set of bars). This experiment demonstrates that knockout of two antigens (CD33 and CD123) protected the cells against CAR cells targeting both antigens. Furthermore, the population of edited cells contained a high enough proportion of cells that were edited at both alleles of both antigens, and had sufficiently low cell surface levels of cell surface antigens, that a statistically significant resistance to both types of CAR cells was achieved.

Figure 36:
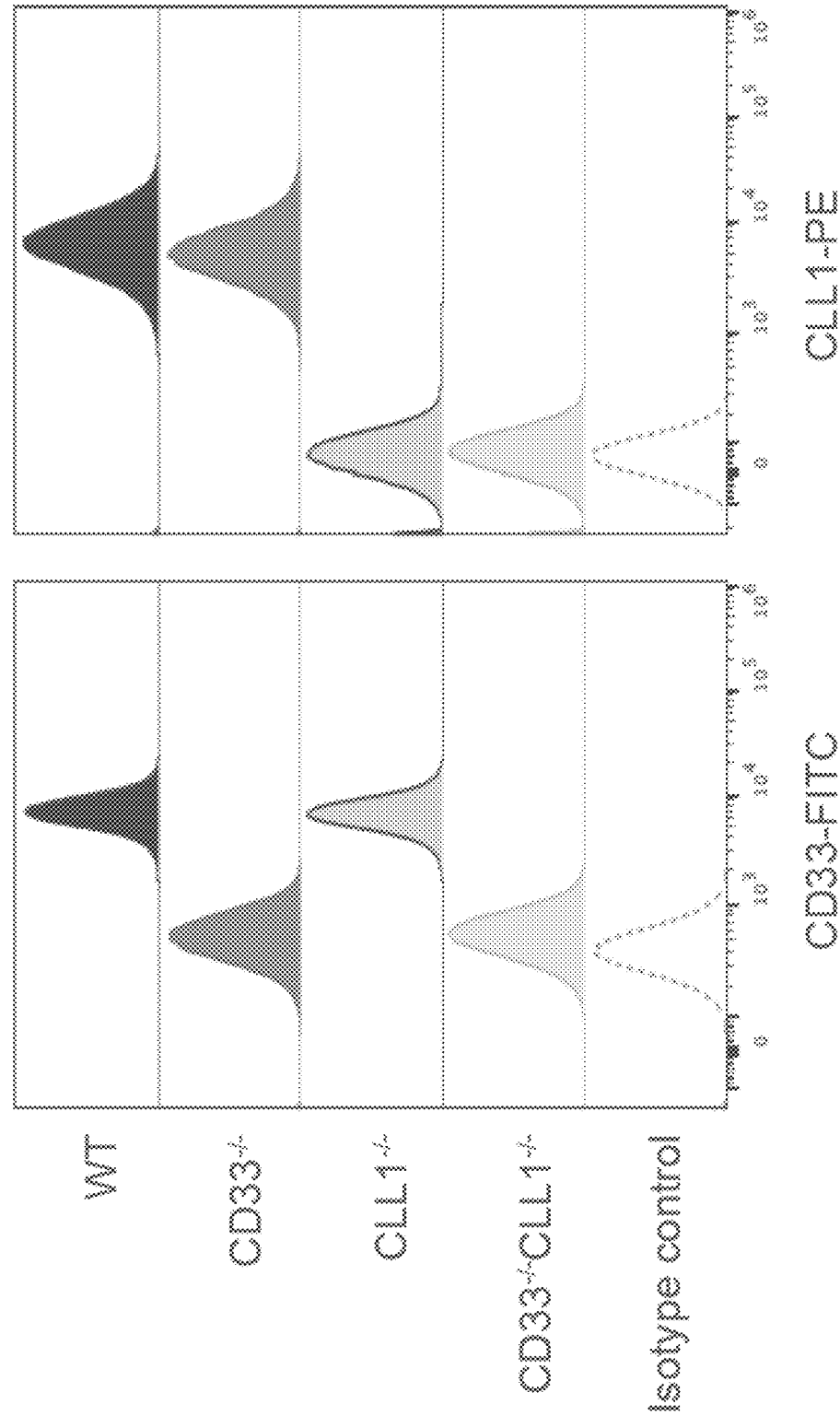
FIG. 36 shows CD33− and CLL1− modified HL-60 cells. The expression of CD33 and CLL1 in wild-type (WT), CD33$^{-/-}$, CLL1$^{-/-}$ and CD33$^{-/-}$ CLL1$^{-/-}$ HL-60 cells was assessed by flow cytometry. For the generation of CD33$^{-/-}$ or CLL1$^{-/-}$ HL-60 cells, WT HL-60 cells were electroporated with CD33− or CLL1− targeting RNP, followed by flow cytometric sorting of CD33− or CLL1− negative cells. CD33$^{-/-}$ CLL1$^{-/-}$ HL-60 cells were generated by electroporating CD33$^{-/-}$ cells with CLL1− targeting RNP and sorted for CLL1− negative population. The X-axis indicates the intensity of antibody staining and the Y-axis corresponds to number of cells.
Figure 37:
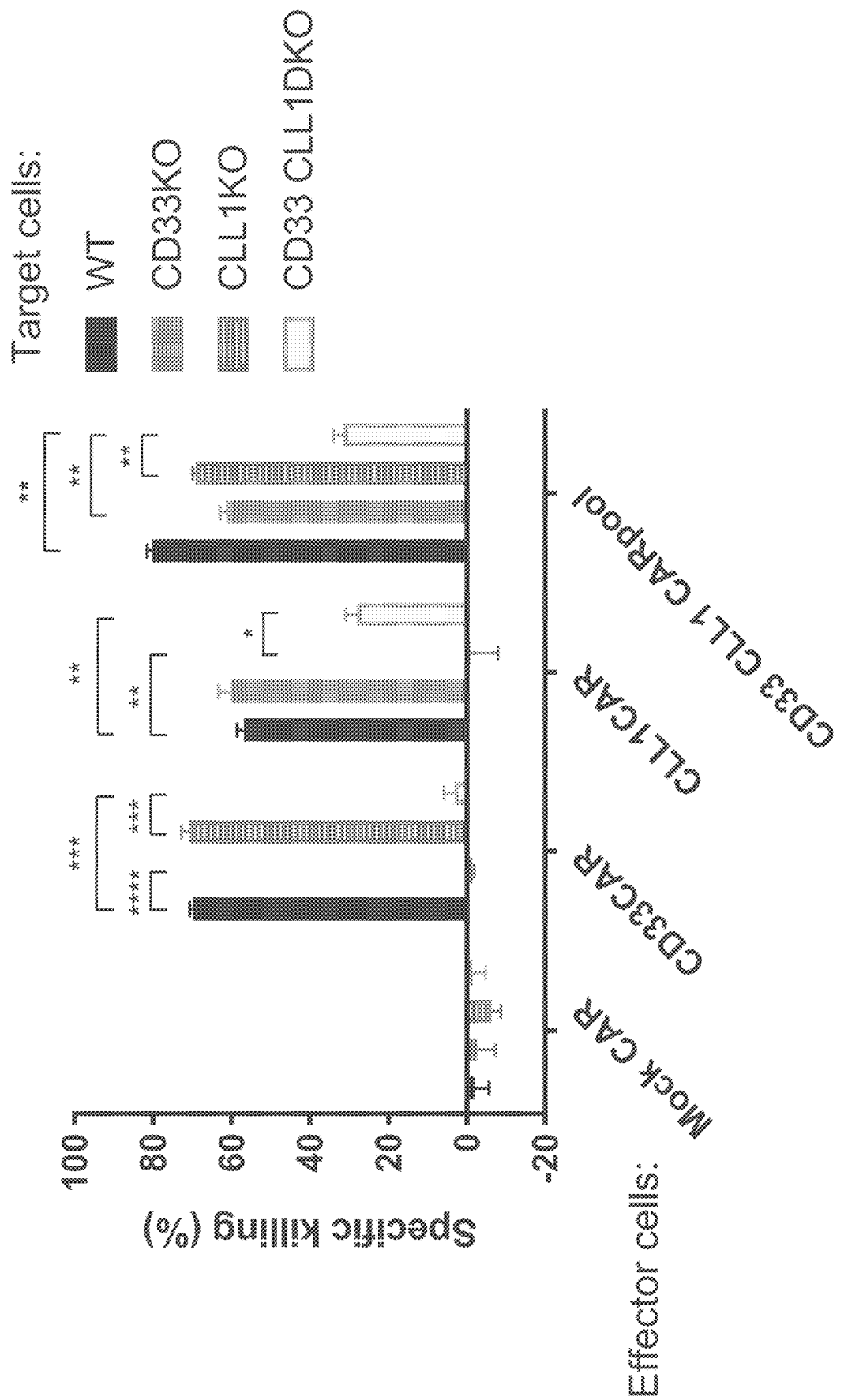
FIG. 37 shows an in vitro cytotoxicity assay of CD33 and CLL1 CAR-Ts. Anti-CD33 CAR-T and anti-CLL1 CAR-T were incubated with wild-type (WT), CD33$^{-/-}$, CLL1$^{-/-}$ and CD33$^{-/-}$ CLL1$^{-/-}$ HL-60 cells, and cytotoxicity was assessed by flow cytometry. Non-transduced T cells were used as mock CAR-T control. The CARpool group was composed of 1:1 pooled combination of anti-CD33 and anti-CLL1 CAR-T cells. Student's t test was used. ns=not significant; *P<0.05; P<0.01, *P<0.001, ****P<0.0001. The Y-axis indicates the percentage of specific killing.

CD33 and CLL1 were mutated in HL-60 using gRNAs and Cas9 as described herein, CD33 and CLL1- modified cells were purified by flow cytometric sorting, and the cell surface levels of CD33 and CLL1 were measured. CD33 and CLL1 levels were high in wild-type HL-60 cells; editing of CD33 only resulted in low CD33 levels; editing of CLL1 only resulted in low CLL1 levels, and editing of both CD33 and CLL1 resulted in low levels of both CD33 and CLL1 (FIG. 36). The edited cells were then tested for resistance to CART effector cells using an in vitro cytotoxicity assay as described herein. All four cell types (wild-type, $CD33^{-/-}$, $CLL1^{-/-}$, and $CD33^{-/-}$ $CLL1^{-/-}$) experienced low levels of specific killing in mock CAR control conditions (FIG. 37, leftmost set of bars). CD33 CAR cells effectively killed wild-type and $CLL1^{-/-}$ cells, while $CD33^{-/-}$ and $CD33^{-/-}$ $CLL1^{-/-}$ cells showed a statistically significant resistance to CD33 CAR (FIG. 37, second set of bars). CLL1 CAR cells effectively killed wild-type and $CD33^{-/-}$ cells, while $CLL1^{-/-}$ and $CD33^{-/-}$ $CLL1^{-/-}$ cells showed a statistically significant resistance to CLL1 CAR (FIG. 37, third set of bars). A pool of CD33 CAR and CLL1 CAR cells effectively killed wild-type cells, $CD33^{-/-}$ cells, and $CLL1^{-/-}$ cells, while $CD33^{-/-}$ $CLL1^{-/-}$ cells showed a statistically significant resistance to the pool of CAR cells (FIG. 37, rightmost set of bars). This experiment demonstrates that knockout of two antigens (CD33 and CLL1) protected the cells against CAR cells targeting both antigens. Furthermore, the population of edited cells contained a high enough proportion of cells that were edited at both alleles of both antigens, and had sufficiently low cell surface levels of cell surface antigens, that a statistically significant resistance to both types of CAR cells was achieved.

Figure 38:
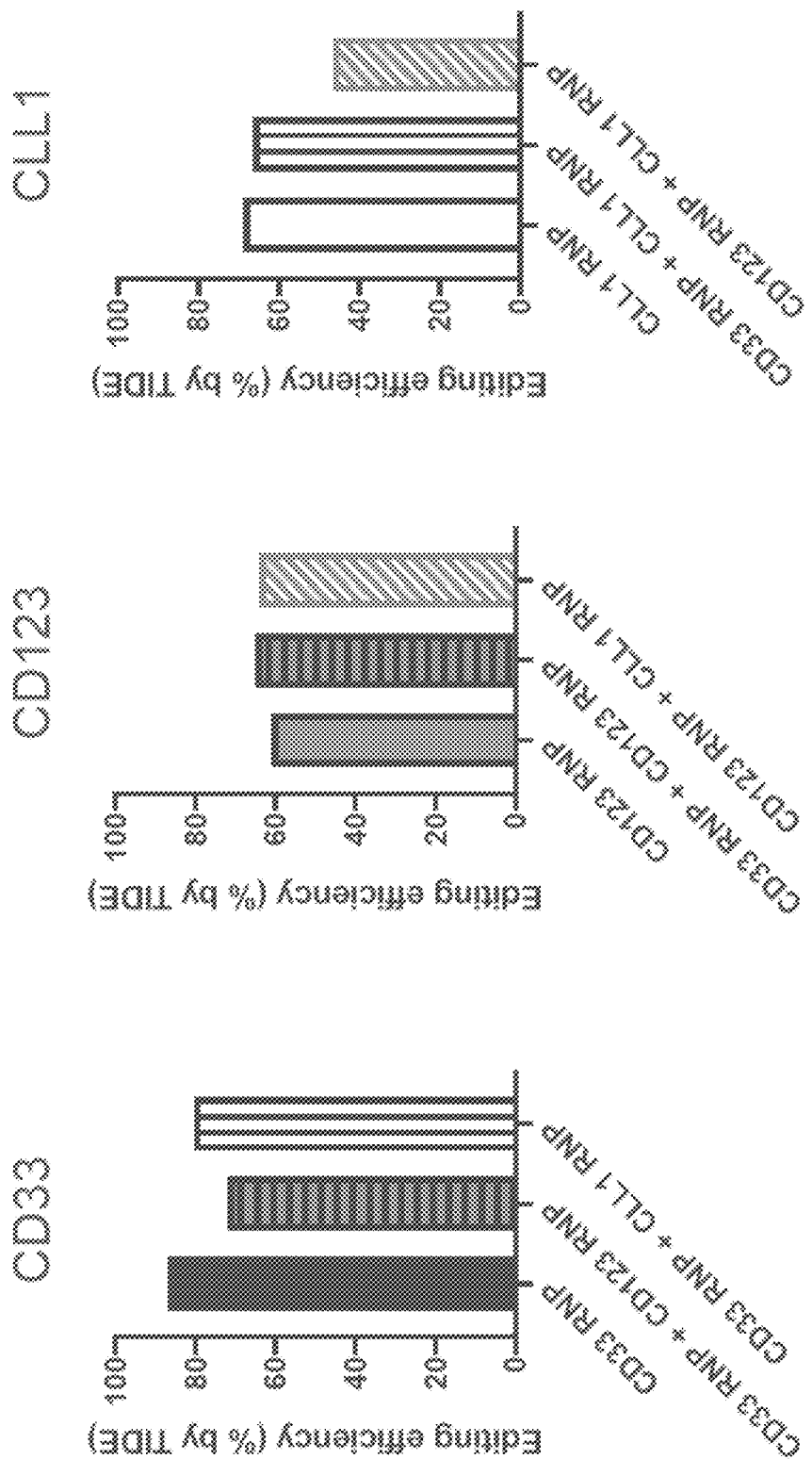
FIG. 38 shows gene-editing efficiency of CD34+ cells. Human CD34+ cells were electroporated with Cas9 protein and CD33−, CD123− or CLL1− targeting gRNAs, either alone or in combination. Editing efficiency of CD33, CD123 or CLL1 locus was determined by Sanger sequencing and TIDE analysis. The Y-axis indicates the editing efficiency (% by TIDE).

The efficiency of gene editing in human CD34+ cells was quantified using TIDE analysis as described herein. At the endogenous CD33 locus, editing efficiency of between about 70-90% was observed when CD33 was targeted alone or in combination with CD123 or CLL1 (FIG. 38, left graph). At the endogenous CD123 locus, editing efficiency of between about 60% was observed when CD123 was targeted alone or in combination with CD33 or CLL1 (FIG. 38, center graph). At the endogenous CLL1 locus, editing efficiency of between about 40-70% was observed when CLL1 was targeted alone or in combination with CD33 or CD123 (FIG. 38, right graph). This experiment illustrates that human CD34+ cells can be edited at a high frequency at two cell surface antigen loci.

Figure 39B:
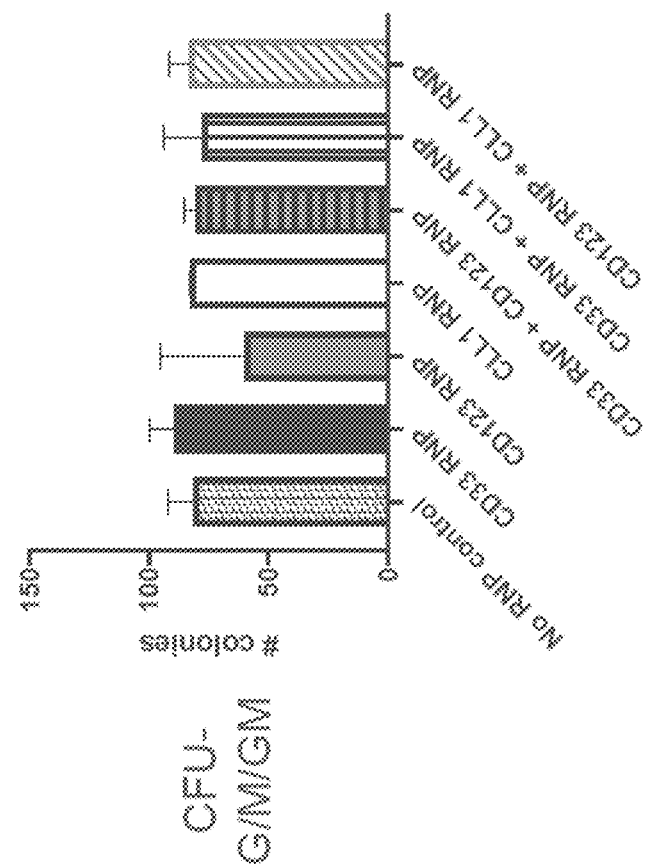
FIGS. 39A-39C show in vitro colony formation of gene-edited CD34+ cells. Control or CD33, CD123, CLL-1-modified CD34+ cells were plated in MethoCult™ 2 days after electroporation and scored for colony formation after 14 days. BFU-E: burst forming unit-erythroid; CFU-GM: colony forming unit-granulocyte/macrophage; CFU- GEMM: colony forming unit of multipotential myeloid progenitor cells (generate granulocytes, erythrocytes, monocytes, and megakaryocytes). Student's t test was used.
Figure 39A:
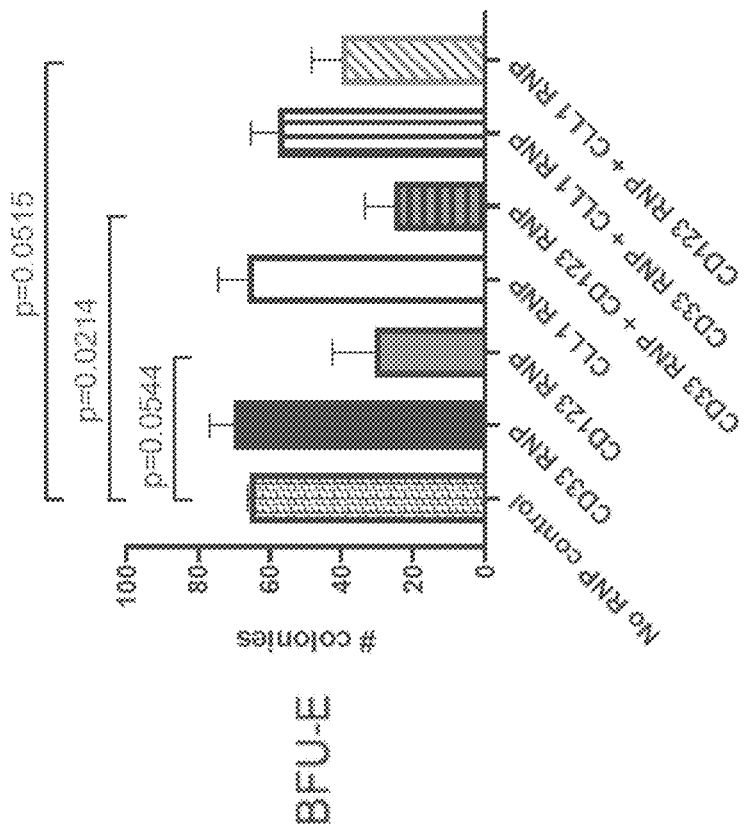
Figure 39C:
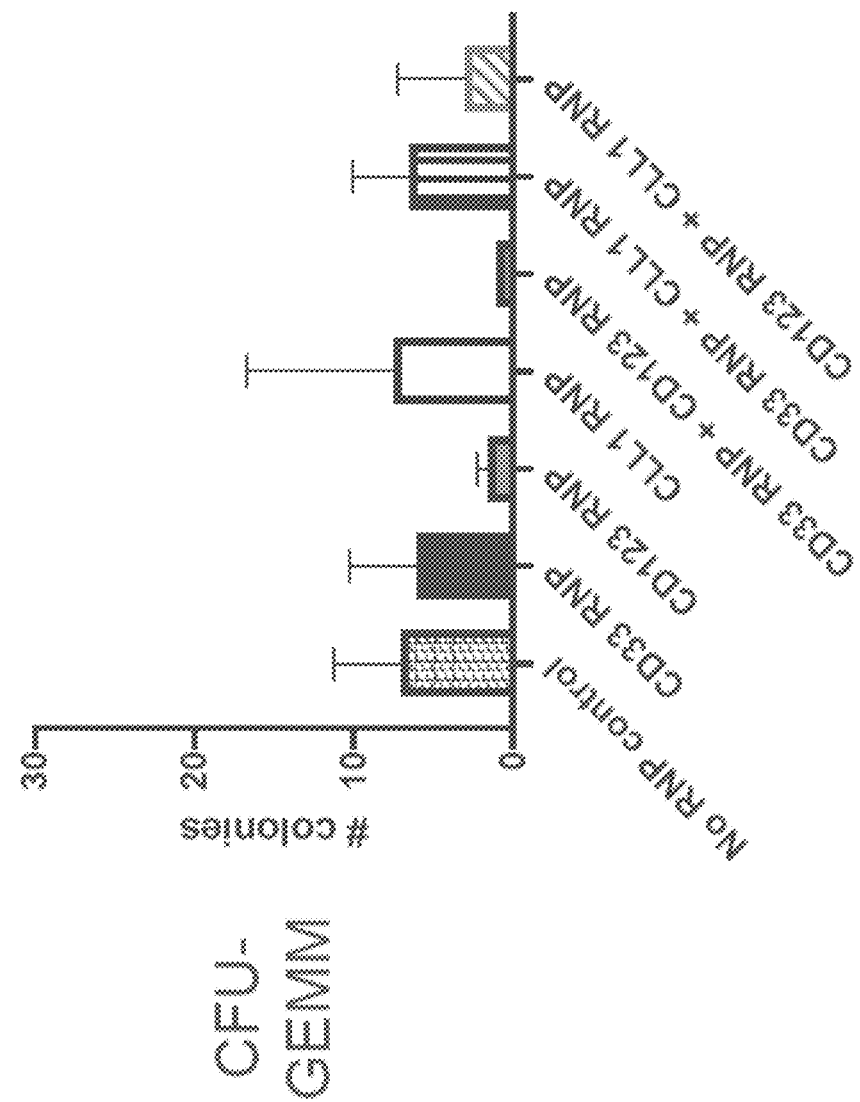

The differentiation potential of gene-edited human CD34+ cells as measured by colony formation assay as described herein. Cells edited for CD33, CD123, or CLL1, individually or in all pairwise combinations, produced BFU-E colonies, showing that the cells retain significant differentiation potential in this assay (FIG. 39A). The edited cells also produced CFU-G/M/GM colonies, showing that the cells retain differentiation potential in this assay that is statistically indistinguishable from the non-edited control (FIG. 39B). The edited cells also produced detectable CFU-GEMM colonies (FIG. 39C). Taken together, the differentiation assays indicate that human CD34+ cells edited at two loci retain the capacity to differentiate into variety of cell types.

Materials and Methods

AML Cell Lines

Human AML cell line HL-60 was obtained from the American Type Culture Collection (ATCC). HL-60 cells were cultured in Iscove's Modified Dulbecco's Medium (IMDM, Gibco™) supplemented with 20% heat-inactivated HyClone™ Fetal Bovine Serum (GE Healthcare®). Human AML cell line MOLM-13 was obtained from AddexBio Technologies™. MOLM-13 cells were cultured in RPMI-1640 media (ATCC®) supplemented with 10% heat-inactivated HyClone™ Fetal Bovine Serum (GE Healthcare®).

Guide RNA Design

All sgRNAs were designed by manual inspection for the SpCas9 PAM (5'-NGG-3') with close proximity to the target region and prioritized according to predicted specificity by minimizing potential off-target sites in the human genome with an online search algorithm (Benchling, Doench et al 2016, Hsu et al 2013). All designed synthetic sgRNAs were purchased from Synthego® with chemically modified nucleotides at the three terminal positions at both the 5' and 3' ends. Modified nucleotides contained 2'-O-methyl-3'-phosphorothioate (abbreviated as "ms") and the ms-sgRNAs were HPLC-purified. Cas9 protein was purchased from Aldervon®.

| Target gene | gRNA name | Sequence | PAM | Target location |
|---|---|---|---|---|
| CD33 | CD33-gRNA37 | CCCCAGGACTACTCACTCCT (SEQ ID NO: 134) | CGG | CD33 exon 3 |
| CD123 | CD123-gRNA19 | TTTCTTGAGCTGCAGCTGGG SEQ ID NO: 135) | CGG | CD123 exon 5 |
|  | CD123-gRNA25 | AGTTCCCACATCCTGGTGCG (SEQ ID NO: 136) | GGG | CD123 exon 6 |
| CLL1 | CLL1-gRNA4 | GGTGGCTATTGTTTGCAGTG (SEQ ID NO: 137) | TGG | CLL1 exon 4 |

AML Cell Line Electroporation

Cas9 protein and ms-sgRNA (at a 1:1 weight ratio) were mixed and incubated at room temperature for 10 minutes prior to electroporation. MOLM-13 and HL-60 cells were electroporated with the Cas9 ribonucleoprotein complex (RNP) using the MaxCyte® ATx™ Electroporator System with program THP-1 and Opt-3, respectively. Cells were incubated at 37° C. for 5-7 days until flow cytometric sorting.

Human CD34+ Cell Culture and Electroporation

Cryopreserved human CD34+ cells were purchased from Hemacare® and thawed according to manufacturer's instructions. Human CD34+ cells were cultured for 2 days in GMP SCGM media (CellGenix™) supplemented with human cytokines (Flt3, SCF, and TPO, all purchased from Peprotech®). CD34+ cells were electroporated with the Cas9 RNP (Cas9 protein and ms-sgRNA at a 1:1 weight ratio) using Lonza® 4D-Nucleofector™ and P3 Primary Cell Kit (Program CA-137). For electroporation with dual ms-sgRNAs, equal amount of each ms-sgRNA was added. Cells were cultured at 37° C. until analysis.

Genomic DNA Analysis

Genomic DNA was extracted from cells 2 days post electroporation using prepGEM DNA extraction kit (Zy-GEM™). Genomic region of interest was amplified by PCR. PCR amplicons were analyzed by Sanger sequencing (Genewiz®) and allele modification frequency was calculated using TIDE (Tracking of Indels by Decomposition) software available on the World Wide Web at tide.deskgen.com.

In Vitro Colony Forming Unit (CFU) Assay

Two days after electroporation, 500 CD34+ cells were plated in 1.1 mL of methylcellulose (MethoCult™ H4034 Optimum, Stem Cell Technologies™) on 6 well plates in duplicates and cultured for two weeks. Colonies were then counted and scored using StemVision™ (Stem Cell Technologies®).

Flow Cytometric Analysis and Sorting

Fluorochrome-conjugated antibodies against human CD33 (P67.6), CD123 (9F5), and CLL1 (REA431) were purchased from Biolegend®, BD Biosciences® and Miltenyi Biotec®, respectively. All antibodies were tested with their respective isotype controls. Cell surface staining was performed by incubating cells with specific antibodies for 30 min on ice in the presence of human TruStain FcX™. For all stains, dead cells were excluded from analysis by DAPI (Biolegend®) stain. All samples were acquired and analyzed with Attune® NxT flow cytometer (ThermoFisher Scientific®) and FlowJo® software (TreeStar).

For flow cytometric sorting, cells were stained with fluorochrome-conjugated antibodies followed by sorting with Moflow Astrios Cell Sorter (Beckman Coulter®).

CAR Constructs and Lentiviral Production

Second-generation CARs were constructed to target CD33, CD123, and CLL-1, with the exception of the anti-CD33 CAR-T used in CD33/CLL-1 multiplex cytotoxicity experiment. Each CAR consisted of an extracellular scFv antigen-binding domain, using CD8α signal peptide, CD8α hinge and transmembrane regions, the 4-1BB costimulatory domain, and the CD34 signaling domain. The anti-CD33 scFv sequence was obtained from clone P67.6 (Mylotarg®); the anti-CD123 scFv sequence from clone 32716; and the CLL-1 scFv sequence from clone 1075.7. The anti-CD33 and anti-CD123 CAR constructs uses a heavy-to-light orientation of the scFv, and the anti-CLL1 CAR construct uses a light-to-heavy orientation. The heavy and light chains were connected by (GGGS)3 linker. CAR cDNA sequences for each target were sub-cloned into the multiple cloning site of the pCDH-EF1α-MCS-T2A-GFP expression vector, and lentivirus was generated following the manufacturer's protocol (System Biosciences®). Lentivirus can be generated by transient transfection of 293TN cells (System Biosciences®) using Lipofectamine™ 3000 (ThermoFisher®). The CAR construct was generated by cloning the light and heavy chain of anti-CD33 scFv (clone My96), to the CD8α hinge domain, the ICOS transmembrane domain, the ICOS signaling domain, the 4-1BB signaling domain and the CD3ξ signaling domain into the lentiviral plasmid pHIV-Zsgreen.

CAR Transduction and Expansion

Human primary T cells were isolated from Leuko Pak (Stem Cell Technologies™) by magnetic bead separation using anti-CD4 and anti-CD8 microbeads according to the manufacturer's protocol (Stem Cell Technologies™). Purified CD4+ and CD8+ T cells were mixed 1:1, and activated using anti-CD3/CD28 coupled Dynabeads™ (Thermo Fisher®) at a 1:1 bead to cell ratio. T cell culture media used was CTS™ Optimizer™ T cell expansion media supplemented with immune cell serum replacement, L-Glutamine and GlutaMAX™ (all purchased from Thermo Fisher®) and 100 IU/mL of IL-2 (Peprotech®). T cell transduction was performed 24 hours post activation by spinoculation in the presence of polybrene (Sigma®). CAR-T cells were cultured for 9 days prior to cryopreservation. Prior to all experiments, T cells were thawed and rested at 37° C. for 4-6 hours.

Flow Cytometry Based CAR-T Cytotoxicity Assay

The cytotoxicity of target cells was measured by comparing survival of target cells relative to the survival of negative control cells. For CD33/CD123 multiplex cytotoxicity assays, wildtype and CRISPR/Cas9 edited MOLM-13 cells were used as target cells, while wildtype and CRISPR/Cas9 edited HL60 cells were used as target cells for CD33/CLL-1 multiplex cytotoxicity assays. Wildtype Raji cell lines (ATCC®) were used as negative control for both experiments. Target cells and negative control cells were stained with CellTrace™ Violet (CTV) and CFSE (Thermo Fisher®), respectively, according to the manufacturer's instructions. After staining, target cells and negative control cells were mixed at 1:1.

Anti-CD33, CD123, or CLL1 CAR-T cells were used as effector T cells. Non-transduced T cells (mock CAR-T) were used as control. For the CARpool groups, appropriate CAR-T cells were mixed at 1:1. The effector T cells were co-cultured with the target cell/negative control cell mixture at a 1:1 effector to target ratio in duplicate. A group of target cell/negative control cell mixture alone without effector T cells was included as control. Cells were incubated at 37° C. for 24 hours before flow cytometric analysis. Propidium iodide (ThermoFisher®) was used as a viability dye. For the calculation of specific cell lysis, the fraction of live target cell to live negative control cell (termed target fraction) was used. Specific cell lysis was calculated as ((target fraction without effector cells–target fraction with effector cells)/(target fraction without effectors))×100%.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of treating a hematopoietic malignancy, comprising administering to a subject in need thereof:
   (a) a plurality of genetically engineered hematopoietic cells (HCs) comprising:
      (i) a genetically engineered gene encoding CD33 that is engineered to have reduced or eliminated expression of CD33, and
      (ii) a genetically engineered gene encoding CD123 that is engineered to have reduced or eliminated expression of CD123; and
   (b) a therapeutically effective amount of at least one agent comprising an anti-CD33 binding domain or an anti-CD123 binding domain;
   wherein the hematopoietic malignancy is acute myeloid leukemia (AML).

2. The method of claim 1, wherein the at least one agent comprises an anti-CD123 binding domain.

3. The method of claim 2, wherein the at least one agent comprises a T cell comprising a chimeric antigen receptor (CAR) comprising the anti-CD123 binding domain, or an antibody or fragment thereof comprising the anti-CD123 binding domain.

4. The method of claim 3, wherein the at least one agent further comprises an anti-CD33 binding domain.

5. The method of claim 4, wherein the at least one agent comprises a T cell comprising a CAR comprising the anti-CD33 binding domain, or an antibody or fragment thereof comprising the anti-CD33 binding domain.

6. The method of claim 1, wherein the genetically engineered gene encoding CD123 or CD33 comprises a frameshift mutation.

7. The method of claim 1, wherein the genetically engineered HCs are genetically engineered using a CRISPR system comprising a guide nucleic acid.

8. The method of claim 7, wherein the guide nucleic acid comprises a sequence according to SEQ ID NO: 67 or a complement thereof.

9. The method of claim 7, wherein the guide nucleic acid comprises a sequence according to SEQ ID NO: 135 or SEQ ID NO: 136 or a complement thereof.

10. The method of claim 2, wherein exon 3 of the genetically engineered gene encoding CD33 is genetically engineered.

11. The method of claim 1, wherein exon 5 or exon 6 of the genetically engineered gene encoding CD123 is genetically engineered.

12. The method of claim 1, wherein the plurality of genetically engineered HCs retains the capacity to differentiate normally compared to a population of HCs that are not genetically engineered.

13. The method of claim 1, wherein each cell of the plurality of genetically engineered HCs comprises the genetically engineered gene encoding CD33 and the genetically engineered gene encoding CD123.

14. The method of claim 1, wherein the plurality of genetically engineered HCs comprises HCs with reduced or no binding to the anti-CD33 binding domain and reduced or no binding to the anti-CD123 binding domain.

15. The method of claim 1, wherein the plurality of genetically engineered HCs is capable of expanding by at least 2-fold over 8 days in culture.

16. The method of claim 1, wherein the method further comprises providing HCs from a biological sample from the subject, and genetically engineering the HCs from the biological sample from the subject, thereby forming the plurality of genetically engineered HCs.

17. The method of claim 1, wherein the plurality of HCs comprises HCs obtained from a healthy donor, or descendants thereof.

18. A method of preparing a population of genetically engineered hematopoietic cells (HCs), the method comprising:
(a) providing a population of HCs obtained from a human subject, wherein the population of HCs or descendants thereof express CD33 and CD123; and
(b) genetically modifying the population of HCs such that
  (i) a gene encoding CD33 is engineered to have reduced or eliminated expression of CD33; and
  (ii) a gene encoding CD123 is engineered to have reduced or eliminated expression of CD123.

19. The method of claim 1, wherein the HCs are hematopoietic stem cells, hematopoietic progenitor cells, or a combination thereof.

20. The method of claim 1, wherein the genetically engineered gene encoding CD33 or CD123 is modified such that an exon is skipped; or wherein the genetically engineered gene encoding CD33 or CD123 comprises an indel mutation.

21. The method of claim 1, wherein the expression level of the genetically engineered gene encoding CD33 or CD123 is less than 50% of the expression level of the corresponding wild-type gene.

22. The method of claim 18, wherein the genetically engineered HCs are genetically engineered using a CRISPR system comprising a guide nucleic acid.

23. The method of claim 22, wherein the guide nucleic acid comprises a sequence according to SEQ ID NO: 67 or a complement thereof.

24. The method of claim 22, wherein the guide nucleic acid comprises a sequence according to SEQ ID NO: 135 or SEQ ID NO: 136 or a complement thereof.

25. The method of claim 18, wherein exon 3 of the genetically engineered gene encoding CD33 is genetically engineered.

26. The method of claim 18, wherein exon 5 or exon 6 of the genetically engineered gene encoding CD123 is genetically engineered.

27. The method of claim 18, wherein the population of genetically engineered HCs comprises HCs with reduced or no binding to at least one agent comprising an anti-CD33 binding domain and reduced or no binding to at least one agent comprising an anti-CD123 binding domain.

28. The method of claim 18, wherein the population of genetically engineered HCs retains the capacity to differentiate normally compared to a population of HCs that are not genetically engineered.

29. The method of claim 18, wherein the population of genetically engineered HCs is capable of engraftment.

30. The method of claim 18, wherein the HCs are hematopoietic stem cells, hematopoietic progenitor cells, or a combination thereof.

31. The method of claim 18, wherein the genetically engineered gene encoding CD33 or CD123 is modified such that an exon is skipped; or wherein the genetically engineered gene encoding CD33 or CD123 comprises an indel mutation.

* * * * *

SEQUENCE LISTING

```
<160> NUMBER OF SEQ ID NOS: 137

<210> SEQ ID NO 1
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 1

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125
```

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 2
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 2

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

```
Tyr Lys Ser Pro Gln Leu Ser Val His Val Thr Asp Leu Thr His Arg
    130                 135                 140
Pro Lys Ile Leu Ile Pro Gly Thr Leu Glu Pro Gly His Ser Lys Asn
145                 150                 155                 160
Leu Thr Cys Ser Val Ser Trp Ala Cys Glu Gln Gly Thr Pro Pro Ile
                165                 170                 175
Phe Ser Trp Leu Ser Ala Ala Pro Thr Ser Leu Gly Pro Arg Thr Thr
            180                 185                 190
His Ser Ser Val Leu Ile Ile Thr Pro Arg Pro Gln Asp His Gly Thr
        195                 200                 205
Asn Leu Thr Cys Gln Val Lys Phe Ala Gly Ala Gly Val Thr Thr Glu
    210                 215                 220
Arg Thr Ile Gln Leu Asn Val Thr Tyr Val Pro Gln Asn Pro Thr Thr
225                 230                 235                 240
Gly Ile Phe Pro Gly Asp Gly Thr Ala Arg Asn Asp Thr Arg Ala Gly
                245                 250                 255
Val Val His Gly Ala Ile Gly Gly Ala Gly Val Thr Ala Leu Leu Ala
            260                 265                 270
Leu Cys Leu Cys Leu Ile Phe Phe Ile Val Lys Thr His Arg Arg Lys
        275                 280                 285
Ala Ala Arg Thr Ala Val Gly Arg Asn Asp Thr His Pro Thr Thr Gly
    290                 295                 300
Ser Ala Ser Pro Lys His Gln Lys Lys Ser Lys Leu His Gly Pro Thr
305                 310                 315                 320
Glu Thr Ser Ser Cys Ser Gly Ala Ala Pro Thr Val Glu Met Asp Glu
                325                 330                 335
Glu Leu His Tyr Ala Ser Leu Asn Phe His Gly Met Asn Pro Ser Lys
            340                 345                 350
Asp Thr Ser Thr Glu Tyr Ser Glu Val Arg Thr Gln
        355                 360

<210> SEQ ID NO 3
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 3

Met Pro Leu Leu Leu Leu Pro Leu Leu Trp Ala Gly Ala Leu Ala
1               5                   10                  15
Met Asp Pro Asn Phe Trp Leu Gln Val Gln Glu Ser Val Thr Val Gln
                20                  25                  30
Glu Gly Leu Cys Val Leu Val Pro Cys Thr Phe Phe His Pro Val Pro
            35                  40                  45
Phe Phe Glu Lys Asn Ser Pro Val His Gly Tyr Trp Phe Arg Glu Gly
        50                  55                  60
Ala Ile Ile Ser Arg Asp Ser Pro Val Ala Thr Asn Lys Leu Asp Gln
65                  70                  75                  80
Glu Val Gln Glu Glu Thr Gln Gly Arg Phe Arg Leu Leu Gly Asp Pro
                85                  90                  95
Ser Arg Asn Asn Cys Ser Leu Ser Ile Val Asp Ala Arg Arg Arg Asp
            100                 105                 110
Asn Gly Ser Tyr Phe Phe Arg Met Glu Arg Gly Ser Thr Lys Tyr Ser
        115                 120                 125
```

```
Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Thr Ala Arg Asn Asp Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 4
<211> LENGTH: 359
<212> TYPE: PRT
<213> ORGANISM: Artificial sequence
<220> FEATURE:
<223> OTHER INFORMATION: Synthetic polypeptide

<400> SEQUENCE: 4

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125
```

```
Tyr Lys Ser Pro Gln Leu Ser Val His Val Thr Asp Leu Thr His Arg
    130                 135                 140
Pro Lys Ile Leu Ile Pro Gly Thr Leu Glu Pro Gly His Ser Lys Asn
145                 150                 155                 160
Leu Thr Cys Ser Val Ser Trp Ala Cys Glu Gln Gly Thr Pro Pro Ile
                165                 170                 175
Phe Ser Trp Leu Ser Ala Ala Pro Thr Ser Leu Gly Pro Arg Thr Thr
            180                 185                 190
His Ser Ser Val Leu Ile Ile Thr Pro Arg Pro Gln Asp His Gly Thr
        195                 200                 205
Asn Leu Thr Cys Gln Val Lys Phe Ala Gly Ala Gly Val Thr Thr Glu
    210                 215                 220
Arg Thr Ile Gln Leu Asn Val Thr Tyr Val Pro Gln Asn Pro Thr Thr
225                 230                 235                 240
Gly Ile Phe Pro Gly Asp Gly Ser Arg Ala Gly Val Val His Gly Ala
                245                 250                 255
Ile Gly Gly Ala Gly Val Thr Ala Leu Leu Ala Leu Cys Leu Cys Leu
            260                 265                 270
Ile Phe Phe Ile Val Lys Thr His Arg Arg Lys Ala Ala Arg Thr Ala
        275                 280                 285
Val Gly Arg Asn Asp Thr His Pro Thr Thr Gly Ser Ala Ser Pro Lys
    290                 295                 300
His Gln Lys Lys Ser Lys Leu His Gly Pro Thr Glu Thr Ser Ser Cys
305                 310                 315                 320
Ser Gly Ala Ala Pro Thr Val Glu Met Asp Glu Glu Leu His Tyr Ala
                325                 330                 335
Ser Leu Asn Phe His Gly Met Asn Pro Ser Lys Asp Thr Ser Thr Glu
            340                 345                 350
Tyr Ser Glu Val Arg Thr Gln
        355

<210> SEQ ID NO 5
<211> LENGTH: 359
<212> TYPE: PRT
<213> ORGANISM: Artificial sequence
<220> FEATURE:
<223> OTHER INFORMATION: Synthetic polypeptide

<400> SEQUENCE: 5

Met Pro Leu Leu Leu Leu Pro Leu Leu Trp Ala Gly Ala Leu Ala
1               5                   10                  15
Met Asp Pro Asn Phe Trp Leu Gln Val Gln Glu Ser Val Thr Val Gln
                20                  25                  30
Glu Gly Leu Cys Val Leu Val Pro Cys Thr Phe Phe His Pro Ile Pro
            35                  40                  45
Tyr Tyr Asp Lys Asn Ser Pro Val His Gly Tyr Trp Phe Arg Glu Gly
        50                  55                  60
Ala Ile Ile Ser Arg Asp Ser Pro Val Ala Thr Asn Lys Leu Asp Gln
65                  70                  75                  80
Glu Val Gln Glu Glu Thr Gln Gly Arg Phe Arg Leu Leu Gly Asp Pro
                85                  90                  95
Ser Arg Asn Asn Cys Ser Leu Ser Ile Val Asp Ala Arg Arg Arg Asp
            100                 105                 110
Asn Gly Ser Tyr Phe Phe Arg Met Glu Arg Gly Ser Thr Lys Tyr Ser
        115                 120                 125
```

```
Tyr Lys Ser Pro Gln Leu Ser Val His Val Thr Asp Leu Thr His Arg
    130                 135                 140
Pro Lys Ile Leu Ile Pro Gly Thr Leu Glu Pro Gly His Ser Lys Asn
145                 150                 155                 160
Leu Thr Cys Ser Val Ser Trp Ala Cys Glu Gln Gly Thr Pro Pro Ile
                165                 170                 175
Phe Ser Trp Leu Ser Ala Ala Pro Thr Ser Leu Gly Pro Arg Thr Thr
            180                 185                 190
His Ser Ser Val Leu Ile Ile Thr Pro Arg Pro Gln Asp His Gly Thr
        195                 200                 205
Asn Leu Thr Cys Gln Val Lys Phe Ala Gly Ala Gly Val Thr Thr Glu
    210                 215                 220
Arg Thr Ile Gln Leu Asn Val Thr Tyr Val Pro Gln Asn Pro Thr Thr
225                 230                 235                 240
Gly Ile Phe Pro Gly Asp Gly Ser Gly Ala Gly Val Val His Gly Ala
                245                 250                 255
Ile Gly Gly Ala Gly Val Thr Ala Leu Leu Ala Leu Cys Leu Cys Leu
            260                 265                 270
Ile Phe Phe Ile Val Lys Thr His Arg Arg Lys Ala Ala Arg Thr Ala
        275                 280                 285
Val Gly Arg Asn Asp Thr His Pro Thr Thr Gly Ser Ala Ser Pro Lys
    290                 295                 300
His Gln Lys Lys Ser Lys Leu His Gly Pro Thr Glu Thr Ser Ser Cys
305                 310                 315                 320
Ser Gly Ala Ala Pro Thr Val Glu Met Asp Glu Glu Leu His Tyr Ala
                325                 330                 335
Ser Leu Asn Phe His Gly Met Asn Pro Ser Lys Asp Thr Ser Thr Glu
            340                 345                 350
Tyr Ser Glu Val Arg Thr Gln
        355

<210> SEQ ID NO 6
<211> LENGTH: 359
<212> TYPE: PRT
<213> ORGANISM: Artificial sequence
<220> FEATURE:
<223> OTHER INFORMATION: Synthetic polypeptide

<400> SEQUENCE: 6

Met Pro Leu Leu Leu Leu Pro Leu Leu Trp Ala Gly Ala Leu Ala
1               5                   10                  15
Met Asp Pro Asn Phe Trp Leu Gln Val Gln Glu Ser Val Thr Val Gln
                20                  25                  30
Glu Gly Leu Cys Val Leu Val Pro Cys Thr Phe Phe His Pro Ile Asn
            35                  40                  45
Ser Pro Val His Gly Tyr Trp Phe Arg Glu Gly Ala Ile Ile Ser Arg
        50                  55                  60
Asp Ser Pro Val Ala Thr Asn Lys Leu Asp Gln Glu Val Gln Glu Glu
65                  70                  75                  80
Thr Gln Gly Arg Phe Arg Leu Leu Gly Asp Pro Ser Arg Asn Asn Cys
                85                  90                  95
Ser Leu Ser Ile Val Asp Ala Arg Arg Arg Asp Asn Gly Ser Tyr Phe
            100                 105                 110
Phe Arg Met Glu Arg Gly Ser Thr Lys Tyr Ser Tyr Lys Ser Pro Gln
        115                 120                 125
```

```
Leu Ser Val His Val Thr Asp Leu Thr His Arg Pro Lys Ile Leu Ile
    130                 135                 140

Pro Gly Thr Leu Glu Pro Gly His Ser Lys Asn Leu Thr Cys Ser Val
145                 150                 155                 160

Ser Trp Ala Cys Glu Gln Gly Thr Pro Pro Ile Phe Ser Trp Leu Ser
                165                 170                 175

Ala Ala Pro Thr Ser Leu Gly Pro Arg Thr Thr His Ser Ser Val Leu
            180                 185                 190

Ile Ile Thr Pro Arg Pro Gln Asp His Gly Thr Asn Leu Thr Cys Gln
        195                 200                 205

Val Lys Phe Ala Gly Ala Gly Val Thr Thr Glu Arg Thr Ile Gln Leu
    210                 215                 220

Asn Val Thr Tyr Val Pro Gln Asn Pro Thr Thr Gly Ile Phe Pro Gly
225                 230                 235                 240

Asp Gly Ser Gly Lys Gln Glu Thr Arg Ala Gly Val Val His Gly Ala
                245                 250                 255

Ile Gly Gly Ala Gly Val Thr Ala Leu Leu Ala Leu Cys Leu Cys Leu
            260                 265                 270

Ile Phe Phe Ile Val Lys Thr His Arg Arg Lys Ala Ala Arg Thr Ala
        275                 280                 285

Val Gly Arg Asn Asp Thr His Pro Thr Thr Gly Ser Ala Ser Pro Lys
    290                 295                 300

His Gln Lys Lys Ser Lys Leu His Gly Pro Thr Glu Thr Ser Ser Cys
305                 310                 315                 320

Ser Gly Ala Ala Pro Thr Val Glu Met Asp Glu Glu Leu His Tyr Ala
                325                 330                 335

Ser Leu Asn Phe His Gly Met Asn Pro Ser Lys Asp Thr Ser Thr Glu
            340                 345                 350

Tyr Ser Glu Val Arg Thr Gln
        355

<210> SEQ ID NO 7
<211> LENGTH: 359
<212> TYPE: PRT
<213> ORGANISM: Artificial sequence
<220> FEATURE:
<223> OTHER INFORMATION: Synthetic polypeptide

<400> SEQUENCE: 7

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125
```

```
                                    -continued

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gly Val Val His Gly Ala
                245                 250                 255

Ile Gly Gly Ala Gly Val Thr Ala Leu Leu Ala Leu Cys Leu Cys Leu
            260                 265                 270

Ile Phe Phe Ile Val Lys Thr His Arg Arg Lys Ala Ala Arg Thr Ala
        275                 280                 285

Val Gly Arg Asn Asp Thr His Pro Thr Thr Gly Ser Ala Ser Pro Lys
290                 295                 300

His Gln Lys Lys Ser Lys Leu His Gly Pro Thr Glu Thr Ser Ser Cys
305                 310                 315                 320

Ser Gly Ala Ala Pro Thr Val Glu Met Asp Glu Glu Leu His Tyr Ala
                325                 330                 335

Ser Leu Asn Phe His Gly Met Asn Pro Ser Lys Asp Thr Ser Thr Glu
            340                 345                 350

Tyr Ser Glu Val Arg Thr Gln
        355

<210> SEQ ID NO 8
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 8

Ser Gly Lys Gln Glu
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 9

Ile Pro Tyr Tyr Asp
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic polypeptide
```

```
<400> SEQUENCE: 10

Gly Lys Gln Glu Thr
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 11

Lys Gln Glu Thr Arg
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 12

Pro Tyr Tyr Asp Lys
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 13

Gln Glu Thr Arg Ala
1               5

<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 14
gaggctggaa acttgagttg                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 15
gagggtaagt tactcagcca                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 16
aaattcagga aagggttgga                                              20
```

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 17
aagggttgga aggactctgc                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 18
agcagaggac tccaaaagct                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 19
cacaccaggt tatagagcag                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 20
ctgctctata acctggtgtg                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 21
acctggtgtg aggagtcggg                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 22
cacagcgtta tctccctctg                                              20

<210> SEQ ID NO 23
<211> LENGTH: 20
<212> TYPE: DNA
<213> ORGANISM: Artificial sequence
<220> FEATURE:

<223> OTHER INFORMATION: Synthetic polynucleotide

<400> SEQUENCE: 23
cggacctctt ctgtccatgg                                          20

<210> SEQ ID NO 24
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 24
ccatggacag aagaggtccg                                          20

<210> SEQ ID NO 25
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 25
gggcgaaact cggagctagg                                          20

<210> SEQ ID NO 26
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 26
gctaggtggg cagactcctg                                          20

<210> SEQ ID NO 27
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 27
gctgtgggga gagggttgt                                           20

<210> SEQ ID NO 28
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 28
ctgtggggag aggggttgtc                                          20

<210> SEQ ID NO 29
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 29
tggggaaacg agggtcagct                                          20

```
<210> SEQ ID NO 30
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 30
gggcccctgt ggggaaacga                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 31
agggcccctg tggggaaacg                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 32
gctgaccctc gtttccccac                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 33
ctgaccctcg tttccccaca                                               20

<210> SEQ ID NO 34
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 34
tgaccctcgt ttccccacag                                               20

<210> SEQ ID NO 35
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 35
ccatagccag ggcccctgtg                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic polynucleotide
```

```
<400> SEQUENCE: 36
gcatgtgaca ggtgaggcac                                          20

<210> SEQ ID NO 37
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 37
tgaggcacag gcttcagaag                                          20

<210> SEQ ID NO 38
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 38
aggcttcaga agtggccgca                                          20

<210> SEQ ID NO 39
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 39
ggcttcagaa gtggccgcaa                                          20

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 40
gtacccatga acttcccttg                                          20

<210> SEQ ID NO 41
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 41
gtggccgcaa gggaagttca                                          20

<210> SEQ ID NO 42
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 42
tggccgcaag ggaagttcat                                          20

<210> SEQ ID NO 43
<211> LENGTH: 20
```

```
<212> TYPE: DNA
<213> ORGANISM: Artificial sequence
<220> FEATURE:
<223> OTHER INFORMATION: Synthetic polynucleotide

<400> SEQUENCE: 43
ggaagttcat gggtactgca                                            20

<210> SEQ ID NO 44
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 44
ttcatgggta ctgcagggca                                            20

<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 45
ctaaacccct cccagtacca                                            20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 46
cactcacctg cccacagcag                                            20

<210> SEQ ID NO 47
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 47
ccctgctgtg ggcaggtgag                                            20

<210> SEQ ID NO 48
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 48
tgggcaggtg agtggctgtg                                            20

<210> SEQ ID NO 49
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 49
```

```
ggtgagtggc tgtggggaga                                              20
```

<210> SEQ ID NO 50
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 50

```
gtgagtggct gtggggagag                                              20
```

<210> SEQ ID NO 51
<211> LENGTH: 556
<212> TYPE: PRT
<213> ORGANISM: Artificial sequence
<220> FEATURE:
<223> OTHER INFORMATION: Synthetic polypeptide

<400> SEQUENCE: 51

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
```

```
            290                 295                 300
Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
                355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 52
<211> LENGTH: 468
<212> TYPE: PRT
<213> ORGANISM: Artificial sequence
<220> FEATURE:
<223> OTHER INFORMATION: Synthetic polypeptide

<400> SEQUENCE: 52

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Gly Glu Leu
                20                  25                  30

Phe Arg Trp Asn Val Ser Asp Leu Gly Gly Leu Gly Cys Gly Leu Lys
            35                  40                  45

Asn Arg Ser Ser Glu Gly Pro Ser Ser Pro Ser Gly Lys Leu Met Ser
        50                  55                  60

Pro Lys Leu Tyr Val Trp Ala Lys Asp Arg Pro Glu Ile Trp Glu Gly
65                  70                  75                  80

Glu Pro Pro Cys Leu Pro Pro Arg Asp Ser Leu Asn Gln Ser Leu Ser
                85                  90                  95

Gln Asp Leu Thr Met Ala Pro Gly Ser Thr Leu Trp Leu Ser Cys Gly
```

100                 105                 110
Val Pro Asp Ser Val Ser Arg Gly Pro Leu Ser Trp Thr His Val
                    115                 120                 125
His Pro Lys Gly Pro Lys Ser Leu Leu Ser Leu Glu Leu Lys Asp Asp
        130                 135                 140
Arg Pro Ala Arg Asp Met Trp Val Met Glu Thr Gly Leu Leu Leu Pro
145                 150                 155                 160
Arg Ala Thr Ala Gln Asp Ala Gly Lys Tyr Tyr Cys His Arg Gly Asn
                    165                 170                 175
Leu Thr Met Ser Phe His Leu Glu Ile Thr Ala Arg Pro Val Leu Trp
                180                 185                 190
His Trp Leu Leu Arg Thr Gly Gly Trp Lys Val Ser Ala Val Thr Leu
                195                 200                 205
Ala Tyr Leu Ile Phe Cys Leu Cys Ser Leu Val Gly Ile Leu His Leu
                210                 215                 220
Gln Arg Ala Leu Val Leu Arg Arg Lys Arg Lys Arg Met Thr Asp Pro
225                 230                 235                 240
Thr Arg Arg Phe Phe Lys Val Thr Pro Pro Pro Gly Ser Gly Pro Gln
                    245                 250                 255
Asn Gln Tyr Gly Asn Val Leu Ser Leu Pro Thr Pro Thr Ser Gly Leu
                    260                 265                 270
Gly Arg Ala Gln Arg Trp Ala Ala Gly Leu Gly Gly Thr Ala Pro Ser
                    275                 280                 285
Tyr Gly Asn Pro Ser Ser Asp Val Gln Ala Asp Gly Ala Leu Gly Ser
                    290                 295                 300
Arg Ser Pro Pro Gly Val Gly Pro Glu Glu Glu Gly Glu Gly Tyr
305                 310                 315                 320
Glu Glu Pro Asp Ser Glu Glu Asp Ser Glu Phe Tyr Glu Asn Asp Ser
                    325                 330                 335
Asn Leu Gly Gln Asp Gln Leu Ser Gln Asp Gly Ser Gly Tyr Glu Asn
                    340                 345                 350
Pro Glu Asp Glu Pro Leu Gly Pro Glu Asp Glu Asp Ser Phe Ser Asn
                    355                 360                 365
Ala Glu Ser Tyr Glu Asn Glu Asp Glu Glu Leu Thr Gln Pro Val Ala
                    370                 375                 380
Arg Thr Met Asp Phe Leu Ser Pro His Gly Ser Ala Trp Asp Pro Ser
385                 390                 395                 400
Arg Glu Ala Thr Ser Leu Ala Gly Ser Gln Ser Tyr Glu Asp Met Arg
                    405                 410                 415
Gly Ile Leu Tyr Ala Ala Pro Gln Leu Arg Ser Ile Arg Gly Gln Pro
                    420                 425                 430
Gly Pro Asn His Glu Glu Asp Ala Asp Ser Tyr Glu Asn Met Asp Asn
                    435                 440                 445
Pro Asp Gly Pro Asp Pro Ala Trp Gly Gly Gly Arg Met Gly Thr
450                 455                 460
Trp Ser Thr Arg
465

<210> SEQ ID NO 53
<211> LENGTH: 43
<212> TYPE: DNA
<213> ORGANISM: Artificial sequence
<220> FEATURE:
<223> OTHER INFORMATION: Synthetic polynucleotide

<400> SEQUENCE: 53
ccggctcctc cactcccagc ccgcggccac aatggagctg gag       43

<210> SEQ ID NO 54
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 54
ccggctcctc cactcccagc tccgcggcca caatggagct ggag       44

<210> SEQ ID NO 55
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 55
gcggccacaa tggagctgga g       21

<210> SEQ ID NO 56
<211> LENGTH: 237
<212> TYPE: PRT
<213> ORGANISM: Artificial sequence
<220> FEATURE:
<223> OTHER INFORMATION: Synthetic polypeptide

<400> SEQUENCE: 56

```
Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220
```

```
Lys Asp Thr Ser Thr Glu Tyr Ser Glu Val Arg Thr Gln
225                 230                 235

<210> SEQ ID NO 57
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 57

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Val Arg
305                 310

<210> SEQ ID NO 58
<211> LENGTH: 183
<212> TYPE: PRT
<213> ORGANISM: Artificial sequence
```

```
<220> FEATURE:
<223> OTHER INFORMATION: Synthetic polypeptide

<400> SEQUENCE: 58

Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Val Arg
            180

<210> SEQ ID NO 59
<211> LENGTH: 53
<212> TYPE: DNA
<213> ORGANISM: Artificial sequence
<220> FEATURE:
<223> OTHER INFORMATION: Synthetic polynucleotide

<400> SEQUENCE: 59
ccctgctgtg ggcaggtgag tggctgtggg gagcagggct gggatgggac cct            53

<210> SEQ ID NO 60
<211> LENGTH: 52
<212> TYPE: DNA
<213> ORGANISM: Artificial sequence
<220> FEATURE:
<223> OTHER INFORMATION: Synthetic polynucleotide

<400> SEQUENCE: 60
ccctgctgtg ggcaggtgaa tggctgcggg gagcagggct gggatgggac cc             52

<210> SEQ ID NO 61
<211> LENGTH: 56
<212> TYPE: DNA
<213> ORGANISM: Artificial sequence
<220> FEATURE:
<223> OTHER INFORMATION: Synthetic polynucleotide

<400> SEQUENCE: 61
ccctgctgtg ggcaggtgag tggctgtggg caggtgagtg gctgggatgg gaccct         56

<210> SEQ ID NO 62
```

```
<211> LENGTH: 61
<212> TYPE: DNA
<213> ORGANISM: Artificial sequence
<220> FEATURE:
<223> OTHER INFORMATION: Synthetic polynucleotide

<400> SEQUENCE: 62
ccctgctgtg ggcaggtgaa tggctgcggg gtactgcagg gcagggctgg gatgggaccc    60
t                                                                   61

<210> SEQ ID NO 63
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 63
ccctgctgtg ggcaggtgaa tggctggatg ggaccct                             37

<210> SEQ ID NO 64
<211> LENGTH: 46
<212> TYPE: DNA
<213> ORGANISM: Artificial sequence
<220> FEATURE:
<223> OTHER INFORMATION: Synthetic polynucleotide

<400> SEQUENCE: 64
ccctgctgtg ggcaggtgaa tggctgcagg gctgggatgg gaccct                   46

<210> SEQ ID NO 65
<211> LENGTH: 27
<212> TYPE: DNA
<213> ORGANISM: Artificial sequence
<220> FEATURE:
<223> OTHER INFORMATION: Synthetic polynucleotide

<400> SEQUENCE: 65
ccctgctgtg ggctgggatg ggaccct                                        27

<210> SEQ ID NO 66
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 66
cacagcgtta tctccctctg                                                20

<210> SEQ ID NO 67
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 67
ccccaggact actcactcct                                                20

<210> SEQ ID NO 68

<400> SEQUENCE: 68

000
```

-continued

<210> SEQ ID NO 69
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 69
ggaacctcta gtggtgaagg                                        20

<210> SEQ ID NO 70
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 70
cacagcgtta tctccctctg                                        20

<210> SEQ ID NO 71
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 71
ggacagggag agataagaca                                        20

<210> SEQ ID NO 72
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 72
aggtagagtt tctctcaact                                        20

<210> SEQ ID NO 73
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 73

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110
```

```
Val Asn Val Glu Gly Ser Gly Glu Leu Phe Arg Trp Asn Val Ser Asp
            115                 120                 125
Leu Gly Gly Leu Gly Cys Gly Leu Lys Asn Arg Ser Ser Glu Gly Pro
        130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Val Leu Trp His Trp Leu
            180                 185                 190
Leu Arg Thr Gly Gly Trp Lys Val Ser Ala Val Thr Leu Ala Tyr Leu
        195                 200                 205
Ile Phe Cys Leu Cys Ser Leu Val Gly Ile Leu His Leu Gln Arg Ala
    210                 215                 220
Leu Val Leu Arg Arg Lys Arg Lys Arg Met Thr Asp Pro Thr Arg Arg
225                 230                 235                 240
Phe Phe Lys Val Thr Pro Pro Gly Ser Gly Pro Gln Asn Gln Tyr
                245                 250                 255
Gly Asn Val Leu Ser Leu Pro Thr Pro Thr Ser Gly Leu Gly Arg Ala
            260                 265                 270
Gln Arg Trp Ala Ala Gly Leu Gly Gly Thr Ala Pro Ser Tyr Gly Asn
        275                 280                 285
Pro Ser Ser Asp Val Gln Ala Asp Gly Ala Leu Gly Ser Arg Ser Pro
290                 295                 300
Pro Gly Val Gly Pro Glu Glu Glu Gly Glu Gly Tyr Glu Glu Pro
305                 310                 315                 320
Asp Ser Glu Glu Asp Ser Glu Phe Tyr Glu Asn Asp Ser Asn Leu Gly
                325                 330                 335
Gln Asp Gln Leu Ser Gln Asp Gly Ser Gly Tyr Glu Asn Pro Glu Asp
            340                 345                 350
Glu Pro Leu Gly Pro Glu Asp Glu Asp Ser Phe Ser Asn Ala Glu Ser
        355                 360                 365
Tyr Glu Asn Glu Asp Glu Glu Leu Thr Gln Pro Val Ala Arg Thr Met
370                 375                 380
Asp Phe Leu Ser Pro His Gly Ser Ala Trp Asp Pro Ser Arg Glu Ala
385                 390                 395                 400
Thr Ser Leu Ala Gly Ser Gln Ser Tyr Glu Asp Met Arg Gly Ile Leu
                405                 410                 415
Tyr Ala Ala Pro Gln Leu Arg Ser Ile Arg Gly Gln Pro Gly Pro Asn
            420                 425                 430
His Glu Glu Asp Ala Asp Ser Tyr Glu Asn Met Asp Asn Pro Asp Gly
        435                 440                 445
Pro Asp Pro Ala Trp Gly Gly Gly Gly Arg Met Gly Thr Trp Ser Thr
450                 455                 460
Arg
465

<210> SEQ ID NO 74
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(27)
```

<223> OTHER INFORMATION: n is a, c, g, or t

<400> SEQUENCE: 74
cacctctctc cctctctctc cacagnnagg gagataacgc tgtgctgcag tgcctcaagg    60
ggacctcaga tggcc    75

<210> SEQ ID NO 75
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(28)
<223> OTHER INFORMATION: n is a, c, g, or t

<400> SEQUENCE: 75
cacctctctc cctctctctc cacagnnnag ggagataacg ctgtgctgca gtgcctcaag    60
gggacctcag atggc    75

<210> SEQ ID NO 76
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(29)
<223> OTHER INFORMATION: n is a, c, g, or t

<400> SEQUENCE: 76
cacctctctc cctctctctc cacagnnnna gggagataac gctgtgctgc agtgcctcaa    60
ggggacctca gatgg    75

<210> SEQ ID NO 77
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(26)
<223> OTHER INFORMATION: n is a, c, g, or t

<400> SEQUENCE: 77
cacctctctc cctctctctc cacagnaggg agataacgct gtgctgcagt gcctcaaggg    60
gacctcagat ggccc    75

<210> SEQ ID NO 78
<211> LENGTH: 73
<212> TYPE: DNA
<213> ORGANISM: Artificial sequence
<220> FEATURE:
<223> OTHER INFORMATION: Synthetic polynucleotide

<400> SEQUENCE: 78
cacctctctc cctctctctc cacagggaga taacgctgtg ctgcagtgcc tcaaggggac    60
ctcagatggc ccc    73

<210> SEQ ID NO 79
<211> LENGTH: 69

```
<212> TYPE: DNA
<213> ORGANISM: Artificial sequence
<220> FEATURE:
<223> OTHER INFORMATION: Synthetic polynucleotide

<400> SEQUENCE: 79
cacctctctc cctctctctc cacagataac gctgtgctgc agtgcctcaa ggggacctca    60
gatggcccc                                                           69

<210> SEQ ID NO 80
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(30)
<223> OTHER INFORMATION: n is a, c, g, or t

<400> SEQUENCE: 80
cacctctctc cctctctctc cacagnnnnn agggagataa cgctgtgctg cagtgcctca    60
aggggacctc agatg                                                    75

<210> SEQ ID NO 81
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(31)
<223> OTHER INFORMATION: n is a, c, g, or t

<400> SEQUENCE: 81
cacctctctc cctctctctc cacagnnnnn nagggagata acgctgtgct gcagtgcctc    60
aaggggacct cagat                                                    75

<210> SEQ ID NO 82
<211> LENGTH: 71
<212> TYPE: DNA
<213> ORGANISM: Artificial sequence
<220> FEATURE:
<223> OTHER INFORMATION: Synthetic polynucleotide

<400> SEQUENCE: 82
cacctctctc cctctctctc cacagagata acgctgtgct gcagtgcctc aaggggacct    60
cagatggccc c                                                        71

<210> SEQ ID NO 83
<211> LENGTH: 74
<212> TYPE: DNA
<213> ORGANISM: Artificial sequence
<220> FEATURE:
<223> OTHER INFORMATION: Synthetic polynucleotide

<400> SEQUENCE: 83
cacctctctc cctctctctc cacaggggag ataacgctgt gctgcagtgc ctcaagggga    60
cctcagatgg cccc                                                     74

<210> SEQ ID NO 84
<211> LENGTH: 75
<212> TYPE: DNA
```

```
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(32)
<223> OTHER INFORMATION: n is a, c, g, or t

<400> SEQUENCE: 84
cacctctctc cctctctctc cacagnnnnn nnagggagat aacgctgtgc tgcagtgcct     60
caaggggacc tcaga                                                     75

<210> SEQ ID NO 85
<211> LENGTH: 74
<212> TYPE: DNA
<213> ORGANISM: Artificial sequence
<220> FEATURE:
<223> OTHER INFORMATION: Synthetic polynucleotide

<400> SEQUENCE: 85
cacctctctc cctctctctc cacaagggag ataacgctgt gctgcagtgc ctcaagggga     60
cctcagatgg cccc                                                      74

<210> SEQ ID NO 86
<211> LENGTH: 72
<212> TYPE: DNA
<213> ORGANISM: Artificial sequence
<220> FEATURE:
<223> OTHER INFORMATION: Synthetic polynucleotide

<400> SEQUENCE: 86
cacctctctc cctctctctc cacaggagat aacgctgtgc tgcagtgcct caaggggacc     60
tcagatggcc cc                                                        72

<210> SEQ ID NO 87
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(27)
<223> OTHER INFORMATION: n is a, c, g, or t

<400> SEQUENCE: 87
cgtggggtga ttatgagcac cgaggnnagt gagtagtcct ggggcccagg gaggtggggg     60
cagctgacaa ccagg                                                     75

<210> SEQ ID NO 88
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(26)
<223> OTHER INFORMATION: n is a, c, g, or t

<400> SEQUENCE: 88
cgtggggtga ttatgagcac cgaggnagtg agtagtcctg ggcccaggg aggtggggc      60 agctgacaac cagga                                                     75
```

```
<210> SEQ ID NO 89
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(28)
<223> OTHER INFORMATION: n is a, c, g, or t

<400> SEQUENCE: 89
cgtggggtga ttatgagcac cgaggnnnag tgagtagtcc tggggcccag ggaggtgggg      60
gcagctgaca accag                                                      75

<210> SEQ ID NO 90
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(29)
<223> OTHER INFORMATION: n is a, c, g, or t

<400> SEQUENCE: 90
cgtggggtga ttatgagcac cgaggnnnna gtgagtagtc ctggggccca gggaggtggg      60
ggcagctgac aacca                                                      75

<210> SEQ ID NO 91
<211> LENGTH: 75
<212> TYPE: DNA
<213> ORGANISM: Artificial sequence
<220> FEATURE:
<223> OTHER INFORMATION: Synthetic polynucleotide

<400> SEQUENCE: 91
cgtggggtga ttatgagcac cgaggagtga gtagtcctgg ggcccaggga ggtggggca      60 gctgacaacc aggag                                                      75

<210> SEQ ID NO 92
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(30)
<223> OTHER INFORMATION: n is a, c, g, or t

<400> SEQUENCE: 92
cgtggggtga ttatgagcac cgaggnnnnn agtgagtagt cctggggccc agggaggtgg      60
gggcagctga caacc                                                      75

<210> SEQ ID NO 93
<211> LENGTH: 68
<212> TYPE: DNA
<213> ORGANISM: Artificial sequence
<220> FEATURE:
<223> OTHER INFORMATION: Synthetic polynucleotide

<400> SEQUENCE: 93
cgtggggtga ttatgagcac cgagtagtcc tggggcccag ggaggtgggg gcagctgaca      60
``` accaggag 68

<210> SEQ ID NO 94
<211> LENGTH: 74
<212> TYPE: DNA
<213> ORGANISM: Artificial sequence
<220> FEATURE:
<223> OTHER INFORMATION: Synthetic polynucleotide

<400> SEQUENCE: 94
cgtggggtga ttatgagcac cgagggtgag tagtcctggg gcccaggag gtgggggcag    60 ctgacaacca ggag                                                    74

<210> SEQ ID NO 95
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(31)
<223> OTHER INFORMATION: n is a, c, g, or t

<400> SEQUENCE: 95
cgtggggtga ttatgagcac cgaggnnnnn nagtgagtag tcctgggcc caggaggtg     60 ggggcagctg acaac                                                   75

<210> SEQ ID NO 96
<211> LENGTH: 68
<212> TYPE: DNA
<213> ORGANISM: Artificial sequence
<220> FEATURE:
<223> OTHER INFORMATION: Synthetic polynucleotide

<400> SEQUENCE: 96
cgtggggtga ttatgagcac tgagtagtcc tggggcccag ggaggtgggg gcagctgaca    60
accaggag                                                           68

<210> SEQ ID NO 97
<211> LENGTH: 73
<212> TYPE: DNA
<213> ORGANISM: Artificial sequence
<220> FEATURE:
<223> OTHER INFORMATION: Synthetic polynucleotide

<400> SEQUENCE: 97
cgtggggtga ttatgagcac cgaggtgagt agtcctgggg cccagggagg tggggcagc    60 tgacaaccag gag                                                     73

<210> SEQ ID NO 98
<211> LENGTH: 68
<212> TYPE: DNA
<213> ORGANISM: Artificial sequence
<220> FEATURE:
<223> OTHER INFORMATION: Synthetic polynucleotide

<400> SEQUENCE: 98
cgtggggtga ttatgagcac cgaggagtcc tggggcccag ggaggtgggg gcagctgaca    60
accaggag                                                           68

<210> SEQ ID NO 99
<211> LENGTH: 72

```
<212> TYPE: DNA
<213> ORGANISM: Artificial sequence
<220> FEATURE:
<223> OTHER INFORMATION: Synthetic polynucleotide

<400> SEQUENCE: 99 cgtgggtga ttatgagcac cgagggagta gtcctggggc ccagggaggt ggggggcagct    60 gacaaccagg ag                                                        72

<210> SEQ ID NO 100
<211> LENGTH: 75
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (26)..(32)
<223> OTHER INFORMATION: n is a, c, g, or t

<400> SEQUENCE: 100 cgtgggtga ttatgagcac cgaggnnnnn nnagtgagta gtcctggggc ccagggaggt    60 ggggggcagct gacaa                                                    75

<210> SEQ ID NO 101
<211> LENGTH: 61
<212> TYPE: DNA
<213> ORGANISM: Artificial sequence
<220> FEATURE:
<223> OTHER INFORMATION: Synthetic polynucleotide

<400> SEQUENCE: 101
cgtggggtga ttgtgagtag tcctggggcc cagggaggtg ggggcagctg acaaccagga    60
g                                                                    61

<210> SEQ ID NO 102
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 102
gtgagtggct gtggggagag                                                20

<210> SEQ ID NO 103
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 103
ttcatgggta ctgcagggca                                                20

<210> SEQ ID NO 104
<211> LENGTH: 6
<212> TYPE: DNA
<213> ORGANISM: Staphylococcus aureus
<220> FEATURE:
<221> NAME/KEY: misc_feature
<222> LOCATION: (1)..(2)
<223> OTHER INFORMATION: n is a, c, g, or t

<400> SEQUENCE: 104
```

```
nngrrt                                                          6

<210> SEQ ID NO 105
<211> LENGTH: 8
<212> TYPE: DNA
<213> ORGANISM: Neisseria meningitidis
<220> FEATURE:
<221> NAME/KEY: misc_feature
<222> LOCATION: (1)..(4)
<223> OTHER INFORMATION: n is a, c, g, or t

<400> SEQUENCE: 105 nnnngatt                                                        8

<210> SEQ ID NO 106
<211> LENGTH: 8
<212> TYPE: DNA
<213> ORGANISM: Neisseria meningitidis
<220> FEATURE:
<221> NAME/KEY: misc_feature
<222> LOCATION: (1)..(4)
<223> OTHER INFORMATION: n is a, c, g, or t

<400> SEQUENCE: 106 nnnnghtt                                                        8

<210> SEQ ID NO 107
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 107 nnagaaw                                                         7

<210> SEQ ID NO 108
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 108 nggng                                                           5

<210> SEQ ID NO 109
<211> LENGTH: 6
<212> TYPE: DNA
<213> ORGANISM: Treponema denticola
<220> FEATURE:
<221> NAME/KEY: misc_feature
<222> LOCATION: (1)..(1)
<223> OTHER INFORMATION: n is a, c, g, or t

<400> SEQUENCE: 109 naaaac                                                          6

<210> SEQ ID NO 110
<211> LENGTH: 3
```

```
<212> TYPE: DNA
<213> ORGANISM: Streptococcus canis
<220> FEATURE:
<221> NAME/KEY: misc_feature
<222> LOCATION: (1)..(2)
<223> OTHER INFORMATION: n is a, c, g, or t

<400> SEQUENCE: 110 nng                                                                 3

<210> SEQ ID NO 111
<211> LENGTH: 8
<212> TYPE: DNA
<213> ORGANISM: Campylobacter jejuni
<220> FEATURE:
<221> NAME/KEY: misc_feature
<222> LOCATION: (1)..(4)
<223> OTHER INFORMATION: n is a, c, g, or t

<400> SEQUENCE: 111 nnnnacac                                                            8

<210> SEQ ID NO 112
<211> LENGTH: 4
<212> TYPE: DNA
<213> ORGANISM: Unknown
<220> FEATURE:
<223> OTHER INFORMATION: PAM sequence
<220> FEATURE:
<221> NAME/KEY: misc_feature
<222> LOCATION: (4)..(4)
<223> OTHER INFORMATION: n is a, c, g, or t

<400> SEQUENCE: 112 tttn                                                                4

<210> SEQ ID NO 113
<211> LENGTH: 5
<212> TYPE: DNA
<213> ORGANISM: Eubacterium rectale
<220> FEATURE:
<221> NAME/KEY: misc_feature
<222> LOCATION: (5)..(5)
<223> OTHER INFORMATION: n is a, c, g, or t

<400> SEQUENCE: 113 ytttn                                                               5

<210> SEQ ID NO 114
<211> LENGTH: 4
<212> TYPE: DNA
<213> ORGANISM: Unknown
<220> FEATURE:
<223> OTHER INFORMATION: PAM sequence
<220> FEATURE:
<221> NAME/KEY: misc_feature
<222> LOCATION: (1)..(1)
<223> OTHER INFORMATION: n is a, c, g, or t

<400> SEQUENCE: 114 ngag                                                                4

<210> SEQ ID NO 115
<211> LENGTH: 4
<212> TYPE: DNA
<213> ORGANISM: Unknown
<220> FEATURE:
<223> OTHER INFORMATION: PAM sequence
<220> FEATURE:
```

```
<221> NAME/KEY: misc_feature
<222> LOCATION: (1)..(1)
<223> OTHER INFORMATION: n is a, c, g, or t

<400> SEQUENCE: 115 ngcg                                                                         4

<210> SEQ ID NO 116
<211> LENGTH: 6
<212> TYPE: DNA
<213> ORGANISM: Unknown
<220> FEATURE:
<223> OTHER INFORMATION: PAM sequence
<220> FEATURE:
<221> NAME/KEY: misc_feature
<222> LOCATION: (1)..(3)
<223> OTHER INFORMATION: n is a, c, g, or t

<400> SEQUENCE: 116 nnnrrt                                                                       6

<210> SEQ ID NO 117
<211> LENGTH: 1674
<212> TYPE: RNA
<213> ORGANISM: Homo sapiens

<400> SEQUENCE: 117
augccaccuc ucgccuccu  cuucuucccuc cucuuccuca  cccccaugga  agucaggccc           60
gaggaaccuc uaguggugaa gguggaagag ggagauaacg cugugcugca gugccucaag            120
gggaccucag auggccccac ucagcagcug accggucuc  gggagucccc  gcuuaaaccc           180
uucuuaaaac ucagccuggg gcugccaggc cugggaaucc acaugaggcc ccuggccauc            240
uggcuuuuca ucuucaacgu cucucaacag auggggggcu ucuaccugug ccagccgggg            300 cccccucug  agaaggccug gcagccuggc uggacaguca augguggaggg cagcggggag            360 cuguccggu  ggaauguuuc ggaccuaggu ggccugggcu guggccugaa gaacaggucc            420
ucagagggcc ccagcucccc uuccgggaag ucaugagcc  ccaagcugua uguguggcc             480 aaagaccgcc cugagaucug ggaggagag  ccuccguguc ucccaccgag ggacagccug            540
aaccagagcc ucagccagga ccucaccaug gccccuggcu ccacacucug gcuguccugu            600 ggggucccc  cugacucugu guccaggggc ccccucuccu ggacccaugu gcaccccaag            660
gggccuaagu cauugcugag ccuagagcug aaggacgauc gcccggccag agauaugugg            720
guaauggaga cgggucuguu guugcccggg gccacagcuc aagacgcugg aaaguauuau            780
ugucaccgug gcaaccugac caugucauuc caccuggaga ucacugcucg gccaguacua            840
uggcacuggc ugcugaggac ugguggcugg aaggucucag cuguugacuuu ggcuuaucug            900 aucuucugcc uguguucccu ugugggcauu cuucaucuuc aaagagcccu gguccugagg            960
aggaaaagaa agcgaaugac ugaccccacc aggagauucu caaaguggac gccucccccca          1020 ggaagcgggc ccagaaacca guacgggaac gugcugcucuc uccccacacc caccucaggc          1080
cucggacgcg cccagcguug ggcgcaggc  cuggggggca cugccccguc uuauggaaac            1140
ccgagcagcg acguccaggc ggauggagcc uggggguccc ggagcccgcc gggaguggc             1200 ccagaagaag aggaaggggaa gggcuaugag gaaccugaca gugaggagga cuccgaguuc          1260
uaugagaacg acuccaaccu uggcaggac  cagcucuccc aggauggcag cggcuacgag            1320
aacccugagg augagccccu gggguccgag gaugaagacu ccuuccaag  cgcugagucu           1380 uaugagaacg aggaugaaga gcugacccag ccggucgcca ggacaaugga cuuccugagc          1440
```

-continued

| | |
|---|---|
| ccucaugggu cagccuggga ccccagccgg gaagcaaccu cccuggcagg gucccaguec | 1500 |
| uaugaggaua ugagaggaau ccuguaugca gcccccage uccgcuccau ucggggccag | 1560 |
| ccuggaccca aucaugagga agaugcagac ucuuaugaga acauggauaa ucccgauggg | 1620 |
| ccagacccag ccuggggagg aggggccgc augggcaccu ggagcaccag guga | 1674 |

<210> SEQ ID NO 118
<211> LENGTH: 1407
<212> TYPE: RNA
<213> ORGANISM: Artificial Sequence
<220> FEATURE:
<223> OTHER INFORMATION: Synthetic polynucleotide

<400> SEQUENCE: 118

| | |
|---|---|
| augccaccuc cucgccuccu cuucuuccuc cucuuccuca cccccaugga agucaggccc | 60 |
| gaggaaccuc uaguggugaa gguggaaggg gagcuguucc gguggaaugu uucggaccua | 120 |
| gguggccugg gcuguggccu gaagaacagg uccucagagg gccccagcuc cccuuccggg | 180 |
| aagcucauga gccccaagcu guaugugugg gccaaagacc gcccugagau cugggaggga | 240 |
| gagccuccgu gucucccacc gagggacagc cugaaccaga gccucagcca ggaccucacc | 300 |
| auggccccug gcuccacacu cuggcugucc ugugggguac ccccugacuc ugguccagg | 360 |
| ggccccucu ccuggaccca ugugcacccc aaggggccua agucauugcu gagccuagag | 420 |
| cugaaggacg aucgcccggc cagagauaug uggguaaugg agacggggucu guuguugccc | 480 |
| cgggccacag cucaagacgc uggaaaguau uauugucacc guggcaaccu gaccaugeca | 540 |
| uuccaccugg agaucacugc ucggccagua cuauggcacu ggcugcugag acugguggc | 600 |
| uggaaggucu cagcugugac uuuggcuuau cugaucuucu gccuguuuc ccuuguggc | 660 |
| auucuucauc uucaaagagc ccugguccug aggaggaaaa gaaagcgaau gacugacccc | 720 |
| accaggagau cuucaaaagu gacgccuccc caggaagcg ggcccagaa ccaguacggg | 780 |
| aacgucugu cucuccccac acccaccuca ggccucggac gcgcccagcg uugggccgca | 840 |
| ggccugggg gcacugcccc gucuuaugga aacccgagca gcgacgucca ggcggaugga | 900 |
| gccuugggu cccggagccc gccgggagug ggccagaag aagaggaagg ggagggcuau | 960 |
| gaggaaccug acagugagga ggacuccgag uucuaugaga acgacuccaa ccuugggcag | 1020 |
| gaccagcucu cccaggaugg cagcggcuac gagaacccug aggaugagcc ccuggguccu | 1080 |
| gaggaugaag acuccuucuc caacgcugag ucuuaugaga acgaggauga agagcugacc | 1140 |
| cagccggucg ccaggacaau ggacuuccug agcccucaug gucagccug gaccccagc | 1200 |
| cgggaagcaa ccucccuggc agggucccag uccuaugagg auaugagagg aauccuguau | 1260 |
| gcagccccc agcuccgcuc cauucgggc cagccuggac caaucauga ggaagaugca | 1320 |
| gacucuuaug agaacaugga uaaucccgau gggccagacc cagccuggg aggaggggc | 1380 |
| cgcaugggca ccuggagcac cagguga | 1407 |

<210> SEQ ID NO 119
<211> LENGTH: 1398
<212> TYPE: DNA
<213> ORGANISM: Artificial Sequence
<220> FEATURE:
<223> OTHER INFORMATION: Synthetic polynucleotide

<400> SEQUENCE: 119

| | |
|---|---|
| atgccacctc ctcgcctcct cttcttcctc ctcttcctca cccccatgga agtcaggccc | 60 |

```
gaggaacctc tagtggtgaa ggtggaagag ggagataacg ctgtgctgca gtgcctcaag    120
gggacctcag atggcccac tcagcagctg acctggtctc gggagtcccc gcttaaaccc    180
ttcttaaaac tcagcctggg gctgccaggc ctgggaatcc acatgaggcc cctggccatc    240
tggcttttca tcttcaacgt ctctcaacag atgggggct tctacctgtg ccagccgggg    300
cccccctctg agaaggcctg gcagcctggc tggacagtca atgtggaggg cagcggggag    360
ctgttccggt ggaatgtttc ggacctaggt ggcctgggct gtggcctgaa gaacaggtcc    420
tcagagggcc ccagctcccc ttccgggaag ctcatgagcc caagctgta tgtgtgggcc    480 aaagaccgcc ctgagatctg ggaggggag cctccgtgtc tcccaccgag ggacagcctg    540
aaccagagcc tcagccaggt actatggcac tggctgctga ggactggtgg ctggaaggtc    600
tcagctgtga ctttggctta tctgatcttc tgcctgtgtt cccttgtggg cattcttcat    660
cttcaaagag ccctggtcct gaggaggaaa agaaagcgaa tgactgaccc caccaggaga    720
ttcttcaaag tgacgcctcc cccaggaagc gggcccaga accagtacgg gaacgtgctg    780
tctctcccca cacccacctc aggcctcgga cgcgcccagc gttgggccgc aggcctgggg    840
ggcactgccc cgtcttatgg aaacccgagc agcgacgtcc aggcggatgg agccttgggg    900
tcccggagcc cgccggagt gggcccagaa gaagaggaag ggagggcta tgaggaacct    960 gacagtgagg aggactccga gttctatgag aacgactcca accttgggca ggaccagctc   1020
tcccaggatg gcagcggcta cgagaaccct gaggatgagc cctgggtcc tgaggatgaa   1080 gactccttct ccaacgctga gtcttatgag aacgaggatg aagagctgac ccagccggtc   1140
gccaggacaa tggacttcct gagccctcat gggtcagcct gggaccccag ccgggaagca   1200
acctccctgg cagggtccca gtcctatgag gatatgagag gaatcctgta tgcagccccc   1260
cagctccgct ccattcgggg ccagcctgga cccaatcatg aggaagatgc agactcttat   1320
gagaacatgg ataatcccga tgggccagac ccagcctggg gaggaggggg ccgcatgggc   1380
acctggagca ccaggtga                                                 1398

<210> SEQ ID NO 120
<211> LENGTH: 1095
<212> TYPE: RNA
<213> ORGANISM: Artificial Sequence
<220> FEATURE:
<223> OTHER INFORMATION: Synthetic polynucleotide

<400> SEQUENCE: 120
augccgcugc ugcuacugcu gccccugcug ugggcagggg cccuggcuau ggauccaaau     60
uucuggcugc aagugcagga gucagugacg guacaggagg guuugugcgu ccucgugccc    120
ugcacuuucu uccaucccau acccuacuac gacaagaacu ccccaguuca ugguuacugg    180
uuccgggaag gagccauuau auccagggac ucuccagugg ccacaaacaa gcuagaucaa    240
gaaguacagg aggagacuca gggcagauuc cgccuccuug gggauccag uaggaacaac    300 ugcucccuga gcaucguaga cgccaggagg agggauaaug uucauacuu cuuucggaug    360 gagagaggaa guaccaaaua caguuacaaa ucuccccagc ucucugugca ugugacagac    420
uugacccaca ggcccaaaau ccucauccu ggcacucuag aacccggcca cuccaaaaac    480
cugaccugcu cugugccug gccugugag cagggaacac cccgaucuu cuccugguug    540 ucagcugccc ccaccucccu ggccccagg acuacucacu cccgcgugcu cauaaucacc    600
ccacggcccc aggaccacgg caccaaccug accgucagug augaaguucg cuggagcuggu    660 gugacuacgg agagaaccau ccagcucaac gucaccuaug uuccacagaa cccaacaacu    720
```

```
gguaucuuuc caggagaugg cucagggaaa caagagacca gagcaggagu gguucauggg    780 gccauggag gagcuggugu uacagcccug cucgcucuuu gucucugccu caucuucuuc    840
auagugaaga cccacaggag gaaagcagcc aggacagcag ugggcaggaa ugacacccac    900
ccuaccacag ggucagccuc cccgaaacac cagaagaagu ccaaguuaca uggcccacu    960 gaaaccucaa gcguucagg ugccgccccu acuguggaga uggaugagga gcugcauuau   1020
gcuucccuca acuuucaugg gaugaauccu ccaaggaca ccuccaccga auacucagag   1080
gucaggaccc aguga                                                    1095
```

<210> SEQ ID NO 121
<211> LENGTH: 714
<212> TYPE: RNA
<213> ORGANISM: Artificial Sequence
<220> FEATURE:
<223> OTHER INFORMATION: Synthetic polynucleotide

<400> SEQUENCE: 121

```
augccgcugc ugcuacugcu gccccugcug ugggcagacu ugacccacag gcccaaaauc     60
cucaucccug gcacucuaga acccggccac uccaaaaacc ugaccugcuc ugugccuggg   120
gccugugagc agggaacacc cccgaucuuc uccugguugu cagcugcccc caccucccug   180
ggccccagga cuacacacuc cucggugcuc auaaucaccc cacggcccca ggaccacggc   240
accaaccuga ccugucaggu gaaguucgcu ggagcuggug ugacacggga gagaaccauc   300
cagcucaacg ucaccuaugu ccacagaac ccaacaacug guaucuuucc aggagauggc   360
ucagggaaac aagagaccag agcaggagug guucauggg ccauuggagg agcuggugu    420 acagcccugc ucgcucuuug ucucugccuc aucuucuuca uagugaagac ccacaggagg   480
aaagcagcca ggacagcagu gggcaggaau gacacccacc cuaccacagg gucagccucc   540
ccgaaacacc agaagaaguc caaguuacau ggccccacug aaaccucaag cguucaggu    600 gccgcccua cuguggagau ggaugaggag cugcauuaug cuucccucaa cuuucauggg   660
augaauccuu ccaaggacac cuccaccgaa uacucagagg ucaggaccca guga         714
```

<210> SEQ ID NO 122
<211> LENGTH: 930
<212> TYPE: RNA
<213> ORGANISM: Artificial Sequence
<220> FEATURE:
<223> OTHER INFORMATION: Synthetic polynucleotide

<400> SEQUENCE: 122

```
augccgcugc ugcuacugcu gccccugcug ugggcagggg cccuggcuau ggauccaaau    60
uucuggcugc aagugcagga gucagugacg guacaggagg guuugugcgu ccucgugccc   120
ugcacuuucu uccauccau acccuacuac gacaagaacu ccccaguuca ugguuacugg   180
uuccgggaag gagccauuau auccaggac ucuccaguggg ccacaaacaa gcuagaucaa   240
gaaguacagg aggagacuca gggcagauuc cgccuccuug gggauccag uaggaacaac   300 ugcucccuga gcaucguaga cgccaggagg agggauaaug guucauacuu cuuucggaug   360
gagagaggaa guaccaaaua caguuacaaa ucuccccagc ucucugugca ugugacagac   420
uugacccaca ggcccaaaau ccucaucccu ggcacucuag aacccggcca cuccaaaaac   480
cugaccugcu cugugccug gccugugagc agggaacacc cccgaucuuc uccgguugc    540 agcugccccc accucccugg gccccaggac uacacacucc ucggugcuca uaaucacccc   600
```

```
acggccccag gaccacggca ccaaccugac cugucaggug aaguucgcug gagcuggugu    660
gacuacggag agaaccaucc agcucaacgu caccuauguu ccacagaacc caacaacugg    720
uaucuuuccg gagauggcuc agggaaacaa gagaccagag caggaguggu caugggggcc    780
auuggaggag cugguguuac agcccugcuc gcucuuuguc ucugccucau cuucuucaua    840
gugaagaccc acaggaggaa agcagccagg acagcagugg gcaggaauga cacccacccu    900
accacagggu cagccucccc gguacguuga                                    930
```

<210> SEQ ID NO 123
<211> LENGTH: 675
<212> TYPE: RNA
<213> ORGANISM: Artificial Sequence
<220> FEATURE:
<223> OTHER INFORMATION: Synthetic polynucleotide

<400> SEQUENCE: 123

```
augccgcugc ugcuacugcu gcccugcug ugggcaagga acaacugcuc ccugagcauc    60
guagacgcca ggaggaggga uaaugguuca uacuucuuuc ggauggagag aggaaguacc   120
aaauacaguu acaaaucucc ccagcucucu gugcauguga cagacuugac ccacaggccc   180
aaaauccuca ucccuggcac ucuagaaccc ggccacucca aaaaccugac cugcucugug   240
uccuggccug ugagcaggga acaccccga ucuuuccgg uugucagcug ccccaccuc     300 ccugggcccc aggacuacuc acuccucggu gcucauaauc accccacggc cccaggacca   360
cggcaccaac cugaccuguc aggugaaguu cgcuggagcu ggugugacua cggagagaac   420
cauccagcuc aacgucaccu auguuccaca gaacccaaca acugguaucu uuccggagau   480
ggcucaggga acaagagac cagagcagga gugguucaug gggccauugg aggagcuggu   540
guuacagccc ugcucgcucu uugucucugc cucaucuucu ucauagugaa gacccacagg   600
aggaaagcag ccaggacagc agugggcagg aaugacaccc acccuaccac aggguucagcc   660 uccccgguac guuga                                                    675
```

<210> SEQ ID NO 124
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent

<400> SEQUENCE: 124

```
Gly Gly Gly Gly Gly Gly Gly Gly Gly Gly Gly Ser Gly Gly Gly
1               5                   10                  15

Gly Gly Gly Gly Gly Gly Gly Gly Gly Ser Gly Gly Gly Gly Gly
            20                  25                  30

Gly Gly Gly Gly Gly Gly Ser
        35
```

<210> SEQ ID NO 125

<211> LENGTH: 52
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent

<400> SEQUENCE: 125

Gly Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly
            20                  25                  30

Gly Gly Gly Gly Gly Gly Ser Gly Gly Gly Gly Gly Gly Gly
        35                  40                  45

Gly Gly Gly Ser
        50

<210> SEQ ID NO 126
<211> LENGTH: 65
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent

<400> SEQUENCE: 126

Gly Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly
            20                  25                  30

Gly Gly Gly Gly Gly Ser Gly Gly Gly Gly Gly Gly Gly Gly
        35                  40                  45

Gly Gly Gly Ser Gly Gly Gly Gly Gly Gly Gly Gly Gly
    50                  55                  60

Ser

<210> SEQ ID NO 127
<211> LENGTH: 78
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent

<400> SEQUENCE: 127

Gly Gly Gly Gly Gly Gly Gly Gly Gly Gly Gly Ser Gly Gly Gly
1               5                   10                  15

Gly Gly Gly Gly Gly Gly Gly Gly Gly Ser Gly Gly Gly Gly Gly
            20                  25                  30

Gly Gly Gly Gly Gly Gly Ser Gly Gly Gly Gly Gly Gly Gly Gly
        35                  40                  45

Gly Gly Gly Ser Gly Gly Gly Gly Gly Gly Gly Gly Gly Gly Gly
    50                  55                  60

Ser Gly Gly Gly Gly Gly Gly Gly Gly Gly Gly Gly Ser
65                  70                  75

<210> SEQ ID NO 128
<211> LENGTH: 91
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:

<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent

<400> SEQUENCE: 128

Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly
            20                  25                  30

Gly Gly Gly Gly Gly Ser Gly Gly Gly Gly Gly Gly Gly Gly
        35                  40                  45

Gly Gly Gly Ser Gly Gly Gly Gly Gly Gly Gly Gly Gly
    50                  55                  60

Ser Gly Gly Gly Gly Gly Gly Gly Gly Gly Gly Ser Gly Gly
65                  70                  75                  80

Gly Gly Gly Gly Gly Gly Gly Gly Gly Ser
                85                  90

<210> SEQ ID NO 129
<211> LENGTH: 104
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent
<220> FEATURE:
<221> NAME/KEY: misc_feature
<222> LOCATION: (95)..(103)
<223> OTHER INFORMATION: may be absent

<400> SEQUENCE: 129

Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly
            20                  25                  30

Gly Gly Gly Gly Gly Ser Gly Gly Gly Gly Gly Gly Gly Gly
        35                  40                  45

Gly Gly Gly Ser Gly Gly Gly Gly Gly Gly Gly Gly
    50                  55                  60

Ser Gly Gly Gly Gly Gly Gly Gly Gly Gly Ser Gly Gly
65                  70                  75                  80

Gly Gly Gly Gly Gly Gly Gly Gly Ser Gly Gly Gly Gly
                85                  90                  95

Gly Gly Gly Gly Gly Gly Gly Ser
            100

<210> SEQ ID NO 130
<211> LENGTH: 117
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent
<220> FEATURE:
<221> NAME/KEY: misc_feature
<222> LOCATION: (95)..(103)
<223> OTHER INFORMATION: may be absent
<220> FEATURE:
<221> NAME/KEY: misc_feature
<222> LOCATION: (108)..(116)
<223> OTHER INFORMATION: may be absent

<400> SEQUENCE: 130

Gly Gly Gly Gly Gly Gly Gly Gly Gly Gly Ser Gly Gly
1               5                   10                  15

Gly Gly Gly Gly Gly Gly Gly Gly Ser Gly Gly Gly Gly
            20                  25                  30

Gly Gly Gly Gly Gly Ser Gly Gly Gly Gly Gly Gly Gly
        35                  40                  45

Gly Gly Gly Ser Gly Gly Gly Gly Gly Gly Gly Gly Gly
    50                  55                  60

Ser Gly Gly Gly Gly Gly Gly Gly Gly Gly Ser Gly Gly
65                  70                  75                  80

Gly Gly Gly Gly Gly Gly Gly Gly Ser Gly Gly Gly Gly
                85                  90                  95

Gly Gly Gly Gly Gly Gly Gly Ser Gly Gly Gly Gly Gly Gly
                100                 105                 110

Gly Gly Gly Gly Ser
        115

<210> SEQ ID NO 131
<211> LENGTH: 130
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent
<220> FEATURE:
<221> NAME/KEY: misc_feature
<222> LOCATION: (95)..(103)
<223> OTHER INFORMATION: may be absent
<220> FEATURE:
<221> NAME/KEY: misc_feature
<222> LOCATION: (108)..(116)
<223> OTHER INFORMATION: may be absent
<220> FEATURE:
<221> NAME/KEY: misc_feature
<222> LOCATION: (121)..(129)
<223> OTHER INFORMATION: may be absent

<400> SEQUENCE: 131

Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly
            20                  25                  30

Gly Gly Gly Gly Gly Ser Gly Gly Gly Gly Gly Gly Gly Gly
        35                  40                  45

Gly Gly Ser Gly Gly Gly Gly Gly Gly Gly Gly Gly Gly Gly
    50                  55                  60

Ser Gly Gly Gly Gly Gly Gly Gly Gly Ser Gly Gly
65                  70                  75              80

Gly Gly Gly Gly Gly Gly Gly Ser Gly Gly Gly Gly
            85                  90                  95

Gly Gly Gly Gly Gly Gly Ser Gly Gly Gly Gly Gly Gly
            100                 105                 110

Gly Gly Gly Gly Ser Gly Gly Gly Gly Gly Gly Gly Gly
        115                 120                 125

Gly Ser
    130

<210> SEQ ID NO 132
<211> LENGTH: 143
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent
<220> FEATURE:
<221> NAME/KEY: misc_feature
<222> LOCATION: (95)..(103)
<223> OTHER INFORMATION: may be absent
<220> FEATURE:
<221> NAME/KEY: misc_feature
<222> LOCATION: (108)..(116)
<223> OTHER INFORMATION: may be absent
<220> FEATURE:
<221> NAME/KEY: misc_feature
<222> LOCATION: (121)..(129)
<223> OTHER INFORMATION: may be absent
<220> FEATURE:
<221> NAME/KEY: misc_feature
<222> LOCATION: (134)..(142)
<223> OTHER INFORMATION: may be absent

<400> SEQUENCE: 132

Gly Gly Gly Gly Gly Gly Gly Gly Gly Gly Gly Ser Gly Gly Gly
1               5                   10                  15

Gly Gly Gly Gly Gly Gly Gly Gly Ser Gly Gly Gly Gly Gly Gly
            20                  25                  30

Gly Gly Gly Gly Gly Gly Ser Gly Gly Gly Gly Gly Gly Gly Gly
        35                  40                  45

Gly Gly Gly Ser Gly Gly Gly Gly Gly Gly Gly Gly Gly Gly Gly
    50                  55                  60

Ser Gly Gly Gly Gly Gly Gly Gly Gly Gly Gly Ser Gly Gly Gly
65                  70                  75                  80

Gly Gly Gly Gly Gly Gly Gly Gly Ser Gly Gly Gly Gly Gly Gly
            85                  90                  95

Gly Gly Gly Gly Gly Gly Gly Ser Gly Gly Gly Gly Gly Gly Gly
        100                 105                 110

Gly Gly Gly Gly Ser Gly Gly Gly Gly Gly Gly Gly Gly Gly Gly
    115                 120                 125

-continued

Gly Ser Gly Gly Gly Gly Gly Gly Gly Gly Gly Ser
        130                 135                 140

<210> SEQ ID NO 133
<211> LENGTH: 156
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(12)
<223> OTHER INFORMATION: may be absent
<220> FEATURE:
<221> NAME/KEY: misc_feature
<222> LOCATION: (17)..(25)
<223> OTHER INFORMATION: may be absent
<220> FEATURE:
<221> NAME/KEY: misc_feature
<222> LOCATION: (30)..(38)
<223> OTHER INFORMATION: may be absent
<220> FEATURE:
<221> NAME/KEY: misc_feature
<222> LOCATION: (43)..(51)
<223> OTHER INFORMATION: may be absent
<220> FEATURE:
<221> NAME/KEY: misc_feature
<222> LOCATION: (56)..(64)
<223> OTHER INFORMATION: may be absent
<220> FEATURE:
<221> NAME/KEY: misc_feature
<222> LOCATION: (69)..(77)
<223> OTHER INFORMATION: may be absent
<220> FEATURE:
<221> NAME/KEY: misc_feature
<222> LOCATION: (82)..(90)
<223> OTHER INFORMATION: may be absent
<220> FEATURE:
<221> NAME/KEY: misc_feature
<222> LOCATION: (95)..(103)
<223> OTHER INFORMATION: may be absent
<220> FEATURE:
<221> NAME/KEY: misc_feature
<222> LOCATION: (108)..(116)
<223> OTHER INFORMATION: may be absent
<220> FEATURE:
<221> NAME/KEY: misc_feature
<222> LOCATION: (121)..(129)
<223> OTHER INFORMATION: may be absent
<220> FEATURE:
<221> NAME/KEY: misc_feature
<222> LOCATION: (134)..(142)
<223> OTHER INFORMATION: may be absent
<220> FEATURE:
<221> NAME/KEY: misc_feature
<222> LOCATION: (147)..(155)
<223> OTHER INFORMATION: may be absent

<400> SEQUENCE: 133

Gly Gly Gly Gly Gly Gly Gly Gly Gly Gly Ser Gly Gly Gly
1               5                   10                  15

Gly Gly Gly Gly Gly Gly Gly Gly Gly Ser Gly Gly Gly Gly Gly
                20                  25                  30

Gly Gly Gly Gly Gly Gly Ser Gly Gly Gly Gly Gly Gly Gly Gly
            35                  40                  45

Gly Gly Gly Ser Gly Gly Gly Gly Gly Gly Gly Gly Gly Gly
        50                  55                  60

Ser Gly Gly Gly Gly Gly Gly Gly Gly Gly Gly Ser Gly Gly
65                  70                  75                  80

Gly Gly Gly Gly Gly Gly Gly Gly Ser Gly Gly Gly Gly
                85                  90                  95

```
Gly Gly Gly Gly Gly Gly Ser Gly Gly Gly Gly Gly Gly
            100                 105                 110

Gly Gly Gly Gly Ser Gly Gly Gly Gly Gly Gly Gly Gly Gly
        115                 120                 125

Gly Ser Gly Gly Gly Gly Gly Gly Gly Gly Gly Gly Ser Gly
    130                 135                 140

Gly Gly Gly Gly Gly Gly Gly Gly Gly Gly Ser
145                 150                 155

<210> SEQ ID NO 134
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 134
ccccaggact actcactcct                                                  20

<210> SEQ ID NO 135
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 135
tttcttgagc tgcagctggg                                                  20

<210> SEQ ID NO 136
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 136
agttcccaca tcctggtgcg                                                  20

<210> SEQ ID NO 137
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 137
ggtggctatt gtttgcagtg                                                  20
```